United States Patent [19]
Johnson

[11] Patent Number: 5,854,043
[45] Date of Patent: Dec. 29, 1998

[54] MEKK-RELATED SIGNAL TRANSDUCTION KINASES

[75] Inventor: Gary L. Johnson, Boulder, Colo.

[73] Assignee: National Jewish Center for Immunology and Respiratory Medicine, Denver, Colo.

[21] Appl. No.: 323,460

[22] Filed: Oct. 14, 1994

Related U.S. Application Data

[63] Continuation-in-part of PCT/US94/04178 Apr. 15, 1994 and continuation-in-part of Ser. No. 49,254, Apr. 15, 1993, Pat. No. 5,405,941.

[51] Int. Cl.$^6$ .............................. C07K 14/435; C12N 9/12
[52] U.S. Cl. .......................... 435/194; 435/69.1; 530/350
[58] Field of Search .............................. 530/350; 435/194, 435/69.1; 514/2

[56] References Cited

PUBLICATIONS

Seger et al., J. Biol. Chem., vol. 267, 25628, 1992.
Wang et al., Molecular and Cellular Biology, vol. 11, 3554, 1991.
Dent et al., pp. 1404–1407, 1992, *Science*, vol. 257.
Kolch et al., "Raf–1 Protein Kinase is Required for Growth of Induced NIH/3T3 Cells", pp. 426–428, 1991, Nature, vol. 349, Jan. 31.
Kyriakis et al., pp. 417–421, 1992, *Nature*, vol. 358.
L'Allemain et. al., "p42/Mitogen–Activated Protein Kinase as a Converging Target for Different Growth Factor Signaling Pathways: Use of Pertussis Toxin as a Discrimination Factor", pp. 675–684, 1991, Cell Reg., vol. 2, Aug.
Leberer et. al., "The Protein Kinase Homologue Ste20p is Required to Link the Yeast Pheromone Response G–protein βγ Subunits to Downstream Signalling Components", pp. 4815–4824, 1992, EMBO J., vol. 11.
Qureshi et. al., "An Inhibitory Mutant of c–Raf–1 Blocks v–Src–induced Activation of the Egr–1 Promoter", pp. 20594–20597, 1991, J. Biol. Chem., vol. 226, No. 31, Nov.
Stevenson et. al., "Constritctive Mutants of the Protein Kinase STE11 Activate the Yeast Pheromone Response Pathway in the Absence of the G Protein", pp. 1293–1304, 1992, Genes & Dev., vol. 6.
Tamaki et. al., "Surface Immunoglobulin–mediated Signal Transduction Involves Rapid Phosphorylation and Activation of the Protooncogene Product Raf–1 in Human B–Cells", pp. 566–570, 1992, Cancer Res., vol. 52, Feb. 1.

*Primary Examiner*—Sally P. Teng
*Attorney, Agent, or Firm*—Lahive & Cockfield, LLP; Giulio A. DeConti, Jr.; Catherine J. Kara

[57] ABSTRACT

The present invention relates to isolated MEKK proteins, nucleic acid molecules having sequences that encode such proteins, and antibodies raised against such proteins. The present invention also includes methods to use such proteins to regulate signal transduction in a cell. The present invention also includes therapeutic compositions comprising such proteins or nucleic acid molecules that encode such proteins and their use to treat animals having medical disorders including cancer, inflammation, neurological disorders, autoimmune diseases, allergic reactions, and hormone-related diseases. When MEKK is expressed, it phosphorylates and activates MEKs including MEK-1, MEK-2 and JEK.

11 Claims, 32 Drawing Sheets

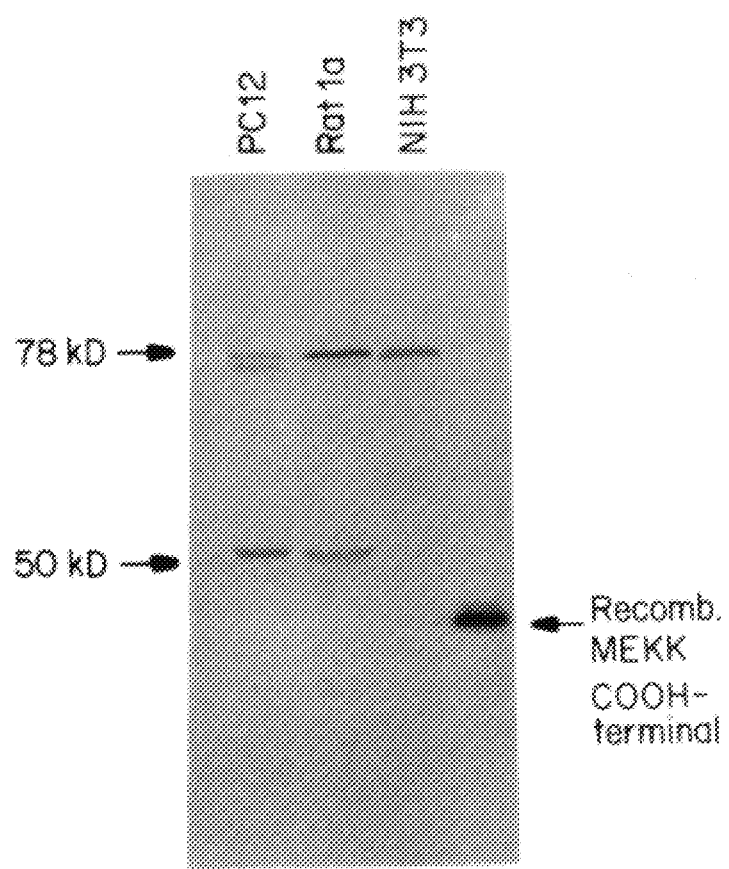

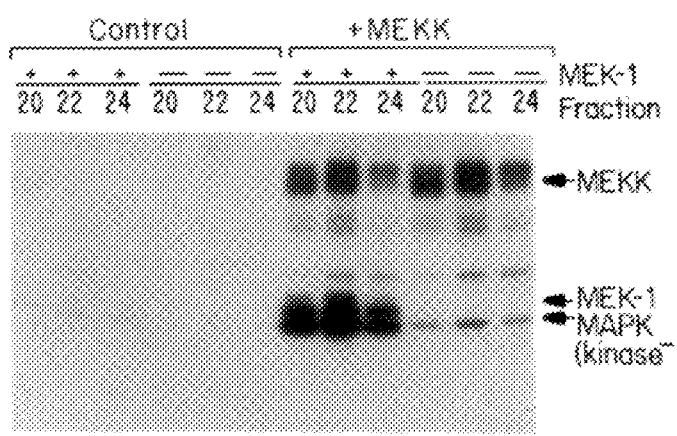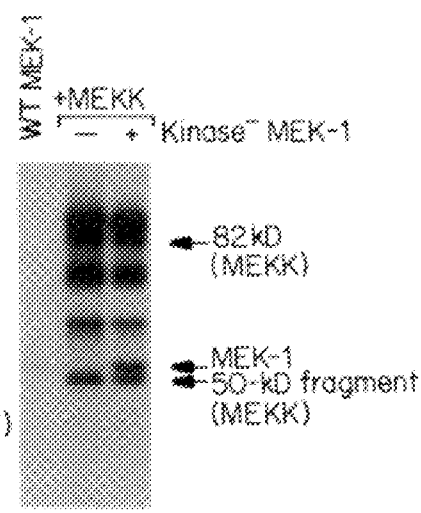

FIG.17A    FIG.17B   FIG.17C
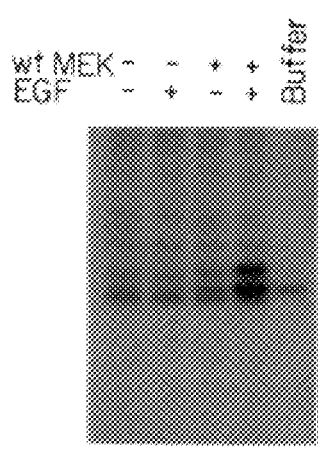
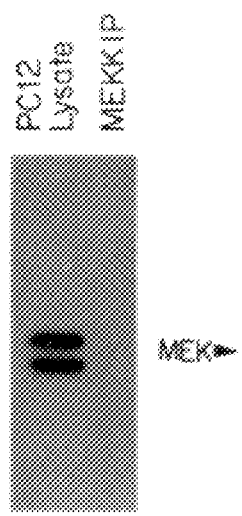

Myc-Gal 4 fusion protein:

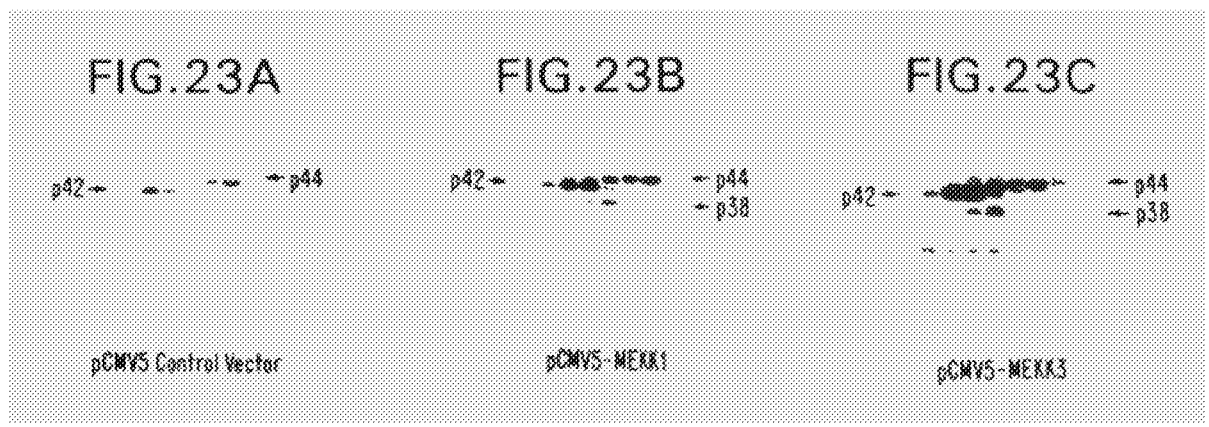

FIG.27A  FIG.27B
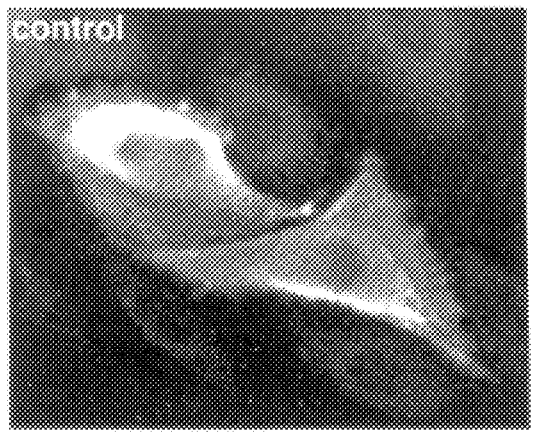 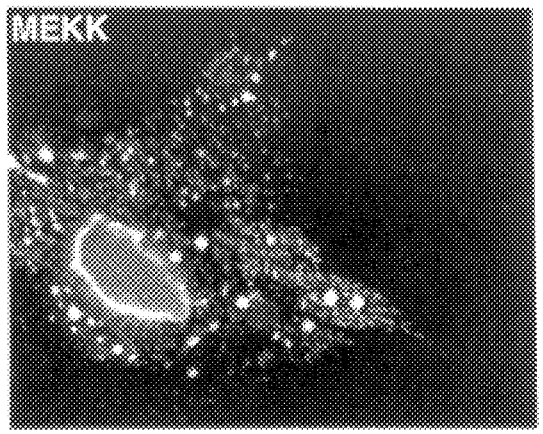
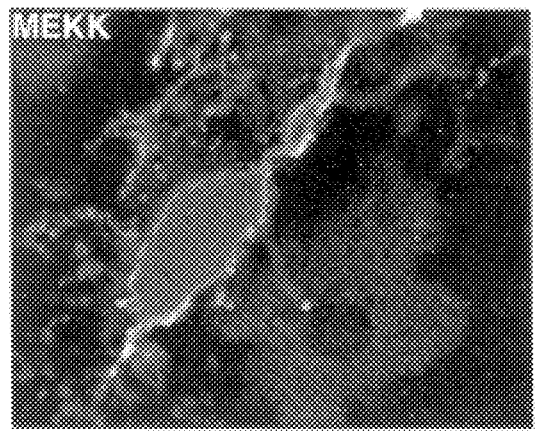 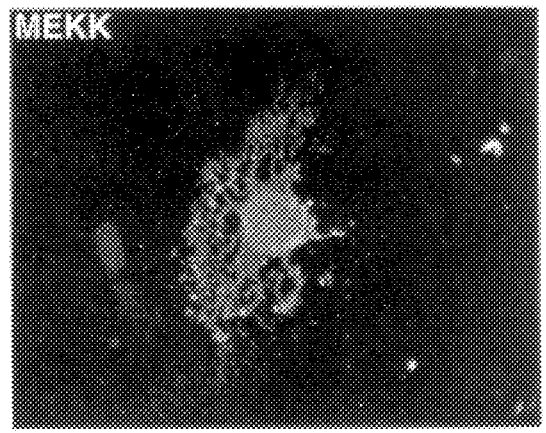
FIG.27C  FIG.27D

MEKK-RELATED SIGNAL TRANSDUCTION KINASES

CROSS-REFERENCE TO RELATED APPLICATIONS

The present application is a continuation-in-part of U.S. patent application Ser. No. 08/049,254 for "Method and Product for Regulating Cell Responsiveness to External Signals", filed Apr. 15, 1993, now U.S. Pat. No. 5,405,941, incorporated herein by this reference in its entirety. The present application is also a continuation-in-part of PCT Application No. PCT/US94/04178 for "Method and Product for Regulating Cell Responsiveness to External Signals", filed Apr. 15, 1994, incorporated herein by this reference in its entirety.

This invention was made in part with government support under USPHS Grant DK37871 and USPHS Grant GM30324, both awarded by the National Institutes of Health. The government has certain rights to this invention.

FIELD OF THE INVENTION

This invention relates to isolated nucleic acid molecules encoding MEKK proteins, substantially pure MEKK proteins, and products and methods for regulating signal transduction in a cell.

SUMMARY OF THE INVENTION

The present invention relates to a substantially pure MEKK protein capable of phosphorylating mammalian MEK protein, in which the MEKK protein comprises a catalytic domain. The present invention includes a substantially pure MEKK protein capable of regulating signals initiated from a growth factor receptor on the surface of a cell by regulating the activity of MAPK protein, the ability to regulate being divergent from Raf protein signal regulation. In particular, the substantially pure MEKK protein comprises at least a portion of an amino acid sequence encoded by a nucleic acid sequence that is capable of hybridizing under stringent conditions with a nucleic acid molecule encoding an amino acid sequence including SEQ ID NO:4, SEQ ID NO:6, SEQ ID NO:8 and SEQ ID NO:10. The substantially pure MEKK protein capable of regulating the activity of MAPK protein, said protein having an amino acid sequence distinct from Raf protein.

The present invention also includes a formulation comprising at least one isolated protein having at least a portion of an amino acid sequence encoded by a nucleic acid sequence that is capable of hybridizing under stringent conditions with a nucleic acid molecule encoding an amino acid sequence including SEQ ID NO:2, SEQ ID NO:4, SEQ ID NO:6, SEQ ID NO:8 and SEQ ID NO:10.

One aspect of the present invention includes an isolated nucleic acid molecule having a sequence encoding a protein capable of phosphorylating mammalian MEK independent of Raf protein and capable of regulating the activity of MAPK protein. In particular, the present invention includes an isolated nucleic acid molecule capable of hybridizing under stringent conditions with a nucleic acid sequence selected from the group consisting of SEQ ID NO:1, SEQ ID NO:3, SEQ ID NO:5, SEQ ID NO:7 and SEQ ID NO:9.

Another aspect of the present invention includes a recombinant molecule, comprising a nucleic acid molecule capable of hybridizing under stringent conditions with a nucleic acid sequence including SEQ ID NO:1, SEQ ID NO:3, SEQ ID NO:5, SEQ ID NO:7 and SEQ ID NO:9, in which the nucleic acid molecule is operatively linked to an expression vector.

Yet another aspect of the present invention is a recombinant cell transformed with a recombinant molecule, comprising a nucleic acid molecule operatively linked to an expression vector, the nucleic acid molecule comprising a nucleic acid sequence capable of hybridizing under stringent conditions with a nucleic acid sequence selected from the group consisting of SEQ ID NO:1, SEQ ID NO:3, SEQ ID NO:5, SEQ ID NO:7 and SEQ ID NO:9 (i.e., the nucleic acid sequence shown in Table 1, Table 2, Table 3, Table 4 and Table 5).

The present invention also includes a method for regulating the homeostasis of a cell comprising regulating the activity of an MEKK-dependent pathway relative to the activity of a Raf-dependent pathway in the cell. In particular, the method comprises regulating the apoptosis of the cell. Such a method is useful for the treatment of a medical disorder. In particular, the method is useful for inhibiting tumorigenesis and autoimmunity.

According to the present invention, the method for treatment of a disease, comprises administering to a patient an effective amount of a therapeutic compound comprising at least one regulatory molecule including a molecule capable of decreasing the activity of a Raf-dependent pathway, a molecule capable of increasing the activity of an MEKK-dependent pathway, and combinations thereof, in which the effective amount comprises an amount which results in the depletion of harmful cells involved in the disease.

Also included in the present invention is a therapeutic compound capable of regulating the activity of an MEKK-dependent pathway in a cell identified by a process, comprising: (a) contacting a cell with a putative regulatory molecule; and (b) determining the ability of the putative regulatory compound to regulate the activity of an MEKK-dependent pathway in the cell by measuring the activation of at least one member of said MEKK-dependent pathway.

One embodiment of the present invention includes a substantially pure protein, in which the protein is isolated using an antibody capable of selectively binding to an MEKK protein capable of phosphorylating mammalian MEK protein and capable of regulating the activity of MAPK protein independent of Raf protein, the antibody capable of being produced by a method comprising: (a) administering to an animal an effective amount of a substantially pure MEKK protein of the present invention; and (b) recovering an antibody capable of selectively binding to the MEKK protein.

Another embodiment of the present invention includes an isolated antibody capable of selectively binding to an MEKK protein, the antibody capable of being produced by a method comprising administering to an animal an effective amount of a substantially pure protein of the present invention, and recovering an antibody capable of selectively binding to the MEKK protein.

BACKGROUND OF THE INVENTION

Mitogen-activated protein kinase (MAPKs) (also called extracellular signal-regulated kinases or ERKs) are rapidly activated in response to ligand binding by both growth factor receptors that are tyrosine kinases (such as the epidermal growth factor (EGF) receptor) and receptors that are coupled to heterotrimeric guanine nucleotide binding proteins (G proteins) such as the thrombin receptor. The MAPKs appear to integrate multiple intracellular signals transmitted by various second messengers. MAPKs phosphorylate and regulate the activity of enzymes and transcription factors including the EGF receptor, Rsk 90, phospholipase $A_2$, c-Myc, c-Jun and Elk-1/TCF. Although the rapid activation of MAPKs by receptors that are tyrosine kinases is dependent on Ras, G protein-mediated activation of MAPK appears to occur through pathways dependent and independent of Ras.

Complementation analysis of the pheromone-induced signaling pathway in yeast has defined a protein kinase system that controls the activity of Spk1 and Fus3-Kss1, the *Schizosaccharomyces pombe* and *Saccharomyces cerevisiae* homologs of MAPK (see for example, B. R. Cairns et al., *Genes and Dev.* 6, 1305 (1992); B. J. Stevenson et al., *Genes and Dev.* 6, 1293 (1992); S. A. Nadin-Davis et al., *EMBO J.* 7, 985 (1988); Y. Wang et al., *Mol. Cell. Biol.* 11, 3554 (1991). In *S. cerevisiae*, the protein kinase Ste7 is the upstream regulator of Fus3-Kss1 activity; the protein kinase Ste11 regulates Ste7. The *S. pombe* gene products Byr1 and Byr2 are homologous to Ste7 and Ste11, respectively. The MEK (MAPK Kinase or ERK Kinase) or MKK (MAP Kinase kinase) enzymes are similar in sequence to Ste7 and Byr1. The MEKs phosphorylate MAPKs on both tyrosine and threonine residues which results in activation of MAPK. The mammalian serine-threonine protein kinase Raf phosphorylates and activates MEK, which leads to activation of MAPK. Raf is activated in response to growth factor receptor tyrosine kinase activity and therefore Raf may activate MAPK in response to stimulation of membrane-associated tyrosine kinases. Raf is unrelated in sequence to Ste11 and Byr2. Thus, Raf may represent a divergence in mammalian cells from the pheromone-responsive protein kinase system defined in yeast. Cell and receptor specific differences in the regulation of MAPKs suggest that other Raf independent regulators of mammalian MEKs exist.

Certain biological functions, such as growth and differentiation, are tightly regulated by signal transduction pathways within cells. Signal transduction pathways maintain the balanced steady state functioning of a cell. Disease states can arise when signal transduction in a cell breaks down, thereby removing the tight control that typically exists over cellular functions. For example, tumors develop when regulation of cell growth is disrupted enabling a clone of cells to expand indefinitely. Because signal transduction networks regulate a multitude of cellular functions depending upon the cell type, a wide variety of diseases can result from abnormalities in such networks. Devastating diseases such as cancer, autoimmune diseases, allergic reactions, inflammation, neurological disorders and hormone-related diseases can result from abnormal signal transduction.

Despite a long-felt need to understand and discover methods for regulating cells involved in various disease states, the complexity of signal transduction pathways has precluded the development of products and processes for regulating cellular function by manipulating signal transduction pathways in a cell. As such, there remains a need for products and processes that permit the implementation of predictable controls of signal transduction in cells, thus enabling the treatment of various diseases that are caused by abnormal cellular function.

BRIEF DESCRIPTION OF THE FIGURES

FIG. 3C shows an immunoblot showing expression of the 78 kD and 50 kD forms of MEKK in rodent cell lines.

FIG. 9A shows the phosphorylation of MAPK by activated MEK-1.

FIG. 9B shows phosphorylation of MEK-1 by immunoprecipitated MEKK.

FIG. 17 shows activation of MEK protein by 98 kD MEKK.

FIG. 23 shows induction of p38 MAPK phosphorylation by MEKK 3.

FIG. 27 shows 3 representative microscopic views of apoptotic REF52 cells expressing MEKK protein.

DETAILED DESCRIPTION OF THE INVENTION

Figure 1:
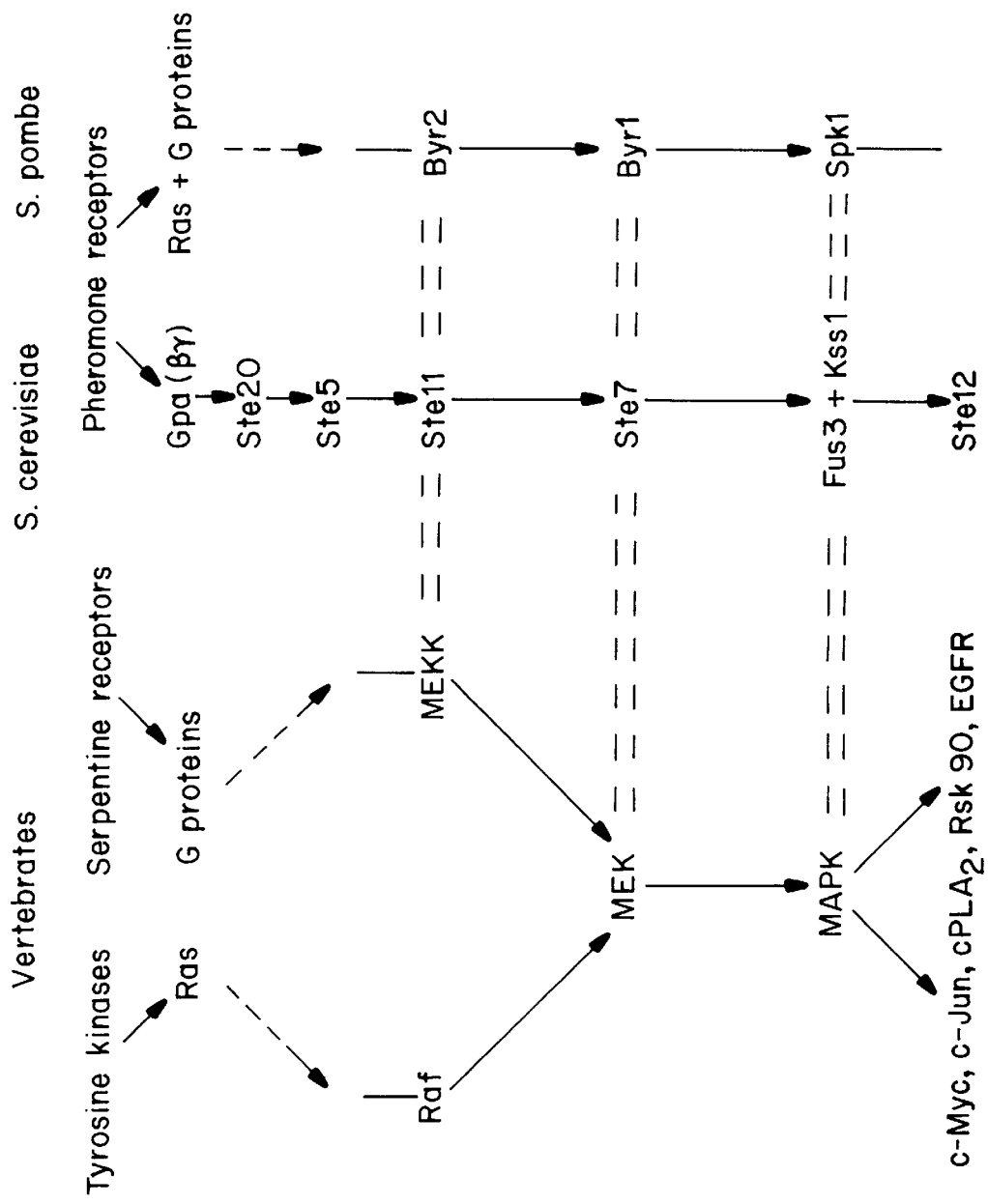
FIG. 1 is a schematic representation of the signal pathways of vertebrates and yeast.

The present invention relates to a novel mitogen ERK kinase kinase protein (MEKK) capable of regulating signal transduction in cells. The present invention includes a novel method for treating disease by regulating the activity of cells involved in such disease. The present invention is particularly advantageous in that the novel product and method of the present invention is capable of regulating a signal transduction pathway that can lead to cellular apoptosis.

One embodiment of the present invention is an isolated MEKK protein. According to the present invention, an isolated protein is a protein that has been removed from its natural milieu. An isolated MEKK protein can, for example, be obtained from its natural source, be produced using recombinant DNA technology, or be synthesized chemically. As used herein, an isolated MEKK protein can be a full-length MEKK protein or any homologue of such a protein, such as an MEKK protein in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycosylphosphatidyl inositol), wherein the modified protein is capable of phosphorylating mitogen ERK kinase (MEK) and/or Jun ERK kinase (JEK). A homologue of an MEKK protein is a protein having an amino acid sequence that is sufficiently similar to a natural MEKK protein amino acid sequence that a nucleic acid sequence encoding the homologue is capable of hybridizing under stringent conditions to (i.e., with) a nucleic acid sequence encoding the natural MEKK protein amino acid sequence. As used herein, stringent hybridization conditions refer to standard hybridization conditions under which nucleic acid molecules, including oligonucleotides, are used to identify similar nucleic acid molecules. Such standard conditions are disclosed, for example, in Sambrook et al., *Molecular Cloning: A Laboratory Manual*, Cold Spring Harbor Labs Press, 1989. A homologue of an MEKK protein also includes a protein having an amino acid sequence that is sufficiently cross-reactive such that the homologue has the ability to elicit an immune response against at least one epitope of a naturally-occurring MEKK protein.

The minimal size of a protein homologue of the present invention is a size sufficient to be encoded by a nucleic acid molecule capable of forming a stable hybrid with the complementary sequence of a nucleic acid molecule encoding the corresponding natural protein. As such, the size of the nucleic acid molecule encoding such a protein homologue is dependent on nucleic acid composition, percent homology between the nucleic acid molecule and complementary sequence, as well as upon hybridization conditions per se (e.g., temperature, salt concentration, and formamide concentration). The minimal size of such nucleic acid molecules is typically at least about 12 to about 15 nucleotides in length if the nucleic acid molecules are GC-rich and at least about 15 to about 17 bases in length if they are AT-rich. As such, the minimal size of a nucleic acid molecule used to encode an MEKK protein homologue of the present invention is from about 12 to about 18 nucleotides in length. There is no limit, other than a practical limit, on the maximal size of such a nucleic acid molecule in that the nucleic acid molecule can include a portion of a gene, an entire gene, or multiple genes, or portions thereof. Similarly, the minimal size of an MEKK protein homologue of the present invention is from about 4 to about 6 amino acids in length, with preferred sizes depending on whether a full-length, multivalent protein (i.e., fusion protein having more than one domain each of which has a function), or a functional portion of such a protein is desired.

MEKK protein homologues can be the result of allelic variation of a natural gene encoding an MEKK protein. A natural gene refers to the form of the gene found most often in nature. MEKK protein homologues can be produced using techniques known in the art including, but not limited to, direct modifications to a gene encoding a protein using, for example, classic or recombinant DNA techniques to effect random or targeted mutagenesis. The ability of an MEKK protein homologue to phosphorylate MEK and/or JEK protein can be tested using techniques known to those skilled in the art. Such techniques include phosphorylation assays described in detail in the Examples section.

In one embodiment, an MEKK protein of the present invention is capable of regulating an MEKK-dependent pathway. According to the present invention, an MEKK-dependent pathway refers generally to a pathway in which MEKK protein regulates a pathway substantially independent of Raf, and a pathway in which MEKK protein regulation converges with common members of a pathway involving Raf protein, in particular, MEK protein (see FIG. 2). A suitable MEKK-dependent pathway includes a pathway involving MEKK protein and JEK protein, but not Raf protein. One of skill in the art can determine that regulation of a pathway by an MEKK protein is substantially independent of Raf protein by comparing the ability of an MEKK protein and a Raf protein to regulate the phosphorylation of a downstream member of such pathway using, for example, the general method described in Example 16. An MEKK protein regulates a pathway substantially independently of Raf protein if the MEKK protein induces phosphorylation of a member of the pathway downstream of MEKK (e.g., proteins including JEK, JNK, Jun and/or ATF-2) by an amount significantly greater than that seen when Raf protein is utilized. For example, MEKK induction of phosphorylation of JNK is preferably at least about 10-fold, more preferably at least about 20-fold and even more preferably at least about 30-fold, greater phosphorylation of JNK protein than the phosphorylation induced when using Raf protein. If MEKK induction of phosphorylation is similar to Raf protein induction of phosphorylation, then one of skill in the art can conclude that regulation of a pathway by an MEKK protein includes members of a signal transduction pathway that could also include Raf protein. For example, MEKK induction of phosphorylation of MAPK is of a similar magnitude as induction of phosphorylation with Raf protein.

A "Raf-dependent pathway" can refer to a signal transduction pathway in which Raf protein regulates a signal transduction pathway substantially independently of MEKK protein, and a pathway in which Raf protein regulation converges with common members of a pathway involving MEKK protein. The independence of regulation of a pathway by a Raf protein from regulation of a pathway by an MEKK protein can be determined using methods similar to those used to determine MEKK independence.

In another embodiment, an MEKK protein is capable of regulating the activity of signal transduction proteins including, but not limited to, mitogen ERK kinase (MEK), mitogen activated protein kinase (MAPK), transcription control factor (TCF), Ets-like-1 transcription factor (Elk-1), Jun ERK kinase (JEK), Jun kinase (JNK), stress activated MAPK proteins, Jun, activating transcription factor-2 (ATF-2) and/or Myc protein. As used herein, the "activity" of a protein can be directly correlated with the phosphorylation state of the protein and/or the ability of the protein to perform a particular function (e.g., phosphorylate another protein or regulate transcription). Preferred MEK proteins regulated by an MEKK protein of the present invention include MEK-1 and/or MEK-2. Preferred MAPK proteins regulated by an MEKK protein of the present invention include p38 MAPK, p42 MAPK and/or p44 MAPK. A preferred MEKK protein that is capable of phosphorylating p38 MAPK protein includes a protein encoded by the nucleic acid sequence represented by SEQ ID NO:5 with a protein having the amino acid sequence represented by SEQ ID NO:7 being more preferred. Preferred stress activated MAPK proteins regulated by an MEKK protein of the present invention include Jun kinase (JNK), stress activated MAPK-$\alpha$ and/or stress activated MAPK-$\beta$. An MEKK protein of the present invention is capable of increasing the activity of an MEK protein over basal levels of MEK (i.e., levels found in nature when not stimulated). For example, an MEKK protein is preferably capable of increasing the phosphorylation of an MEK protein by at least about 2-fold, more preferably at least about 3-fold, and even more preferably at least about 4-fold over basal levels when measured under conditions described in Example 9.

A preferred MEKK protein of the present invention is also capable of increasing the activity of an MAPK protein over basal levels of MAPK (i.e., levels found in nature when not stimulated). For example, an MEKK protein of the present invention is preferably capable of increasing MAPK activity at least 2-fold, more preferably at least about 3-fold, and even more preferably at least about 4-fold over basal activity when measured under the conditions described in Example 3.

Moreover, an MEKK protein of the present invention is capable of increasing the activity of a JNK protein. JNK regulates the activity of the transcription factor JUN which is involved in controlling the growth and differentiation of different cell types, such as T cells, neural cells or fibroblasts. JNK shows structural and regulatory homologies with MAPK. For example, an MEKK protein of the present invention is preferably capable of inducing the phosphorylation of JNK protein at least about 30 times more than Raf, more preferably at least about 40 times more than Raf, and even more preferably at least about 50 times more than Raf, when measured under conditions described in Example 16.

A preferred MEKK protein of the present invention is additionally capable of inducing the phosphorylation of a c-Myc transcriptional transactivation domain protein in such a manner that the phosphorylated transcriptional transactivation domain of c-Myc is capable of regulating gene transcription. The ability of an MEKK protein to regulate phosphorylation of a c-Myc transcriptional transactivation domain protein exceeds the ability of Raf protein or cyclic AMP-dependent protein kinase to regulate a c-Myc protein. For example, an MEKK protein of the present invention is preferably capable of inducing luciferase gene transcription by phosphorylated c-Myc transcriptional transctivation domain protein at least about 25-fold, more preferably at least about 35-fold, and even more preferably at least about 45-fold, over Raf induction when measured under the conditions described in Example 17.

Another aspect of the present invention relates to the ability of MEKK activity to be stimulated by growth factors including, but not limited to, epidermal growth factor (EGF), neuronal growth factor (NGF), tumor necrosis factor (TNF), C5A, interleukin-8 (IL-8), monocyte chemotactic protein 1 (MIP1$\alpha$), monocyte chemoattractant protein 1 (MCP-1), platelet activating factor (PAF), N-Formyl-methionyl-leucyl-phenylalanine (FMLP), leukotriene $B_4$ ($LTB_4R$), gastrin releasing peptide (GRP), IgE, major histocompatibility protein (MHC), peptide, superantigen, antigen, vasopressin, thrombin, bradykinin and acetylcholine. In addition, the activity of an MEKK protein of the present invention is capable of being stimulated by compounds including phorbol esters such as TPA. A preferred MEKK protein is also capable of being stimulated by EGF, NGF and TNF (especially TNF$\alpha$).

Preferably, the activity of an MEKK protein of the present invention is capable of being stimulated at least 2-fold over basal levels (i.e., levels found in nature when not stimulated), more preferably at least about 4-fold over basal levels and even more preferably at least about 6-fold over basal levels, when a cell producing the MEKK protein is contacted with EGF under the conditions described in Example 3.

Similarly, the activity of an MEKK protein of the present invention is capable of being stimulated at least 1-fold over basal levels, more preferably at least about 2-fold over basal levels and even more preferably at least about 3-fold over basal levels by NGF stimulation, when a cell producing the MEKK protein is contacted with NGF under the conditions described in Example 9.

Preferably, an MEKK protein of the present invention is capable of being stimulated at least 0.5-fold over basal levels, more preferably at least about 1-fold over basal levels and even more preferably at least about 2-fold over basal levels by TPA stimulation when a cell producing the MEKK protein is contacted with TPA under the conditions described in Example 9.

TNF is capable of regulating cell death and other functions in different cell types. The present inventor discovered that MEKK stimulation by TNF is independent of Raf. Similarly, the present inventor is the first to appreciate that an MEKK protein can be directly stimulated by ultraviolet light (UV) damage of cells while a Raf-dependent pathway cannot. Therefore, both TNF and UV stimulate MEKK activity without substantially activating Raf. In addition, both UV and TNF activation of MEKK is Ras dependent.

Another aspect of the present invention is the recognition that an MEKK protein of the present invention is capable of regulating the apoptosis of a cell, an ability not shared by Raf protein. As used herein, apoptosis refers to the form of cell death that comprises: progressive contraction of cell volume with the preservation of the integrity of cytoplasmic organelles; condensation of chromatin, as viewed by light or electron microscopy; and DNA cleavage, as determined by centrifuged sedimentation assays. Cell death occurs when the membrane integrity of the cell is lost and cell lysis occurs. Apoptosis differs from necrosis in which cells swell and eventually rupture.

A preferred MEKK protein of the present invention is capable of inducing the apoptosis of cells, such that the cells have characteristics substantially similar to cytoplasmic shrinkage and/or nuclear condensation as shown in FIGS. 24, 25, 26, 27 and 28. The apoptotic cells in FIGS. 24 through 28 were obtained when cells were microinjected with expression plasmids encoding MEKK protein. Injected cells were identified using anti-$\beta$-Gal antibody and the DNA of the cells were stained with propidium iodide. Cytoplasmic organization was monitored using an anti-tubulin antibody. The cells were then imaged by differential fluorescent imaging microscopy using techniques standard in the art. The cells demonstrated apoptosis by displaying a morphology having cytoplasmic shrinkage and nuclear condensation.

Figure 2:
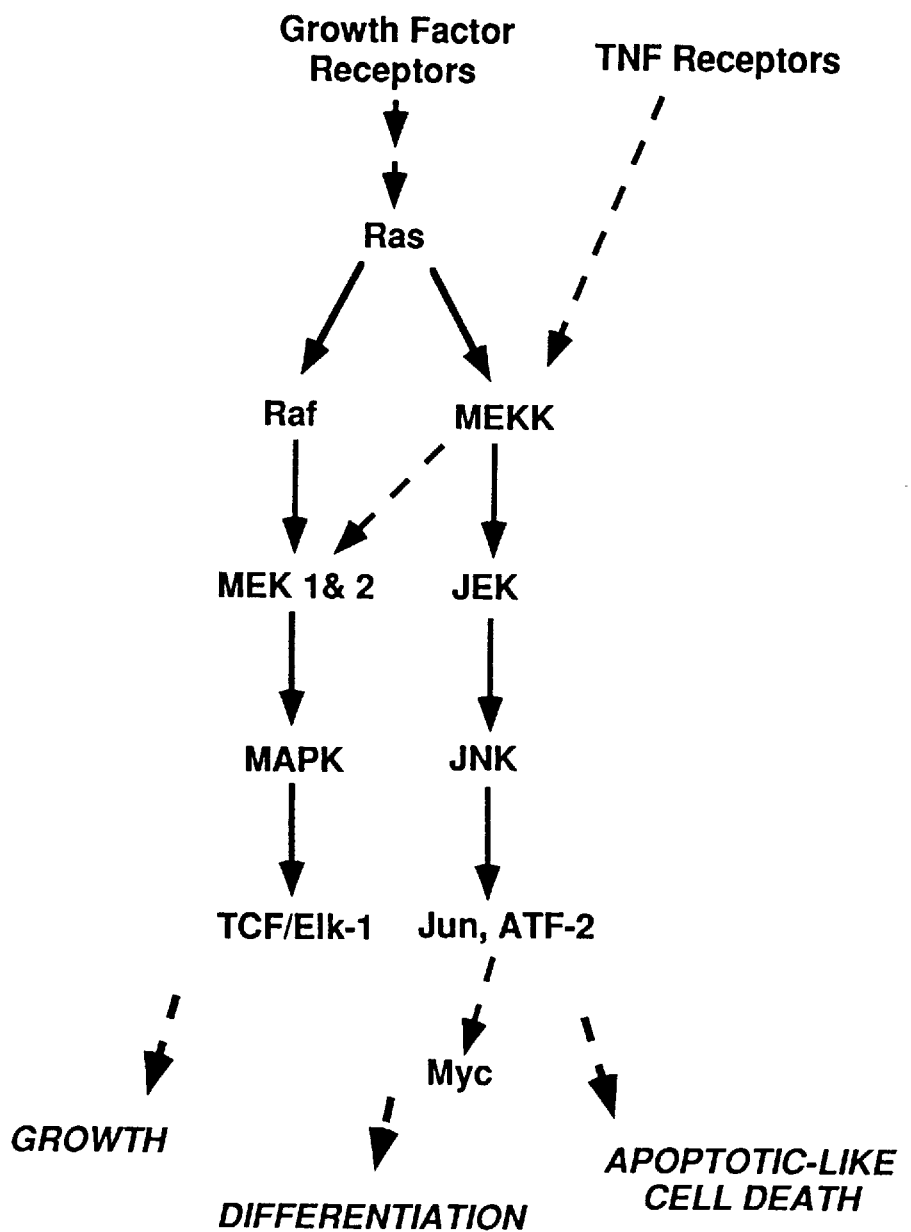
FIG. 2 is a schematic representation of the dual MEKK and Raf pathways divergent from Ras protein pathway.

A schematic representation of the cell growth regulatory signal transduction pathway that is MEKK dependent is shown in FIG. 2. An MEKK protein of the present invention is capable of regulating the activity of JEK protein, JNK protein, Jun protein and/or ATF-2 protein, and Myc protein, such regulation being substantially, if not entirely, independent of Raf protein. Such Raf-independent regulation can regulate the growth characteristics of a cell, including the apoptosis of a cell. In addition, an MEKK protein of the present invention is capable of regulating the activity of MEK protein, which is also capable of being regulated by Raf protein. As such, an MEKK protein of the present invention is capable of regulating the activity of MAPK protein and members of the Ets family of transcription factors, such as TCF protein, also referred to as Elk-1 protein.

Referring to FIG. 2, an MEKK protein of the present invention is capable of being activated by a variety of growth factors capable of activating Ras protein. In addition, an MEKK protein is capable of activating JNK protein which is also activated by Ras protein, but is not activated by Raf protein. As such, an MEKK protein of the present invention comprises a protein kinase at a divergence point in a signal transduction pathway initiated by different cell surface receptors. An MEKK protein is also capable of being regulated by TNF protein independent of Raf, thereby indicating an association of MEKK protein to a novel signal transduction pathway which is independent of Ras protein and Raf protein.

Thus, an MEKK protein is capable of performing numerous unique functions independent of or by-passing Raf protein in one or more signal transduction pathways. An MEKK protein is capable of regulating the activity of MEK and/or JEK activity. As such, an MEKK protein is capable of regulating the activity of members of a signal transduction pathway that does not substantially include Raf activity. Such members include, but are not limited to, JNK, Jun, ATF and Myc protein. In addition, an MEKK protein is capable of regulating the members of a signal transduction pathway that does involve Raf, such members including, but are not limited to, MEK, MAPK and TCF. An MEKK protein of the present invention is thus capable of regulating the apoptosis of a cell independent of significant involvement by Raf protein.

In addition to the numerous functional characteristics of an MEKK protein, an MEKK protein of the present invention comprises numerous unique structural characteristics. For example, in one embodiment, an MEKK protein of the present invention includes at least one of two different structural domains having particular functional characteristics. Such structural domains include an $NH_2$-terminal regulatory domain that serves to regulate a second structural domain comprising a COOH-terminal protein kinase catalytic domain that is capable of phosphorylating an MEK protein and/or JEK protein.

According to the present invention, an MEKK protein of the present invention includes a full-length MEKK protein, as well as at least a portion of an MEKK protein capable of performing at least one of the functions defined above. The phrase "at least a portion of an MEKK protein" refers to a portion of an MEKK protein encoded by a nucleic acid molecule that is capable of hybridizing, under stringent conditions, with a nucleic acid encoding a full-length MEKK protein of the present invention. Preferred portions of MEKK proteins are useful for regulating apoptosis in a cell. Additional preferred portions have activities useful for regulating MEKK kinase activity. Suitable sizes for portions of an MEKK protein of the present invention are as disclosed for MEKK protein homologues of the present invention.

In another embodiment, an MEKK protein of the present invention includes at least a portion of an MEKK protein having molecular weights ranging from about 70 kD to about 250 kD as determined by Tris-glycine SDS-PAGE, preferably using an 8% polyacrylamide SDS gel (SDS-PAGE) and resolved using methods standard in the art. A preferred MEKK protein has a molecular weight ranging from about 75 kD to about 225 kD and even more preferably from about 80 kD to about 200 kD.

In yet another embodiment, an MEKK protein of the present invention comprises at least a portion of an MEKK protein encoded by an mRNA (messenger ribonucleic acid) ranging from about 3.5 kb to about 12.0 kb, more preferably ranging from about 4.0 kb to about 11.0 kb, and even more preferably ranging from about 4.5 kb to about 10.0 kb. Particularly preferred MEKK proteins comprise at least a portion of an MEKK protein encoded by an mRNA having a size ranging from about 4.5 kb to about 5.0 kb, a size ranging from about 6.0 kb to about 6.5 kb, a size of about 7.0 kb, or a size ranging from about 8.0 kb to about 10.0 kb.

In another embodiment, an $NH_2$-terminal regulatory domain of the present invention includes an $NH_2$-terminal comprising about 400 amino acids having at least about 10% serine and/or threonine residues, more preferably about 400 amino acids having at least about 15% serine and/or threonine residues, and even more preferably about 400 amino acids having at least about 20% serine and/or threonine residues.

A preferred an $NH_2$-terminal regulatory domain of the present invention includes an $NH_2$-terminal comprising about 360 amino acids having at least about 10% serine and/or threonine residues, more preferably about 360 amino acids having at least about 15% serine and/or threonine residues, and even more preferably about 360 amino acids having at least about 20% serine and/or threonine residues.

Another preferred an $NH_2$-terminal regulatory domain of the present invention includes an $NH_2$-terminal comprising about 370 amino acids having at least about 10% serine and/or threonine residues, more preferably about 370 amino acids having at least about 15% serine and/or threonine residues, and even more preferably about 370 amino acids having at least about 20% serine and/or threonine residues.

In one embodiment, an MEKK protein of the present invention is devoid of SH2 and SH3 domains.

In another embodiment, an MEKK protein of the present invention includes at least a portion of an MEKK protein homologue preferably having at least about 50%, more preferably at least about 75%, and even more preferably at least about 85% amino acid homology (identity within comparable regions) with the kinase catalytic domain of a naturally occurring MEKK protein. Another MEKK protein of the present invention also includes at least a portion of an MEKK homologue of the present invention has at least about 10%, more preferably at least about 20%, and even more preferably at least about 30% amino acid homology with the $NH_2$-terminal regulatory domain of an MEKK protein of a naturally occurring MEKK protein.

The sequences comprising the catalytic domain of an MEKK protein are involved in phosphotransferase activity, and therefore display a relatively conserved amino acid sequence. The NH$_2$-terminal regulatory domain of an MEKK protein, however, can be substantially divergent. The lack of significant homology between MEKK protein NH$_2$-terminal regulatory domains is related to the regulation of each of such domains by different upstream regulatory proteins. For example, an MEKK protein can be regulated by the protein Ras, while others can be regulated independent of Ras. In addition, some MEKK proteins can be regulated by the growth factor TNFA, while others cannot. As such, the NH$_2$-terminal regulatory domain of an MEKK protein provides selectivity for upstream signal transduction regulation, while the catalytic domain provides for MEKK substrate selectivity function.

A preferred MEKK homologue has at least about 50%, more preferably at least about 75% and even more preferably at least about 85% amino acid homology with the kinase catalytic domain of an MEKK protein having an amino acid sequence represented by SEQ ID NO:2, SEQ ID NO:4, SEQ ID NO:6, SEQ ID NO:8 or SEQ ID NO:10. Another preferred MEKK homologue has at least about 10%, more preferably at least about 20% and even more preferably at least about 30% amino acid homology with the NH$_2$-terminal regulatory domain of an MEKK protein having an amino acid sequence represented by SEQ ID NO:2, SEQ ID NO:4, SEQ ID NO:6, SEQ ID NO:8 or SEQ ID NO:10.

In a preferred embodiment, an MEKK protein of the present invention includes at least a portion of an MEKK protein homologue of the present invention that is encoded by a nucleic acid molecule having at least about 50%, more preferably at least about 75%, and even more preferably at least about 85% homology with a nucleic acid molecule encoding the kinase catalytic domain of an MEKK protein. Another preferred MEKK protein homologue is encoded by a nucleic acid molecule having at least about 10%, more preferably at least about 20%, and even more preferably at least about 30% homology with a nucleic acid molecule encoding the NH$_2$-terminal regulatory domain of an MEKK protein.

Still another preferred MEKK homologue is encoded by a nucleic acid molecule having at least about 50%, more preferably at least about 75% and even more preferably at least about 85% amino acid homology with the kinase catalytic domain of an MEKK protein encoded by a nucleic acid sequence represented by SEQ ID NO:1, SEQ ID NO:3, SEQ ID NO:5, SEQ ID NO:7 or SEQ ID NO:9. An MEKK homologue also includes those encoded by a nucleic acid molecule having at least about 10%, more preferably at least about 20% and even more preferably at least about 30% amino acid homology with the NH$_2$-terminal regulatory domain of an MEKK protein encoded by a nucleic acid sequence represented by SEQ ID NO:1, SEQ ID NO:3, SEQ ID NO:5, SEQ ID NO:7 or SEQ ID NO:9.

An MEKK protein of the present invention, referred to here as MEKK 1, includes an MEKK protein having (i.e., including) at least a portion of the nucleic acid and/or an amino acid sequence shown in Table 1 and represented by SEQ ID NO:1 and SEQ ID NO:2, respectively.

TABLE 1

```
TACACTCCTT GCCACAGTCT GGCAGAAAGA ATCAAACTTC AGAGACTCCT CCGGCCAGTT    60
GTAGACACTA TCCTTGTCAA GTGTGCAGAT CCAACAGCCG CACGAGTCAG CTGTCCATAT   120
CTACAGTGCT GGAACTCTGC AAGGGCCAAG CAGGAGAGCT GGCGGTTGGG AGAGAAATAC   180
TTAAAGCTGG GTCCATCGGG GTTGGTGGTG TCGATTACGT CTTAAGTTGT ATCCTTGGAA   240
ACCAAGCTGA ATCAAACAAC TGGCAAGAAC TGCTGGGTCG CCTCTGTCTT ATAGACAGGT   300
TGCTGTTGGA ATTTCCTGCT GAATTCTATC CTCATATTGT CAGTACTGAT GTCTCACAAG   360
CTGAGCCTGT TGAAATCAGG TACAAGAAGC TGCTCTCCCT CTTAACCTTT GCCTTGCAAT   420
CCATTGACAA TTCCCACTCG ATGGTTGGCA AGCTCTCTCG GAGGATATAT CTGAGCTCTG   480
```

| | | | | | | | | | | | | | | | |
|---|---|---|---|---|---|---|---|---|---|---|---|---|---|---|---|
| CCAGG | ATG | GTG | ACC | GCA | GTG | CCC | GCT | GTG | TTT | TCC | AAG | CTG | GTA | ACC | 527 |
| | Met | Val | Thr | Ala | Val | Pro | Ala | Val | Phe | Ser | Lys | Leu | Val | Thr | |
| | 1 | | | | 5 | | | | | 10 | | | | | |
| ATG | CTT | AAT | GCT | TCT | GGC | TCC | ACC | CAC | TTC | ACC | AGG | ATG | CGC | CGG | CGT | 575 |
| Met | Leu | Asn | Ala | Ser | Gly | Ser | Thr | His | Phe | Thr | Arg | Met | Arg | Arg | Arg | |
| 15 | | | | | 20 | | | | | 25 | | | | | 30 | |
| CTG | ATG | GCT | ATC | GCG | GAT | GAG | GTA | GAA | ATT | GCC | GAG | GTC | ATC | CAG | CTG | 623 |
| Leu | Met | Ala | Ile | Ala | Asp | Glu | Val | Glu | Ile | Ala | Glu | Val | Ile | Gln | Leu | |
| | | | | 35 | | | | | 40 | | | | | 45 | | |
| GGT | GTG | GAG | GAC | ACT | GTG | GAT | GGG | CAT | CAG | GAC | AGC | TTA | CAG | GCC | GTG | 671 |
| Gly | Val | Glu | Asp | Thr | Val | Asp | Gly | His | Gln | Asp | Ser | Leu | Gln | Ala | Val | |
| | | | 50 | | | | | 55 | | | | | 60 | | | |
| GCC | CCC | ACC | AGC | TGT | CTA | GAA | AAC | AGC | TCC | CTT | GAG | CAC | ACA | GTC | CAT | 719 |
| Ala | Pro | Thr | Ser | Cys | Leu | Glu | Asn | Ser | Ser | Leu | Glu | His | Thr | Val | His | |
| | | 65 | | | | | 70 | | | | | 75 | | | | |
| AGA | GAG | AAA | ACT | GGA | AAA | GGA | CTA | AGT | GCT | ACG | AGA | CTG | AGT | GCC | AGC | 767 |
| Arg | Glu | Lys | Thr | Gly | Lys | Gly | Leu | Ser | Ala | Thr | Arg | Leu | Ser | Ala | Ser | |
| | | 80 | | | | 85 | | | | | 90 | | | | | |
| TCG | GAG | GAC | ATT | TCT | GAC | AGA | CTG | GCC | GGC | GTC | TCT | GTA | GGA | CTT | CCC | 815 |
| Ser | Glu | Asp | Ile | Ser | Asp | Arg | Leu | Ala | Gly | Val | Ser | Val | Gly | Leu | Pro | |
| 95 | | | | | 100 | | | | | 105 | | | | | 110 | |
| AGC | TCA | ACA | ACA | ACA | GAA | CAA | CCA | AAG | CCA | GCG | GTT | CAA | ACA | AAA | GGC | 863 |
| Ser | Ser | Thr | Thr | Thr | Glu | Gln | Pro | Lys | Pro | Ala | Val | Gln | Thr | Lys | Gly | |
| | | | | 115 | | | | | 120 | | | | | 125 | | |

TABLE 1-continued

| | | | | | | | | | | | | | | | | |
|---|---|---|---|---|---|---|---|---|---|---|---|---|---|---|---|---|
| AGA | CCC | CAC | AGT | CAG | TGT | TTG | AAC | TCC | TCC | CCT | TTG | TCT | CAT | GCT | CAA | 911 |
| Arg | Pro | His | Ser 130 | Gln | Cys | Leu | Asn | Ser 135 | Ser | Pro | Leu | Ser | His 140 | Ala | Gln | |
| TTA | ATG | TTC | CCA | GCA | CCA | TCA | GCC | CCT | TGT | TCC | TCT | GCC | CCG | TCT | GTC | 959 |
| Leu | Met | Phe 145 | Pro | Ala | Pro | Ser | Ala 150 | Pro | Cys | Ser | Ser | Ala 155 | Pro | Ser | Val | |
| CCA | GAT | ATT | TCT | AAG | CAC | AGA | CCC | CAG | GCA | TTT | GTT | CCC | TGC | AAA | ATA | 1007 |
| Pro | Asp 160 | Ile | Ser | Lys | His | Arg 165 | Pro | Gln | Ala | Phe | Val 170 | Pro | Cys | Lys | Ile | |
| CCT | TCC | GCA | TCT | CCT | CAG | ACA | CAG | CGC | AAG | TTC | TCT | CTA | CAA | TTC | CAG | 1055 |
| Pro 175 | Ser | Ala | Ser | Pro | Gln 180 | Thr | Gln | Arg | Lys | Phe 185 | Ser | Leu | Gln | Phe | Gln 190 | |
| AGG | AAC | TGC | TCT | GAA | CAC | CGA | GAC | TCA | GAC | CAG | CTC | TCC | CCA | GTC | TTC | 1103 |
| Arg | Asn | Cys | Ser | Glu 195 | His | Arg | Asp | Ser | Asp 200 | Gln | Leu | Ser | Pro | Val 205 | Phe | |
| ACT | CAG | TCA | AGA | CCC | CCA | CCC | TCC | AGT | AAC | ATA | CAC | AGG | CCA | AAG | CCA | 1151 |
| Thr | Gln | Ser | Arg 210 | Pro | Pro | Pro | Ser | Ser 215 | Asn | Ile | His | Arg | Pro 220 | Lys | Pro | |
| TCC | CGA | CCC | GTT | CCG | GGC | AGT | ACA | AGC | AAA | CTA | GGG | GAC | GCC | ACA | AAA | 1199 |
| Ser | Arg | Pro 225 | Val | Pro | Gly | Ser | Thr 230 | Ser | Lys | Leu | Gly | Asp 235 | Ala | Thr | Lys | |
| AGT | AGC | ATG | ACA | CTT | GAT | CTG | GGC | AGT | GCT | TCC | AGG | TGT | GAC | GAC | AGC | 1247 |
| Ser | Ser 240 | Met | Thr | Leu | Asp | Leu 245 | Gly | Ser | Ala | Ser | Arg 250 | Cys | Asp | Asp | Ser | |
| TTT | GGC | GGC | GGC | GGC | AAC | AGT | GGC | AAC | GCC | GTC | ATA | CCC | AGC | GAC | GAG | 1295 |
| Phe 255 | Gly | Gly | Gly | Gly | Asn 260 | Ser | Gly | Asn | Ala | Val 265 | Ile | Pro | Ser | Asp | Glu 270 | |
| ACA | GTG | TTC | ACG | CCG | GTG | GAG | GAC | AAG | TGC | AGG | TTA | GAT | GTG | AAC | ACC | 1343 |
| Thr | Val | Phe | Thr | Pro 275 | Val | Glu | Asp | Lys | Cys 280 | Arg | Leu | Asp | Val | Asn 285 | Thr | |
| GAG | CTC | AAC | TCC | AGC | ATC | GAG | GAC | CTT | CTT | GAA | GCA | TCC | ATG | CCT | TCA | 1391 |
| Glu | Leu | Asn | Ser 290 | Ser | Ile | Glu | Asp | Leu 295 | Leu | Glu | Ala | Ser | Met 300 | Pro | Ser | |
| AGT | GAC | ACG | ACA | GTC | ACT | TTC | AAG | TCC | GAA | GTC | GCC | GTC | CTC | TCT | CCG | 1439 |
| Ser | Asp | Thr 305 | Thr | Val | Thr | Phe | Lys 310 | Ser | Glu | Val | Ala | Val 315 | Leu | Ser | Pro | |
| GAA | AAG | GCC | GAA | AAT | GAC | GAC | ACC | TAC | AAA | GAC | GAC | GTC | AAT | CAT | AAT | 1487 |
| Glu | Lys 320 | Ala | Glu | Asn | Asp | Asp 325 | Thr | Tyr | Lys | Asp | Asp 330 | Val | Asn | His | Asn | |
| CAA | AAG | TGC | AAA | GAA | AAG | ATG | GAA | GCT | GAA | GAG | GAG | GAG | GCT | TTA | GCG | 1535 |
| Gln 335 | Lys | Cys | Lys | Glu | Lys 340 | Met | Glu | Ala | Glu | Glu 345 | Glu | Glu | Ala | Leu | Ala 350 | |
| ATC | GCC | ATG | GCG | ATG | TCA | GCG | TCT | CAG | GAT | GCC | CTC | CCC | ATC | GTC | CCT | 1583 |
| Ile | Ala | Met | Ala | Met 355 | Ser | Ala | Ser | Gln | Asp 360 | Ala | Leu | Pro | Ile | Val 365 | Pro | |
| CAG | CTG | CAG | GTG | GAA | AAT | GGA | GAA | GAT | ATT | ATT | ATC | ATT | CAG | CAG | GAC | 1631 |
| Gln | Leu | Gln | Val 370 | Glu | Asn | Gly | Glu | Asp 375 | Ile | Ile | Ile | Ile | Gln 380 | Gln | Asp | |
| ACA | CCA | GAA | ACT | CTT | CCA | GGA | CAT | ACC | AAA | GCG | AAA | CAG | CCT | TAC | AGA | 1679 |
| Thr | Pro | Glu 385 | Thr | Leu | Pro | Gly | His 390 | Thr | Lys | Ala | Lys | Gln 395 | Pro | Tyr | Arg | |
| GAA | GAC | GCT | GAG | TGG | CTG | AAA | GGC | CAG | CAG | ATA | GGC | CTC | GGA | GCA | TTT | 1727 |
| Glu | Asp | Ala 400 | Glu | Trp | Leu | Lys | Gly 405 | Gln | Gln | Ile | Gly | Leu 410 | Gly | Ala | Phe | |
| TCT | TCC | TGT | TAC | CAA | GCA | CAG | GAT | GTG | GGG | ACT | GGG | ACT | TTA | ATG | GCT | 1775 |
| Ser 415 | Ser | Cys | Tyr | Gln | Ala 420 | Gln | Asp | Val | Gly | Thr 425 | Gly | Thr | Leu | Met | Ala 430 | |
| GTG | AAA | CAG | GTG | ACG | TAC | GTC | AGA | AAC | ACA | TCC | TCC | GAG | CAG | GAG | GAG | 1823 |
| Val | Lys | Gln | Val | Thr 435 | Tyr | Val | Arg | Asn | Thr 440 | Ser | Ser | Glu | Gln | Glu 445 | Glu | |

TABLE 1-continued

| Codons | Position |
|---|---|
| GTG GTG GAA GCG TTG AGG GAA GAG ATC CGG ATG ATG GGT CAC CTC AAC<br>Val Val Glu Ala Leu Arg Glu Glu Ile Arg Met Met Gly His Leu Asn<br>              450                            455                            460 | 1871 |
| CAT CCA AAC ATC ATC CGG ATG CTG GGG GCC ACG TGC GAG AAG AGC AAC<br>His Pro Asn Ile Ile Arg Met Leu Gly Ala Thr Cys Glu Lys Ser Asn<br>         465                             470                            475 | 1919 |
| TAC AAC CTC TTC ATT GAG TGG ATG GAG GGA GGA TCT GTG GCT CAC CTC<br>Tyr Asn Leu Phe Ile Glu Trp Met Ala Gly Gly Ser Val Ala His Leu<br>     480                          485                        490 | 1967 |
| TTG AGT AAA TAC GGA GCT TTC AAG GAG TCA GTC GTC ATT AAC TAC ACT<br>Leu Ser Lys Tyr Gly Ala Phe Lys Glu Ser Val Val Ile Asn Tyr Thr<br>495                      500                     505                  510 | 2015 |
| GAG CAG TTA CTG CGT GGC CTT TCC TAT CTC CAC GAG AAC CAG ATC ATT<br>Glu Gln Leu Leu Arg Gly Leu Ser Tyr Leu His Glu Asn Gln Ile Ile<br>              515                     520                     525 | 2063 |
| CAC AGA GAC GTC AAA GGT GCC AAC CTG CTC ATT GAC AGC ACC GGT CAG<br>His Arg Asp Val Lys Gly Ala Asn Leu Leu Ile Asp Ser Thr Gly Gln<br>              530                     535                     540 | 2111 |
| AGG CTG AGA ATT GCA GAC TTT GGA GCT GCT GCC AGG TTG GCA TCA AAA<br>Arg Leu Arg Ile Ala Asp Phe Gly Ala Ala Ala Arg Leu Ala Ser Lys<br>       545                         550                     555 | 2159 |
| GGA ACC GGT GCA GGA GAG TTC CAG GGA CAG TTA CTG GGG ACA ATT GCA<br>Gly Thr Gly Ala Gly Glu Phe Gln Gly Gln Leu Leu Gly Thr Ile Ala<br>     560                          565                     570 | 2207 |
| TTC ATG GCG CCT GAG GTC CTA AGA GGT CAG CAG TAT GGT AGG AGC TGT<br>Phe Met Ala Pro Glu Val Leu Arg Gly Gln Gln Tyr Gly Arg Ser Cys<br>575                      580                     585                  590 | 2255 |
| GAT GTA TGG AGT GTT GGC TGC GCC ATT ATA GAA ATG GCT TGT GCA AAA<br>Asp Val Trp Ser Val Gly Cys Ala Ile Ile Glu Met Ala Cys Ala Lys<br>              595                     600                   605 | 2303 |
| CCA CCT TGG AAT GCA GAA AAA CAC TCC AAT CAT CTC GCC TTG ATA TTT<br>Pro Pro Trp Asn Ala Glu Lys His Ser Asn His Leu Ala Leu Ile Phe<br>          610                        615                   620 | 2351 |
| AAG ATT GCT AGC GCA ACT ACT GCA CCG TCC ATC CCG TCA CAC CTG TCC<br>Lys Ile Ala Ser Ala Thr Thr Ala Pro Ser Ile Pro Ser His Leu Ser<br>        625                           630                    635 | 2399 |
| CCG GGT CTC CGC GCA GTG GCG GTG CGC TGC TTA GAA CTT CAG CCT CAG<br>Pro Gly Leu Arg Asp Val Ala Val Arg Cys Leu Glu Leu Gln Pro Gln<br>     640                      645                     650 | 2447 |
| GAC CGG CCT CCG TCC AGA GAG CTG CTG AAA CAT CCG GTC TTC CGT ACC<br>Asp Arg Pro Pro Ser Arg Glu Leu Leu Lys His Pro Val Phe Arg Thr<br>655                      660                     665                  670 | 2495 |
| ACG TGG TAGTTAATTG TTCAGATCAG CTCTAATGGA GACAGGATAT CGAACCGGGA<br>Thr Trp | 2551 |
| GAGAGAAAAG AGAACTTGTG GGCGACCATG CCGCTAACCG CAGCCCTCAC GCCACTGAAC | 2611 |
| AGCCAGAAAC GGGGCCAGCG GGGAACCGTA CCTAAGCATG TGATTGACAA ATCATGACCT | 2671 |
| GTACCTAAGC TCGATATGCA GACATCTACA GCTCGTGCAG GAACTGCACA CCGTGCCTTT | 2731 |
| CACAGGACTG GCTCTGGGGG ACCAGGAAGG CGATGGAGTT TGCATGACTA AAGAACAGAA | 2791 |
| GCATAAATTT ATTTTTGGAG CACTTTTTCA GTTACCATGT ACATCAACAT | 2851 |
| GCCCGCCACA TTTCAAACTC AGACTGTCCC AGATGTCAAG ATCCACTGTG TTTGAGTTTG | 2911 |
| TTTGCAGTTC CCTCAGCTTG CTGGTAATTG TGGTGTTTTG TTTTCGATGC AAATGTGATG | 2971 |
| TAATATTCTT ATTTTCTTTG GATCAAAGCT GGACTGAAAA TTGTACTGTG TAATTATTTT | 3031 |
| TGTGTTTTTA ATGTTATTTG GTACTCGAAT TGTAAATAAC GTCTACTGCT GTTTATTCCA | 3091 |
| GTTTCTACTA CCTCAGGTGT CCTATAGATT TTTCTTCACA CAAAGTTCAC TCTCAGAATG | 3151 |
| AAATTCTACG TGCTGTGTGA CTATGACTCC TAAGACTTCC AGGGCTTAAG GGCTAACTCC | 3211 |
| TATTAGCACC TTACTATGTA AGCAAATGCT ACAAAAAAAA AAAAAAAA | 3260 |

An MEKK protein of the present invention, referred to here as MEKK 2, includes an MEKK protein having at least a portion of the nucleic acid and/or amino acid sequence shown in Table 2 and represented by SEQ ID NO:3 and SEQ ID NO:4, respectively.

TABLE 2

```
GGTGGCGGCC GCTCTAGAAC TAGTGGATCC CCCGGGCTGC AGGAATTCGG CACGAGGGAC    60
GATCCAGCGG CAGAGTCGCC GCTTCCGCTT CGCTGCTTCT CCGGTCGGCG ACGCGGGCCC   120
GGGGCTTCCT TTTCATCGGC CCAGCTTATT CCGCGGGCCC CGGGGCTGCA GCTACCCAGA   180
AGCGGCGAAG AGGCCCTGGG CTGCGCGCCC GCTGTCCCAT GTGAAGCAGG TTGGGCCTGG   240
TCCCCGGCCC GTGCCCGGTT GTCTGCGGCC CTTCAGGCCT CAGGGACCCC CGCGAGGCGC   300
TGCTCCTGGG GGGCGCGGTG ACAGGCCGTG CGGGGGCGGA GGGGCCAGCT CGGTGGCCTC   360
CTCTCGGCCC TCGCGTCCGC GATCCCGCCC AGCGGCGGGC AATAAAGAA TGTTGATGGG    420

AGAACCATTT TCCTAATTTT CAAATTATTG AGCTGGTCGC GCATA ATG GAT GAT       474
                                                  Met Asp Asp
                                                    1
```

| | | | | | | | | | | | | | | | |
|---|---|---|---|---|---|---|---|---|---|---|---|---|---|---|---|
| CAG | CAA | GCT | TTG | AAT | TCA | ATC | ATG | CAA | GAT | TTG | GCT | GTC | CTT | CAT | AAG | 522
| Gln | Gln | Ala | Leu | Asn | Ser | Ile | Met | Gln | Asp | Leu | Ala | Val | Leu | His | Lys |
| | 5 | | | | 10 | | | | | 15 | | | | | |

| CCA | GTC | GGC | CAG | CAT | TAT | CTT | TAC | AAG | AAA | CCA | GGA | AAG | CAA | AAC | CTT | 570
|---|---|---|---|---|---|---|---|---|---|---|---|---|---|---|---|
| Pro | Val | Gly | Gln | His | Tyr | Leu | Tyr | Lys | Lys | Pro | Gly | Lys | Gln | Asn | Leu |
| 20 | | | | | 25 | | | | | 30 | | | | | 35 |

| CAT | CAC | CAA | AAA | AAC | AGA | ATG | ATG | TTC | GAG | TCA | AAT | TTG | AAC | ATA | GAG | 618
|---|---|---|---|---|---|---|---|---|---|---|---|---|---|---|---|
| His | His | Gln | Lys | Asn | Arg | Met | Met | Phe | Glu | Ser | Asn | Leu | Asn | Ile | Glu |
| | | | | 40 | | | | | 45 | | | | | 50 | |

| GAG | GAA | AAA | AGG | ATC | CTG | CAG | GTT | ACT | AGA | CCA | GTT | AAA | CTA | GAA | GAC | 666
|---|---|---|---|---|---|---|---|---|---|---|---|---|---|---|---|
| Glu | Glu | Lys | Arg | Ile | Leu | Gln | Val | Thr | Arg | Pro | Val | Lys | Leu | Glu | Asp |
| | | | 55 | | | | | 60 | | | | | 65 | | |

| CTG | AGA | TCT | AAG | TCT | AAG | ATC | GCC | TTT | GGG | CAG | TCT | ATG | GAT | CTA | CAC | 714
|---|---|---|---|---|---|---|---|---|---|---|---|---|---|---|---|
| Leu | Arg | Ser | Lys | Ser | Lys | Ile | Ala | Phe | Gly | Gln | Ser | Met | Asp | Leu | His |
| | | 70 | | | | | 75 | | | | | 80 | | | |

| TAT | ACC | AAC | AAT | GAG | TTG | GTA | ATT | CCG | TTA | ACT | ACC | CAA | GAT | GAC | TTG | 762
|---|---|---|---|---|---|---|---|---|---|---|---|---|---|---|---|
| Tyr | Thr | Asn | Asn | Glu | Leu | Val | Ile | Pro | Leu | Thr | Thr | Gln | Asp | Asp | Leu |
| | 85 | | | | | 90 | | | | | 95 | | | | |

| GAC | AAA | GCT | GTG | GAA | CTG | CTG | GAT | CGC | AGT | ATT | CAC | ATG | AAG | AGT | CTC | 810
|---|---|---|---|---|---|---|---|---|---|---|---|---|---|---|---|
| Asp | Lys | Ala | Val | Glu | Leu | Leu | Asp | Arg | Ser | Ile | His | Met | Lys | Ser | Leu |
| 100 | | | | | 105 | | | | | 110 | | | | | 115 |

| AAG | ATA | TTA | CTT | GTA | GTA | AAT | GGG | AGT | ACA | CAG | GCT | ACT | AAT | TTA | GAA | 858
|---|---|---|---|---|---|---|---|---|---|---|---|---|---|---|---|
| Leu | Ile | Leu | Leu | Val | Val | Asn | Gly | Ser | Thr | Gln | Ala | Thr | Asn | Leu | Gln |
| | | | | 120 | | | | | 125 | | | | | 130 | |

| CCA | TCA | CCG | TCA | CCA | GAA | GAT | TTG | AAT | AAT | ACA | CCA | CTT | GGT | GCA | GAG | 906
|---|---|---|---|---|---|---|---|---|---|---|---|---|---|---|---|
| Pro | Ser | Pro | Ser | Pro | Glu | Asp | Leu | Asn | Asn | Thr | Pro | Leu | Gly | Ala | Glu |
| | | | 135 | | | | | 140 | | | | | 145 | | |

| AGG | AAA | AAG | CGG | CTA | TCT | GTA | GTA | GGT | CCC | CCT | AAT | AGG | GAT | AGA | AGT | 954
|---|---|---|---|---|---|---|---|---|---|---|---|---|---|---|---|
| Arg | Lys | Lys | Arg | Leu | Ser | Val | Val | Gly | Pro | Pro | Asn | Arg | Asp | Arg | Ser |
| | | 150 | | | | | 155 | | | | | 160 | | | |

| TCC | CCT | CCT | CCA | GGA | TAC | ATT | CCA | GAC | ATA | CTA | CAC | CAG | ATT | GCC | CGG | 1002
|---|---|---|---|---|---|---|---|---|---|---|---|---|---|---|---|
| Ser | Pro | Pro | Pro | Gly | Tyr | Ile | Pro | Asp | Ile | Leu | His | Gln | Ile | Ala | Arg |
| | 165 | | | | | 170 | | | | | 175 | | | | |

| AAT | GGG | TCA | TTC | ACT | AGC | ATC | AAC | AGT | GAA | GGA | GAG | TTC | ATT | CCA | GAG | 1050
|---|---|---|---|---|---|---|---|---|---|---|---|---|---|---|---|
| Asn | Gly | Ser | Phe | Thr | Ser | Ile | Asn | Ser | Glu | Gly | Glu | Phe | Ile | Pro | Glu |
| 180 | | | | | 185 | | | | | 190 | | | | | 195 |

| AGC | ATG | GAC | CAA | ATG | CTG | GAT | CCA | TTG | TCT | TTA | AGC | AGC | CCT | GAA | AAT | 1098
|---|---|---|---|---|---|---|---|---|---|---|---|---|---|---|---|
| Ser | Met | Asp | Gln | Met | Leu | Asp | Pro | Leu | Ser | Leu | Ser | Ser | Pro | Glu | Asn |
| | | | | 200 | | | | | 205 | | | | | 210 | |

| TCT | GGC | TCA | GGA | AGC | TGT | CCG | TCA | CTT | GAT | AGT | CCT | TTG | GAT | GGA | GAA | 1146
|---|---|---|---|---|---|---|---|---|---|---|---|---|---|---|---|
| Ser | Gly | Ser | Gly | Ser | Cys | Pro | Ser | Leu | Asp | Ser | Pro | Leu | Asp | Gly | Glu |
| | | | 215 | | | | | 220 | | | | | 225 | | |

| AGC | TAC | CCA | AAA | TCA | CGG | ATG | CCT | AGG | GCA | CAG | AGC | TAC | CCA | GAT | AAT | 1194
|---|---|---|---|---|---|---|---|---|---|---|---|---|---|---|---|
| Ser | Tyr | Pro | Lys | Ser | Arg | Met | Pro | Arg | Ala | Gln | Ser | Tyr | Pro | Asp | Asn |
| | | 230 | | | | | 235 | | | | | 240 | | | |

| CAT | CAG | GAG | TTT | ACA | GAC | TAT | GAT | AAC | CCC | ATT | TTT | GAG | AAA | TTT | GGA | 1242
|---|---|---|---|---|---|---|---|---|---|---|---|---|---|---|---|
| His | Gln | Glu | Phe | Thr | Asp | Tyr | Asp | Asn | Pro | Ile | Phe | Glu | Lys | Phe | Gly |
| | 245 | | | | | 250 | | | | | 255 | | | | |

| AAA | GGA | GGA | ACA | TAT | CCA | AGA | AGG | TAC | CAC | GTT | TCC | TAT | CAT | CAC | CAG | 1290
|---|---|---|---|---|---|---|---|---|---|---|---|---|---|---|---|
| Lys | Gly | Gly | Thr | Tyr | Pro | Arg | Arg | Tyr | His | Val | Ser | Tyr | His | His | Gln |
| 260 | | | | | 265 | | | | | 270 | | | | | 275 |

TABLE 2-continued

| | | | | | | | | | | | | | | | | |
|---|---|---|---|---|---|---|---|---|---|---|---|---|---|---|---|---|
| GAG | TAT | AAT | GAC | GGT | CGG | AAG | ACT | TTT | CCA | AGA | GCT | AGA | AGG | ACC | CAG | 1338 |
| Glu | Tyr | Asn | Asp | Gly 280 | Arg | Lys | Thr | Phe | Pro 285 | Arg | Ala | Arg | Arg | Thr 290 | Gln | |
| GGC | ACC | AGT | TTC | CGG | TCT | CCT | GTG | AGC | TTC | AGT | CCT | ACT | GAT | CAC | TCC | 1386 |
| Gly | Thr | Ser | Phe 295 | Arg | Ser | Pro | Val | Ser | Phe 300 | Ser | Pro | Thr | Asp | His 305 | Ser | |
| TTA | AGC | ACT | AGT | AGT | GGA | AGC | AGT | GTC | TTT | ACC | CCA | GAG | TAT | GAC | GAC | 1434 |
| Leu | Ser | Thr 310 | Ser | Ser | Gly | Ser | Ser 315 | Val | Phe | Thr | Pro | Glu 320 | Tyr | Asp | Asp | |
| AGT | CGA | ATA | AGA | AGA | CGG | GGG | AGT | GAC | ATA | GAC | AAT | CCT | ACT | TTG | ACT | 1482 |
| Ser | Arg 325 | Ile | Arg | Arg | Arg | Gly 330 | Ser | Asp | Ile | Asp | Asn 335 | Pro | Thr | Leu | Thr | |
| GTC | ACA | GAC | ATC | AGC | CCA | CCC | AGC | CGT | TCA | CCT | CGA | GCT | CCG | ACC | AAC | 1530 |
| Val 340 | Thr | Asp | Ile | Ser | Pro 345 | Pro | Ser | Arg | Ser | Pro 350 | Arg | Ala | Pro | Thr | Asn 355 | |
| TGG | AGA | CTG | GGC | AAG | CTG | CTT | GGC | CAA | GGA | GCT | TTT | GGT | AGG | GTC | TAC | 1578 |
| Trp | Arg | Leu | Gly | Lys 360 | Leu | Leu | Gly | Gln | Gly 365 | Ala | Phe | Gly | Arg | Val 370 | Tyr | |
| CTC | TGC | TAT | GAT | GTT | GAT | ACC | GGA | AGA | GAG | CTG | GCT | GTT | AAG | CAA | GTT | 1626 |
| Leu | Cys | Tyr | Asp 375 | Val | Asp | Thr | Gly | Arg 380 | Glu | Leu | Ala | Val | Lys 385 | Gln | Val | |
| CAG | TTT | AAC | CCT | GAG | AGC | CCA | GAG | ACC | AGC | AAG | GAA | GTA | AAT | GCA | CTT | 1674 |
| Gln | Phe | Asn 390 | Pro | Glu | Ser | Pro | Glu 395 | Thr | Ser | Lys | Glu | Val 400 | Asn | Ala | Leu | |
| GAG | TGT | GAA | ATT | CAG | TTG | TTG | AAA | AAC | TTG | TTG | CAT | GAG | CGA | ATT | GTT | 1722 |
| Glu | Cys 405 | Glu | Ile | Gln | Leu | Leu 410 | Lys | Asn | Leu | Leu | His 415 | Glu | Arg | Ile | Val | |
| CAG | TAT | TAT | GGC | TGT | TTG | AGG | GAT | CCT | CAG | GAG | AAA | ACA | CTT | TCC | ATC | 1770 |
| Gln 420 | Tyr | Tyr | Gly | Cys | Leu 425 | Arg | Asp | Pro | Gln | Glu 430 | Lys | Thr | Leu | Ser | Ile 435 | |
| TTT | ATG | GAG | CTC | TCG | CCA | GGG | GGT | TCA | ATT | AAG | GAC | CAA | CTA | AAA | GCC | 1818 |
| Phe | Met | Glu | Leu | Ser 440 | Pro | Gly | Gly | Ser | Ile 445 | Lys | Asp | Gln | Leu | Lys 450 | Ala | |
| TAC | GGA | GCT | CTT | ACT | GAG | AAC | GTG | ACG | AGG | AAG | TAC | ACC | CGT | CAG | ATT | 1866 |
| Tyr | Gly | Ala | Leu 455 | Thr | Glu | Asn | Val | Thr 460 | Arg | Lys | Tyr | Thr | Arg 465 | Gln | Ile | |
| CTG | GAG | GGG | GTC | CAT | TAT | TTG | CAT | AGT | AAT | ATG | ATT | GTC | CAT | AGA | GAT | 1914 |
| Leu | Glu | Gly 470 | Val | His | Tyr | Leu | His 475 | Ser | Asn | Met | Ile | Val 480 | His | Arg | Asp | |
| ATC | AAA | GGA | GCA | AAT | ATC | TTA | AGG | GAT | TCC | ACA | GGC | AAT | ATC | AAG | TTA | 1962 |
| Ile | Lys 485 | Gly | Ala | Asn | Ile | Leu 490 | Arg | Asp | Ser | Thr | Gly 495 | Asn | Ile | Lys | Leu | |
| GGA | GAC | TTT | GGG | GCT | AGT | AAA | CGG | CTT | CAG | ACC | ATC | TGT | CTC | TCA | GGC | 2010 |
| Gly 500 | Asp | Phe | Gly | Ala | Ser 505 | Lys | Arg | Leu | Gln | Thr 510 | Ile | Cys | Leu | Ser | Gly 515 | |
| ACA | GGA | ATG | AAG | TCT | GTC | ACA | GGC | ACG | CCA | TAC | TGG | ATG | AGT | CCT | GAG | 2058 |
| Thr | Gly | Met | Lys | Ser 520 | Val | Thr | Gly | Thr | Pro 525 | Tyr | Trp | Met | Ser | Pro 530 | Glu | |
| GTC | ATC | AGT | GGA | GAA | GGC | TAT | GGA | AGA | AAA | GCA | GAC | ATC | TGG | AGT | GTA | 2106 |
| Val | Ile | Ser | Gly 535 | Glu | Gly | Tyr | Gly | Arg 540 | Lys | Ala | Asp | Ile | Trp 545 | Ser | Val | |
| GCA | TGT | ACT | GTG | GTA | GAA | ATG | CTA | ACT | GAA | AAG | CCA | CCT | TGG | GCT | GAA | 2154 |
| Ala | Cys | Thr 550 | Val | Val | Glu | Met | Leu 555 | Thr | Glu | Lys | Pro | Pro 560 | Trp | Ala | Glu | |
| TTT | GAA | GCA | ATG | GCT | GCC | ATC | TTT | AAG | ATC | GCC | ACT | CAG | CCA | ACG | AAC | 2202 |
| Phe | Glu | Ala | Met 565 | Ala | Ala | Ile | Phe | Lys 570 | Ile | Ala | Thr | Gln | Pro 575 | Thr | Asn | |
| CCA | AAG | CTG | CCA | CCT | CAT | GTC | TCA | GAC | TAT | ACT | CGG | GAC | TTC | CTC | AAA | 2250 |
| Pro 580 | Lys | Leu | Pro | Pro | His 585 | Val | Ser | Asp | Tyr | Thr 590 | Arg | Asp | Phe | Leu | Lys 595 | |

TABLE 2-continued

```
CGG ATT TTT GTA GAG GCC AAA CTT CGA CCT TCA GCG GAG GAG CTC TTG        2298
Arg Ile Phe Val Glu Ala Lys Leu Arg Pro Ser Ala Glu Glu Leu Leu
                600                 605                 610

CGG CAC ATG TTT GTG CAT TAT CAC TAGCAGCGGC GGCTTCGGTC CTCCACCAGC       2352
Arg His Met Phe Val His Tyr His
            615                 620

TCCATCCTCG CGGCCACCTT CTCTCTTACT GCACTTTCCT TTTTTATAAA AAAGAGAGAT      2412
GGGGAGAAAA AGACAAGAGG GAAAATATTT CTCTTGATTC TTGGTTAAAT TTGTTTAATA      2472
ATAATAGTAA ACTAAAAAAA AAAAAAAAAA A                                     2503
```

An MEKK protein of the present invention, referred to here as MEKK 3, includes an MEKK protein having at least a portion of the nucleic acid and/or amino acid sequence shown in Table 3 and represented by SEQ ID NO:5 and SEQ ID NO:6, respectively.

TABLE 3

```
AGGGAACAAA AGCTGGAGCT CCACCGCGGT GGCGGCCGCT CTAGAACTAG TGGATCCCCC        60
GGGCTGCAGG AATTCGGCAC GAGGAACAGT GGCCGGTCGG AGCGTCTTCT GGACTTCAGG       120
ACTCGCAGGC GGCCCGGTCG AGTGGCGCCG CCGAGGCCGG GTTGGGCCGA GCCTGGGAGC       180
GCCGGGGATG TAGCGGGCCA ACCTGCTCAT GCCACAGCGC CCGGCCGCGG CCGAGCCGGA       240
GCCTGGGGAG GCGGCGGGGG CCCCGAGCGC AGCCCACGGC CCCCGCGCGG AGCCAGGCCC       300
GCTGCCGTCC CCGCCGCCCG CTCCCCCGGC ATGCAGCCCC GGCTGCGGAG GTGACACTTC       360

TGGGCTGTAG TCGCCACCGC CGCCTCCGCC ATCGCCACC ATG GAT GAA CAA GAG          414
                                            Met Asp Glu Gln Glu
                                             1                5

GCA TTA GAC TCG ATC ATG AAG GAC CTG GTG GCC CTC CAG ATG AGC CGA        462
Ala Leu Asp Ser Ile Met Lys Asp Leu Val Ala Leu Gln Met Ser Arg
                10                  15                  20

CGA ACC CGG TTG TCT GGA TAT GAG ACC ATG AAG AAT AAG GAC ACA GGT        510
Arg Thr Arg Leu Ser Gly Tyr Glu Thr Met Lys Asn Lys Asp Thr Gly
                25                  30                  35

CAC CCA AAC AGG CAG AGT GAC GTC AGA ATC AAG TTT GAA CAC AAT GGG        558
His Pro Asn Arg Gln Ser Asp Val Arg Ile Lys Phe Glu His Asn Gly
            40                  45                  50

GAG AGA CGA ATT ATA GCA TTC AGC CGG CCT GTG AGA TAC GAA GAT GTG        606
Glu Arg Arg Ile Ile Ala Phe Ser Arg Pro Val Arg Tyr Glu Asp Val
        55                  60                  65

GAG CAC AAG GTG ACA ACA GTC TTT GGG CAG CCT CTT GAT TTG CAT TAT        654
Glu His Lys Val Thr Thr Val Phe Gly Gln Pro Leu Asp Leu His Tyr
70                  75                  80                  85

ATG AAT AAT GAG CTC TCC ATC CTG TTG AAA AAC CAA GAT GAT CTC GAT        702
Met Asn Asn Glu Leu Ser Ile Leu Leu Lys Asn Gln Asp Asp Leu Asp
                90                  95                 100

AAA GCC ATT GAC ATT TTG GAT AGA AGC TCA AGT ATG AAA AGC CTT AGG        750
Lys Ala Ile Asp Ile Leu Asp Arg Ser Ser Ser Met Lys Ser Leu Arg
            105                 110                 115

ATA CTA CTG TTA TCC CAA GAC AGA AAC CAT ACT AGT TCC TCT CCC CAC        798
Ile Leu Leu Leu Ser Gln Asp Arg Asn His Thr Ser Ser Ser Pro His
        120                 125                 130

TCT GGA GTG TCC AGG CAG GTT CGG ATC AAG CCT TCC CAG TCT GCA GGG        846
Ser Gly Val Ser Arg Gln Val Arg Ile Lys Pro Ser Gln Ser Ala Gly
    135                 140                 145

GAT ATA AAT ACC ATC TAC CAA GCT CCT GAG CCC AGA AGC AGG CAC CTG        894
Asp Ile Asn Thr Ile Tyr Gln Ala Pro Glu Pro Arg Ser Arg His Leu
150                 155                 160                 165

TCT GTC AGC TCC CAG AAC CCT GGC CGA AGC TCT CCT CCC CCG GGA TAT        942
Ser Val Ser Ser Gln Asn Pro Gly Arg Ser Ser Pro Pro Pro Gly Tyr
                170                 175                 180

GTA CCT GAG CGA CAA CAG CAC ATT GCC CGG CAA GGA TCC TAT ACG AGC        990
Val Pro Glu Arg Gln Gln His Ile Ala Arg Gln Gly Ser Tyr Thr Ser
            185                 190                 195
```

TABLE 3-continued

| | | | | | | | | | | | | | | | |
|---|---|---|---|---|---|---|---|---|---|---|---|---|---|---|---|
| ATC | AAC | AGC | GAA | GGT | GAA | TTC | ATC | CCA | GAG | ACC | AGC | GAA | CAG | TGT | ATG | 1038 |
| Ile | Asn | Ser 200 | Glu | Gly | Glu | Phe | Ile 205 | Pro | Glu | Thr | Ser | Glu 210 | Gln | Cys | Met |
| CTA | GAT | CCC | CTC | AGC | AGT | GCC | GAA | AAT | TCC | TTG | TCA | GGA | AGC | TGC | CAA | 1086 |
| Leu | Asp 215 | Pro | Leu | Ser | Ser | Ala 220 | Glu | Asn | Ser | Leu | Ser 225 | Gly | Ser | Cys | Gln |
| TCC | TTG | GAC | AGG | TCA | GCA | GAC | AGC | CCA | TCC | TTC | AGG | AAA | TCA | CAA | ATG | 1134 |
| Ser 230 | Leu | Asp | Arg | Ser | Ala 235 | Asp | Ser | Pro | Ser | Phe 240 | Arg | Lys | Ser | Gln | Met 245 |
| TCC | CGA | GCC | CGG | AGC | TTC | CCA | GAC | AAC | AGA | AAG | GAA | TGC | TCA | GAT | CGG | 1182 |
| Ser | Arg | Ala | Arg | Ser 250 | Phe | Pro | Asp | Asn | Arg 255 | Lys | Glu | Cys | Ser | Asp 260 | Arg |
| GAG | ACC | CAG | CTC | TAT | GAT | AAA | GGT | GTC | AAA | GGT | GGA | ACC | TAT | CCC | AGG | 1230 |
| Glu | Thr | Gln | Leu 265 | Tyr | Asp | Lys | Gly | Val 270 | Lys | Gly | Gly | Thr | Tyr 275 | Pro | Arg |
| CGC | TAC | CAT | GTG | TCT | GTG | CAT | CAC | AAA | GAC | TAC | AAT | GAT | GGC | AGA | AGA | 1278 |
| Arg | Tyr | His 280 | Val | Ser | Val | His | Lys 285 | Asp | Tyr | Asn | Asp | Gly 290 | Arg | Arg |
| ACA | TTT | CCC | CGA | ATA | CGA | CGG | CAT | CAA | GGC | AAC | CTA | TTC | ACT | CTG | GTG | 1326 |
| Thr | Phe 295 | Pro | Arg | Ile | Arg | Arg 300 | His | Gln | Gly | Asn | Leu 305 | Phe | Thr | Leu | Val |
| CCC | TCA | AGT | CGC | TCC | TTG | AGC | ACA | AAT | GGC | GAG | AAC | ATG | GGT | GTA | GCT | 1374 |
| Pro 310 | Ser | Ser | Arg | Ser | Leu 315 | Ser | Thr | Asn | Gly | Glu 320 | Asn | Met | Gly | Val | Ala 325 |
| GTG | CAA | TAC | CTG | GAC | CCC | CGT | GGG | CGC | CTA | CGG | AGT | GCA | GAC | AGT | GAG | 1422 |
| Val | Gln | Tyr | Leu | Asp 330 | Pro | Arg | Gly | Arg | Leu 335 | Arg | Ser | Ala | Asp | Ser 340 | Glu |
| AAT | GCC | CTC | ACT | GTG | CAG | GAA | AGG | AAT | GTG | CCA | ACC | AAA | TCT | CCT | AGT | 1470 |
| Asn | Ala | Leu | Thr 345 | Val | Gln | Glu | Arg | Asn 350 | Val | Pro | Thr | Lys | Ser 355 | Pro | Ser |
| GCT | CCC | ATC | AAT | TGG | CGT | CGG | GGG | AAG | CTC | CTG | GGT | CAA | GGT | GCC | TTC | 1518 |
| Ala | Pro | Ile | Asn 360 | Trp | Arg | Arg | Gly | Lys 365 | Leu | Leu | Gly | Gln | Gly 370 | Ala | Phe |
| GGC | AGG | GTC | TAC | TTG | TGC | TAT | GAT | GTG | GAC | ACA | GGA | CGT | GAA | CTT | GCT | 1566 |
| Gly | Arg 375 | Val | Tyr | Leu | Cys | Tyr 380 | Asp | Val | Asp | Thr | Gly 385 | Arg | Glu | Leu | Ala |
| TCT | AAG | CAG | GTC | CAG | TTT | GAC | CCA | GAT | AGT | CCT | GAG | ACA | AGC | AAG | GAG | 1614 |
| Ser | Lys | Gln | Val | Gln 390 | Phe 395 | Asp | Pro | Asp | Ser | Pro 400 | Glu | Thr | Ser | Lys | Glu 405 |
| GTG | AGT | GCT | CTG | GAG | TGT | GAG | ATC | CAG | TTG | CTG | AAG | AAC | CTG | CAG | CAT | 1662 |
| Val | Ser | Ala | Leu | Glu 410 | Cys | Glu | Ile | Gln | Leu 415 | Leu | Lys | Asn | Leu | Gln 420 | His |
| GAG | CGC | ATT | GTG | CAG | TAC | TAC | GGC | TGC | CTG | CGG | GAC | CGT | GCT | GAG | AAG | 1710 |
| Glu | Arg | Ile | Val 425 | Gln | Tyr | Tyr | Gly | Cys 430 | Leu | Arg | Asp | Arg | Ala 435 | Glu | Lys |
| ATC | CTC | ACC | ATC | TTT | ATG | GAG | TAT | ATG | CCA | GGG | GGC | TCT | GTA | AAA | GAC | 1758 |
| Ile | Leu | Thr 440 | Ile | Phe | Met | Glu | Tyr 445 | Met | Pro | Gly | Gly | Ser 450 | Val | Lys | Asp |
| CAG | TTG | AAG | GCC | TAC | GGA | GCT | CTG | ACA | GAG | AGT | GTG | ACC | CGC | AAG | TAC | 1806 |
| Gln | Leu 455 | Lys | Ala | Tyr | Gly 460 | Ala | Leu | Thr | Glu | Ser 465 | Val | Thr | Arg | Lys | Tyr |
| ACC | CGG | CAG | ATT | CTG | GAG | GGC | ATG | TCA | TAC | CTG | CAC | AGC | AAC | ATG | ATT | 1854 |
| Thr 470 | Arg | Gln | Ile | Leu | Glu 475 | Gly | Met | Ser | Tyr | Leu 480 | His | Ser | Asn | Met | Ile 485 |
| GTG | CAT | CGG | GAC | ATC | AAG | GGA | GCC | AAT | ATC | CTC | CGA | GAC | TCA | GCT | GGG | 1902 |
| Val | His | Arg | Asp | Ile 490 | Lys | Gly | Ala | Asn | Ile 495 | Leu | Arg | Asp | Ser | Ala 500 | Gly |
| AAT | GTG | AAG | CTT | GGG | GAT | TTT | GGG | GCC | AGC | AAA | CGC | CTA | CAG | ACC | ATC | 1950 |
| Asn | Val | Lys | Leu 505 | Gly | Asp | Phe | Gly | Ala 510 | Ser | Lys | Arg | Leu | Gln 515 | Thr | Ile |

TABLE 3-continued

| | | | | | | | | | | | | | | | | |
|---|---|---|---|---|---|---|---|---|---|---|---|---|---|---|---|---|
| TGC | ATG | TCA | GGG | ACA | GGC | ATT | CGC | TCT | GTC | ACT | GGC | ACA | CCC | TAC | TGG | 1998 |
| Cys | Met | Ser 520 | Gly | Thr | Gly | Ile | Arg 525 | Ser | Val | Thr | Gly | Thr 530 | Pro | Tyr | Trp | |
| ATG | AGT | CCT | GAA | GTC | ATC | AGT | GGC | GAG | GGC | TAT | GGA | AGA | AAG | GCA | GAC | 2046 |
| Met | Ser 535 | Pro | Glu | Val | Ile | Ser 540 | Gly | Glu | Gly | Tyr | Gly 545 | Arg | Lys | Ala | Asp | |
| GTG | TGG | AGC | CTG | GGC | TGT | ACT | GTG | GTG | GAA | ATG | CTG | ACA | GAG | AAA | CCA | 2094 |
| Val 550 | Trp | Ser | Leu | Gly | Cys 555 | Thr | Val | Val | Glu | Met 560 | Leu | Thr | Glu | Lys | Pro 565 | |
| CCT | TGG | GCA | GAG | TAT | GAA | GCT | ATG | GCT | GCC | ATT | TTC | AAG | ATT | GCC | ACC | 2142 |
| Pro | Trp | Ala | Glu | Tyr 570 | Glu | Ala | Met | Ala | Ala 575 | Ile | Phe | Lys | Ile | Ala 580 | Thr | |
| CAG | CCT | ACC | AAT | CCT | CAG | CTG | CCC | TCT | CAC | ATC | TCA | GAA | CAC | GGC | AGG | 2190 |
| Gln | Pro | Thr | Asn 585 | Pro | Gln | Leu | Pro | Ser | His 590 | Ile | Ser | Glu | His | Gly 595 | Arg | |
| GAC | TTC | CTG | AGG | CGC | ATA | TTT | GTG | GAA | GCT | CGT | CAG | AGA | CCC | TCA | GCT | 2238 |
| Asp | Phe | Leu 600 | Arg | Arg | Ile | Phe | Val 605 | Glu | Ala | Arg | Gln | Arg 610 | Pro | Ser | Ala | |
| GAG | GAG | CTG | CTC | ACA | CAC | CAC | TTT | GCA | CAG | CTA | GTG | TAC | TGAGCTCTCA | | | 2287 |
| Glu | Glu 615 | Leu | Leu | Thr | His | His 620 | Phe | Ala | Gln | Leu | Val 625 | Tyr | | | | |
| AGGCTATCAG | GCTGCCAGCT | GCCACCTGCT | GAGCAGGCAA | GGGGCTGCTG | TCAGGCTCAG | | | | | | | | | | | 2347 |
| TGAAGTTGCT | GCTTCTTCCA | GGCAAGGCTA | TGACCAGTGG | AGCATCGGTC | CAGCCATTGT | | | | | | | | | | | 2407 |
| TTGTCTGTGC | CCCATCTGCC | ACTGGGACTC | AAAGCCAGGA | TGGGATAGCT | CTGGCATCAA | | | | | | | | | | | 2467 |
| GACTGGGAGC | TCCAGCCTGT | AAGACCCAAG | AGCTTTAGCA | CCTTAAGCTC | AGTATGGCGG | | | | | | | | | | | 2527 |
| GAAGGGCTGG | AAACAGTATG | CAAGACTGCC | ATGGGTCCTG | CCTACCCTCA | GATGTGTCCT | | | | | | | | | | | 2587 |
| AACACTGCAG | ACAGCACTGA | AGTCAAGAGG | GACTGGGGCA | CAGGAGGTCC | TCAAGGGTAT | | | | | | | | | | | 2647 |
| GAATAGTGTT | ACTTCATTCA | GAGTGTTACT | TTGTTTCTCT | CCCAATGTTT | GGAGACCACC | | | | | | | | | | | 2707 |
| AGCCTGTCTC | TGGGCTGCAA | GCCTGAGGTA | AAGCCCAGCA | TCCCCCAGCC | AACAGAAGGT | | | | | | | | | | | 2767 |
| AGAGGTTTGG | GCTACCCCAC | TATAGCTTCC | AGGTATTCGG | TGTCAGTCCT | GTCTTACCAA | | | | | | | | | | | 2827 |
| AGATGAATGA | AGCAAATGTT | ACACTGCCTT | ATTCTGGAGA | GGAGGAGCTA | CTCGGATAAG | | | | | | | | | | | 2887 |
| CAGGGCCTGA | GAGATGGAGC | TGCCTCCAGA | AACTGGGGAG | ACCCAGTCTT | GTCAATGCAA | | | | | | | | | | | 2947 |
| TTGTCTCTGT | TTTACAAGTT | GGAGTCACTC | TTATGCTGTT | CCCAGTTTTA | AAACTGGAGA | | | | | | | | | | | 3007 |
| CTTTGCCCTC | TGAGCTCTGG | AGACCCATGT | GGGCTTAGGC | TTGGACTGGA | TGGAAGAGCT | | | | | | | | | | | 3067 |
| GATGGCCTCT | GCCCCTGGCC | TG | | | | | | | | | | | | | | 3089 |

An MEKK protein of the present invention can also include an MEKK protein having at least a portion of the nucleic acid and/or amino acid sequence shown in Table 4 and represented by SEQ ID NO:7 and SEQ ID NO:8, respectively, and is referred to as MEKK 4.

TABLE 4

| | | | | | | |
|---|---|---|---|---|---|---|
| AATTCGGCAC | GAGAACCTAT | CAGACATTGG | CTGGCCAGTG | TTTGAAATCC | CCTCCCCTCG | 60 |
| GCCGTCCAAG | GGCTACGAGC | CAGAGGACGA | GGTCGAGGAC | ACGGAGGTTG | AGCTGAGGGA | 120 |
| GCTGGAGAGC | GGGACGGAGG | AGAGTGACGA | GGAGCCAACC | CCCAGTCCCA | GGGTGCCAGA | 180 |
| GCTCAGGCTG | TCCACAGACA | CCATCTTGGA | CAGTCGCTCC | CAGGGCTGCG | TCTCCAGGAA | 240 |
| GCTGGAGAGG | CTCGAGTCAG | AGGAAGATTC | CATAGGCTGG | GGGACAGCGG | ACTGTGGCCC | 300 |
| TGAAGCCAGC | AGGCATTGTT | TGACTTCTAT | CTATAGACCA | TTCGTGGACA | AAGCACTGAA | 360 |
| GCAAATGGGG | CTAAGAAAGT | TAATTTTACG | ACTTCATAAG | CTTATGAAGT | GGTCCTTGCA | 420 |
| AAGAGCTCGT | GTAGCTCTGG | TGAAGGACAA | CCGTCAGTGG | AGTTCTCTGA | CTTTCCAGGT | 480 |
| CCCATGTGGG | GCTCGGATTA | TGTGCAGTTG | TCGGGAACAC | CTCCTTCCTC | AGAGCAGAAG | 540 |
| TGTAGCGCTG | TGTCCTGGGA | AGAACTGAGA | GCCATGGACC | TGCCTTCCTT | TGAGCCCGCC | 600 |
| TTCCTGGTGC | TCTGTCGGGT | CCTGCTGAAC | GTGATCCACG | AGTGCCTGAA | GCTGCGGCTG | 660 |
| GAACAGAGGC | TGCCGGGGAG | CCTTCCCTCT | TGAGTATCAA | ACAGCTAGTG | CGAGAGTGTA | 720 |

| | | | | | | |
|---|---|---|---|---|---|---|
| AAGAGGTCCT | AAAGGGCGGG | CTCCTG ATG AAG CAG TAT TAC CAG TTC ATG CTG | | | | 773 |
| | | Met Lys Gln Tyr Tyr Gln Phe Met Leu | | | | |
| | | 1       5 | | | | |

| | | | | | | |
|---|---|---|---|---|---|---|
| CAG GAG GTC CTG GGC GGA CTG GAG AAG ACC GAC TGC AAC ATG GAT GCC | | | | | | 821 |
| Gln Glu Val Leu Gly Gly Leu Glu Lys Thr Asp Cys Asn Met Asp Ala | | | | | | |
| 10           15            20            25 | | | | | | |

| | | | | | | |
|---|---|---|---|---|---|---|
| TTT GAG GAG GAC CTG CAG AAG ATG CTG ATG GTG TAT TTT GAT TAC ATG | | | | | | 869 |
| Phe Glu Glu Asp Leu Gln Lys Met Leu Met Val Tyr Phe Asp Tyr Met | | | | | | |
| 30            35            40 | | | | | | |

TABLE 4-continued

| | | | | | | | | | | | | | | | | |
|---|---|---|---|---|---|---|---|---|---|---|---|---|---|---|---|---|
| AGA | AGC | TGG | ATC | CAA | ATG | CTA | CAG | CAG | TTA | CCT | CAG | GCT | TCC | CAT | AGC | 917 |
| Arg | Ser | Trp | Ile 45 | Gln | Met | Leu | Gln | Gln 50 | Leu | Pro | Gln | Ala | Ser 55 | His | Ser | |
| TTA | AAA | AAC | CTG | CTA | GAA | GAG | GAA | TGG | AAT | TTC | ACC | AAA | GAA | ATA | ACC | 965 |
| Leu | Lys | Asn 60 | Leu | Leu | Glu | Glu | Glu 65 | Trp | Asn | Phe | Thr | Lys 70 | Glu | Ile | Thr | |
| CAT | TAT | ATC | CGT | GGC | GGA | GAA | GCG | CAG | GCT | GGA | AAG | CTT | TTC | TGT | GAC | 1013 |
| His | Tyr 75 | Ile | Arg | Gly | Gly | Glu | Ala 80 | Gln | Ala | Gly | Lys 85 | Leu | Phe | Cys | Asp | |
| ATC | GCA | GGG | ATG | CTG | CTG | AAA | TCC | ACA | GGG | AGC | TTT | CTG | GAA | TCC | GGC | 1061 |
| Ile 90 | Ala | Gly | Met | Leu | Leu 95 | Lys | Ser | Thr | Gly | Ser 100 | Phe | Leu | Glu | Ser | Gly 105 | |
| CTG | CAG | GAG | AGC | TGT | GCT | GAG | CTG | TGG | ACC | AGN | GCC | GAC | GAC | AAC | GGT | 1109 |
| Leu | Gln | Glu | Ser | Cys 110 | Ala | Glu | Leu | Trp | Thr 115 | Xaa | Ala | Asp | Asp | Asn 120 | Gly | |
| GCT | GCC | GAC | GAG | CTA | AGG | AGA | TCT | GTC | ATC | GAG | ATC | AGC | CGA | GCA | CTC | 1157 |
| Ala | Ala | Asp | Glu 125 | Leu | Arg | Arg | Ser | Val 130 | Ile | Glu | Ile | Ser 135 | Arg | Ala | Leu | |
| AAG | GAG | CTC | TTC | CAC | GAA | GCC | AGG | GAA | AGA | GCC | TCC | AAG | GCC | CTG | GGC | 1205 |
| Lys | Glu | Leu 140 | Phe | His | Glu | Ala | Arg 145 | Glu | Arg | Ala | Ser | Lys 150 | Ala | Leu | Gly | |
| TTT | GCT | AAA | ATG | CTG | AGG | AAG | GAC | CTA | GAA | ATA | GCA | GCA | GAG | TTC | GTG | 1253 |
| Phe | Ala 155 | Lys | Met | Leu | Arg | Lys 160 | Asp | Leu | Glu | Ile | Ala 165 | Ala | Glu | Phe | Val | |
| CTA | TCT | GCA | TCA | GCC | CGA | GAG | CTC | CTG | GAC | GCT | CTG | AAA | GCA | AAG | CAG | 1301 |
| Leu 170 | Ser | Ala | Ser | Ala | Arg 175 | Glu | Leu | Leu | Asp | Ala 180 | Leu | Lys | Ala | Lys | Gln 185 | |
| TAT | GTT | AAG | GTA | CAG | ATT | CCC | GGG | TTA | GAG | AAT | TTG | CAC | GTG | TTT | GTC | 1349 |
| Tyr | Val | Lys | Val | Gln 190 | Ile | Pro | Gly | Leu | Glu 195 | Asn | Leu | His | Val | Phe 200 | Val | |
| CCC | GAC | AGC | CTC | GCT | GAG | GAG | AAG | AAA | ATT | ATT | TTG | CAG | CTA | CTC | AAT | 1397 |
| Pro | Asp | Ser | Leu 205 | Ala | Glu | Glu | Lys | Lys 210 | Ile | Ile | Leu | Gln 215 | Leu | Leu | Asn | |
| GCT | GCC | ACA | GGA | AAG | GAC | TGC | TCA | AAG | GAT | CCA | GAC | GAC | GTC | TTC | ATG | 1445 |
| Ala | Ala | Thr 220 | Gly | Lys | Asp | Cys | Ser 225 | Lys | Asp | Pro | Asp | Asp 230 | Val | Phe | Met | |
| GAT | GCC | TTC | CTG | CTC | CTG | ACC | AAG | CAT | GGG | GAC | CGA | GCC | CGT | GAC | TCA | 1493 |
| Asp | Ala 235 | Phe | Leu | Leu | Leu | Thr 240 | Lys | His | Gly | Asp | Arg 245 | Ala | Arg | Asp | Ser | |
| GAA | GAT | GGC | TGG | GGC | ACA | TGG | GAA | GCT | CGG | GCT | GTC | AAA | ATT | GTG | CCT | 1541 |
| Glu 250 | Asp | Gly | Trp | Gly | Thr 255 | Trp | Glu | Ala | Arg | Ala 260 | Val | Lys | Ile | Val | Pro 265 | |
| CAG | GTG | GAG | ACT | GTG | GAC | ACC | CTG | AGA | AGC | ATG | CAG | GTG | GAC | AAC | CTT | 1589 |
| Gln | Val | Glu | Thr | Val 270 | Asp | Thr | Leu | Arg | Ser 275 | Met | Gln | Val | Asp | Asn 280 | Leu | |
| CTG | CTG | GTT | GTC | ATG | GAG | TCT | GCT | CAC | CTC | GTA | CTT | CAG | AGA | AAA | GCC | 1637 |
| Leu | Leu | Val | Val 285 | Met | Glu | Ser | Ala | His 290 | Leu | Val | Leu | Gln | Arg 295 | Lys | Ala | |
| TTC | CAG | CAG | TCC | ATT | GAG | GGG | CTG | ATG | ACT | GTA | CGC | CAT | GAG | CAG | ACA | 1685 |
| Phe | Gln | Gln 300 | Ser | Ile | Glu | Gly | Leu 305 | Met | Thr | Val | Arg | His 310 | Glu | Gln | Thr | |
| TCT | AGC | CAG | CCC | ATC | ATC | GCC | AAA | GGT | TTG | CAG | CAG | CTC | AAG | AAC | GAT | 1733 |
| Ser | Ser 315 | Gln | Pro | Ile | Ile | Ala 320 | Lys | Gly | Leu | Gln | Gln 325 | Leu | Lys | Asn | Asp | |
| GCA | CTT | GAG | CTA | TGC | AAC | AGA | ATC | AGC | GAT | GCC | ATC | GAC | CGT | GTG | GAC | 1781 |
| Ala 330 | Leu | Glu | Leu | Cys | Asn 335 | Arg | Ile | Ser | Asp | Ala 340 | Ile | Asp | Arg | Val | Asp 345 | |
| CAC | ATG | TTC | ACC | CTG | GAG | TTC | GAT | GCT | GAG | GTC | GAG | GAG | TCT | GAG | TCG | 1829 |
| His | Met | Phe | Thr | Leu 350 | Glu | Phe | Asp | Ala | Glu 355 | Val | Glu | Glu | Ser | Glu 360 | Ser | |

TABLE 4-continued

| | | | | | | | | | | | | | | | |
|---|---|---|---|---|---|---|---|---|---|---|---|---|---|---|---|
| GCC | ACG | CTG | CAG | CAG | TAC | TAC | CGA | GAA | GCC | ATG | ATT | CAG | GGC | TAC | AAC | 1877 |
| Ala | Thr | Leu | Gln 365 | Gln | Tyr | Tyr | Arg | Glu 370 | Ala | Met | Ile | Gln | Gly 375 | Tyr | Asn | |
| TTT | GGG | TTT | GAG | TAT | CAT | AAA | GAA | GTT | GTT | CGT | TTG | ATG | TCT | GGG | GAA | 1925 |
| Phe | Gly | Phe 380 | Glu | Tyr | His | Lys | Glu 385 | Val | Val | Arg | Leu | Met 390 | Ser | Gly | Glu | |
| TTC | AGG | CAG | AAG | ATA | GGA | GAC | AAA | TAT | ATA | ACG | TTC | GCC | CAG | AAG | TGG | 1973 |
| Phe | Arg 395 | Gln | Lys | Ile | Gly | Asp 400 | Lys | Tyr | Ile | Thr | Phe 405 | Ala | Gln | Lys | Trp | |
| ATG | AAT | TAC | GTG | CTG | ACC | AAA | TGC | GAG | AGC | GGC | AGA | GGC | ACA | AGA | CCC | 2021 |
| Met 410 | Asn | Tyr | Val | Leu | Thr 415 | Lys | Cys | Glu | Ser | Gly 420 | Arg | Gly | Thr | Arg | Pro 425 | |
| AGA | TGG | GCC | ACC | CAA | GGA | TTT | GAT | TTC | CTA | CAA | GCC | ATT | GAA | CCT | GCC | 2069 |
| Arg | Trp | Ala | Thr | Gln 430 | Gly | Phe | Asp | Phe | Leu 435 | Gln | Ala | Ile | Glu | Pro 440 | Ala | |
| TTT | ATT | TCA | GCT | TTA | CCA | GAA | GAT | GAC | TTC | TTG | AGT | TTG | CAA | GCC | CTG | 2117 |
| Phe | Ile | Ser | Ala 445 | Leu | Pro | Glu | Asp | Asp 450 | Phe | Leu | Ser | Leu | Gln 455 | Ala | Leu | |
| ATG | AAT | GAG | TGC | ATC | GGG | CAC | GTC | ATA | GGA | AAG | CCA | CAC | AGC | CCT | GTC | 2165 |
| Met | Asn | Glu 460 | Cys | Ile | Gly | His | Val 465 | Ile | Gly | Lys | Pro | His 470 | Ser | Pro | Val | |
| ACA | GCT | ATC | CAT | CGG | AAC | AGC | CCC | CGC | CCT | GTG | AAG | GTG | CCC | CGA | TGC | 2213 |
| Thr | Ala 475 | Ile | His | Arg | Asn | Ser 480 | Pro | Arg | Pro | Val | Lys 485 | Val | Pro | Arg | Cys | |
| CAC | AGT | GAC | CCT | CCT | AAC | CCT | CAC | CTC | ATC | ATC | CCG | ACT | CCA | GAG | GGA | 2261 |
| His 490 | Ser | Asp | Pro | Pro | Asn 495 | Pro | His | Leu | Ile | Ile 500 | Pro | Thr | Pro | Glu | Gly 505 | |
| TTC | AGG | GGT | TCC | AGT | GTC | CCT | GAA | AAC | GAC | CGC | TTG | GCC | TCC | ATA | GCT | 2309 |
| Phe | Arg | Gly | Ser | Ser 510 | Val | Pro | Glu | Asn | Asp 515 | Arg | Leu | Ala | Ser | Ile 520 | Ala | |
| GCA | GAA | CTG | CAG | TTC | AGG | TCT | CTG | AGT | CGG | CAC | TCA | AGC | CCC | ACG | GAA | 2357 |
| Ala | Glu | Leu | Gln 525 | Phe | Arg | Ser | Leu | Ser 530 | Arg | His | Ser | Ser | Pro 335 | Thr | Glu | |
| GAG | CGA | GAC | GAG | CCA | GCG | TAT | CCT | CGG | AGT | GAC | TCA | AGT | GGA | TCA | ACT | 2405 |
| Glu | Arg | Asp 540 | Glu | Pro | Ala | Tyr | Pro 545 | Arg | Ser | Asp | Ser | Ser 550 | Gly | Ser | Thr | |
| CGG | AGA | AGC | TGG | GAA | CTT | CGA | ACA | CTC | ATC | AGC | CAG | ACC | AAA | GAC | TCG | 2453 |
| Arg | Arg 555 | Ser | Trp | Glu | Leu | Arg 560 | Thr | Leu | Ile | Ser | Gln 565 | Thr | Lys | Asp | Ser | |
| GCC | TCT | AAG | CAG | GGG | CCC | ATA | GAA | GCT | ATC | CAG | AAG | TCA | GTC | CGA | CTG | 2501 |
| Ala 570 | Ser | Lys | Gln | Gly | Pro 575 | Ile | Glu | Ala | Ile | Gln 580 | Lys | Ser | Val | Arg | Leu 585 | |
| TTT | GAA | GAG | AGG | AGG | TAT | CGA | GAG | ATG | AGG | AGA | AAG | AAT | ATC | ATC | GGC | 2549 |
| Phe | Glu | Glu | Arg | Arg 590 | Tyr | Arg | Glu | Met | Arg 595 | Arg | Lys | Asn | Ile | Ile 600 | Gly | |
| CAA | GTG | TGC | GAT | ACC | CCT | AAG | TCC | TAT | GAT | AAC | GTC | ATG | CAT | GTT | GGA | 2597 |
| Gln | Val | Cys | Asp 605 | Thr | Pro | Lys | Ser | Tyr 610 | Asp | Asn | Val | Met | His 615 | Val | Gly | |
| CTG | AGG | AAG | GTG | ACA | TTT | AAG | TGG | CAA | AGA | GGA | AAC | AAA | ATT | GGA | GAA | 2645 |
| Leu | Arg | Lys 620 | Val | Thr | Phe | Lys | Trp 625 | Gln | Arg | Gly | Asn | Lys 630 | Ile | Gly | Glu | |
| GGA | CAG | TAT | GGA | AAA | GTA | TAC | ACC | TGC | ATC | AGT | GTT | GAC | ACA | GGG | GAG | 2693 |
| Gly | Gln | Tyr 635 | Gly | Lys | Val | Tyr | Thr 640 | Cys | Ile | Ser | Val | Asp 645 | Thr | Gly | Glu | |
| CTG | ATG | GCC | ATG | AAG | GAG | ATT | CGA | TTT | CAG | CCT | AAC | GAC | CAC | AAG | ACT | 2741 |
| Leu 650 | Met | Ala | Met | Lys | Glu 655 | Ile | Arg | Phe | Gln | Pro 660 | Asn | Asp | His | Lys | Thr 665 | |
| ATC | AAG | GAG | ACT | GCA | GAC | GAG | TTG | AAA | ATA | TTT | GAA | GGC | ATC | AAG | CAC | 2789 |
| Ile | Lys | Glu | Thr | Ala 670 | Asp | Glu | Leu | Lys | Ile 675 | Phe | Glu | Gly | Ile | Lys 680 | His | |

| | | | | | | | | | | | | | | | | |
|---|---|---|---|---|---|---|---|---|---|---|---|---|---|---|---|---|
| CCC | AAC | CTG | GTC | CGG | TAT | TTT | GGC | GTG | GAG | CTT | CAC | AGG | GAA | GAG | ATG | 2837 |
| Pro | Asn | Leu | Val | Arg | Tyr | Phe | Gly | Val | Glu | Leu | His | Arg | Glu | Glu | Met | |
| | | | 685 | | | | | 690 | | | | 695 | | | | |
| TAC | ATC | TTC | ATG | GAG | TAC | TGT | GAT | GAG | GGT | ACA | CTA | GAG | GAG | GTG | TCA | 2885 |
| Tyr | Ile | Phe | Met | Glu | Tyr | Cys | Asp | Glu | Gly | Thr | Leu | Glu | Glu | Val | Ser | |
| | | 700 | | | | | 705 | | | | | 710 | | | | |
| CGA | CTG | GGC | CTG | CAG | GAG | CAC | GTC | ATC | AGG | TTA | TAT | ACC | AAG | CAG | ATC | 2933 |
| Arg | Leu | Gly | Leu | Gln | Glu | His | Val | Ile | Arg | Leu | Tyr | Thr | Lys | Gln | Ile | |
| | 715 | | | | | 720 | | | | | 725 | | | | | |
| ACT | GTC | GCC | ATC | AAC | GTC | CTC | CAT | GAG | CAC | GGC | ATC | GTT | CAC | CGA | GAC | 2981 |
| Thr | Val | Ala | Ile | Asn | Val | Leu | His | Glu | His | Gly | Ile | Val | His | Arg | Asp | |
| 730 | | | | | 735 | | | | | 740 | | | | | 745 | |
| ATC | AAA | GGT | GCC | AAT | ATC | TTC | CTT | ACG | TCA | TCT | GGA | CTA | ATC | AAG | CTG | 3029 |
| Ile | Lys | Gly | Ala | Asn | Ile | Phe | Leu | Thr | Ser | Ser | Gly | Leu | Ile | Lys | Leu | |
| | | | | 750 | | | | | 755 | | | | | 760 | | |
| GGA | GAT | TTT | GGA | TGC | TCT | GTA | AAA | CTT | AAA | AAC | AAC | GCC | CAG | ACC | ATG | 3077 |
| Gly | Asp | Phe | Gly | Cys | Ser | Val | Lys | Leu | Lys | Asn | Asn | Ala | Gln | Thr | Met | |
| | | | 765 | | | | | 770 | | | | | 775 | | | |
| CCC | GGA | GAG | GTG | AAC | AGC | ACC | CTA | GGG | ACA | GCA | GCT | TAC | ATG | GCC | CCT | 3125 |
| Pro | Gly | Glu | Val | Asn | Ser | Thr | Leu | Gly | Thr | Ala | Ala | Tyr | Met | Ala | Pro | |
| | | 780 | | | | | 785 | | | | | 790 | | | | |
| GAA | GTT | ATT | ACC | CGA | GCC | AAA | GGA | GAA | GGC | CAC | GGA | CGT | GCG | GCA | GAT | 3173 |
| Glu | Val | Ile | Thr | Arg | Ala | Lys | Gly | Glu | Gly | His | Gly | Arg | Ala | Ala | Asp | |
| | 795 | | | | | 800 | | | | | 805 | | | | | |
| ATC | TGG | AGT | CTG | GGG | TGC | GTC | GTC | ATA | GAG | ATG | GTG | ACT | GGC | AAG | CGG | 3221 |
| Ile | Trp | Ser | Leu | Gly | Cys | Val | Val | Ile | Glu | Met | Val | Thr | Gly | Lys | Arg | |
| 810 | | | | | 815 | | | | | 820 | | | | | 825 | |
| CCT | TGG | CAT | GAG | TAT | GAA | CAC | AAC | TTT | CAG | ATT | ATG | TAC | AAG | GTG | GGG | 3269 |
| Pro | Trp | His | Glu | Tyr | Glu | His | Asn | Phe | Gln | Ile | Met | Tyr | Lys | Val | Gly | |
| | | | | 830 | | | | | 835 | | | | | 840 | | |
| ATG | GGA | CAC | AAG | CCA | CCA | ATC | CCG | GAA | AGG | CTA | AGC | CCT | GAA | GGA | AAG | 3317 |
| Met | Gly | His | Lys | Pro | Pro | Ile | Pro | Glu | Arg | Leu | Ser | Pro | Glu | Gly | Lys | |
| | | | 845 | | | | | 850 | | | | | 855 | | | |
| GCC | TTT | CTC | TCG | CAC | TGC | CTG | GAA | AGT | GAC | CCG | AAG | ATA | CGG | TGG | ACA | 3365 |
| Ala | Phe | Leu | Ser | His | Cys | Leu | Glu | Ser | Asp | Pro | Lys | Ile | Arg | Trp | Thr | |
| | | 860 | | | | | 865 | | | | | 870 | | | | |
| GCC | AGC | CAG | CTC | CTC | GAC | CAC | GCT | TTT | GTC | AAG | GTT | TGC | ACA | GAT | GAA | 3413 |
| Ala | Ser | Gln | Leu | Leu | Asp | His | Ala | Phe | Val | Lys | Val | Cys | Thr | Asp | Glu | |
| | 875 | | | | | 880 | | | | | 885 | | | | | |
| GAG | T | GAAGTGAACC | AGTCCGTGGC | CTAGTAGTGT | GTGGACAGAA | TCCCGTGATC | | | | | | | | | | 3467 |
| Glu | | | | | | | | | | | | | | | | |
| 890 | | | | | | | | | | | | | | | | |

| | | | | | |
|---|---|---|---|---|---|
| ACTACTGTAT | GTAATATTTA | CATAAAGACT | GCAGCGCAGG | CGGCCTTCCT | AACCTCCCAG | 3527 |
| GACTGAAGAC | TACAGGGGTG | ACAAGCCTCA | CTTCTGCTGC | TCCTGTCGCC | TGCTGAGTGA | 3587 |
| CAGTGCTGAG | GTTAAAGGAG | CCGCACGTTA | AGTGCCATTA | CTACTGTACA | CGGCCACCGC | 3647 |
| CTCTGTCCCC | TCCGACCCTC | TCGTGACTGA | GAACCAACCG | TGTCATCAGC | ACAGTGTTTT | 3707 |
| TGAGCTCCTG | GGGTTCAGAA | GAACATGTAG | TGTTCCCGGG | TGTCCGGGAC | GTTTATTTCA | 3767 |
| ACCTCCTGGT | CGTTGGCTCT | GACTGTGGAG | CCTCCTTGTT | CGAAAGCTGC | AGGTTTGTTA | 3827 |
| TGCAAAGGCT | CGTAAGTGAA | GCTGAAGAAA | AGGTTCTTTT | TCAATAAATG | GTTTATTTTA | 3887 |
| GGAAAGCGAA | AAAAAAAAAA | AAAAAA | | | | 3913 |

An MEKK protein of the present invention, referred to here as MEKK 5, includes an MEKK protein having at least a portion of the nucleic acid and/or amino acid sequence shown in Table 5 and represented by SEQ ID NO:9 and SEQ ID NO:10, respectively.

TABLE 5

| | | | | | |
|---|---|---|---|---|---|
| AAGAAGAAGG | ACAGGGAGCA | GAGGGGACAA | GAAAACACGG | CTGCTTTCTG | GTTCAACCGA | 60 |
| TCGAACGAAC | TGATCTGGTT | AGAACTGCAG | GCCTGGCACG | CGGGCCGCAC | CATCAATGAC | 120 |
| CAGGACCTCT | TTCTCTACAC | AGCCCGCCAG | GCCATCCCAG | ACATCAATCAA | TGAGATCCTC | 180 |
| ACCTTCAAAG | TTAACTACGG | GAGCATTGCC | TTCTCCAGCA | ATGGAGCCGG | TTTCAACGGG | 240 |
| CCCTTGGTAG | AAGGCCAGTG | CAGAACCCCT | CAGGAGACAA | ACCGTGTGGG | CTGCTCATCG | 300 |
| TACCACGAGC | ACCTCCAGCG | CCAGAGGGTC | TCGTTTGAGC | AGGTGAAGCG | GATA ATG | 357 |
| | | | | | Met |
| | | | | | 1 |

```
GAG CTG CTG GAG TAC ATG GAG GCA CTT TAC CCA TCC TTG CAG GCT CTG       405
Glu Leu Leu Glu Tyr Met Glu Ala Leu Tyr Pro Ser Leu Gln Ala Leu
            5               10              15

CAG AAG GAC TAT GAA CGG TAC GCC GCC AAG GAC TTT GAG GAC AGA GTG       453
Gln Lys Asp Tyr Glu Arg Tyr Ala Ala Lys Asp Phe Glu Asp Arg Val
        20              25              30

CAG GCG CTC TGC CTG TGG CTC AAC ATC ACG AAA GAT CTA AAT CAG AAG       501
Gln Ala Leu Cys Leu Trp Leu Asn Ile Thr Lys Asp Leu Asn Gln Lys
    35              40              45

CTG CGG ATC ATG GGC ACC GTG CTG GGC ATC AAG TTC CTA TCA GAC ATT       549
Leu Arg Ile Met Gly Thr Val Leu Gly Ile Lys Phe Leu Ser Asp Ile
50              55              60              65

GGC TGG CCA GTG AAA GAA ATC CCC TCC CCT CGG CCG TCC AAG GGC TAC       597
Gly Trp Pro Val Lys Glu Ile Pro Ser Pro Arg Pro Ser Lys Gly Tyr
            70              75              80

GAG CCA GAG GAC GAG GTC GAG GAC ACG GAG GTT GAG CTG AGG GAG CTG       645
Glu Pro Glu Asp Glu Val Glu Asp Thr Glu Val Glu Leu Arg Glu Leu
        85              90              95

GAG AGC GGG ACG GAG GAG AGT GAC GAG GAG CCA ACC CCC AGT CCG AGG       693
Glu Ser Gly Thr Glu Glu Ser Asp Glu Glu Pro Thr Pro Ser Pro Arg
        100             105             110

GTG CCA GAG CTC AGG CTG TCC ACA GAC ACC ATC TTG GAC AGT CGC TCC       741
Val Pro Glu Leu Arg Leu Ser Thr Asp Thr Ile Leu Asp Ser Arg Ser
    115             120             125

CAG GGC TGC GTC TCC AGG AAG CTG GAG AGG CTC GAG TCA GAG GAA GAT       789
Gln Gly Cys Val Ser Arg Lys Leu Glu Arg Leu Glu Ser Glu Glu Asp
130             135             140             145

TCC ATA GGC TGG GGG ACA GCG GAC TGT GGC CCT GAA GCC AGC AGG CAT       837
Ser Ile Gly Trp Gly Thr Ala Asp Cys Gly Pro Glu Ala Ser Arg His
            150             155             160

TGT TTG ACT TCT ATC TAT AGA CCA TTC GTG GAC AAA GCA CTG AAG CAA       885
Cys Leu Thr Ser Ile Tyr Arg Pro Phe Val Asp Lys Ala Leu Lys Gln
        165             170             175

ATG GGG CTA AGA AAG TTA ATT TTA CGA CTT CAT AAG CTT ATG AAT GGG       933
Met Gly Leu Arg Lys Leu Ile Leu Arg Leu His Lys Leu Met Asn Gly
        180             185             190

TCC TTG CAA AGA GCT CGT GTA GCT CTG GTG AAG GAC GAC CGT CCA GTG       981
Ser Leu Gln Arg Ala Arg Val Ala Leu Val Lys Asp Asp Arg Pro Val
    195             200             205

GAG TTC TCT GAC TTT CCA GGT CCC ATG TGG GGC TCG GAT TAT GTG CAG      1029
Glu Phe Ser Asp Phe Pro Gly Pro Met Trp Gly Ser Asp Tyr Val Gln
210             215             220             225

TTG TCG GGA ACA CCT CCT TCC TCA GAG CAG AAG TGT AGC GCT GTG TCC      1077
Leu Ser Gly Thr Pro Pro Ser Ser Glu Gln Lys Cys Ser Ala Val Ser
            230             235             240

TGG GAA GAA CTG AGA GCC ATG GAC CTG CCT TCC TTT GAG CCC GCC TTC      1125
Trp Glu Glu Leu Arg Ala Met Asp Leu Pro Ser Phe Glu Pro Ala Phe
        245             250             255

CTG GTG CTC TGT CGG GTC CTG CTG AAC GTG ATC CAC GAG TGC CTG AAG      1173
Leu Val Leu Cys Arg Val Leu Leu Asn Val Ile His Glu Cys Leu Lys
        260             265             270

CTG CGG CTG GAA CAG AGG CCT GCC GGG GAG CCT TCC CTC TTG AGT ATC      1221
Leu Arg Leu Glu Gln Arg Pro Ala Gly Glu Pro Ser Leu Leu Ser Ile
        275             280             285
```

TABLE 5-continued

| | | | | | | | | | | | | | | | | |
|---|---|---|---|---|---|---|---|---|---|---|---|---|---|---|---|---|
| AAA | CAG | CTA | GTG | CGA | GAG | TGT | AAA | GAG | GTC | CTA | AAG | GGC | GGG | CTC | CTG | 1269 |
| Lys | Gln | Leu | Val | Arg | Glu | Cys | Lys | Glu | Val | Leu | Lys | Gly | Gly | Leu | Leu | |
| 290 | | | | | 295 | | | | | 300 | | | | | 305 | |
| ATG | AAG | CAG | TAT | TAC | CAG | TTC | ATG | CTG | CAG | GAG | GTC | CTG | GGC | GGA | CTG | 1317 |
| Met | Lys | Gln | Tyr | Tyr | Gln | Phe | Met | Leu | Gln | Glu | Val | Leu | Gly | Gly | Leu | |
| | | | | 310 | | | | | 315 | | | | | 320 | | |
| GAG | AAG | ACC | GAC | TGC | AAC | ATG | GAT | GCC | TTT | GAG | GAG | GAC | CTG | CAG | AAG | 1365 |
| Glu | Lys | Thr | Asp | Cys | Asn | Met | Asp | Ala | Phe | Glu | Glu | Asp | Leu | Gln | Lys | |
| | | | 325 | | | | | 330 | | | | | 335 | | | |
| ATG | CTG | ATG | GTG | TAT | TTT | GAT | TAC | ATG | AGA | AGC | TGG | ATC | CAA | ATG | CTA | 1413 |
| Met | Leu | Met | Val | Tyr | Phe | Asp | Tyr | Met | Arg | Ser | Trp | Ile | Gln | Met | Leu | |
| | | 340 | | | | | 345 | | | | | 350 | | | | |
| CAG | CAG | TTA | CCT | CAG | GCT | TCC | CAT | AGC | TTA | AAA | AAC | CTG | CTA | GAA | GAG | 1461 |
| Gln | Gln | Leu | Pro | Gln | Ala | Ser | His | Ser | Leu | Lys | Asn | Leu | Leu | Glu | Glu | |
| | 355 | | | | | 360 | | | | | 365 | | | | | |
| GAA | TGG | AAT | TTC | ACC | AAA | GAA | ATA | ACC | CAT | TAT | ATC | CGT | GGC | GGA | GAA | 1509 |
| Glu | Trp | Asn | Phe | Thr | Lys | Glu | Ile | Thr | His | Tyr | Ile | Arg | Gly | Gly | Glu | |
| 370 | | | | | 375 | | | | | 380 | | | | | 385 | |
| GCG | CAG | GCT | GGA | AAG | CTT | TTC | TGT | GAC | ATC | GCA | GGG | ATG | CTG | CTG | AAA | 1557 |
| Ala | Gln | Ala | Gly | Lys | Leu | Phe | Cys | Asp | Ile | Ala | Gly | Met | Leu | Leu | Lys | |
| | | | | 390 | | | | | 395 | | | | | 400 | | |
| TCC | ACA | GGG | AGC | TTT | CTG | GAA | TCC | GGC | CTG | CAG | GAG | AGC | TGT | GCT | GAG | 1605 |
| Ser | Thr | Gly | Ser | Phe | Leu | Glu | Ser | Gly | Leu | Gln | Glu | Ser | Cys | Ala | Glu | |
| | | | 405 | | | | | 410 | | | | | 415 | | | |
| CTG | TGG | ACC | AGC | GCC | GAC | GAC | AAC | GGT | GCT | GCC | GAC | GAG | CTA | AGG | AGA | 1653 |
| Leu | Trp | Thr | Ser | Ala | Asp | Asp | Asn | Gly | Ala | Ala | Asp | Glu | Leu | Arg | Arg | |
| | | 420 | | | | | 425 | | | | | 430 | | | | |
| TCT | GTC | ATC | GAG | ATC | AGC | CGA | GCA | CTC | AAG | GAG | CTC | TTC | CAC | GAA | GCC | 1701 |
| Ser | Val | Ile | Glu | Ile | Ser | Arg | Ala | Leu | Lys | Glu | Leu | Phe | His | Glu | Ala | |
| | 435 | | | | | 440 | | | | | 445 | | | | | |
| AGG | GAA | AGA | GCC | TCC | AAG | GCC | CTG | GGC | TTT | GCT | AAA | ATG | CTG | AGG | AAG | 1749 |
| Arg | Glu | Arg | Ala | Ser | Lys | Ala | Leu | Gly | Phe | Ala | Lys | Met | Leu | Arg | Lys | |
| 450 | | | | | 455 | | | | | 460 | | | | | 465 | |
| GAC | CTA | GAA | ATA | GCA | GCA | GAG | TTC | GTG | CTA | TCT | GCA | TCA | GCC | CGA | GAG | 1797 |
| Asp | Leu | Glu | Ile | Ala | Ala | Glu | Phe | Val | Leu | Ser | Ala | Ser | Ala | Arg | Glu | |
| | | | | 470 | | | | | 475 | | | | | 480 | | |
| CTC | CTG | GAC | GCT | CTG | AAA | GCA | AAG | CAG | TAT | GTT | AAG | GTA | CAG | ATT | CCC | 1845 |
| Leu | Leu | Asp | Ala | Leu | Lys | Ala | Lys | Gln | Tyr | Val | Lys | Val | Gln | Ile | Pro | |
| | | | 485 | | | | | 490 | | | | | 495 | | | |
| GGG | TTA | GAG | AAT | TTG | CAC | GTG | TTT | GTC | CCC | GAC | AGC | CTC | GCT | GAG | GAG | 1893 |
| Gly | Leu | Glu | Asn | Leu | His | Val | Phe | Val | Pro | Asp | Ser | Leu | Ala | Glu | Glu | |
| | | 500 | | | | | 505 | | | | | 510 | | | | |
| AAG | AAA | ATT | ATT | TTG | CAG | CTA | CTC | AAT | GCT | GCC | ACA | GGA | AAG | GAC | TGC | 1941 |
| Lys | Lys | Ile | Ile | Leu | Gln | Leu | Leu | Asn | Ala | Ala | Thr | Gly | Lys | Asp | Cys | |
| | 515 | | | | | 520 | | | | | 525 | | | | | |
| TCA | AAG | GAT | CCA | GAC | GAC | GTC | TTC | ATG | GAT | GCC | TTC | CTG | CTC | CTG | ACC | 1989 |
| Ser | Lys | Asp | Pro | Asp | Asp | Val | Phe | Met | Asp | Ala | Phe | Leu | Leu | Leu | Thr | |
| 530 | | | | | 535 | | | | | 540 | | | | | 545 | |
| AAG | CAT | GGG | GAC | CGA | GCC | CGT | GAC | TCA | GAA | GAT | GGC | TGG | GGC | ACA | TGG | 2037 |
| Lys | His | Gly | Asp | Arg | Ala | Arg | Asp | Ser | Glu | Asp | Gly | Trp | Gly | Thr | Trp | |
| | | | | 550 | | | | | 555 | | | | | 560 | | |
| GAA | GCT | CGG | GCT | GTC | AAA | ATT | GTG | CCT | CAG | GTG | GAG | ACT | GTG | GAC | ACC | 2085 |
| Glu | Ala | Arg | Ala | Val | Lys | Ile | Val | Pro | Gln | Val | Glu | Thr | Val | Asp | Thr | |
| | | | 565 | | | | | 570 | | | | | 575 | | | |
| CTG | AGA | AGC | ATG | CAG | GTG | GAC | AAC | CTT | CTG | CTG | GTT | GTC | ATG | GAG | TCT | 2133 |
| Leu | Arg | Ser | Met | Gln | Val | Asp | Asn | Leu | Leu | Leu | Val | Val | Met | Glu | Ser | |
| | | 580 | | | | | 585 | | | | | 590 | | | | |
| GCT | CAC | CTC | GTA | CTT | CAG | AGA | AAA | GCC | TTC | CAG | CAG | TCC | ATT | GAG | GGG | 2181 |
| Ala | His | Leu | Val | Leu | Gln | Arg | Lys | Ala | Phe | Gln | Gln | Ser | Ile | Glu | Gly | |
| | 595 | | | | | 600 | | | | | 605 | | | | | |

TABLE 5-continued

| | | | | | | | | | | | | | | | | |
|---|---|---|---|---|---|---|---|---|---|---|---|---|---|---|---|---|
| CTG | ATG | ACT | GTA | CGC | CAT | GAG | CAG | ACA | TCT | AGC | CAG | CCC | ATC | ATC | GCC | 2229 |
| Leu | Met | Thr | Val | Arg | His | Glu | Gln | Thr | Ser | Ser | Gln | Pro | Ile | Ile | Ala | |
| 610 | | | | 615 | | | | | 620 | | | | | 625 | | |
| AAA | GGT | TTG | CAG | CAG | CTC | AAG | AAC | GAT | GCA | CTT | GAG | CTA | TGC | AAC | AGA | 2277 |
| Lys | Gly | Leu | Gln | Gln | Leu | Lys | Asn | Asp | Ala | Leu | Glu | Leu | Cys | Asn | Arg | |
| | | | | 630 | | | | | 635 | | | | 640 | | | |
| ATC | AGC | GAT | GCC | ATC | GAC | CGT | GTG | GAC | CAC | ATG | TTC | ACC | CTG | GAG | TTC | 2325 |
| Ile | Ser | Asp | Ala | Ile | Asp | Arg | Val | Asp | His | Met | Phe | Thr | Leu | Glu | Phe | |
| | | | 645 | | | | | 650 | | | | | 655 | | | |
| GAT | GCT | GAG | GTC | GAG | GAG | TCT | GAG | TCG | GCC | ACG | CTG | CAG | CAG | TAC | TAC | 2373 |
| Asp | Ala | Glu | Val | Glu | Glu | Ser | Glu | Ser | Ala | Thr | Leu | Gln | Gln | Tyr | Tyr | |
| | | 660 | | | | | 665 | | | | | 670 | | | | |
| CGA | GAA | GCC | ATG | ATT | CAG | GGC | TAC | AAC | TTT | GGG | TTT | GAG | TAT | CAT | AAA | 2421 |
| Arg | Glu | Ala | Met | Ile | Gln | Gly | Tyr | Asn | Phe | Gly | Phe | Glu | Tyr | His | Lys | |
| | 675 | | | | | 680 | | | | | 685 | | | | | |
| GAA | GTT | GTT | CGT | TTG | ATG | TCT | GGG | GAA | TTC | AGG | CAG | AAG | ATA | GGA | GAC | 2469 |
| Glu | Val | Val | Arg | Leu | Met | Ser | Gly | Glu | Phe | Arg | Gln | Lys | Ile | Gly | Asp | |
| 690 | | | | | 695 | | | | | 700 | | | | | 705 | |
| AAA | TAT | ATA | AGC | TTC | GCC | CAG | AAG | TGG | ATG | AAT | TAC | GTG | CTG | ACC | AAA | 2517 |
| Lys | Tyr | Ile | Ser | Phe | Ala | Gln | Lys | Trp | Met | Asn | Tyr | Val | Leu | Thr | Lys | |
| | | | | 710 | | | | | 715 | | | | | 720 | | |
| TGC | GAG | AGC | GGC | AGA | GGC | ACA | AGA | CCC | AGA | TGG | GCC | ACC | CAA | GGA | TTT | 2565 |
| Cys | Glu | Ser | Gly | Arg | Gly | Thr | Arg | Pro | Arg | Trp | Ala | Thr | Gln | Gly | Phe | |
| | | | 725 | | | | | 730 | | | | | 735 | | | |
| GAT | TTC | CTA | CAA | GCC | ATT | GAA | CCT | GCC | TTT | ATT | TCA | GCT | TTA | CCA | GAA | 2613 |
| Asp | Phe | Leu | Gln | Ala | Ile | Glu | Pro | Ala | Phe | Ile | Ser | Ala | Leu | Pro | Glu | |
| | | 740 | | | | | 745 | | | | | 750 | | | | |
| GAT | GAC | TTC | TTG | AGT | TTG | CAA | GCC | CTG | ATG | AAT | GAG | TGC | ATC | GGG | CAC | 2661 |
| Asp | Asp | Phe | Leu | Ser | Leu | Gln | Ala | Leu | Met | Asn | Glu | Cys | Ile | Gly | His | |
| | 735 | | | | | 760 | | | | | 765 | | | | | |
| GTC | ATA | GGA | AAG | CCA | CAC | AGC | CCT | GTC | ACA | GCT | ATC | CAT | CGG | AAC | AGC | 2709 |
| Val | Ile | Gly | Lys | Pro | His | Ser | Pro | Val | Thr | Ala | Ile | His | Arg | Asn | Ser | |
| 770 | | | | | 775 | | | | | 780 | | | | | 785 | |
| CCC | CGC | CCT | GTG | AAG | GTG | CCC | CGA | TGC | CAC | AGT | GAC | CCT | CCT | AAC | CCT | 2757 |
| Pro | Arg | Pro | Val | Lys | Val | Pro | Arg | Cys | His | Ser | Asp | Pro | Pro | Asn | Pro | |
| | | | | 790 | | | | | 795 | | | | | 800 | | |
| CAC | CTC | ATC | ATC | CCG | ACT | CCA | GAG | GGA | TTC | AGC | ACC | CGG | AGC | GTG | CCT | 2805 |
| His | Leu | Ile | Ile | Pro | Thr | Pro | Glu | Gly | Phe | Ser | Thr | Arg | Ser | Val | Pro | |
| | | | 805 | | | | | 810 | | | | | 815 | | | |
| TCC | GAC | GCT | CGG | ACC | CAT | GGC | AAC | TCT | GTT | GCT | GCT | GCT | GCT | GCT | GTT | 2853 |
| Ser | Asp | Ala | Arg | Thr | His | Gly | Asn | Ser | Val | Ala | Ala | Ala | Ala | Ala | Val | |
| | | 820 | | | | | 825 | | | | | 830 | | | | |
| CGT | GCC | GCC | GCC | ACC | ACT | GCT | GCT | GGC | CGC | CCT | GGC | CCA | GGT | GGT | GGT | 2901 |
| Arg | Ala | Ala | Ala | Thr | Thr | Ala | Ala | Gly | Arg | Pro | Gly | Pro | Gly | Gly | Gly | |
| | 835 | | | | | 840 | | | | | 845 | | | | | |
| GAC | TCT | GTG | CCA | GCC | AAA | CCT | GTC | AAC | ACT | GCC | CCT | GAT | ACC | AGG | GGT | 2949 |
| Asp | Ser | Val | Pro | Ala | Lys | Pro | Val | Asn | Thr | Ala | Pro | Asp | Thr | Arg | Gly | |
| 850 | | | | | 855 | | | | | 860 | | | | | 865 | |
| TCC | AGT | GTC | CCT | GAA | AAC | GAC | CGC | TTG | GCC | TCC | ATA | GCT | GCA | GAA | CTG | 2997 |
| Ser | Ser | Val | Pro | Glu | Asn | Asp | Arg | Leu | Ala | Ser | Ile | Ala | Ala | Glu | Leu | |
| | | | | 870 | | | | | 875 | | | | | 880 | | |
| CAG | TTC | AGG | TCT | CTG | AGT | CGG | CAC | TCA | AGC | CCC | ACG | GAA | GAG | CGA | GAC | 3045 |
| Gln | Phe | Arg | Ser | Leu | Ser | Arg | His | Ser | Ser | Pro | Thr | Glu | Glu | Arg | Asp | |
| | | | 885 | | | | | 890 | | | | | 895 | | | |
| GAG | CCA | GCG | TAT | CCT | CGG | AGT | GAC | TCA | AGT | GGA | TCA | ACT | CGG | AGA | AGC | 3093 |
| Glu | Pro | Ala | Tyr | Pro | Arg | Ser | Asp | Ser | Ser | Gly | Ser | Thr | Arg | Arg | Ser | |
| | | 900 | | | | | 905 | | | | | 910 | | | | |
| TGG | GAA | CTT | CGA | ACA | CTC | ATC | AGC | CAG | ACC | AAA | GAC | TCG | GCC | TCT | AAG | 3141 |
| Trp | Glu | Leu | Arg | Thr | Leu | Ile | Ser | Gln | Thr | Lys | Asp | Ser | Ala | Ser | Lys | |
| | 915 | | | | | 920 | | | | | 925 | | | | | |

TABLE 5-continued

| | | | | | | | | | | | | | | | | |
|---|---|---|---|---|---|---|---|---|---|---|---|---|---|---|---|---|
| CAG | GGG | CCC | ATA | GAA | GCT | ATC | CAG | AAG | TCA | GTC | CGA | CTG | TTT | GAA | GAG | 3189 |
| Gln | Gly | Pro | Ile | Glu | Ala | Ile | Gln | Lys | Ser | Val | Arg | Leu | Phe | Glu | Glu | |
| 930 | | | | | 935 | | | | | 940 | | | | | 945 | |
| AGG | AGG | TAT | CGA | GAG | ATG | AGG | AGA | AAG | AAT | ATC | ATC | GGC | CAA | GTG | TGC | 3237 |
| Arg | Arg | Tyr | Arg | Glu | Met | Arg | Arg | Lys | Asn | Ile | Ile | Gly | Gln | Val | Cys | |
| | | | | 950 | | | | | 955 | | | | | 960 | | |
| GAT | ACC | CCT | AAG | TCC | TAT | GAT | AAC | GTC | ATG | CAT | GTT | GGA | CTG | AGG | AAG | 3285 |
| Asp | Thr | Pro | Lys | Ser | Tyr | Asp | Asn | Val | Met | His | Val | Gly | Leu | Arg | Lys | |
| | | | 965 | | | | | 970 | | | | | 975 | | | |
| GTG | ACA | TTT | AAG | TGG | CAA | AGA | GGA | AAC | AAA | ATT | GGA | GAA | GGA | CAG | TAT | 3333 |
| Val | Thr | Phe | Lys | Trp | Gln | Arg | Gly | Asn | Lys | Ile | Gly | Glu | Gly | Gln | Tyr | |
| | | 980 | | | | | 985 | | | | | 990 | | | | |
| GGA | AAA | GTA | TAC | ACC | TGC | ATC | AGT | GTT | GAC | ACA | GGG | GAG | CTG | ATG | GCC | 3381 |
| Gly | Lys | Val | Tyr | Thr | Cys | Ile | Ser | Val | Asp | Thr | Gly | Glu | Leu | Met | Ala | |
| | 995 | | | | | 1000 | | | | | 1005 | | | | | |
| ATG | AAG | GAG | ATT | CGA | TTT | CAG | CCT | AAC | GAC | CAC | AAG | ACT | ATC | AAG | GAG | 3429 |
| Met | Lys | Glu | Ile | Arg | Phe | Gln | pro | Asn | Asp | His | Lys | Thr | Ile | Lys | Glu | |
| 1010 | | | | | 1015 | | | | | 1020 | | | | | 1025 | |
| ACT | GCA | GAC | GAG | TTG | AAA | ATA | TTT | GAA | GGC | ATC | AAG | CAC | CCC | AAC | CTG | 3477 |
| Thr | Ala | Asp | Glu | Leu | Lys | Ile | Phe | Glu | Gly | Ile | Lys | his | Pro | Asn | Leu | |
| | | | | 1030 | | | | | 1035 | | | | | 1040 | | |
| GTC | CGG | TAT | TTT | GGC | GTG | GAG | CTT | CAC | AGG | GAA | GAG | ATG | TAC | ATC | TTC | 3525 |
| Val | Arg | Tyr | Phe | Gly | Val | Glu | Leu | His | Arg | Glu | Glu | Met | Tyr | Ile | Phe | |
| | | | 1045 | | | | | 1050 | | | | | 1055 | | | |
| ATG | GAG | TAC | TGT | GAT | GAG | GGT | ACA | CTA | GAG | GAG | GTG | TCA | CGA | CTG | GGC | 3573 |
| Met | Glu | Tyr | Cys | Asp | Glu | Gly | Thr | Leu | Glu | Glu | Val | Ser | Arg | Leu | Gly | |
| | | 1060 | | | | | 1065 | | | | | 1070 | | | | |
| CTG | CAG | GAG | CAC | GTC | ATC | AGG | TTA | TAT | ACC | AAG | CAG | ATC | ACT | GTC | GCC | 3621 |
| Leu | Gln | Glu | His | Val | Ile | Arg | Leu | Tyr | Thr | Lys | Gln | Ile | Thr | Val | Ala | |
| | 1075 | | | | | 1080 | | | | | 1085 | | | | | |
| ATC | AAC | GTC | CTC | CAT | GAG | CAC | GGC | ATC | GTT | CAC | CGA | GAC | ATC | AAA | GGT | 3669 |
| Ile | Asn | Val | Leu | His | Glu | His | Gly | Ile | Val | His | Arg | Asp | Ile | Lys | Gly | |
| 1090 | | | | | 1095 | | | | | 1100 | | | | | 1105 | |
| GCC | AAT | ATC | TTC | CTT | ACG | TCA | TCT | GGA | CTA | ATC | AAG | CTG | GGA | GAT | TTT | 3717 |
| Ala | Asn | Ile | Phe | Leu | Thr | Ser | Ser | Gly | Leu | Ile | Lys | Leu | Gly | Asp | Phe | |
| | | | | 1110 | | | | | 1115 | | | | | 1120 | | |
| GGA | TGC | TCT | GTA | AAA | CTT | AAA | AAC | AAC | GCC | CAG | ACC | ATG | CCC | GGA | GAG | 3765 |
| Gly | Cys | Ser | Val | Lys | Leu | Lys | Asn | Asn | Ala | Gln | Thr | Met | Pro | Gly | Glu | |
| | | | 1125 | | | | | 1130 | | | | | 1135 | | | |
| GTG | AAC | AGC | ACC | CTA | GGG | ACA | GCA | GCT | TAC | ATG | GCC | CCT | GAA | GTT | ATT | 3813 |
| Val | Asn | Ser | Thr | Leu | Gly | Thr | Ala | Ala | Tyr | Met | Ala | Pro | Glu | Val | Ile | |
| | | | 1140 | | | | | 1145 | | | | | 1150 | | | |
| ACC | CGA | GCC | AAA | GGA | GAA | GGC | CAC | GGA | CGT | GCG | GCA | GAT | ATC | TGG | AGT | 3861 |
| Thr | Arg | Ala | Lys | Gly | Glu | Gly | His | Gly | Arg | Ala | Ala | Asp | Ile | Trp | Ser | |
| | | 1155 | | | | | 1160 | | | | | 1165 | | | | |
| CTG | GGG | TGC | GTC | GTC | ATA | GAG | ATG | GTG | ACT | GGC | AAG | CGG | CCT | TGG | CAT | 3909 |
| Leu | Gly | Cys | Val | Val | Ile | Glu | Met | Val | Thr | Gly | Lys | Arg | Pro | Trp | His | |
| 1170 | | | | | 1175 | | | | | 1180 | | | | | 1185 | |
| GAG | TAT | GAA | CAC | AAC | TTT | CAG | ATT | ATG | TAC | AAG | GTG | GGG | ATG | GGA | CAC | 3957 |
| Glu | Tyr | Glu | His | Asn | Phe | Gln | Ile | Met | Tyr | Lys | Val | Gly | Met | Gly | His | |
| | | | | 1190 | | | | | 1195 | | | | | 1200 | | |
| AAG | CCA | CCA | ATC | CCG | GAA | AGG | CTA | AGC | CCT | GAA | GGA | AAG | GCC | TTT | CTC | 4005 |
| Lys | Pro | Pro | Ile | Pro | Glu | Arg | Leu | Ser | Pro | Glu | Gly | Lys | Ala | Phe | Leu | |
| | | | 1205 | | | | | 1210 | | | | | 1215 | | | |
| TCG | CAC | TGC | CTG | GAA | AGT | GAC | CCG | AAG | ATA | CGG | TGG | ACA | GCC | AGC | CAG | 4053 |
| Ser | His | Cys | Leu | Glu | Ser | Asp | Pro | Lys | Ile | Arg | Trp | Thr | Ala | Ser | Gln | |
| | | 1220 | | | | | 1225 | | | | | 1230 | | | | |
| CTC | CTC | GAC | CAC | GCT | TTT | GTC | AAG | GTT | TGC | ACA | GAT | GAA | GAG | | | 4095 |
| Leu | Leu | Asp | His | Ala | Phe | Val | Lys | Val | Cys | Thr | Asp | Glu | Glu | | | |
| | 1235 | | | | | 1240 | | | | | 1245 | | | | | |

TABLE 5-continued

| | | | | | |
|---|---|---|---|---|---|
| TGAAGTGAAC | CAGTCCGTGG | CCTAGTAGTG | TGTGGACAGA | ATCCCGTGAT | CACTACTGTA 4155 |
| TGTAATATTT | ACATAAAGAC | TGCAGCGCAG | GCGGCCTTCC | TAACCTCCCA | GGACTGAAGA 4215 |
| CTACAGGGGT | GACAAGCCTC | ACTTCTGCTG | CTCCTGTCGC | CTGCTGAGTG | ACAGTGCTGA 4275 |
| GGTTAAAGGA | GCCGCACGTT | AAGTGCCATT | ACTACTGTAC | ACGGCCACCG | CCTCTGTCCC 4335 |
| CTCCGACCCT | CTCGTGACTG | AGAACCAACC | GTGTCATCAG | CACAGTGTTT | TTGAGCTCCT 4395 |
| GGGGTTCAGA | AGAACATGTA | GTGTTCCCGG | GTGTCCGGGA | CGTTTATTTC | AACCTCCTGG 4455 |
| TCGTTGGCTC | TGACTGTGGA | GCCTCCTTGT | TCGAAAGCTG | CAGGTTTGTT | ATGCAAAGGC 4515 |
| TCGTAAGTGA | AGCTGAAGAA | AAGGTTCTTT | TTCAATAAAT | GGTTTATTTT | AGGAAAGCGA 4575 |
| AAAAAAAAAA | AAAAAAA | | | | 4592 |

MEKK 5 represents a splice variant of MEKK 4. The splice insert is shown by the underlined portion of the sequence shown in Table 5.

The amino acid sequences for MEKK 2 and MEKK 3 compared with the amino acid sequence of MEKK 1 are shown in Table 6.

TABLE 6

| | |
|---|---|
| MVTAVPAVFSKLVTMLNASGSTHFTRMRRRLMAIADEVEIAEVIQLGVEDTVDGHQDSL | MEKK 1 |
| MDDQQALNSIMQDI - - - - - - - - - - - - - | 2 |
| MDEQEALDSIMKDLVALQMSRRTRL- | 3 |
| | |
| AVAPTSCLENSSLEHTVHREKTGKGLSATRLSASSEDISDRLAGVSVGLPSSTTTEQPKP | 1 |
| AVLHKPVGQHYLYKKPGKQNLHHQKNRMMFESNLNIEEEKRILQVTRPVKLEDLRSKSKI | 2 |
| S - - GYETM NKDTGHPNRQSDVRIKFEHNGERRI - IAFSRPVRYEDVEHKVTTVFGQPLD | 3 |
| | |
| AVQTKGRPHSQCLNSS - PLSHAQLMFPAPSAPCSSAPSVPDISKHRPQAFVPCKIPSASP | 1 |
| AFGQSMDLHYTNNELVIPLTTQDDLDKAVELLDRSIHMKSL - KILLVVNGSTQA - TNLEP | 2 |
| LHYMNNELSILLKNQDDLDKAIDILDRSSSMKSLRILLLSQDRNHTSSSPHSGVSRQVRI | 3 |
| | |
| QTQRKFSLQFQRNCSEHRDSDQLSPVFTQS - RPPPSSNIHRPKPSRPVPGSTSKLGDATK | 1 |
| SPSPEDLNNTPLGAERKKRLSVVGPPNR - - DRSSPPPGYIPDILHQIARNGSFTSINSEG | 2 |
| KPSQSAGDINTIYQAPEPRSRHLSVSSQNPGRSSPPPGYVPERQQHIARQGSYTSINSEG | 3 |
| | |
| SSMTLDLGSASRCDDSFGGGGNSGNAVIPSDETVFTPVEDKCRLDVNTELNSSIEDLLEA | 1 |
| EFIPESMDQ - MLDPLSLSSPENSGSGSCPSLDSPLDGESYPKSRMPRAQSYPDNHQEFTD | 2 |
| EFIPETSEQCMLDPLSSAENSLSGSCQSLDRSADSPSFRKSQMSRARSFPDNR - - - ECSD | 3 |
| | |
| SMPSSDTTVTFKSEVAVLSPEKAENDDTYKDDVNHNQKCKEKMEAEEEEALAIAMAMSAS | 1 |
| YDNPIFEKFGKGGTYPRRYHVSYHHQEYNDGRKTFPRARRTQGTSFRSPVSFSPTDHSLS | 2 |
| K - - - - RETQLYDKGVKGGTYPRRYHVSVHHKDYNDGRRTFPRIRRHQGNLFTLVPSSRSL | 3 |
| | |
| QDALPIVPQLQVENGEDIIIIQQDTPETLPGHTKAKQPYRE*DAEWLKGQQIGLGAFSSCY* | 1 |
| TSSGSSVFTPEYDDSRIRRRGSDIDNPTLTVTDISPPSRSP*RAPTNWRLGKLLGQGAFGR* | 2 |
| STNGENMGVAVQYLDPRGRLRSADSENALTVQERNVPTKSP*SAPINWRRGKLLGQGAFGR* | 3 |
| | |
| *QAQDVGTGTLMAVKQVTYVRNTSSEQEEVVEALREEIRMMGHLNHPNIIRMLGATCEKSN* | 1 |
| *VYLCYDVDTGRELAVKQVQFNPESPETSKEVNALECEIQLLKNLLHERIVQYYGCLRDPQ* | 2 |
| *VYLCYDVDTGRELASKQVQFDPDSPETSKEVSALECEIQLLKNLQHERIVQYYGCLRDRA* | 3 |
| | |
| *YNLFIEWMAGGSVAHLLSKYGAFKESVVINYTEQLLRGLSYLHEN - - Q - IIHRDVKGANL* | 1 |
| *EKTLSIFMELSPGGSIKDQLKAYGALTENVTRKYTRQILEGVHYLHSNMIVHRDIKGANI* | 2 |
| *EKILTIFMEYMPGGSVKDQLKAYGALTESVTRKYTRQILEGMSYLHSNMIVHRDIKGANI* | 3 |
| | |
| *LIDSTGQ - RLRIADFGAAARLASK - GTGAGEFQGQLLGTIAFMAPEVLRGQQYGRSCDVW* | 1 |
| *LRDSTGNIKLGDFGASKRLQTICLSGTGMKSVTG - PY - - - - WMSPEVISGEGYGRKADIW* | 2 |
| *LRDSAGNVKLGDFGASKRLQTICMSGTGIRSVTGTPY - - - - WMSPEVISGEGYGRKADVW* | 3 |
| | |
| *SVGCAIIEMACAKPPWNAEKHSNHLALIFKIASATTAPSIPSHLSPGLRDVAVRCLELQP* | 1 |
| *SVACTVVEMLTEKPPW - AEFEA - MAA - IFKIATQPTNPKLPPHVSDYTRDFLKRIFVEAK* | 2 |
| *SLGCTVVEMLTEKPPW - AEYEA - MAA - IFKIATQPTNPQLPSHISEHGRDFLRRIFVEAR* | 3 |
| | |
| *QDRPPSRE - LLKHPVFRTTW* | 1 |
| *L - RP - SAEELLRHMFVHYH* | 2 |
| *Q - RP - SAEELLTHHFAQLVY* | 3 |

TABLE 6-continued

Bold Amino Terminus- Regulatory Domain
(corresponding to Met1-Arg210 of SEQ ID No. 2;
Met1-Arg162 of SEQ ID No. 4; and Met1-Arg174 of SEQ ID No. 6)
Underline sequence- Regulatory hinge Sequence
(corresponding to Pro211-Ser215 of SEQ ID No. 2;
Ser163-Pro167 of SEQ ID No. 4;
and Ser175-Pro179 of SEQ ID No. 6)

*Bold Italics- Catalytic Domain.*

(corresponding to Asp400-Trp672 of SEQ ID No. 2;
Arg351-His351-His619 of SEQ ID No. 4;
and Ser357-Tyr626 of SEQ ID No. 6)

Table 7 shows the amino acid sequence of the kinase domain of MEKK 4 (corresponding to Ile656-Val742 of SEQ ID No. 8) compared with the kinase domains of MEKK 1, MEKK 2 and MEKK 3 (corresponding to Thr435-Ile526 of SEQ ID No. 2, Gln386-Val480 of SEQ ID No. 4 and Gln392-Val486 of SEQ ID No. 6, respectively).

TABLE 7

| | |
|---|---|
| . . I R F Q P N D H K T I  K E T A D E E L K I  F E G I  K H P  N L  V R Y F G V. . E L H R E E M. YI | MEKK4 |
| T Y V R N T S S E Q E E V V E A L R E E I  R M M G H L N H P  N I  I  R M L G A T C E K S  N Y N L F I  E | MEKK1 |
| Q V Q F N P  E S  P E T S  K E V N A L E C E I  Q L L K N L L H E R I  V Q Y Y G C L R D P  Q E K T L S  I | MEKK2 |
| Q V Q F  D P  D S  P E T S  K E V S  A L E C E   Q L L K N L Q H E R I  V Q Y Y G C L R D R A E K I  L T I | MEKK3 |
| I  F  M E  Y C D E  G T L E E V S  R L G L Q E H V.  I . R L Y T K Q I  T V A I  N V L H E H G N V | MEKK4 |
| . W M A G G S  V A H L L S  K Y G A F  K E S  V V. I  N. . Y T E Q L L R G L S  Y L H E N Q I  I | MEKK1 |
| . F M E L S  P  G G S  I  K D Q L K A Y G A L T E N V T R K Y T R Q I  L E G V H Y L H S  N M I  V | MEKK2 |
| . F  M E  Y M P  G G S  V K D Q L K A Y G A L T E S  V T R K Y T R Q I  L E G M S  Y L H S  N M I  V | MEKK3 |

The foregoing SEQ ID NO's represent sequences deduced according to methods disclosed in the Examples. It should be noted that since nucleic acid and amino acid sequencing technology is not entirely error-free, the foregoing SEQ ID NO's, at best, represent apparent nucleic acid and amino acid sequences of MEKK proteins of the present invention.

According to the present invention, an MEKK protein of the present invention can include MEKK proteins that have undergone post-translational modification. Such modification can include, for example, glycosylation (e.g., including addition of N-linked and/or O-linked oligosaccharides) or post-translational conformational changes or post-translational deletions.

Another embodiment of the present invention is an isolated nucleic acid molecule capable of hybridizing, under stringent conditions, with an MEKK protein gene encoding an MEKK protein of the present invention. In accordance with the present invention, an isolated nucleic acid molecule is a nucleic acid molecule that has been removed from its natural milieu (i.e., that has been subject to human manipulation). As such, "isolated" does not reflect the extent to which the nucleic acid molecule has been purified. An isolated nucleic acid molecule can include DNA, RNA, or derivatives of either DNA or RNA.

An isolated nucleic acid molecule of the present invention can be obtained from its natural source either as an entire (i.e., complete) gene or a portion thereof capable of forming a stable hybrid with that gene. As used herein, the phrase "at least a portion of" an entity refers to an amount of the entity that is at least sufficient to have the functional aspects of that entity. For example, at least a portion of a nucleic acid sequence, as used herein, is an amount of a nucleic acid sequence capable of forming a stable hybrid with a particular desired gene (e.g., MEKK genes) under stringent hybridization conditions. An isolated nucleic acid molecule of the present invention can also be produced using recombinant DNA technology (e.g., polymerase chain reaction (PCR) amplification, cloning) or chemical synthesis. Isolated MEKK protein nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications do not substantially interfere with the nucleic acid molecule's ability to encode an MEKK protein of the present invention or to form stable hybrids under stringent conditions with natural nucleic acid molecule isolates of MEKK.

Preferred modifications to an MEKK protein nucleic acid molecule of the present invention include truncating a full-length MEKK protein nucleic acid molecule by, for example: deleting at least a portion of an MEKK protein nucleic acid molecule encoding a regulatory domain (examples illustrated in Table 6) to produce a constitutively active MEKK protein; deleting at least a portion of an MEKK protein nucleic acid molecule encoding a catalytic domain (examples illustrated in Table 6) to produce an inactive MEKK protein; and modifying the MEKK protein to achieve desired inactivation and/or stimulation of the protein, for example, substituting a codon encoding a lysine residue in the catalytic domain (i.e., phosphotransferase domain) with a methionine residue to inactivate the catalytic domain.

A preferred truncated MEKK nucleic acid molecule encodes a form of an MEKK protein containing a catalytic domain but that lacks a regulatory domain. Preferred catalytic domain truncated MEKK nucleic acid molecules encode residues from about 352 to about 672 of MEKK 1, from about 352 to about 619 of MEKK 2, from about 358 to about 626 of MEKK 3, from about 811 to about 1195 of MEKK 4 or from about 863 to about 1247 of MEKK 5.

Another preferred truncated MEKK nucleic acid molecule encodes a form of an MEKK protein comprising an NH$_2$-terminal regulatory domain but lacking a catalytic domain. Preferred regulatory domain truncated MEKK nucleic acid molecules encode residues from about 1 to about 369 for MEKK 1, from about 1 to about 335 for MEKK 2, from about 1 to about 360 for MEKK 3, from about 1 to about 825 for MEKK 4 and from about 1 to about 875 for MEKK 5, thereby removing the catalytic domain to form the truncated MEKK molecule.

An isolated nucleic acid molecule of the present invention can include a nucleic acid sequence that encodes at least one MEKK protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides that comprise the nucleic acid molecule, the two phrases can be used interchangeably. As heretofore disclosed, MEKK proteins of the present invention include, but are not limited to, proteins having full-length MEKK protein coding regions, portions thereof, and other MEKK protein homologues.

As used herein, an MEKK protein gene includes all nucleic acid sequences related to a natural MEKK protein gene such as regulatory regions that control production of an MEKK protein encoded by that gene (including, but not limited to, transcription, translation or post-translation control regions) as well as the coding region itself. A nucleic acid molecule of the present invention can be an isolated natural MEKK protein nucleic acid molecule or a homologue thereof. A nucleic acid molecule of the present invention can include one or more regulatory regions, full-length or partial coding regions, or combinations thereof. The minimal size of an MEKK protein nucleic acid molecule of the present invention is the minimal size capable of forming a stable hybrid under stringent hybridization conditions with a corresponding natural gene.

An MEKK protein nucleic acid molecule homologue can be produced using a number of methods known to those skilled in the art (see, e.g., Sambrook et al., ibid.). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid (e.g., the ability of a homologue to phosphorylate MEK protein or JEK protein) and/or by hybridization with isolated MEKK protein nucleic acids under stringent conditions.

One embodiment of the present invention is an MEKK protein nucleic acid molecule capable of encoding at least a portion of an MEKK protein, or a homologue thereof, as described herein. A preferred nucleic acid molecule of the present invention includes, but is not limited to, a nucleic acid molecule that encodes a protein having at least a portion of an amino acid sequence represented by SEQ ID NO:2, SEQ ID NO:4, SEQ ID NO:6, SEQ ID NO:8 and SEQ ID NO:10, or homologues thereof.

A preferred nucleic acid molecule of the present invention is capable of hybridizing under stringent conditions to a nucleic acid that encodes at least a portion of an MEKK protein, or a homologue thereof. Also preferred is an MEKK protein nucleic acid molecule that includes a nucleic acid sequence having at least about 50%, preferably at least about 75%, and more preferably at least about 85% homology with the corresponding region(s) of the nucleic acid sequence encoding the catalytic domain of an MEKK protein, or a homologue thereof. Also preferred is an MEKK protein nucleic acid molecule that includes a nucleic acid sequence having at least about 20%, preferably at least about 30%, and more preferably at least about 40% homology with the corresponding region(s) of the nucleic acid sequence encoding the NH$_2$-terminal regulatory domain of an MEKK protein, or a homologue thereof. A particularly preferred nucleic acid sequence is a nucleic acid sequence having at least about 50%, preferably at least about 75%, and more preferably at least about 85% homology with a nucleic acid sequence encoding the catalytic domain of an amino acid sequence represented by SEQ ID NO:2, SEQ ID NO:4, SEQ ID NO:6, SEQ ID NO:8 and SEQ ID NO:10. Another particularly preferred nucleic acid sequence is a nucleic acid sequence having at least about 20%, preferably at least about 30%, and more preferably at least about 40% homology with a nucleic acid sequence encoding the NH$_2$-terminal regulatory domain of an amino acid sequence represented by SEQ ID NO:2, SEQ ID NO:4, SEQ ID NO:6, SEQ ID NO:8 and SEQ ID NO:10.

Such nucleic acid molecules can be a full-length gene and/or a nucleic acid molecule encoding a full-length protein, a hybrid protein, a fusion protein, a multivalent protein or a truncation fragment. More preferred nucleic acid molecules of the present invention comprise isolated nucleic acid molecules having a nucleic acid sequence as represented by SEQ ID NO:1, SEQ ID NO:3, SEQ ID NO:5, SEQ ID NO:7 or SEQ ID NO: 9.

Knowing a nucleic acid molecule of an MEKK protein of the present invention allows one skilled in the art to make copies of that nucleic acid molecule as well as to obtain additional portions of MEKK protein-encoding genes (e.g., nucleic acid molecules that include the translation start site and/or transcription and/or translation control regions), and/or MEKK protein nucleic acid molecule homologues. Knowing a portion of an amino acid sequence of an MEKK protein of the present invention allows one skilled in the art to clone nucleic acid sequences encoding such an MEKK protein.

The present invention also includes nucleic acid molecules that are oligonucleotides capable of hybridizing, under stringent conditions, with complementary regions of other, preferably longer, nucleic acid molecules of the present invention that encode at least a portion of an MEKK protein, or a homologue thereof. A preferred oligonucleotide is capable of hybridizing, under stringent conditions, with a nucleic acid molecule that is capable of encoding at least a portion of an amino acid sequence represented by SEQ ID NO:2, SEQ ID NO:4, SEQ ID NO:6, SEQ ID NO:8 and SEQ ID NO:10, or homologues thereof. A more preferred oligonucleotide is capable of hybridizing to a nucleic acid molecule having a nucleic acid sequence as represented by SEQ ID NO:1, SEQ ID NO:3, SEQ ID NO:5, SEQ ID NO:7 and SEQ ID NO:9, or complements thereof.

Oligonucleotides of the present invention can be RNA, DNA, or derivatives of either. The minimal size of such oligonucleotides is the size required to form a stable hybrid between a given oligonucleotide and the complementary sequence on another nucleic acid molecule of the present invention. Minimal size characteristics are disclosed herein.

The size of the oligonucleotide must also be sufficient for the use of the oligonucleotide in accordance with the present invention. Oligonucleotides of the present invention can be used in a variety of applications including, but not limited to, as probes to identify additional nucleic acid molecules, as primers to amplify or extend nucleic acid molecules or in therapeutic applications to inhibit, for example, expression of MEKK proteins by cells. Such therapeutic applications include the use of such oligonucleotides in, for example, antisense-, triplex formation-, ribozyme- and/or RNA drug-based technologies. The present invention, therefore, includes use of such oligonucleotides and methods to interfere with the production of MEKK proteins.

In one embodiment, an isolated MEKK protein of the present invention is produced by culturing a cell capable of expressing the protein under conditions effective to produce the protein, and recovering the protein. A preferred cell to culture is a recombinant cell that is capable of expressing the MEKK protein, the recombinant cell being produced by transforming a host cell with one or more nucleic acid molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained.

The present invention also includes a recombinant vector which includes at least one MEKK protein nucleic acid molecule of the present invention inserted into any vector capable of delivering the nucleic acid molecule into a host cell. Such a vector contains heterologous nucleic acid sequences, for example nucleic acid sequences that are not naturally found adjacent to MEKK protein nucleic acid molecules of the present invention. The vector can be either RNA or DNA, and either prokaryotic or eukaryotic, and is typically a virus or a plasmid. Recombinant vectors can be used in the cloning, sequencing, and/or otherwise manipulating of MEKK protein nucleic acid molecules of the present invention. One type of recombinant vector, herein referred to as a recombinant molecule and described in more detail below, can be used in the expression of nucleic acid molecules of the present invention. Preferred recombinant vectors are capable of replicating in the transformed cell.

Preferred nucleic acid molecules to insert into a recombinant vector includes a nucleic acid molecule that encodes at least a portion of an MEKK protein, or a homologue thereof. A more preferred nucleic acid molecule to insert into a recombinant vector includes a nucleic acid molecule encoding at least a portion of an amino acid sequence represented by SEQ ID NO:2, SEQ ID NO:4, SEQ ID NO:6, SEQ ID NO:8 and/or SEQ ID NO:10, or homologues thereof. An even more preferred nucleic acid molecule to insert into a recombinant vector includes a nucleic acid molecule represented by SEQ ID NO:1, SEQ ID NO:3, SEQ ID NO:5, SEQ ID NO:7 and/or SEQ ID NO:9, or complements thereof.

Suitable host cells for transforming a cell can include any cell capable of producing MEKK proteins of the present invention after being transformed with at least one nucleic acid molecule of the present invention. Host cells can be either untransformed cells or cells that are already transformed with at least one nucleic acid molecule. Suitable host cells of the present invention can include bacterial, fungal (including yeast), insect, animal and plant cells. Preferred host cells include bacterial, yeast, insect and mammalian cells, with mammalian cells being particularly preferred.

A recombinant cell is preferably produced by transforming a host cell with one or more recombinant molecules, each comprising one or more nucleic acid molecules of the present invention operatively linked to an expression vector containing one or more transcription control sequences. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, insect, animal, and/or plant cells. As such, nucleic acid molecules of the present invention can be operatively linked to expression vectors containing regulatory sequences such as promoters, operators, repressors, enhancers, termination sequences, origins of replication, and other regulatory sequences that are compatible with the recombinant cell and that control the expression of nucleic acid molecules of the present invention. As used herein, a transcription control sequence includes a sequence which is capable of controlling the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, and mammalian cells, such as, but not limited to, tac, lac, trp, trc, oxy-pro, omp/lpp, rrnB, bacteriophage lambda (λ) (such as $\lambda p_L$ and $\lambda p_R$ and fusions that include such promoters), bacteriophage T7, T7lac, bacteriophage T3, bacteriophage SP6, bacteriophage SP01, metallothionein, alpha mating factor, baculovirus, vaccinia virus, herpesvirus, poxvirus, adenovirus, simian virus 40, retrovirus actin, retroviral long terminal repeat, Rous sarcoma virus, heat shock, phosphate and nitrate transcription control sequences, as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with a DNA sequence encoding an MEKK protein.

Preferred nucleic acid molecules for insertion into an expression vector include nucleic acid molecules that encode at least a portion of an MEKK protein, or a homologue thereof. A more preferred nucleic acid molecule for insertion into an expression vector includes a nucleic acid molecule encoding at least a portion of an amino acid sequence represented by SEQ ID NO:2, SEQ ID NO:4, SEQ ID NO:6, SEQ ID NO:8 and/or SEQ ID NO:10, or homologues thereof. An even more preferred nucleic acid molecule for insertion into an expression vector includes a nucleic acid molecule represented by SEQ ID NO:1, SEQ ID NO:3, SEQ ID NO:5, SEQ ID NO:7 and/or SEQ ID NO:9, or complements thereof.

Expression vectors of the present invention may also contain fusion sequences which lead to the expression of inserted nucleic acid molecules of the present invention as fusion proteins. Inclusion of a fusion sequence as part of an MEKK nucleic acid molecule of the present invention can enhance the stability during production, storage and/or use of the protein encoded by the nucleic acid molecule. Furthermore, a fusion segment can function as a tool to simplify purification of an MEKK protein, such as to enable purification of the resultant fusion protein using affinity chromatography. A suitable fusion segment can be a domain of any size that has the desired function (e.g., increased stability and/or purification tool). It is within the scope of the present invention to use one or more fusion segments. Fusion segments can be joined to amino and/or carboxyl termini of an MEKK protein. Linkages between fusion segments and MEKK proteins can be constructed to be susceptible to cleavage to enable straight-forward recovery of the MEKK proteins. Fusion proteins are preferably produced by culturing a recombinant cell transformed with a fusion nucleic acid sequence that encodes a protein including the fusion segment attached to either the carboxyl and/or amino terminal end of an MEKK protein.

A recombinant cell of the present invention includes any cells transformed with at least one of any nucleic acid molecule of the present invention. A preferred recombinant cell is a cell transformed with at least one nucleic acid molecule that encodes at least a portion of an MEKK protein, or a homologue thereof. A more preferred recombinant cell is transformed with at least one nucleic acid molecule that is capable of encoding at least a portion of an amino acid sequence represented by SEQ ID NO:2, SEQ ID NO:4, SEQ ID NO:6 SEQ ID NO:8 and/or SEQ ID NO:10, or homologues thereof. An even more preferred recombinant cell is transformed with at least one nucleic acid molecule represented by SEQ ID NO:1, SEQ ID NO:3, SEQ ID NO:5, SEQ ID NO:7 and/or SEQ ID NO:9, or complements thereof. Particularly preferred recombinant cells include mammalian cells involved in a disease transformed with at least one of the aforementioned nucleic acid molecules.

It may be appreciated by one skilled in the art that use of recombinant DNA technologies can improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant protein production during fermentation. The activity of an expressed recombinant protein of the present invention may be improved by fragmenting, modifying, or derivatizing the resultant protein.

As used herein, amplifying the copy number of a nucleic acid sequence in a cell can be accomplished either by increasing the copy number of the nucleic acid sequence in the cell's genome or by introducing additional copies of the nucleic acid sequence into the cell by transformation. Copy number amplification is conducted in a manner such that greater amounts of enzyme are produced, leading to enhanced conversion of substrate to product. For example, recombinant molecules containing nucleic acids of the present invention can be transformed into cells to enhance enzyme synthesis. Transformation can be accomplished using any process by which nucleic acid sequences are inserted into a cell. Prior to transformation, the nucleic acid sequence on the recombinant molecule can be manipulated to encode an enzyme having a higher specific activity.

In accordance with the present invention, recombinant cells can be used to produce an MEKK protein of the present invention by culturing such cells under conditions effective to produce such a protein, and recovering the protein. Effective conditions to produce a protein include, but are not limited to, appropriate media, bioreactor, temperature, pH and oxygen conditions that permit protein production. An appropriate, or effective, medium refers to any medium in which a cell of the present invention, when cultured, is capable of producing an MEKK protein. Such a medium is typically an aqueous medium comprising assimilable carbohydrate, nitrogen and phosphate sources, as well as appropriate salts, minerals, metals and other nutrients, such as vitamins. The medium may comprise complex nutrients or may be a defined minimal medium.

Cells of the present invention can be cultured in conventional fermentation bioreactors, which include, but are not limited to, batch, fed-batch, cell recycle, and continuous fermentors. Culturing can also be conducted in shake flasks, test tubes, microtiter dishes, and petri plates. Culturing is carried out at a temperature, pH and oxygen content appropriate for the recombinant cell. Such culturing conditions are well within the expertise of one of ordinary skill in the art.

Depending on the vector and host system used for production, resultant MEKK proteins may either remain within the recombinant cell or be secreted into the fermentation medium. The phrase "recovering the protein" refers simply to collecting the whole fermentation medium containing the protein and need not imply additional steps of separation or purification. MEKK proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, chromatofocusing and differential solubilization.

In addition, an MEKK protein of the present invention can be produced by isolating the MEKK protein from cells expressing the MEKK protein recovered from an animal. For example, a cell type, such as T cells, can be isolated from the thymus of an animal. MEKK protein can then be isolated from the isolated T cells using standard techniques described herein.

The present invention also includes a method to identify compounds capable of regulating signals initiated from a receptor on the surface of a cell, such signal regulation involving in some respect, MEKK protein. Such a method comprises the steps of: (a) contacting a cell containing an MEKK protein with a putative regulatory compound; (b) contacting the cell with a ligand capable of binding to a receptor on the surface of the cell; and (c) assessing the ability of the putative regulatory compound to regulate cellular signals by determining activation of a member of an MEKK-dependent pathway of the present invention. A preferred method to perform step (c) comprises measuring the phosphorylation of a member of an MEKK-dependent pathway. Such measurements can be performed using immunoassays having antibodies specific for phosphotyrosines, phosphoserines and/or phosphothreonines. Another preferred method to perform step (c) comprises measuring the ability of the MEKK protein to phosphorylate MEK protein and/or JEK protein using methods described herein.

In another embodiment, a method to identify compounds capable of regulating signal transduction in a cell can comprise the steps of: (a) contacting a putative inhibitory compound with an MEKK protein to form a reaction mixture; (b) contacting the reaction mixture with MEK protein; and (c) assessing the ability of the putative inhibitory compound to inhibit phosphorylation of the MEK protein by the MEKK protein. The results obtained from step (c) can be compared with the ability of a putative inhibitory compound to inhibit the ability of Raf protein to phosphorylate MEK protein, to determine if the compound can selectively regulate signal transduction involving MEKK protein independent of Raf protein. MEKK, MEK and Raf proteins used in the foregoing methods can be recombinant proteins or naturally-derived proteins.

Moreover, one can determine whether the site of inhibitory action along a particular signal transduction pathway involves both Raf and MEKK proteins by carrying out experiments set forth above (i.e., see discussion on MEKK-dependent pathways).

Another aspect of the present invention includes a kit to identify compounds capable of regulating signals initiated from a receptor on the surface of a cell, such signals involving in some respect, MEKK protein. Such kits include: (a) at least one cell containing MEKK protein; (b) a ligand capable of binding to a receptor on the surface of the cell; and (c) a means for assessing the ability of a putative regulatory compound to alter phosphorylation of the MEKK protein. Such a means for detecting phosphorylation include methods and reagents known to those of skill in the art, for example, phosphorylation can be detected using antibodies specific for phosphorylated amino acid residues, such as tyrosine, serine and threonine. Using such a kit, one is capable of determining, with a fair degree of specificity, the location along a signal transduction pathway of particular pathway constituents, as well as the identity of the constituents involved in such pathway, at or near the site of regulation.

In another embodiment, a kit of the present invention can includes: (a) MEKK protein; (b) MEK protein; and (c) a means for assessing the ability of a putative inhibitory compound to inhibit phosphorylation of the MEK protein by the MEKK protein. A kit of the present invention can further comprise Raf protein and a means for detecting the ability of a putative inhibitory compound to inhibit the ability of Raf protein to phosphorylate the MEK protein.

Another aspect of the present invention relates to the treatment of an animal having a medical disorder that is subject to regulation or cure by manipulating a signal transduction pathway in a cell involved in the disorder. Such medical disorders include disorders which result from abnormal cellular growth or abnormal production of secreted cellular products. In particular, such medical disorders include, but are not limited to, cancer, autoimmune disease, inflammatory responses, allergic responses and neuronal disorders, such as Parkinson's disease and Alzheimer's disease. Preferred cancers subject to treatment using a method of the present invention include, but are not limited to, small cell carcinomas, non-small cell lung carcinomas with overexpressed EGF receptors, breast cancers with overexpressed EGF or Neu receptors, tumors having overexpressed growth factor receptors of established autocrine loops and tumors having overexpressed growth factor receptors of established paracrine loops. According to the present invention, the term treatment can refer to the regulation of the progression of a medical disorder or the complete removal of a medical disorder (e.g., cure). Treatment of a medical disorder can comprise regulating the signal transduction activity of a cell in such a manner that a cell involved in the medical disorder no longer responds to extracellular stimuli (e.g., growth factors or cytokines), or the killing of a cell involved in the medical disorder through cellular apoptosis.

One aspect of the present invention involves the recognition that an MEKK protein of the present invention is capable of regulating the homeostasis of a cell by regulating cellular activity such as cell growth cell death, and cell function (e.g., secretion of cellular products). Such regulation, in most cases, is independent of Raf, however, as discussed above (and as shown in FIG. 2), some pathways capable of regulation by MEKK protein may be subject to upstream regulation by Raf protein. Therefore, it is within the scope of the present invention to either stimulate or inhibit the activity of Raf protein and/or MEKK protein to achieve desired regulatory results. Without being bound by theory, it is believed that the regulation of Raf protein and MEKK protein activity at the divergence point from Ras protein (see FIG. 2) can be controlled by a "2-hit" mechanism. For example, a first "hit" can comprise any means of stimulating Ras protein, thereby stimulating a Ras-dependent pathway, including, for example, contacting a cell with a growth factor which is capable of binding to a cell surface receptor in such a manner that Ras protein is activated. Following activation of Ras protein, a second "hit" can be delivered that is capable of increasing the activity of JNK activity compared with MAPK activity, or vice versa. A second "hit" can include, but is not limited to, regulation of JNK or MAPK activity by compounds capable of stimulating or inhibiting the activity of MEKK, JEK, Raf and/or MEK. For example, compounds such as protein kinase C or phospholipase C kinase, can provide the second "hit" needed to drive the divergent Ras-dependent pathway down the MEKK-dependent pathway in such a manner that JNK is preferentially activated over MAPK.

One embodiment of the present invention comprises a method for regulating the homeostasis of a cell comprising regulating the activity of an MEKK-dependent pathway relative to the activity of a Raf-dependent pathway in the cell. As used herein, the term "homeostasis" refers to the tendency of a cell to maintain a normal state using intracellular systems such as signal transduction pathways. Regulation of the activity of an MEKK-dependent pathway includes increasing the activity of an MEKK-dependent pathway relative to the activity of a Raf-dependent pathway by regulating the activity of a member of an MEKK-dependent pathway, a member of a Raf-dependent pathway, and combinations thereof, to achieve desired regulation of phosphorylation along a given pathway, and thus effect apoptosis. Preferred regulated members of an MEKK-dependent pathway or a Raf-dependent pathway to regulate include, but are not limited to, proteins including MEKK, Raf, JEK, MEK, MAPK, JNK, TCF, ATF-2, Jun and Myc, and combinations thereof.

In one embodiment, the activity of a member of an MEKK-dependent pathway, a member of a Raf-dependent pathway, and combinations thereof, are regulated by altering the concentration of such members in a cell. One preferred regulation scheme involves altering the concentration of proteins including MEKK, Raf, JEK, MEK, MAPK, JNK, TCF, Jun, ATF-2, and Myc, and combinations thereof. A more preferred regulation scheme involves increasing the concentration of proteins including MEKK, JEK, JNK, Jun, ATF-2, and Myc, and combinations thereof. Another more preferred regulation scheme involves decreasing the concentration of proteins including Raf, MEK, MAPK, and TCF, and combinations thereof. It is also within the scope of the present invention that the regulation of protein concentrations in two or more of the foregoing regulation schemes can be combined to achieve an optimal apoptotic effect in a cell.

A preferred method for increasing the concentration of a protein in a regulation scheme of the present invention includes, but is not limited to, increasing the copy number of a nucleic acid sequence encoding such protein within a cell, improving the efficiency with which the nucleic acid sequence encoding such protein is transcribed within a cell, improving the efficiency with which a transcript is translated into such a protein, improving the efficiency of post-translational modification of such protein, contacting cells capable of producing such protein with anti-sense nucleic acid sequences, and combinations thereof.

In a preferred embodiment of the present invention, the homeostasis of a cell is controlled by regulating the apoptosis of a cell. A suitable method for regulating the apoptosis of a cell is to regulate the activity of an MEKK-dependent pathway in which the MEKK protein regulates the pathway substantially independent of Raf. A particularly preferred method for regulating the apoptosis of a cell comprises increasing the concentration of MEKK protein by contacting a cell with a nucleic acid molecule encoding an MEKK protein that possesses unregulated kinase activity. A preferred nucleic acid molecule with which to contact a cell includes a nucleic acid molecule encoding an MEKK protein represented by SEQ ID NO:2, SEQ ID NO:4, SEQ ID NO:6, SEQ ID NO:8 and SEQ ID NO:10, and combinations thereof. A more preferred nucleic acid molecule with which to contact a cell includes a nucleic acid molecule encoding a truncated MEKK protein having only the kinase catalytic domain (i.e., no regulatory domain) of an MEKK protein represented by SEQ ID NO:2, SEQ ID NO:4, SEQ ID NO:6, SEQ ID NO:8 and/or SEQ ID NO:10. An even more preferred nucleic acid molecule with which to contact a cell includes a nucleic acid molecule including $MEKK1_{352-672}$, $MEKK2_{352-619}$, $MEKK3_{358-626}$, $MEKK4_{811-1195}$, $MEKK5_{863-1247}$, and combinations thereof. Again, suitable variations of MEKK proteins described herein comprise those proteins encoded by a nucleic acid molecule that are able to hybridize to any of the above sequences under stringent conditions.

It is within the scope of the invention that the foregoing method can further comprise the step of decreasing the activity of MEK protein in the cell by contacting the cell with a compound capable of inhibiting MEK activity. Such compounds can include: peptides capable of binding to the kinase domain of MEK in such a manner that phosphorylation of MAPK protein by the MEK protein is inhibited; and/or peptides capable of binding to a portion of a MAPK protein in such a manner that phosphorylation of the MAPK protein is inhibited.

In another embodiment, the activity of a member of an MEKK-dependent pathway, a member of a Raf-dependent pathway, and combinations thereof, can be regulated by directly altering the activity of such members in a cell. A preferred method for altering the activity of a member of an MEKK-dependent pathway, includes, but is not limited to, contacting a cell with a compound capable of directly interacting with a protein including MEKK, JEK, JNK, Jun, ATF-2, and Myc, and combinations thereof, in such a manner that the proteins are activated; and/or contacting a cell with a compound capable of directly interacting with a protein including Raf, MEK, MAPK, TCF protein, and combinations thereof in such a manner that the activity of the proteins are inhibited. A preferred compound with which to contact a cell that is capable of regulating a member of an MEKK-dependent pathway includes a peptide capable of binding to the regulatory domain of proteins including MEKK, JEK, JNK, Jun, ATF-2, and Myc, in which the peptide inhibits the ability of the regulatory domain to regulate the activity of the kinase domains of such proteins. Another preferred compound with which to contact a cell includes TNFα, growth factors regulating tyrosine kinases, hormones regulating G protein-coupled receptors and FAS ligand.

A preferred compound with which to contact a cell that is capable of regulating a member of a Raf-dependent pathway includes a peptide capable of binding to the kinase catalytic domain of a protein selected from the group consisting of Raf, MEK-1, MEK-2, MAPK, and TCF, in which the peptide inhibits the ability of the protein to be phosphorylated or to phosphorylate a substrate.

One aspect of the present invention relates to the recognition that an MEKK protein is capable of activating MAPK. MAPK is known to be involved in various cellular pathways in mammalian systems. MAPK is known to be involved in cellular mitogenesis, DNA synthesis, cell division and differentiation. MAPK is also recognized as being involved in the activation of oncogenes, such as c-jun and c-myc. While not bound by theory, the present inventor believes that MAPK is also intimately involved in various abnormalities having a genetic origin. MAPK is known to cross the nuclear membrane and is believed to be at least partially responsible for regulating the expression of various genes. As such, MAPK is believed to play a significant role in the instigation or progression of cancer, neuronal diseases, autoimmune diseases, allergic reactions, wound healing and inflammatory responses. The present inventor, by being first to identify nucleic acid sequences encoding MEKK, recognized that it is now possible to regulate the expression of MEKK, and thus regulate the activation of MAPK.

The present invention also includes a method for regulating the homeostasis of a cell comprising injecting an area of a subject's body with an effective amount of a naked plasmid DNA compound. A naked plasmid DNA compound comprises a nucleic acid molecule encoding an MEKK protein of the present invention, operatively linked to a naked plasmid DNA vector capable of being taken up by and expressed in a recipient cell located in the body area. A preferred naked plasmid DNA compound of the present invention comprises a nucleic acid molecule encoding a truncated MEKK protein having deregulated kinase activity. Preferred naked plasmid DNA vectors of the present invention include those known in the art. When administered to a subject, a naked plasmid DNA compound of the present invention transforms cells within the subject and directs the production of at least a portion of an MEKK protein or RNA nucleic acid molecule that is capable of regulating the apoptosis of the cell.

A naked plasmid DNA compound of the present invention is capable of treating a subject suffering from a medical disorder including cancer, autoimmune disease, inflammatory responses, allergic responses and neuronal disorders, such as Parkinson's disease and Alzheimer's disease. For example, a naked plasmid DNA compound can be administered as an anti-tumor therapy by injecting an effective amount of the plasmid directly into a tumor so that the plasmid is taken up and expressed by a tumor cell, thereby killing the tumor cell. As used herein, an effective amount of a naked plasmid DNA to administer to a subject comprises an amount needed to regulate or cure a medical disorder the naked plasmid DNA is intended to treat, such mode of administration, number of doses and frequency of dose capable of being decided upon, in any given situation, by one of skill in the art without resorting to undue experimentation.

Therapeutic compounds for use with a treatment method of the present invention can further comprise suitable excipients. A therapeutic compound for use with a treatment method of the present invention can be formulated in an excipient that the subject to be treated can tolerate. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful excipients include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In another embodiment, a therapeutic compound for use with a treatment method of the present invention can also comprise a carrier. Carriers are typically compounds that increase the half-life of a therapeutic compound in the treated animal. Suitable carriers include, but are not limited to, liposomes, micelles, cells, polymeric controlled release formulations, biodegradable implants, bacteria, viruses, oils, esters, and glycols. Preferred carriers include liposomes and micelles.

A therapeutic compound for use with a treatment method of the present invention can be administered to any subject having a medical disorder as herein described. Acceptable protocols by which to administer therapeutic compounds of the present invention in an effective manner can vary according to individual dose size, number of doses, frequency of dose administration, and mode of administration. Determination of such protocols can be accomplished by those skilled in the art without resorting to undue experimentation. An effective dose refers to a dose capable of treating a subject for a medical disorder as described herein. Effective doses can vary depending upon, for example, the therapeutic compound used, the medical disorder being treated, and the size and type of the recipient animal. Effective doses to treat a subject include doses administered over time that are capable of regulating the activity, including growth, of cells involved in a medical disorder. For example, a first dose of a naked plasmid DNA compound of the present invention can comprise an amount of that causes a tumor to decrease in size by about 10% over 7 days when administered to a subject having a tumor. A second dose can comprise at least the same the same therapeutic compound than the first dose.

Another aspect of the present invention includes a method for prescribing treatment for subjects having a medical disorder as described herein. A preferred method for prescribing treatment comprises: (a) measuring the MEKK protein activity in a cell involved in the medical disorder to determine if the cell is susceptible to treatment using a method of the present invention; and (b) prescribing treatment comprising regulating the activity of an MEKK-dependent pathway relative to the activity of a Raf-dependent pathway in the cell to induce the apoptosis of the cell. The step of measuring MEKK protein activity can comprise: (1) removing a sample of cells from a subject; (2) stimulating the cells with a TNFA; and (3) detecting the state of phosphorylation of JEK protein using an immunoassay using antibodies specific for phosphothreonine and/or phosphoserine.

The present invention also includes antibodies capable of selectively binding to an MEKK protein of the present invention. Such an antibody is herein referred to as an anti-MEKK antibody. Polyclonal populations of anti-MEKK antibodies can be contained in an MEKK antiserum. MEKK antiserum can refer to affinity purified polyclonal antibodies, ammonium sulfate cut antiserum or whole antiserum. As used herein, the term "selectively binds to" refers to the ability of such an antibody to preferentially bind to MEKK proteins. Binding can be measured using a variety of methods known to those skilled in the art including immunoblot assays, immunoprecipitation assays, enzyme immunoassays (e.g., ELISA), radioimmunoassays, immunofluorescent antibody assays and immunoelectron microscopy; see, for example, Sambrook et al., *Molecular Cloning: A Laboratory Manual*, Cold Spring Harbor Labs Press, 1989.

Antibodies of the present invention can be either polyclonal or monoclonal antibodies and can be prepared using techniques standard in the art. Antibodies of the present invention include functional equivalents such as antibody fragments and genetically-engineered antibodies, including single chain antibodies, that are capable of selectively binding to at least one of the epitopes of the protein used to obtain the antibodies. Preferably, antibodies are raised in response to proteins that are encoded, at least in part, by a MEKK nucleic acid molecule. More preferably antibodies are raised in response to at least a portion of an MEKK protein, and even more preferably antibodies are raised in response to either the amino terminus or the carboxyl terminus of an MEKK protein. Preferably, an antibody of the present invention has a single site binding affinity of from about $10^3 M^{-1}$ to about $10^{12} M^{-1}$ for an MEKK protein of the present invention.

A preferred method to produce antibodies of the present invention includes administering to an animal an effective amount of an MEKK protein to produce the antibody and recovering the antibodies. Antibodies of the present invention have a variety of potential uses that are within the scope of the present invention. For example, such antibodies can be used to identify unique MEKK proteins and recover MEKK proteins.

Another aspect of the present invention comprises a therapeutic compound capable of regulating the activity of an MEKK-dependent pathway in a cell identified by a process, comprising: (a) contacting a cell with a putative regulatory molecule; and (b) determining the ability of the putative regulatory compound to regulate the activity of an MEKK-dependent pathway in the cell by measuring the activation of at least one member of said MEKK-dependent pathway. Preferred methods to measure the activation of a member of an MEKK-dependent pathway include measuring the transcription regulation activity of c-Myc protein, measuring the phosphorylation of a protein selected from the group consisting of MEKK, JEK, JNK, Jun, ATF-2, Myc, and combinations thereof.

The following examples are provided for the purposes of illustration and are not intended to limit the scope of the present invention.

EXAMPLES

Example 1

This example describes the structural characterization of MEKK 1 protein.

A. MEKK 1 Nucleotide Sequence

MEKK 1 protein was cloned by the following method. Unique degenerate inosine oligodeoxynucleotides were designed to correspond to regions of sequence identity between the yeast Ste11 and Byr2 genes. With primers and cDNA templates derived from polyadenylated RNA from NIH 3T3 cells, a polymerase chain reaction (PCR) amplification product of 320 base pairs (bp) was isolated. This 320 bp cDNA was used as a probe to identify an MEKK 1 cDNA of 3260 bp from a mouse brain cDNA library using standard methods in the art. The MEKK 1 nucleotide sequence was determined by dideoxynucleotide sequencing of double-stranded DNA using standard methods in the art.

Referring to Table 6, based on the Kozak consensus sequence for initiation codons, the starting methionine can be predicted to occur at nucleotide 486. With this methionine at the start, the cDNA encodes a protein of 672 amino acids, corresponding to a molecular size of 73 kD. There is another in-frame methionine at position 441, which does not follow the Kozak rule, but would yield a protein of 687 amino acid residues (74.6 kD). Also referring to Table 6, 20% of the $NH_2$-terminal 400 amino acids are serine or threonine and there are only two tyrosines. Several potential sites of phosphorylation by protein kinase C are apparent in the $NH_2$-terminal region. The kinase catalytic domain is located in the COOH-terminal half of the MEKK 1.

B. Northern Blot Analysis of MEKK1 Transcript

Figure 3A:
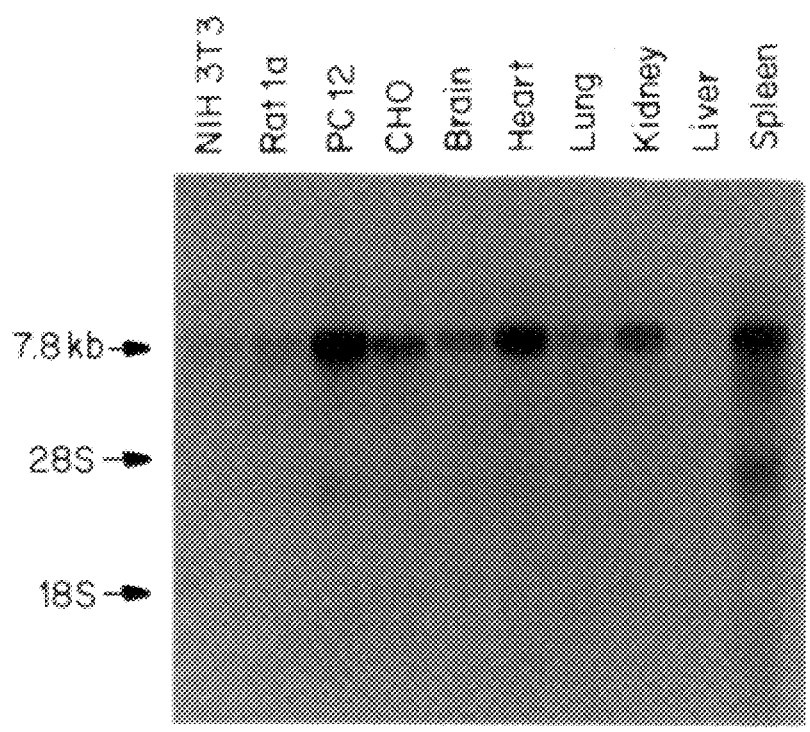
FIG. 3A shows a Northern (RNA) blot of a single 7.8 kb MEKK mRNA in several cell lines and mouse tissues.

Equal amounts (20 μg) of total RNA were loaded onto the gel as indicated by ethidium bromide staining. Blots were probed with either a 320-bp cDNA fragment encoding a portion of the MEKK1 kinase domain or an 858-bp fragment encoding a portion of the $NH_2$ terminal region of MEKK1 using standard methods in the art. Referring to FIG. 3A, a 7.8 kb mRNA was identified with probes derived from both the 5' and 3' ends of the MEKK1 cDNA in several cell lines and mouse tissues. The MEKK1 mRNA was highly expressed in mouse heart and spleen, an in lower amounts in liver.

C. Southern Blot Analysis

Figure 3B:
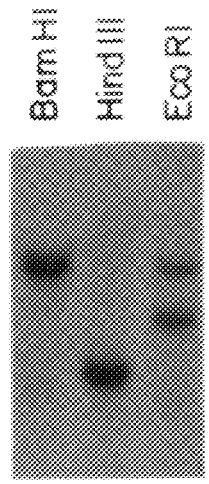
FIG. 3B shows a Southern (DNA) blot of the MEKK gene.

Mouse genomic DNA (10 μg) was digested with either Bam HI, Hind III or Eco RI and applied to gels using standard methods in the art. Blots were probed with a 320-bp fragment of the MEKK1 gene. FIG. 3B shows the appearance of one band in the Bam HI and Hind III digests which indicates that MEKK is encoded by one gene. The appearance of two bands in the Eco RI digest indicates the likely presence of an Eco RI site within an intron sequence spanned by the probe.

D. Immunoblots Using Anti-MEKK Antibodies

Three polyclonal antisera were prepared using three different antigens. A first polyclonal antiserum was prepared using an antigen comprising a 15 amino acid peptide DRPPSRELLKHPVER derived from the COOH-terminus of MEKK1 corresponding to amino acids 655 to 669 of SEQ ID NO:2. NZW rabbits were immunized with the peptide and antisera was recovered using standard methods known in the art. This first polyclonal antiserum is hereinafter referred to as the DRPP antiserum.

A second polyclonal antiserum was produced using a DNA clone comprising an MEKK1 cDNA digested with EcoR1 and PstI, thereby creating a 1270 bp fragment that encodes the amino terminus of MEKK1. This fragment was cloned into pRSETC to form the recombinant molecule $pMEKK_{1-369}$ comprising amino acid residues 1 to 369 of MEKK 1. The $pMEKK1_{369}$ recombinant molecule was expressed in E. coli and protein encoded by the recombinant molecule was recovered and purified using standard methods known in the art. NZW rabbits were immunized with the purified recombinant $MEKK1_{1-369}$ protein and antisera was recovered using standard methods known in the art. This second polyclonal antiserum is hereinafter referred to as the $MEKK1_{1-369}$ antiserum.

A third polyclonal antiserum was produced using a DNA clone comprising an MEKK1 cDNA digested with Pst I and Kpn 1, thereby creating a 1670 bp fragment that encodes the catalytic domain of MEKK1. This fragment was cloned into pRSETC to form the recombinant molecule $pMEKK_{370-672}$ comprising amino acid residues 370 to 672 of MEKK1 (encoded by base pairs 1592–3260). The $pMEKK1_{370-672}$ recombinant molecule was expressed in E. coli and protein encoded by the recombinant molecule was recovered and purified using standard methods known in the art. NZW rabbits were immunized with the purified recombinant $MEKK1_{370-672}$ protein and antisera was recovered using standard methods known in the art. This second polyclonal antiserum is hereinafter referred to as the $MEKK1_{370-672}$ antiserum.

The DRPP antiserum was used to probe Western Blots of soluble cellular protein derived from several rodent cell lines. Soluble cellular protein (100 μg) or recombinant MEKK COOH-terminal fusion protein (30 ng) was loaded onto a 10% Tris Glycine SDS-PAGE gel and the protein transferred to a nylon filter using methods standard in the art. The nylon filter was immunoblotted with affinity purified DRPP antiserum (1:300 dilution). Referring to FIG. 3C, a 78 kD immunoreactive protein was identified in the samples comprising protein from Pheochromocytoma (PC12), Rat 1a, and NIH 3T3 cells. A prominent 50 kD immunoreactive band was also commonly present but varied in intensity from preparation to preparation indicating the band is a proteolytic fragment. Visualization of both the 78 kD and 50 kD immunoreactive bands on immunoblots was inhibited by pre-incubation of the 15 amino acid peptide antigen with the affinity purified DRPP antiserum. The MEKK protein detected by immunoblotting is similar to the molecular size predicted from the open reading frame of the MEKK1 cDNA.

Figure 4:
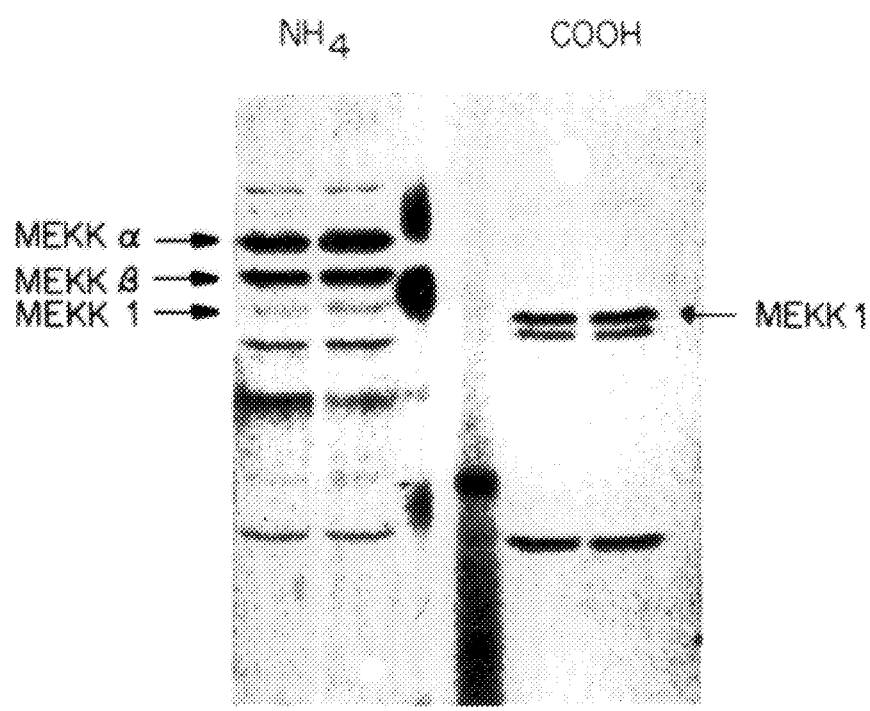
FIG. 4 shows immunprecipitates of MEKK protein using MEKK antiserum.

In a second immunoblot experiment, PC12 cells stimulated or not stimulated with EGF were lysed and resolved on 10% Tris Glycine SDS-PAGE gel as described above. MEKK proteins contained in the cell lysates were identified by immunoblot using affinity purified MEKK1$_{1-369}$ antiserum (1:300) using methods standard in the art. Referring to FIG. 4, MEKK 1 and two higher molecular weight proteins having MEKK activity, MEKK α and MEKK β, were identified using the affinity purified MEKK1$_{1-369}$ antiserum. MEKK 1, and not MEKK α and MEKK β, were identified using the affinity purified MEKK1$_{370-672}$ antiserum.

Figure 5A:
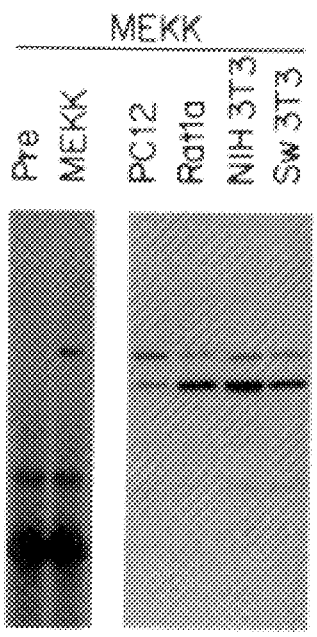
FIG. 5 shows immunoblotting of MEKK protein in immunoprecipitates and cell lysates.
Figure 5B:
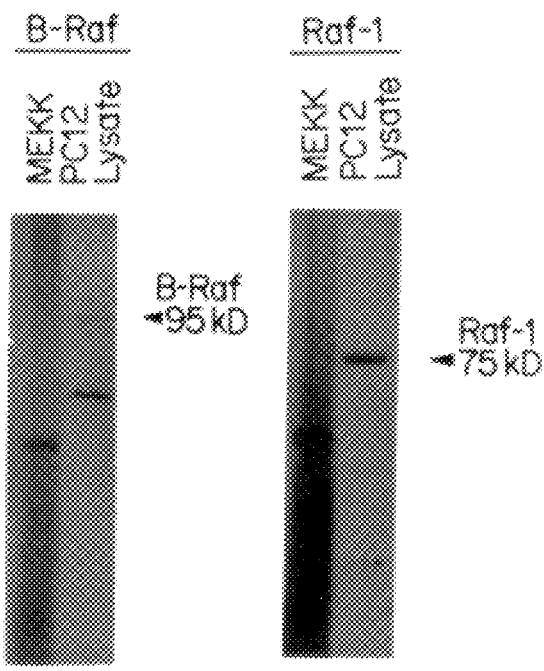

Using the same procedure described above, two MEKK immunoreactive species of approximately 98 kD and 82 kD present in PC12, Rat1a, NIH3T3, and Swiss3T3 cell lysates were recognized by affinity purified MEKK1$_{1-369}$ antiserum as shown in FIG. 5. It should be noted that the 98 kD MEKK protein described herein was originally identified as a 95 kD MEKK protein in the related PCT application (International application no. PCT/US94/04178). Visualization of both of these proteins was inhibited by incubation of the affinity purified MEKK1$_{1-369}$ antiserum with purified recombinant MEKK1$_{1-369}$ fusion protein antigen. A single 98 kD MEKK protein was present in MEKK immunoprecipitates, but not in immunoprecipitates using preimmune serum. More of the 98 kD MEKK was expressed in PC12 cells relative to fibroblast cell lines. Immunoblotting with antibodies that specifically recognize Raf-1 or Raf-B indicated that neither of these enzymes were present as contaminants of MEKK immunoprecipitates. 98 kD MEKK in MEKK immunoprecipitates did not comigrate with Raf-1 or Raf-B in PC12 cell lysates and no cross-reactivity between MEKK and Raf antibodies was observed.

Example 2

This example describes the isolation of nucleic acid sequences encoding MEKK 2, MEKK 3 and MEKK 4 protein.

PCR primers were designed based on the nucleotide sequence of MEKK 1. PCR amplification of fragments from DNA isolated from reverse transcriptase reactions of RNA isolated form PC12 and HL60 cells was conducted using standard techniques. The resultant PCR products were cloned into the pGEX cloning vector (Promega, Wis.) using standard procedures and submitted to DNA sequence analysis using standard techniques.

Example 3

This example describes the expression of MEKK 1 protein in COS-1 cells to define its function in regulating the signaling system that includes MAPK.

COS cells in 100-mm culture dishes were transfected with either the pCVMV5 expression vector alone (1 μg: control) or the pCVMV5 MEKK construct (1 μg: MEKK). After 48 hours, the cells were placed in serum-free medium containing bovine serum albumin (0.1 percent) for 16 to 18 hours to induce quiescence. Cells were then treated with human EGF (30 ng/ml) (+EGF) or buffer (control) for 10 minutes, washed twice in cold phosphate buffered saline (PBS), and lysed in cell lysis buffer containing 50 mM β-glycerophosphate (pH 7.2), 100 μM sodium vanadate, 2 mM MgCl$_2$, 1 mM EGTA Triton X-100 (0.5 percent), leupeptin (2 μg/ml), aprotinin (2 μg/ml), and 1 mM dithiothreitol (600 μl). After centrifugation for 10 minutes at maximum speed in a microfuge, COS cell lysates containing 0.5 to 1 mg of soluble protein were subjected to FPLC on a MONO Q column, and eluted fractions were assayed for MAPK activity according to the method described in Heasley et al., p. 545, 1992, Mol. Biol. Cell, Vol. 3.

Figure 6A:
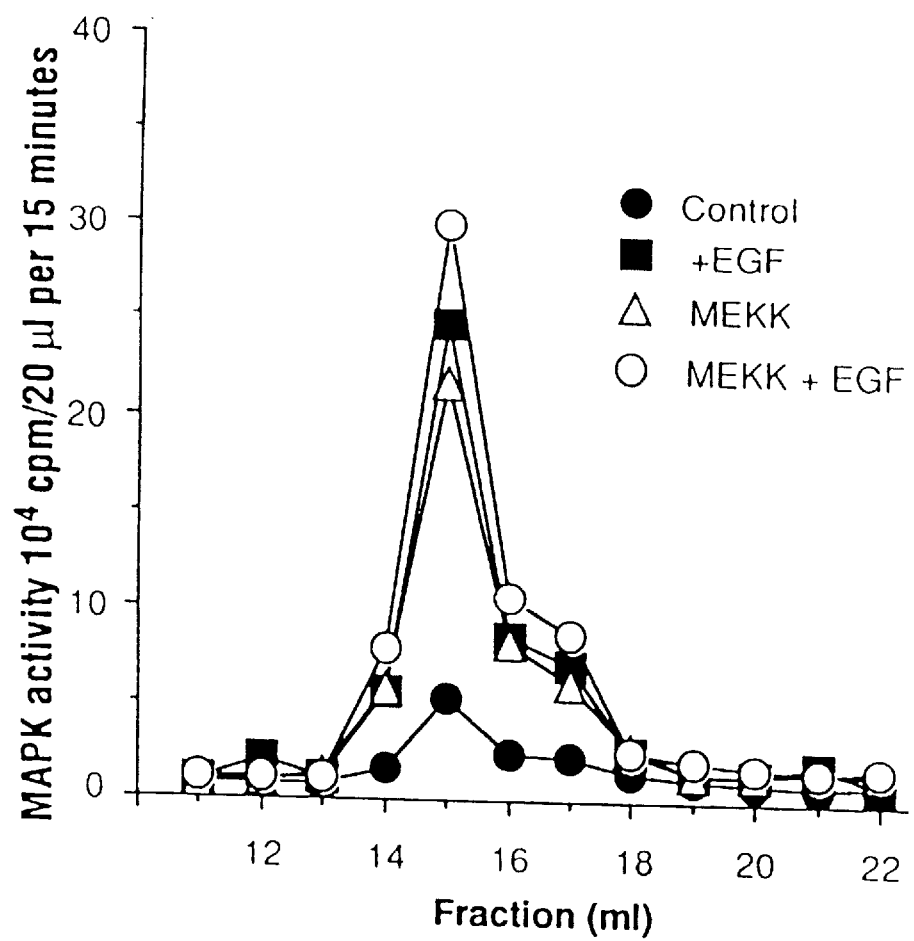
FIG. 6A shows the activation of MAPK in COS cells transfected with MEKK.

Referring to FIG. 6A, when MEKK 1 was overexpressed in COS 1 cells, MAPK activity was four to five times greater than that in control cells transfected with plasmid lacking an MEKK 1 cDNA insert. The activation of MAPK occurred in COS cells deprived of serum and in the absence of any added growth factor. The activity of MAPK was similar to that observed after stimulation of control cells with EGF. Stimulation of COS cells transiently overexpressing MEKK with EGF resulted in only a slight increase in MAPK activity compared to that observed with MEKK expression alone.

Figure 6B:
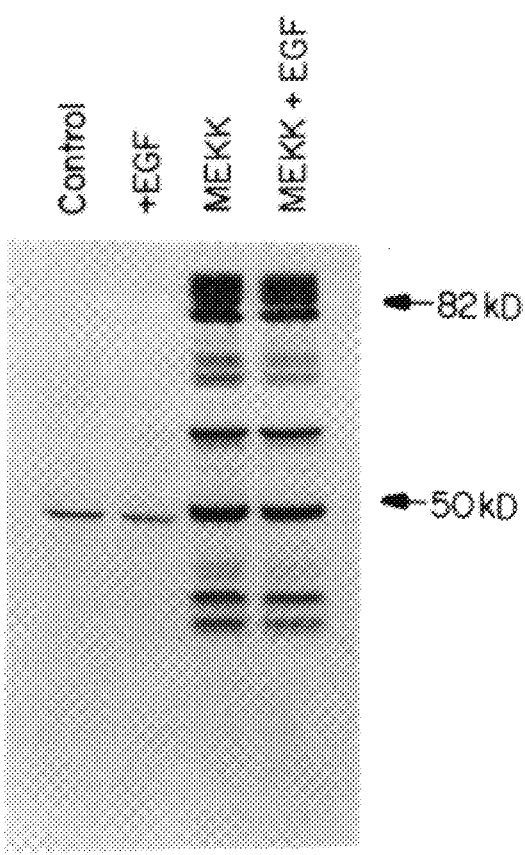
FIG. 6B is an immunoblot showing expression of MEKK in cells either treated or not treated with EGF.

To ensure that MEKK protein was present in the samples tested for MAPK activity, protein from cell lysates of the transfected COS 1 cells were immunoblotted with MEKK specific antiserum. Equal amounts (100 μg) of soluble protein lysate from COS cells were placed on the gel for immunoblotting using the methods described in Example 1. The filters were immunoblotted using the affinity purified DRPP antiserum (1:300) and affinity purified MEKK$_{1-369}$ antiserum (1:300). Referring to FIG. 6B, the results indicate that expression of MEKK in cells transfected with vector encoding MEKK that were treated with or without EGF. Only the 50 kD MEKK immunoreactive fragment was detected in lysates from control COS cells using the DRPP antiserum. Transient expression of MEKK in COS cells yielded a predominant 82 kD band that was slightly larger than that observed in PC12, Rat 1a, or NIH 3T3 cells. Addition of the 15 amino acid DRPP peptide antigen to the antiserum during immunoblotting prevented detection of all of the immunoreactive bands; these bands were not detected in extracts of control COS cells, an indication that they were derived from the expressed MEKK protein.

Example 4

This Example describes the expression of MEKK 1 in COS cells to test the ability of MEKK protein to activate MEK protein.

Recombinant MAPK was used to assay MEK activity in COS cell lysates that had been fractionated by fast protein liquid chromatography (FPLC) on a Mono S column. A cDNA encoding p42 MAPK from Xenopus laevis was cloned into the pRSETB expression vector. This construct was used for expression in the LysS strain of Escherichia coli BL21(DE3) of a p42 MAPK fusion protein containing a polyhistidine sequence at the NH$_2$-terminus. Cultures containing the expression plasmid were grown at 37° C. to an optical density of 0.7 to 0.9 at 600 nM. Isopropyl-β-thiogalactopyranoside (0.5 mM) was added to induce fusion protein synthesis and the cultures were incubated for 3 hours. The cells were then collected and lysed by freezing, thawing, and sonication. The lysate was centrifuged at 10,000 g for 15 minutes at 4° C. The supernatant was then passed over a Ni$^{2+}$- charged Sepharose resin and the soluble recombinant MAPK was eluted in sodium phosphate buffer (pH 4.5). The purified recombinant MAPK was more than 80 percent pure. The purified recombinant MAPK served as a substrate for MEK and catalyzed the phosphorylation of a peptide consisting of residues 662 to 681 of the EGF receptor (EGFR$^{662-681}$).

Soluble cell lysates from COS cells transiently transfected with MEKK, mock-transfected (control), or mock-transfected and treated with EGF (30 ng/ml) (+EGF), were fractionated by FPLC on a Mono S column and endogenous MEK activity was measured. Endogenous MAPK eluted in fractions 2 to 4, whereas MEK was contained in fractions 9 to 13. For assaying endogenous MEK activity, cells were washed twice in cold PBS and lysed in 650 μl of a solution containing 50 mM β-glycerophosphate, 10 mM 2-N-morpholinoethane-sulfonic acid (pH 6.0), 100 μM sodium vanadate, 2 mM MgCl$_2$, 1 mM EGTA, Triton X-100 (0.5 percent), leupeptin (5 µg/ml), aprotinin (2 µg/ml), and 1 mM dithiothreitol. After centrifugation at maximum speed for 10 minutes in a microfuge, soluble cell lysates (1 to 2 mg of protein) were applied to a Mono S column equilibrated in elution buffer (50 mM β-glycerophosphate, 10 mM MES (pH 6.0), 100 µM sodium vanadate, 2 mM MgCl$_2$, 1 mM EGTA, and 1 mM dithiothreitol. The column was washed with buffer (2 ml) and bound proteins were eluted with a 30 ml linear gradient of 0 to 350 mM NaCl in elution buffer. A portion (30 µl) of each fraction was assayed for MEK activity by mixing with buffer (25 mM β-glycerophosphate, 40 mM N-(2-hydroxyethyl)piperazine-N'-(2-ethanolsulfonic acid) (pH7.2) 50 mM sodium vanadate, 10 mM MgCl$_2$, 100 µM γ-$^{32}$P-ATP (3000 to 4000 cpm/pmol), inhibitor protein-20 (IP-20; TTYADFIASGRTGRRNAIHD; 25 µg/ml), 0.5 mM EGTA, recombinant MAP kinase (7.5 µg/ml), and 200 µM EGFR$^{662-681}$) in a final volume of 40 µl. After incubation at 30° C. for 20 minutes, the incorporation of γ-$^{32}$P-ATP into EGFR$^{662-681}$ was measured. In this assay, the ability of each column fraction to activate added recombinant MAPK was measured by the incorporation of γ-$^{32}$P-ATP into the MAPK substrate, a peptide derived from the EGF receptor (EGFR).

Figure 7:
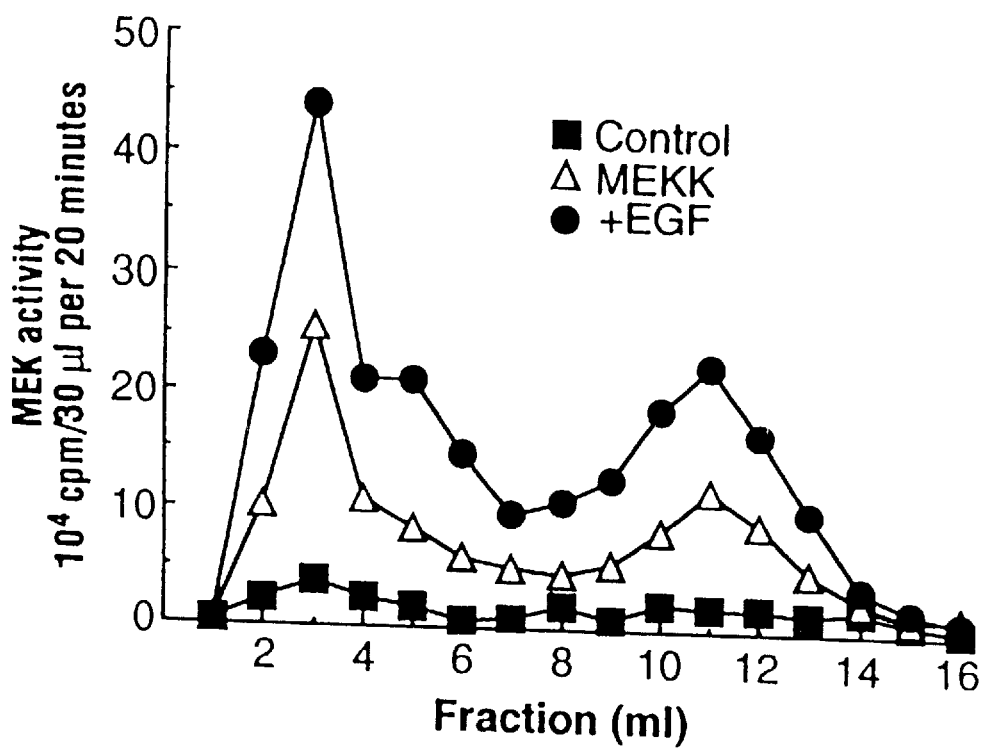
FIG. 7 shows the activation and phosphorylation of MEK in COS cells transfected with MEKK.

Referring to FIG. 7, the first peak of activity eluted represents endogenous activated MAPK, which directly phosphorylates the EGFR peptide substrate. The second peak of activity represents the endogenous MEK in COS cells.

COS cell lysates were fractionated by FPLC on a Mono Q column to partially purify the expressed MEKK. Purified recombinant MEK-1 was then used as a substrate for MEKK in the presence of γ-$^{32}$P-ATP to determine whether MEKK directly phosphorylates MEK-1.

A cDNA encoding MEK-1 was obtained from mouse B cell cDNA templates with the polymerase chain reaction and oligodeoxynucleotide primers corresponding to portions of the 5' coding region and 3' untranslated region of MEK-1. The catalytically inactive MEK-1 was generated by site-directed mutagenesis of Lys$^{343}$ to Met. The wild-type MEK-1 and catalytically inactive MEK-1 proteins were expressed in pRSETA as recombinant fusion proteins containing a polyhistidine sequence at their NH$_2$-termini.

Lysates from COS cells transfected with MEKK or mock-transfected (control) were subjected to FPLC on a Mono Q column as described above. Portions (20 µl) of fractions containing MEKK were mixed with buffer containing 50 mM β-glycerophosphate (pH 7.2), 100 µM sodium vanadate, 2 mM MgCl$_2$, 1 mM EGTA, 50 µM ATP, IP-20 (50 µg/ml), and 10 µl γ-$^{32}$P-ATP in a reaction volume of 40 µl and incubated for 40 minutes in the presence (+) or absence (−) of recombinant, catalytically inactive MEK-1 (150 ng) (kinase-MEK-1). Reactions were stopped by the addition of 5×SDS sample buffer (10 µl), 1×SDS buffer contains 2 percent SDS, 5 percent glycerol, 62.5 mM tris-HCl (pH 6.8), 5 percent β-mercaptoethanol, and 0.001 percent bromophenol blue. The samples were boiled for 3 minutes and subjected to SDS-PAGE and autoradiography.

Figure 8A:
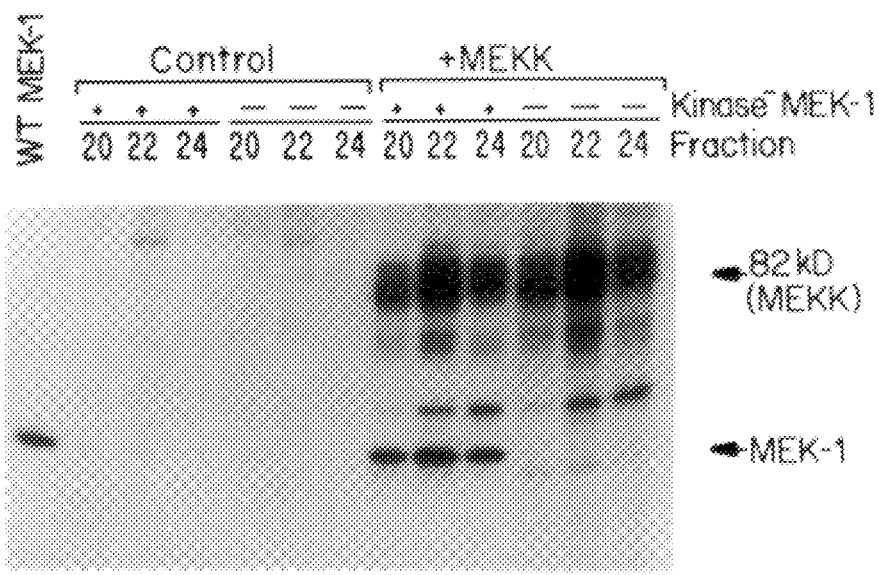
FIG. 8A shows the phosphorylation of MEK-1 by MEKK.

Referring to FIG. 8A, autophosphorylated recombinant wild-type MEK-1 (WT MEK-1) comigrated with phosphorylated catalytically inactive MEK-1. Thus, MEKK was capable of phosphorylating MEK-1. Corresponding fractions of lysates from control cells, however, were not able to phosphorylate MEK-1.

Example 5

Figure 8B:
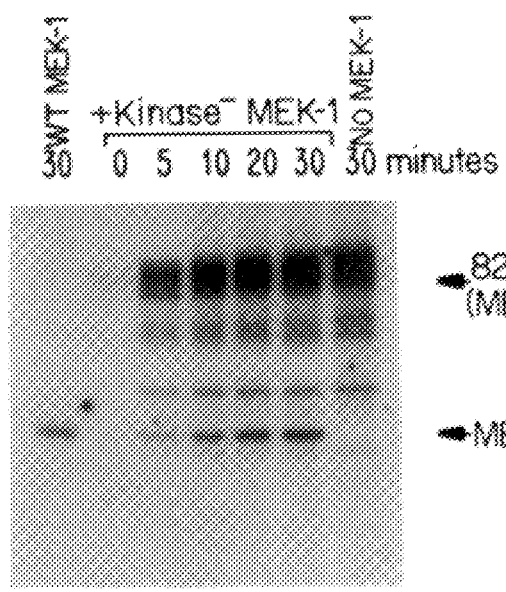
FIG. 8B shows the time course of phosphorylation of MEK-1 by MEKK expressed in COS cells.
Figure 8C:
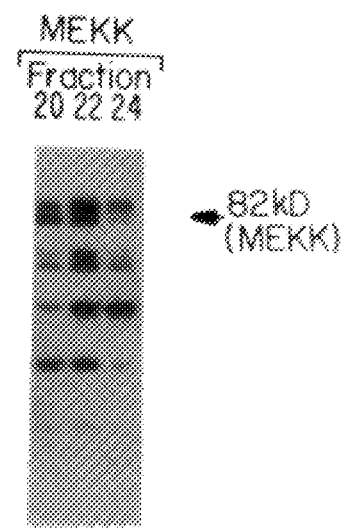
FIG. 8C is an immunoblot of MEKK overexpressed in COS cells.

Phosphorylation of catalytically inactive MEK-1 by MEKK was time dependent (FIG. 8B); MEKK was also phosphorylated. Fraction 22 from FPLC on a Mono Q column (20 µl) was incubated with or without recombinant catalytically inactive MEK-1 (0.15 µg) for the indicated times. Referring to FIG. 8B, phosphorylation of kinase MEK-1 and MEKK was visable after 5 minutes and maximal after about 20 minutes. The time-dependent increase in MEKK phosphorylation correlated with a decreased mobility of the MEKK protein during SDS-PAGE. Referring to FIG. 8C, immunoblotting demonstrated that the MEKK protein co-eluted (after FPLC on a Mono Q column) with the peak of activity (fraction 22) that phosphorylated MEK. The slowly migrating species of MEKK were also detected by immunoblotting. Thus, expression of MEKK appears to activate MAPK by activating MEK.

Example 6

This Example describes that the phosphorylation of MEK by overexpressed MEKK resulted in activation of MEK, recombinant wild-type MEK-1 and a modified form of MAPK that is catalytically inactive.

COS cell lysates were separated by Mono Q-FPLC and fractions containing MEKK were assayed for their ability to activate added wild-type MEK-1 such that it would phosphorylate catalytically inactive recombinant MAPK in the presence of γ-$^{32}$P-ATP. Lysates from COS cells transfected with MEKK or mock-transfected (control) were fractionated by FPLC on a Mono Q column and portions (20 µl) of fractions containing MEKK were mixed with buffer. Each fraction was incubated in the presence (+) or absence (−) of purified recombinant wild-type MEK-1 (150 ng) and in the presence of purified recombinant, catalytically inactive (kinase$^-$) MAPK (300 ng). Referring to FIG. 9A, fractions 20 to 24 from lysates of COS cells transfected with MEKK activated MEK-1. Thus, MEKK phosphorylated and activated MEK-1, leading to MAPK phosphorylation.

Example 7

This Example describes studies demonstrating that MEKK activated MEK directly, and not through the activation of one or more other kinases contained in the column fractions.

Overexpressed MEKK was immunoprecipitated from COS cell lysates with affintiy purified MEKK$_{1-369}$ antiserum. Immunoprecipitated MEKK was resuspended in 10 to 15 µl of PAN (10 mM piperazine-N,N'-bis-2-ethanesulfonic acid (Pipes) (pH 7.0), 100 mM NaCl, and aprotinin (20 µg/ml) and incubated with (+) or without (−) catalytically inactive MEK-1 (150 ng) and 25 µCi of γ-$^{32}$P-ATP in 20 mM pipes (pH 7.0), 10 mM MnCl$_2$, and aprotinin (20 µg/ml) in a final volume of 20 µl for 15 minutes 30° C. Reactions were stopped by the addition of 5×SDS sample buffer (5 µl). The samples were boiled for 3 minutes and subjected to SDS-PAGE and autoradiography.

Referring to FIG. 9B, MEKK phosphorylated catalytically inactive MEK-1, which comigrated with wild-type MEK-1 on SDS-PAGE. Several phosphorylated bands of overexpressed MEKK were detected in the immunoprecipitates. These bands probably resulted from autophosphorylation of MEKK and corresponded to the forms of MEKK identified by immunoblotting of lysates from COS cells transfected with MEKK. Immunoprecipitates obtained with pre-immune serum contained no MEKK and did not phosphorylate MEK-1. Thus, MEKK appears to directly phosphorylate MEK.

Taken together, the results from Examples 4 through 7 show that MEKK can phosphorylate and activate MEK, which in turn phosphorylates and activates MAPK.

Example 8

This Example demonstrates that Raf can also phosphorylate and activate MEK.

Figure 10A:
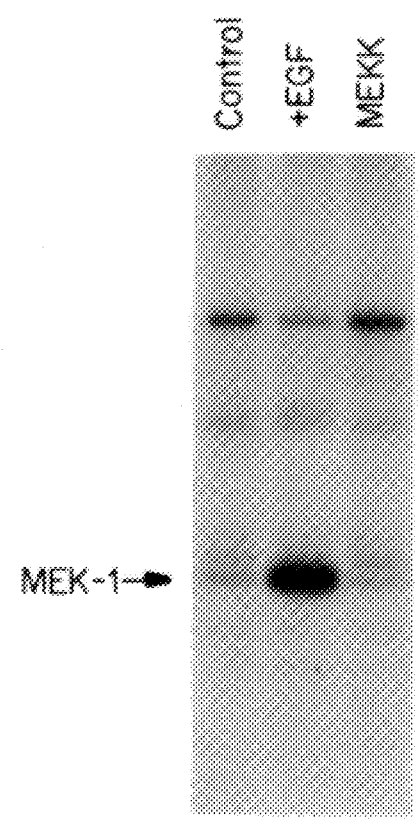
FIG. 10A shows the phosphorylation of MEK-1 by activated Raf.
Figure 10B:
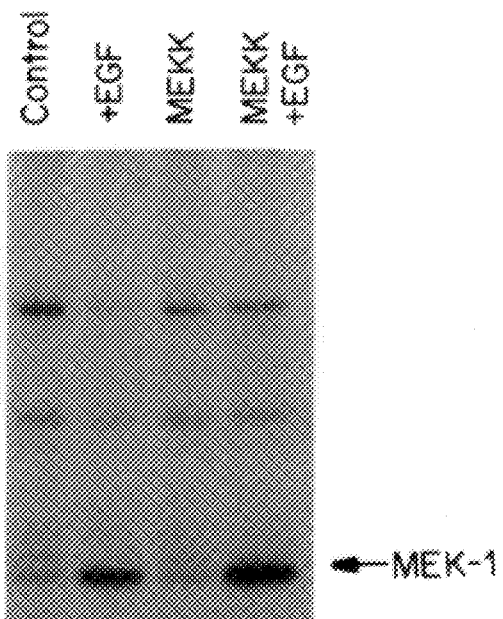
FIG. 10B shows the phosphorylation state of Raf isolated from COS cells which are overexpressing MEKK and have been treated with EGF.

COS cells deprived of serum were stimulated with EGF, and Raf was immunoprecipitated with an antibody to the COOH-terminus of Raf-1. Cos cells were transiently transfected with vector alone (control) or with the PCV/M5-MEKK construct (MEKK). Quiescent control cells were treated with or without human EGF (30 ng/ml) for 10 minutes and Raf was immunoprecipitatd from cell lysates with an antibody to a COOH-terminal peptide from Raf. Immunoprecipitated Raf was incubated with catalytically inactive MEK-1 (150 ng) and 25 $\mu$l of $\gamma$-$^{32}$P-ATP. The immunoprecipitated Raf phosphorylated MEK-1 in the presence of $\gamma$-$^{32}$P-ATP (FIG. 10A). Little or no phosphorylation of MEK-1 by Raf was observed in immunoprecipitates of Raf from COS cells overexpressing MEKK. Treatment of COS cells overexpressing MEKK with EGF resulted in a similar degree of phosphorylation of MEK-1 by immunoprecipitated Raf (FIG. 10B). Cells transfected with MEKK and deprived of serum were treated with EGF, and Raf was immunoprecipitated and incubated with catalytically inactive MEK-1. Equal amounts of Raf were immunoprecipitated in each sample as demonstrated by immunoblotting with antibodies to Raf. The slowest migrating band represents an immunoprecipitated phosphoprotein that is unrelated to Raf or MEK-1. The amount of Raf in the immunoprecipitates from control cells and cells transfected with MEKK was similar as shown by subsequent SDS-PAGE and immunoblotting with the antibody to Raf. Thus, both MEKK and Raf can independently activate MEK.

Example 9

This Example describes the activation of a 98 kD MEKK protein isolated from PC12 cells in response to stimulation of cells containing MEKK protein by growth factors.

PC12 cells were deprived of serum by incubation in starvation media (DMEM, 0.1% BSA) for 18–20 hours and MEKK was immunoprecipitated from lysates containing equal amounts of protein from untreated controls or cells treated with EGF (30 ng/ml) or NGF (100 ng/ml) for 5 minutes with the above-described anti-MEKK antibodies speicific for the NH$_4$-terminal portion of MEKK. Immunoprecipitated MEKK was resuspended in 8 $\mu$l of PAN (10 mM piperazine-N,N'-bis-2-ethanesulfonic acid (Pipes) (pH 7.0), 10 mM NaCl, and aprotinin (20 $\mu$g/ml)) and incubated with catalytically inactive MEK-1 (150 ng) and 40 $\mu$Ci of ($\gamma$-$^{32}$P) ATP in universal kinase buffer (20 mM piperazine-N,N'-bis-2-ethanesulfonic acid (Pipes) (pH 7.0), 10 mM MnCl$_2$, and aprotinin (20 $\mu$g/ml)) in a final volume of 20 $\mu$l for 25 minutes at 30° C. Reactions were stopped by the addition of 2× SDS sample buffer (20 $\mu$l). The samples were boiled for 3 minutes and subjected to SDS-PAGE and autoradiography. Raf-B was immunoprecipitated from the same untreated and treated PC12 cell lysates as above with an antiserum to a COOH-terminal peptide of Raf-B (Santa Cruz Biotechnology, Inc.) and assayed similarly. Raf-1 was immunoprecipitated with an antiserum to the 12 COOH-terminal amino acids of Raf-1 (Santa Cruz Biotechnology, Inc.). Epidermal growth factor (EGF) treatment of serum starved PC12 cells resulted in increased MEKK activity.

Figure 11:
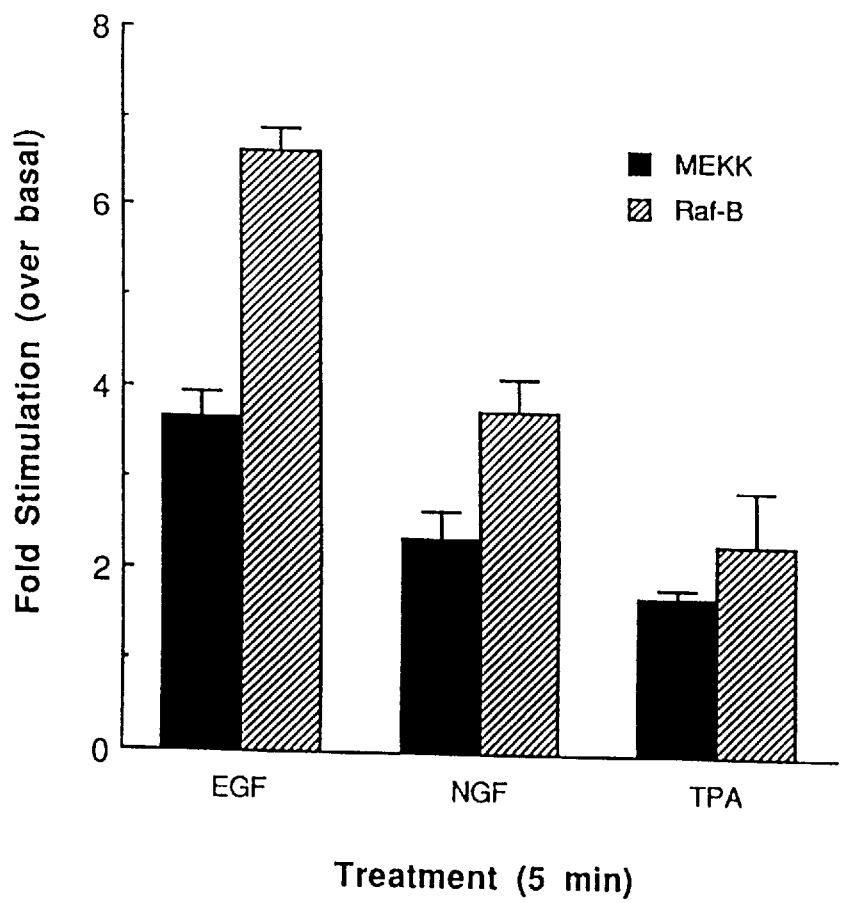
FIG. 11 shows the relative ability of immunoprecipitated MEKK and Raf-B to phosphorylate kinase inactive MEK-1.

Referring to FIG. 11, the results were obtained by measuring the phosphorylation of purified MEK-1 (a kinase inactive form) by immunoprecipitates of MEKK in in vitro kinase assays. NGF stimulated a slight increase in MEKK activity compared to control immunoprecipitates from untreated cells. Stimulation of MEKK activity by NGF and EGF was similar to Raf-B activation by these agents, although Raf-B exhibited a high basal activity. Activation of c-Raf-1 by NGF and EGF was almost negligible in comparison to that of MEKK or Raf-B.

Figure 12:
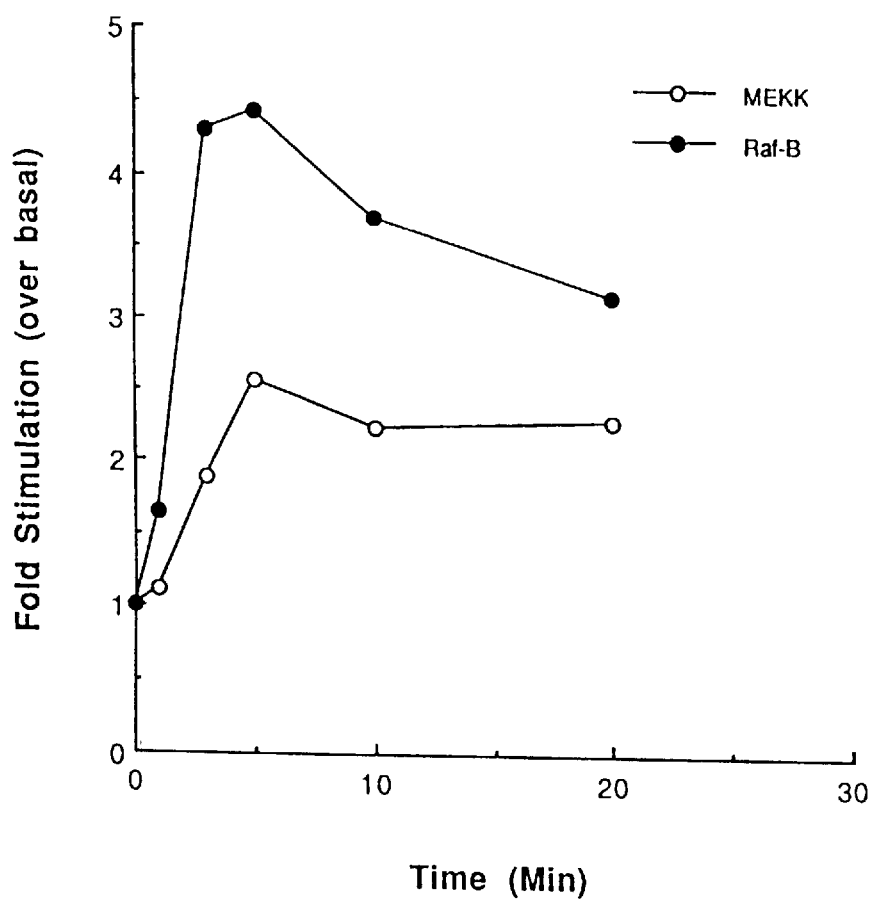
FIG. 12 shows a time course of EGF-stimulated MEKK and Raf-B activation.

A timecourse of MEKK stimulation by EGF was established by immunoprecipitating MEKK or Raf-B protein from lysates of PC12 cells treated with EGF (30 ng/ml) for 0, 1, 3, 5, 10, or 20 minutes and incubating the protein with catalytically inactive MEK-1 (150 ng) and ($\gamma$-$^{32}$P)ATP as described above. Data represent the relative magnitude of the response for each timepoint as quantitated by phosphorimager analysis of radioactive gels from a typical experiment. A timecourse of EGF treatment indicated that MEKK activation reached maximal levels following 5 minutes and persisted for at least 30 minutes (FIG. 12). Raf-B exhibited a similar timecourse; peak activity occurred within 3–5 minutes following EGF treatment and was persistent for up to 20 minutes.

Figure 13:
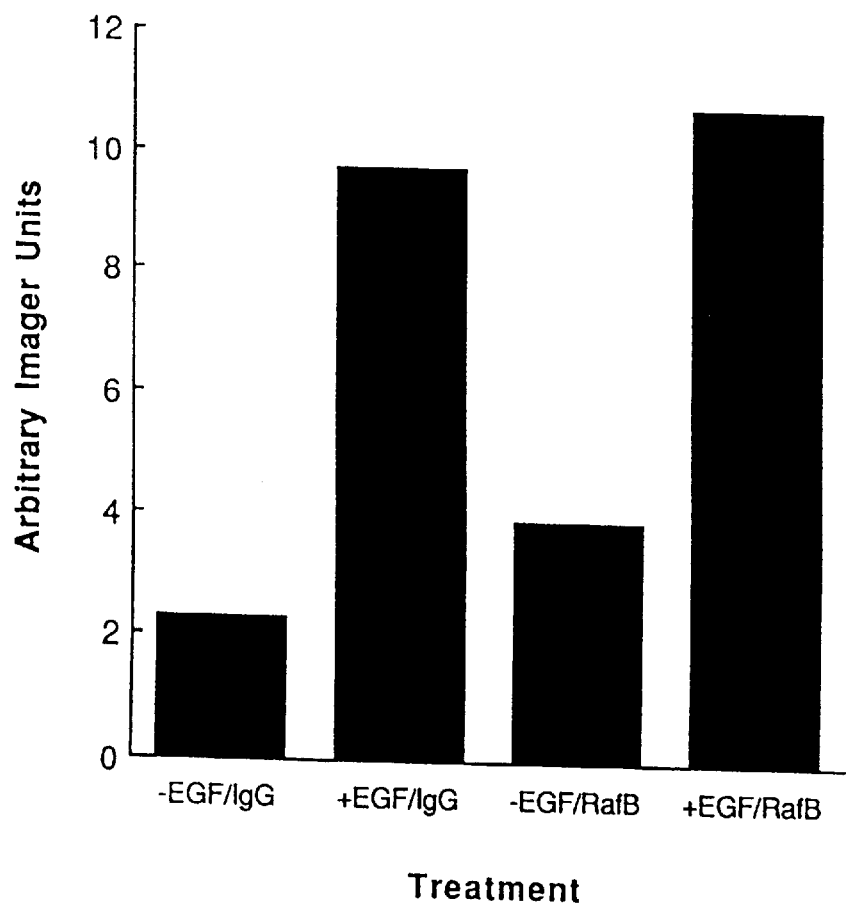
FIG. 13 shows that the immunodepletion of Raf-B from MEKK immunoprecipitates has no effect on MEKK activity.
Figure 14:
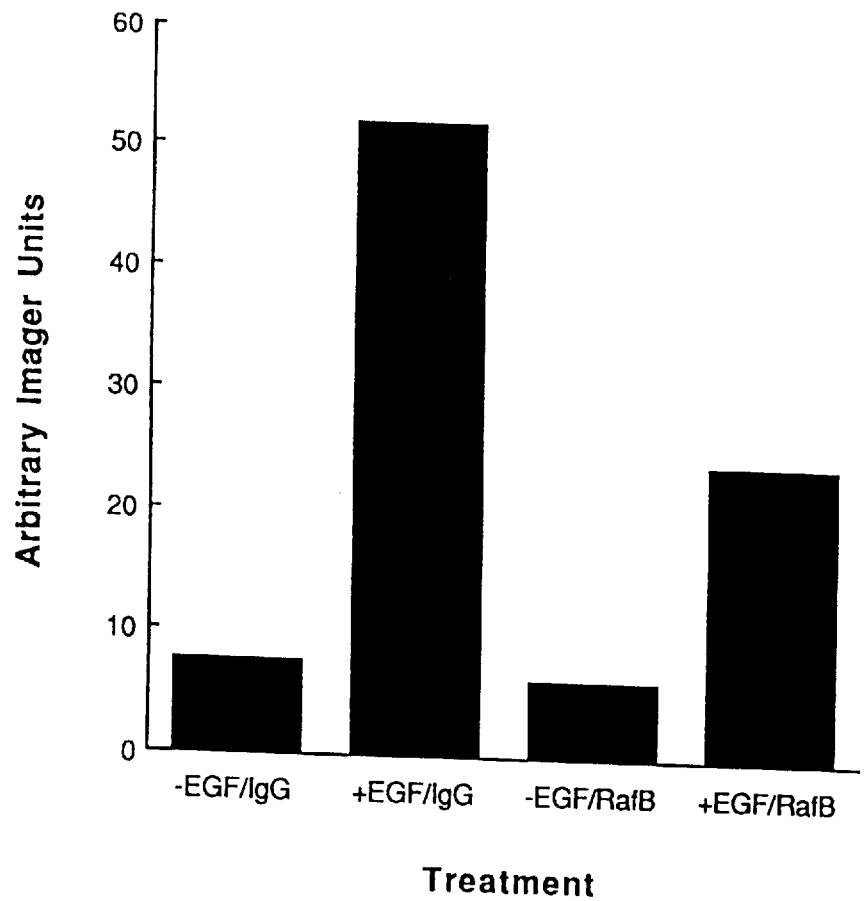
FIG. 14 shows that the immunodepletion of Raf-B from MEKK immunoprecipitates decreases Raf-B activity.

To further dissociate EGF-stimulated MEKK activity from that of Raf-B, Raf-B was immunodepleted from cell lysates prior to MEKK immunoprecipitation. Raf-B was pre-cleared from lysates of serum-starved PC12 cells which had been either treated or not treated with EGF (30 ng/ml) for 5 minutes. Raf-B was pre-cleared two times using antisera to Raf-B or using preimmune IgG antisera as a control. The pre-cleared supernatant was then immunoprecipitated with either MEKK or Raf-B antisera and incubated with catalytically inactive MEK-1 and ($\gamma$-$^{32}$P)ATP as described in detail above. EGF-stimulated and unstimulated PC12 cell lysates were precleared with either IgG or Raf-B antisera and then subjected to immunoprecipitation with MEKK antiserum or Raf-B antibodies. The results shown in FIG. 14 indicate that pre-clearing with Raf-B resulted in a 60% diminution of Raf-B activity as measured by phosphorimager analysis of Raf-B in vitro kinase assays. FIG. 13 shows that EGF-stimulated MEKK activity was unaffected by Raf-B depletion, suggesting that Raf-B is not a component of MEKK immunoprecipitates. At least 40% of the Raf-B activity is resistant to preclearing with Raf-B antibodies. Recombinant wild type MEKK over-expressed in COS cells readily autophosphorylates on serine and threonine residues and the amino-terminus of MEKK is highly serine and threonine rich. MEKK contained in immunoprecipitates of PC12 cells were tested for selective phosphorylation of purified recombinant MEKK amino-terminal fusion protein in in vitro kinase assays.

Serum-starved PC12 cells were treated with EGF (30 ng/ml) for 5 minutes and equal amounts of protein from the same cell lysates were immunoprecipitated with either MEKK, Raf-B, or preimmune antiserum as a control. Immunoprecipitates were incubated with purified recombinant MEKK NH$_2$-terminal fusion protein (400 ng) and ($\gamma$-$^{32}$P) ATP as described above. MEKK immunoprecipitated from lysates of EGF-stimulated and unstimulated PC12 cells robustly phosphorylated the inert 50 kD MEKK NH$_2$-fusion protein, while Raf-B or preimmune immunoprecipitates from EGF-stimulated or unstimulated cells did not use the MEKK NH$_2$-fusion protein as a substrate. Thus, the EGF-stimulated MEKK activity contained in MEKK immunoprecipites is not due to contaminating Raf kinases.

Example 10

This Example describes MEKK activity in FPLC Mono Q ino-exchnage column fractions of PC12 cell lysates.

Figure 15A:
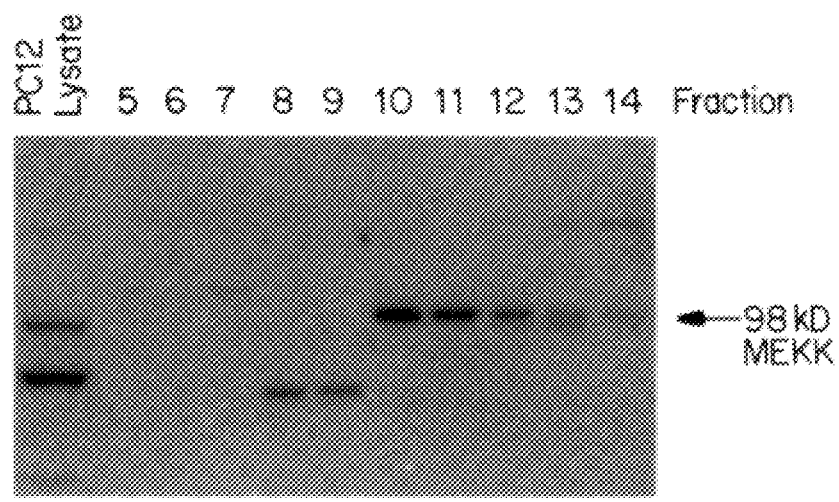
FIG. 15 shows MEKK activity in FPLC Mono Q ion-exchange column fractions of PC12 cell lysates.

Cell lysates were prepared from EGF-stimulated PC12 cells. Portions (900 $\mu$l) of 1 ml column fractions (1 to 525 mM NaCl gradient) were concentrated by precipitation with trichloroacetic acid and loaded on gels as described above. The gels were blotted and then immunoblotted with MEKK specific antibody. The results are shown in FIG. 15A indicate that 98 kD MEKK immunoreactivity eluted in fractions 10 to 12. The peak of B-Raf immunoreactivity eluted in fraction 14, whereas Raf-1 was not detected in the eulates from the column.

Figure 15B:
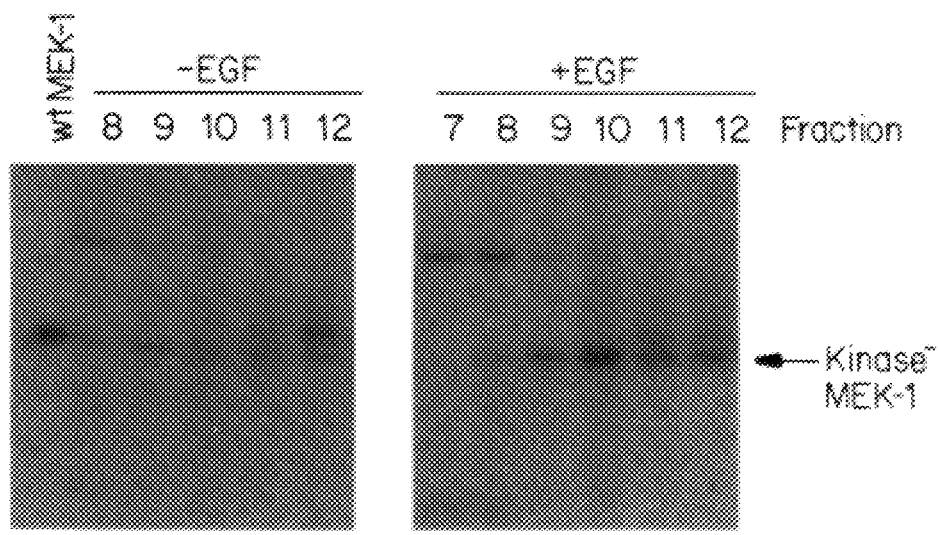

Portions (30 $\mu$l) of each fraction from the PC12 lysates of unstimulated control cells or EGF-treated cells were assayed as described above in buffer containing purified recombinant MEK-1 (150 ng) as a substrate. The results shown in FIG. 15B indicate that the peak of MEKK activity eluted in fractions 10 to 12 from EGF-stimulated PC12 cells phosphorylated MEK, whereas little MEK phosphorylation occurred in fractions from unstimulated cells.

Example 11

This Example describes studies demonstrating that the phosphorylation of both MEK-1 and the MEKK $NH_2$-terminal fusion protein were due to the activity of the 98 kD PC12 cell MEKK.

Cell lysates prepared from EGF-stimulated and unstimulated cells were fractionated by FPLC on a Mono-Q column to partially purify the endogenous MEKK. Lysates from unstimulated control PC12 cells or cells treated with EGF (30 ng/ml) for 5 minutes were fractionated by FPLC on a Mono Q column using a linear gradient of 0 to 525 mM NaCl. A portion (30 $\mu$l) of each even numbered fraction was mixed with buffer (20 mM piperazine-N,N'-bis-2-ethanesulfonic acid (Pipes) (pH 7.0), 10 mM $MnCl_2$, aprotinin (20 $\mu$g/ml), 50 mM β-glycerophosphate (pH 7.2), 1 mM EGTA, IP-20 (5 $\mu$g/ml), 50 mM NaF, and 30 $\mu$Ci ($\gamma$-$^{32}$P)ATP) containing purified recombinant MEK-1 (150 ng) as a substrate in a final volume of 40 $\mu$l and incubated at 30° C. for 25 minutes. Reactions were stopped by the addition of 2× SDS sample buffer (40 $\mu$l), boiled and subjected to SDS-PAGE and autoradiography. The peak of MEKK activity eluted in fractions 10–12. Portions (30 $\mu$l) of each even numbered fraction from lysates of EGF-treated PC12 cells were mixed with buffer as described above except containing purified recombinant MEKK $NH_2$-terminal fusion protein (400 ng) as a substrate instead of MEK-1. Purified recombinant kinase inactive MEK-1 or the MEKK $NH_2$-terminal fusion protein were then used as substrates in the presence of ($\gamma$-$^{32}$P)ATP to determine whether 98 kD MEKK directly phosphorylates either substrate. Fractions 10–14 of lysate from PC12 cells treated with EGF phosphorylated MEK-1 while little MEK-1 phosphorylation occurred in untreated control fractions. The MEKK $NH_2$-terminal fusion protein was also phosphorylated in the same fractions as was MEK-1, although the peak of activity was slightly broader (fractions 8–16).

Immunoblotting of column fractions demonstrated that the 98 kD MEKK protein co-eluted with the peak of activity that phosphorylated either exogenously added kinase inactive MEK-1 or the 50 kD MEKK $NH_2$-terminal fusion protein. Portions (900 $\mu$l) of even numbered column fractions were concentrated by precipitation with trichloroacetic acid and immunoblotted with MEKK antibody. The peak of immunoreactivity eluted in fractions 10–12.

Example 12

This Example describes the activation of MEK by a 98 kD MEKK.

98 kD MEKK was immunoprecipitated using the $MEKK_{1-369}$ antiserum described in Example 1 from untreated (−) or EGF-treated (+) PC12 cell lysates. The immunoprecipitates were incubated in the presence (+) or absence (−) of purified recombinant wild-type MEK (150 ng) and in the presence of purified recombinant catalytically inactive MAPK (300 ng) and ($\gamma$-$^{32}$P)ATP. The results shown in FIG. 17A indicate that immunoprecipitated MEKK from EGF-stimulated cells phosphorylated and activated MEK, leading to MAPK phosphorylation. No phosphorylation of MAPK occurred in the absence of added recombinant MEK. Immunoblotting demonstrated that there was no contaminating MAPK (FIG. 17B) or contaminating MEK (FIG. 17C) in the MEKK immunoprecipitates from the EGF-stimulated PC12 cells. Thus, phosphorylation and activation of MEK is due to EGF stimulation of MEKK activity measured in the immunoprecipitates.

Example 13

This Example describes whether 98 kD PC12 cell MEKK and Raf-B require functional Ras proteins for growth factor mediated signalling.

Figure 16:
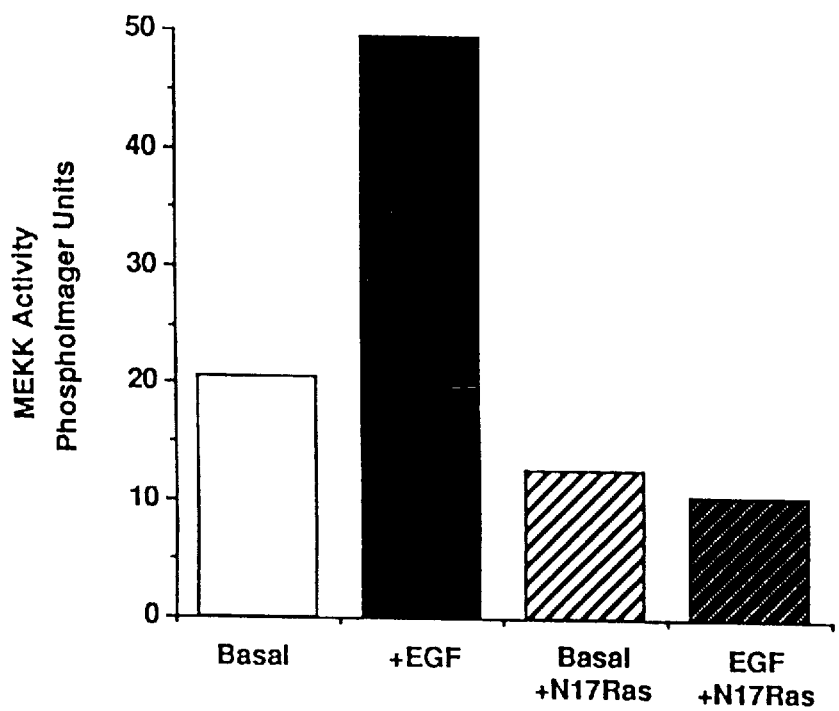
FIG. 16 shows inhibition of MEKK activation by dominant negative $N^{17}RAS$ expression.
Figure 18:
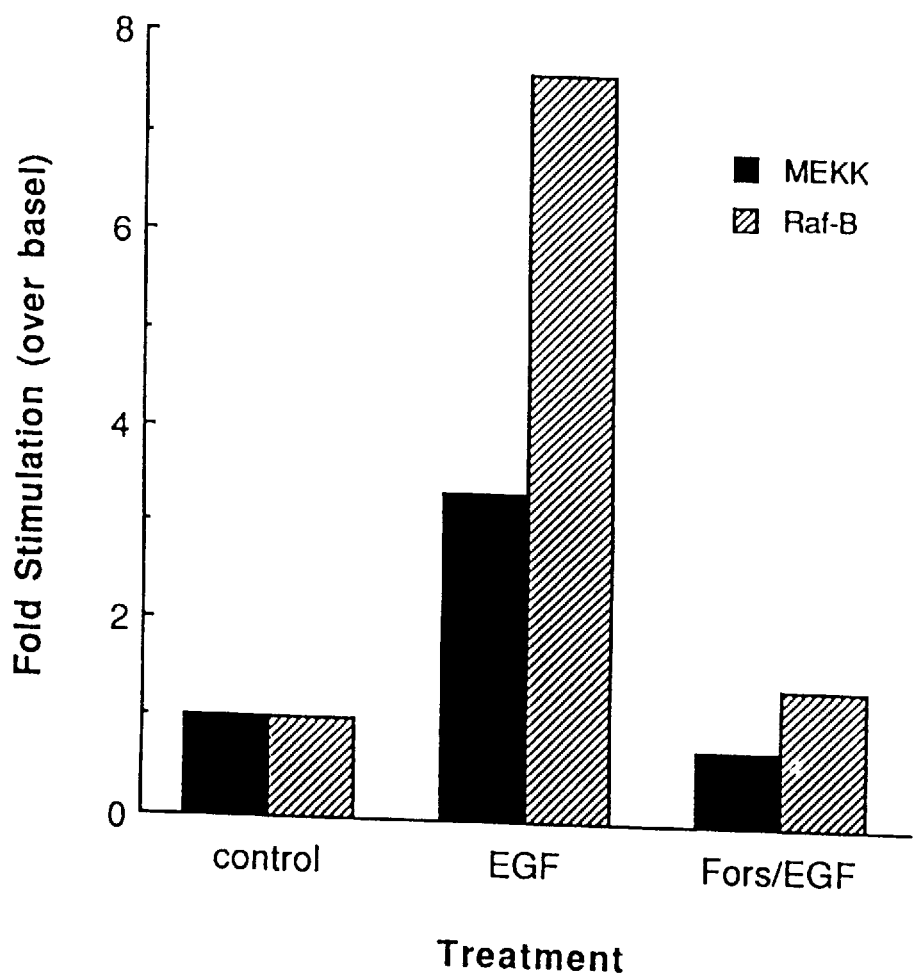
FIG. 18 shows inhibition of EGF activation of MEKK by forskolin.

Dominant negative Ha-ras(Asn 17) ($N^{17}$Ras) was expressed in PC12 cells and EGF-stimulated MEKK or Raf-B activation was assayed in immunoprecipitates using kinase inactive MEK-1 as a substrate. PC12 cells stably expressing dexamethasone inducible $N^{17}$Ras were serum starved for 18–20 hours in media containing 0.1% BSA with or without 1 $\mu$M dexamethasone and then untreated or treated with EGF (30 ng/ml) for 5 minutes. Equal amounts of soluble protein from cell lysates was immunoprecipitated with either MEKK or Raf-B antisera and incubated with purified recombinant catalytically inactive MEK-1 and ($\gamma$-$^{32}$P)ATP as described above. Expression of $N^{17}$Ras was induced in PC12 clones stabley transfected with the $N^{17}$Ras gene by the addition of dexamethasone to the starvation media. FIG. 16 shows that $N^{17}$Ras expression inhibited the activation of MEKK by EGF as measured by its ability to phosphorylate kinase inactive MEK. EGF-mediated activation of Raf-B was also greatly reduced in $N^{17}$Ras expressing PC12 cells compared to uninduced $N^{17}$Ras transfectants. Addition of dexamethasone to wild type PC12 cells had no effect on the magnitude of MEKK or Raf-B activation elicited by EGF. PC12 cell clones stably transfected with the $N^{17}$Ras gene are less responsive to EGF-mediated activation of MEKK activity than are wild type PC12 cells. These results indicate that functional Ras is required for growth factor stimulated activation of both Raf-B and MEKK in PC12 cells, suggesting that Ras may mediate its effects on cell growth and differentiation through the activation of multiple protein kinase effectors from both the Raf and MEKK families. Thus, EGF stimulated a peak of MEKK activity within 5 minutes which persisted for at least 30 minutes following treatment, and was similar to the time-course of Raf-B activation. Nerve growth factor (NGF) and the phorbol ester TPA also activated MEKK, although to a lesser degree than EGF. MEKK activity in immunoprecipitates or column fractions was dissociable from that of EGF-stimulated c-Raf-1 and Raf-B activities. Forskolin pretreatment abolished both MEKK and Raf-B activation by EGF, NGF, and TPA (FIG. 18). Both MEKK and Raf-B activation in response to EGF was inhibited by stable expression of dominant negative $N^{17}$ Ras. These findings represent the first demonstration of Ras-dependent MEKK regulation by growth factors and suggest the emergence of a complex intracellular kinase network in which Ras may alternately couple between members of the Raf and MEKK families.

To determine whether the growth factor-mediated activation of 98 kD PC12 cell MEKK was inhibited by PKA, forskolin was used to elevate intracellular cAMP and activate PKA. Serum-starved PC12 cells were pretreated with or without forskolin (50 μM) for 3 minutes to activate protein kinase A and then with EGF (30 ng/ml), NGF (100 ng/ml), or TPA (200 nM) for 5 minutes and MEKK was immunoprecipitated from equal amounts of soluble protein from cell lysates and incubated with purified recombinant catalytically inactive MEK-1 and ($\gamma$-$^{32}$P)ATP as described above. Raf-B activity was also assayed from the same cell lysates to test whether its regulation differed from that of MEKK. Raf-B was immunoprecipitated from the same cell lysates as described above and assayed for its ability to phosphorylate MEK-1 as described above. Forskolin pretreatment abolished the activation of both MEKK and Raf-B by EGF, NGF, and TPA, as measured by their ability to phosphorylate kinase-inactive MEK-1 (FIG. 18). Forskolin treatment alone had no appreciable effect on either kinase. These results demonstrate that in addition to Raf-1 and Raf-B, PKA activation inhibits growth factor stimulation of 98 kD PC12 cell MEKK, suggesting the existence of a common regulatory control point for PKA action which lies between or downstream of Ras and upstream or at the level of each of these three kinases.

Example 14

This Example describes the determination of whether a similar or distinct MEK activity is involved in activation of MAPK though $G_i$ protein coupled receptors by measuring MEK activity in cell lysates from thrombin stimulated Rat 1a cells.

Thrombin stimulated cells exhibited a MEK activity which co-fractionated with the major MEK peak detected in EGF stimulated cells. The magnitude of MEK activity from thrombin challenged cells was generally two to three-fold less than that observed with EGF stimulation, which correlates with the smaller MAPK response the present inventors have observed in thrombin challenged cells.

Differential regulation of MEK in Rat 1a and NIH3T3 cells expressing gip2, v-src, v-ras, or v-raf led the present inventor to investigate the protein kinases that are putative regulators of MEK-1. Recently, it was shown that Raf-1 can phosphorylate and activate MEK. Raf activation was assayed in the following manner. Cells were serum starved and challenged in the presence or absence of the appropriate growth factors, as described above. Serum starved Rat 1a cells were challenged with buffer alone or with EGF and Raf was immunoprecipitated using an antibody recognizing the C terminus of Raf. Cells were lysed by scraping in ice cold RIPA buffer (50 mM Tris, pH 7.2, 150 mM NaCl, 0.1% SDS, 0.5% sodium deoxycholate, 1.0% Triton X 100, 10 mM sodium pyrophosphate, 25 mM sodium glycerophosphate, 2mM sodium vanadate, 2.1 μg/ml aprotinin) and were microfuged for 10 min to remove nuclei. The supernatants were normalized for protein content and precleared with protein A Sepharose prior to immunoprecipitation with rabbit antiserum to the C terminus of Raf-1 and protein A Sepharose for 2–3 h at 4° C. The beads were washed twice with ice cold RIPA and twice with PAN (10 mM Pipes, pH 7.0, 100 mM NaCl, 21 μg/ml aprotinin). A portion of the immunoprecipitate was diluted with SDS sample buffer and used for immunoblot analysis. The remainder was resuspended in kinase buffer (20 mM Pipes pH 7.0, 10 mM MnCl$_2$, 150 ng kinase-inactive MEK-1, 30 μCi $\gamma$-$^{32}$P-ATP and 20 μg/ml aprotinin) in a final volume of 50 μl for 30 min at 30° C. Wild type recombinant MEK-1 was autophosphorylated in parallel as a marker. Reactions were terminated by the addition of 12.5 μl 5× SDS sample buffer, boiled for 5 minutes and subjected to SDS-PAGE and autoradiography.

The immunoprecipitated Raf, in the presence of $\gamma$-$^{32}$P-ATP, was able to phosphorylate MEK-1. The recombinant MEK-1 used in this assay was kinase inactive to ensure it did not autophosphorylate as is observed with wild type MEK-1. Little or no phosphorylation of MEK-1 by Raf was observed in immunoprecipitates from control cells. EGF challenge clearly stimulated Raf catalyzed phosphorylation of MEK-1; in contrast, thrombin challenge of Rat 1a cells did not measurably activate Raf even though endogenous MEK was clearly activated. EGF stimulated Raf phosphorylation of recombinant MEK-1 by approximately 2.6-fold over basal. Little phosphorylation of MEK by Raf was observed in Raf immunoprecipitates from Gip2 or v-Src expressing Rat 1a cells. EGF stimulation was still capable of activating Raf catalyzed phosphorylation of MEK-1 in these cell lines by 1.8 and 1.4-fold, respectively. The blunting of the EGF response in Gip2 and v-Src expressing cells is likely a result of desensitization of the EGF receptor upon constitutive activation of MAPK. The amount of Raf in the immunoprecipitates was shown to be similar by subsequent SDS-PAGE and immunoblotting using Raf antibody. Since thrombin stimulation of MEK is two to three-fold over basal, at least a 1.5-fold stimulation of MEK phosphorylation is expected if Raf significantly contributed to MEK activation by this growth factor. This level of activation was detectable in the EGF stimulated Gip2 and v-Src expressing cells lines. Thus, it is unlikely that the failure to detect thrombin activation of Raf is due to the sensitivity of the assay. Thrombin stimulation of MAPK is maximal at 3 minutes. Stimulation of Rat 1a cells for 1 or 5 minutes with thrombin did not increase Raf activity.

In NIH3T3 cells, as in Rat 1a cells, EGF activates Raf approximately 2.7-fold, while thrombin does not. V-Raf expressing NIH3T3 cells showed no increase in MEK-1 phosphorylation. This result was unexpected since MEK was clearly activated in v-Raf expressing NIH3T3 cells. Both the p90 and p75 gag-raf fusion proteins in addition to c-Raf-1 were immunoprecipitated from v-Raf NIH3T3 cells by the antisera. P75gag-raf has been shown to exhibit protein kinase activity, but it is possible that the NH$_2$ terminal gag fusion protein sterically hinders Raf phosphorylation of recombinant MEK-1 in the in vitro assay system. Further studies will have to be done to measure v-Raf kinase activity. The results argue that activation of MEK cannot be accounted for exclusively by the activation of Raf. Additional regulatory kinases for MEK must exist which contribute to MEK activation in thrombin stimulated, $G_i$ protein coupled pathways and in gip2 and v-src transfected cells.

Example 15

This Example demonstrates the ability of a PPPSS-trunc and Nco1-trunc of MEKK protein to activate MAPK activity compared with full-length MEKK protein and a negative control protein.

Figure 19:
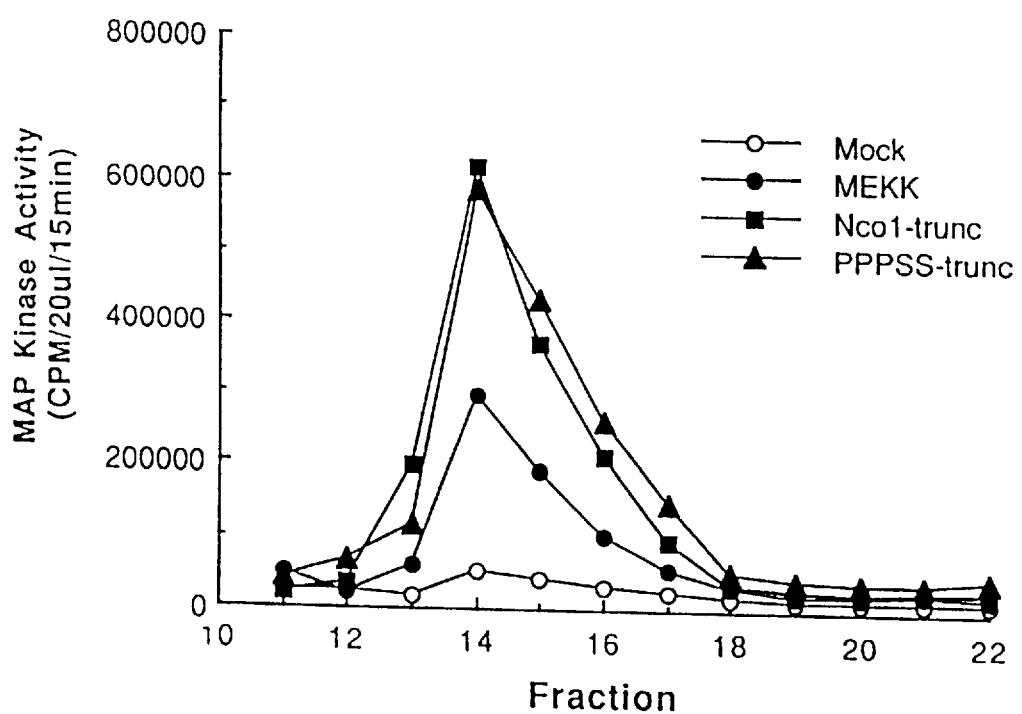
FIG. 19 shows improved MEKK activity by truncated MEKK molecules.

The results shown in FIG. 19 indicate that the truncated MEKK molecules were more active than the full-length MEKK. Indeed, the truncated MEKK molecules were at least about 1.5 times more active than full-length MEKK protein. Thus, removal of the regulatory domain of MEKK deregulates the activity of the catalytic domain resulting in improved enzyme activity.

Example 16

This example describes the preferential activation of JNK by MEKK compared with Raf.

Figure 20:
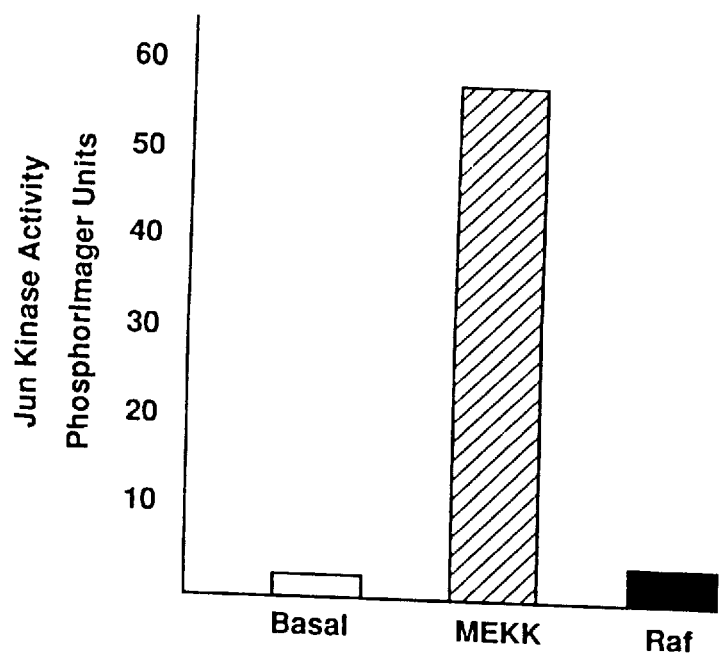
FIG. 20 shows JNK activation by MEKK protein.

HeLa cells were transiently transfected with truncated MEKK$_{370-672}$ under control of an inducible mammary tumor virus promoter, together with epitope tagged JNK1 (described in detail in Derijard et al., p. 1028, 1994, *Cell*, Vol. 76). Other HeLa cells were also transiently transfected with truncated BXB-Raf under control of an inducible mammary tumor virus promoter, together with epitope tagged JNK1 (Derijard et al., ibid.). The following day, MEKK$_{370-672}$ expression and BXB-Raf expression were induced by administration of dexamethasone (10 μM) for 17 hours. Cell extracts were then prepared and assayed for JNK activity using an immune complex kinase assay (detailed in Derijard et al., ibid.). Phosphorylation was quantitated by phosphorimager analysis. The results shown in FIG. 20 indicate that MEKK stimulated about 30-fold to about 50-fold activation more JNK activity over unstimulated cells (basal) and about 15-fold to about 25-fold JNK activity over Raf stimulated cells.

Example 17

This example describes that the phosphorylation of c-Myc transactivation domain in response to MEKK expression activates MYC-GAL 4 transcriptional activity.

Two separate expression plasmids were constructed as follows. The expression plasmid pLNCX was ligated to a cDNA clone comprising c-myc (1–103) ligated to GAL4 (1–147) (Seth et al., pp. 23521–23524, 1993, *J. Biol. Chem.*, Vol. 266) to form the recombinant molecule pMYC-GAL 4. The expression plasmid UAS$_G$-TK Luciferase (Sadowski et al., pp. 563–564, 1988, *Nature*, Vol. 335) was transfected with either pMYC-GAL 4 or pLU-GAL into Swiss 3T3 cells using standard methods in the art to form recombinant cells herein referred to as LU/GAL cells. Recombinant control cells were also produced by transfecting in pGAL4-Control plasmids containing GAL4 (1–147) alone in the absence of c-myc (1–103).

LU/Gal cells were transfected with either pMEKK$_{370-672}$, PMEKK (encoding full-length MEKK$_{1-672}$), BXB-Raf, pMyc-Gal4, pCREB-Gal4 (encoding CREB$_{1-261}$ fused to Gal 4$_{1-147}$; Hoeffler et al., pp. 868–880, 1989, *Mol. Endocrinol.*, Vol. 3), pGal4, or CREB fusion protein referred to as GAL4.

Figure 21:
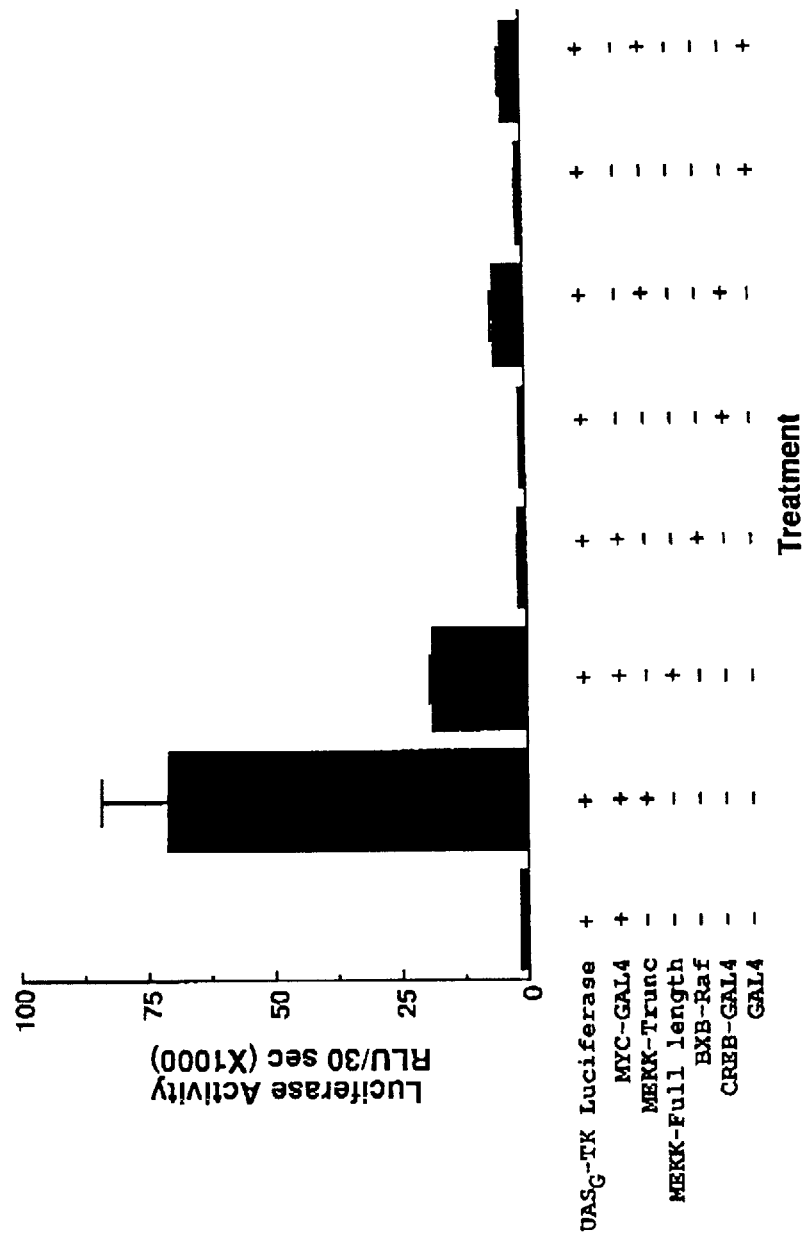
FIG. 21 shows regulation of c-Myc controlled transcription and not CREB controlled transcription by MEKK protein.
Figure 22A:
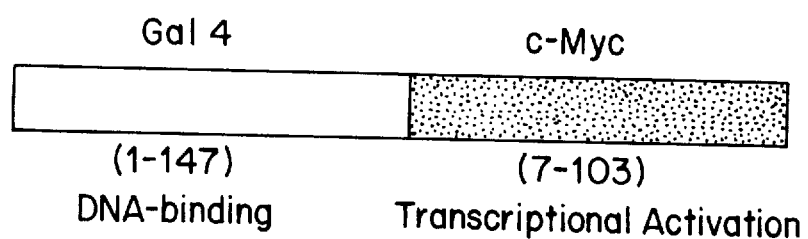
FIG. 22 is a schematic representation of MEKK regulation of c-Myc controlled transcription.
Figure 22B:
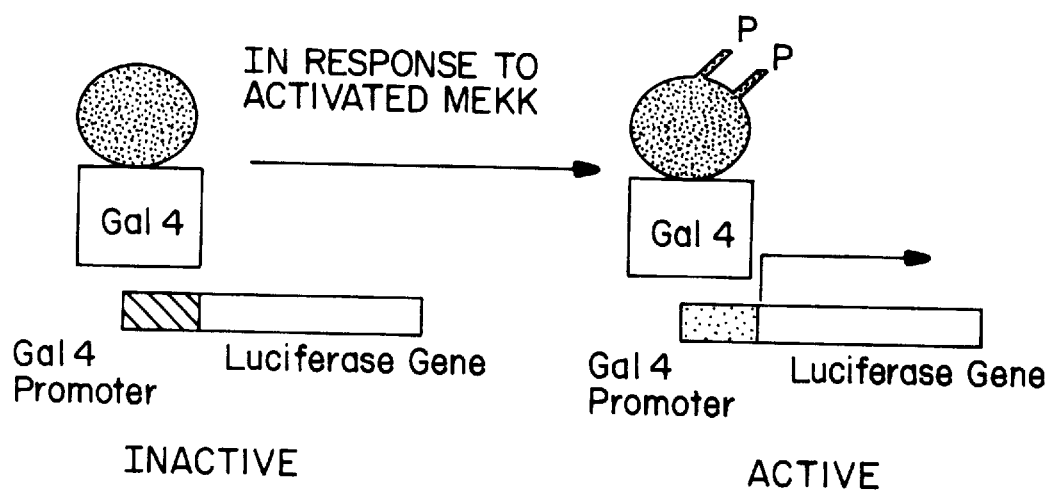
Figures 24A, 24B:
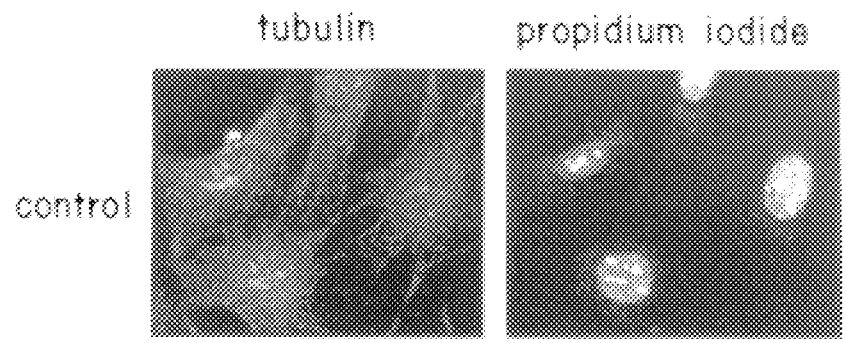
FIG. 24 shows induction of cellular apoptosis in Swiss 3T3 and REF52 cells by beauvericin.
Figures 24C, 24D:
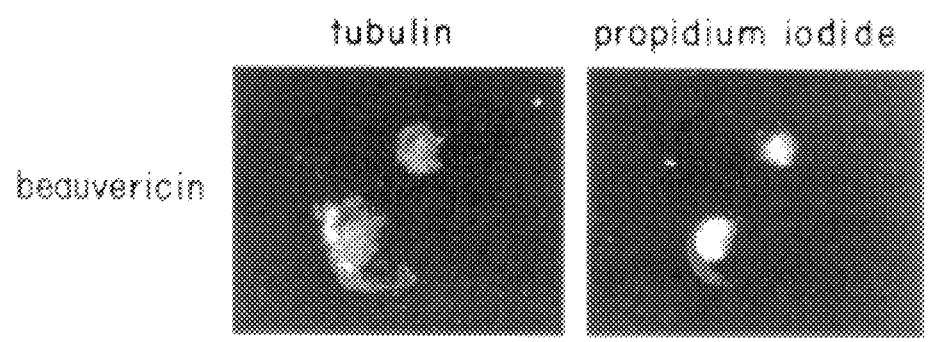
Figures 24E, 24F:
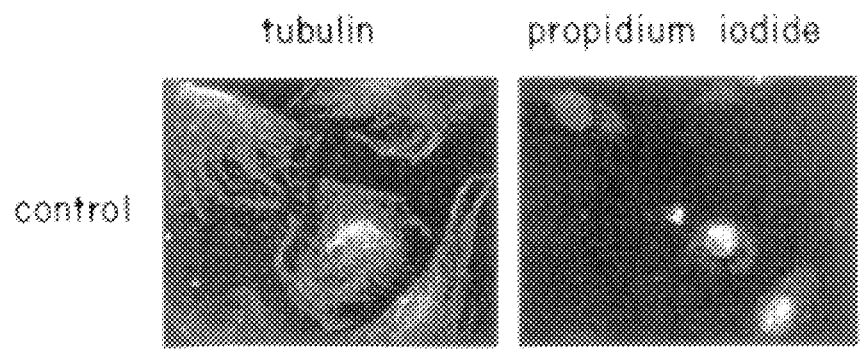
Figures 24G, 24H:
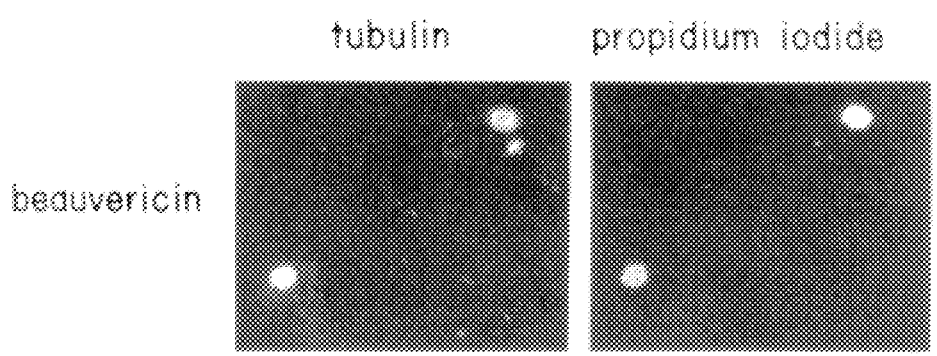

The transfected cells were incubated overnight and then lysed using methods standard in the art. The luciferase activity of each cell lysate was measure on a luminometer. The results shown in FIG. 21 indicate that MEKK is selectively capable of stimulating the phosphorylation of c-Myc transactivation domain in such a manner that the c-Myc domain is activated and induces transcription of the transfected luciferase gene. In addition, the results indicate that MEKK does not stimulate CREB activation. Also, activated Raf is unable to stimulate Myc activation. A schematic representation of the activation mechanism of c-Myc protein by MEKK is shown in FIG. 22.

Example 18

This Example describes the phosphorylation of p38 MAPK protein by MEKK 3 protein and not MEKK 1 protein.

COS cells were transfected with the expression plasmid pCVM5 ligated to cDNA clones encoding either MEKK 1 or MEKK 3 protein, or a control pCVM5 plasmid lacking MEKK cDNA inserts. Forty-eight hours after transfection, the COS cells were lysed and the lysate fractionated on a Mono Q FPLC column using conditions described in Example 4. The fractions were analyzed for tyrosine phosphorylation of MAP kinase-like enzymes using the kinase assay described in Example 4. Referring to FIG. 23, expression of MEKK 3 induces tyrosine phosphorylation of p38 MAPK and the p42 and p44 forms of MAPK. MEKK 1, however, only induces weak phosphorylation of p38 MAPK but does induce phosphorylation of p42 and p44 MAPK.

Example 19

This example describes MEKK-induced apoptosis.

Cells were prepared for the apoptosis studies as follows. Swiss 3T3 cells and REF52 cells were transfected with an expression plasmid encoding β-Galactoctosidase (β-Gal). One set of β-Gal transfected cells were then microinjected with an expression vector encoding MEKK$_{370-672}$ protein. Another set of β-Gal transfected cells were then microinjected with an expression vector encoding truncated BXB-Raf protein.

A. Beauvericin-induced apoptosis

A first group of transfected Swiss 3T3 cells and REF52 cells were treated with 50 μM beauvericin for 6 hours at 37° C. Beauvericin is a compound known to induce apoptosis in mammalian cells. A second group of cells were treated with a control buffer lacking beauvericin. The treated cells were then fixed in paraformaldehyde and permeabilized with saponin using protocols standard in the art. The permeabilized cells were then labelled by incubating the cells with a fluorescein-labelled anti-tubulin antibody (1:500; obtained from GIBCO, Gaithersburg, Md.) to detect cytoplasmic shrinkage or 10 μM propidium iodide (obtained from Sigma, St. Louis, Mo.) to stain DNA to detect nuclear condensation. The labelled cells were then viewed by differential fluorescent imaging using a Nikon Diaphot fluorescent microscope. FIG. 24 shows two fields of Swiss 3T3 cells and REF52 cells, one field representing cells treated with the control buffer and a second field representing cells treated with beauvericin. The cells treated with beauvericin demonstrated cytoplasmic shrinkage (monitored by the anti-tubulin antibodies) and nuclear condensation (monitored by the propidium iodide) characteristic of apoptosis.

B. MEKK-induced apoptosis

Figures 25A, 25B:
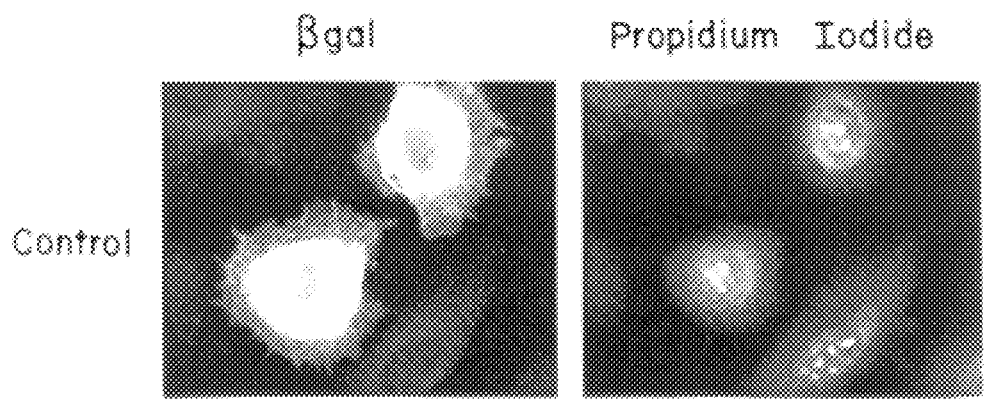
FIG. 25 shows induction of cellular apoptosis in REF52 cells by MEKK.
Figures 25C, 25D:
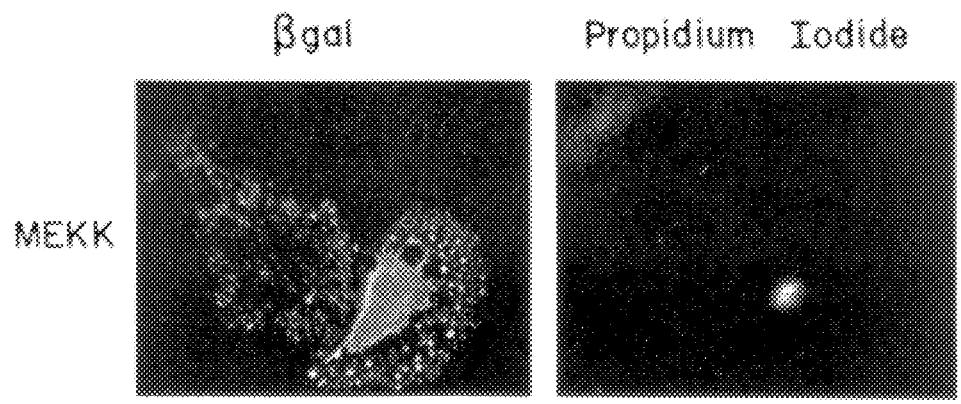
Figures 25E, 25F:
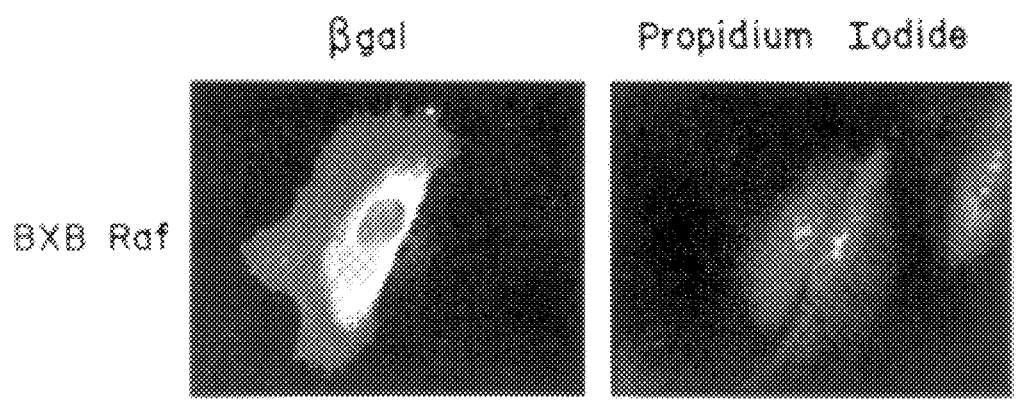
Figures 26A, 26B:
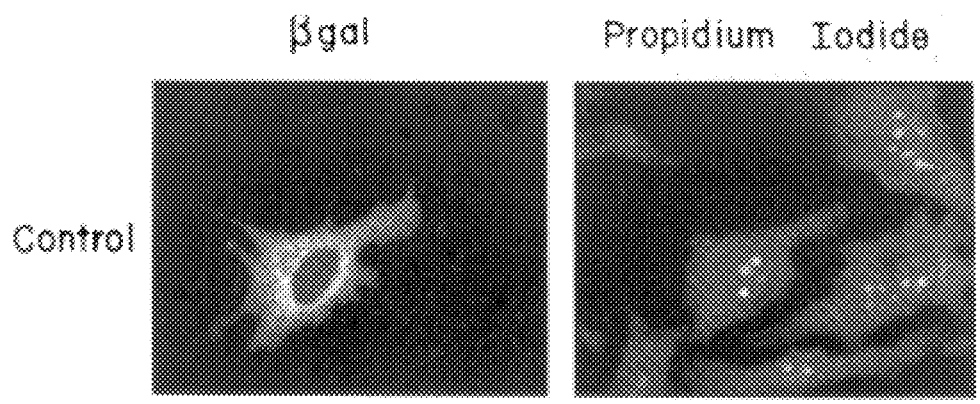
FIG. 26 shows induction of cellular apoptosis in Swiss 3T3 cells by MEKK.
Figures 26C, 26D:
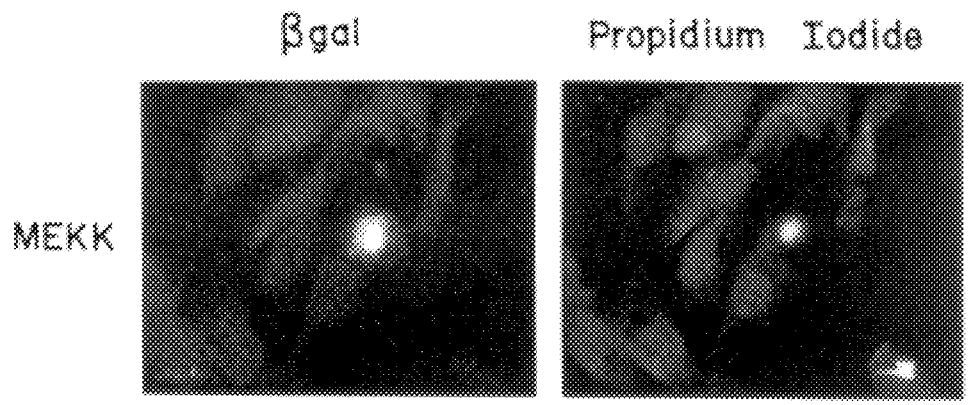
Figures 26E, 26F:
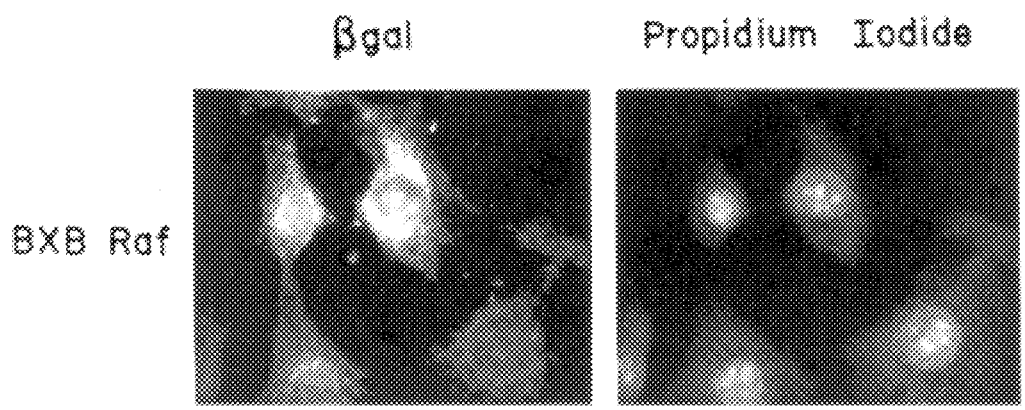
Figure 28A:
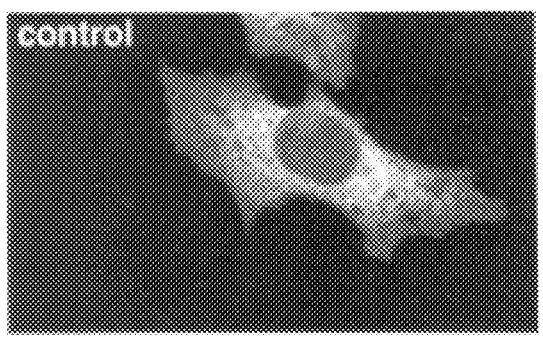
FIG. 28 shows 3 representative microscopic views of apoptotic Swiss 3T3 cells expressing MEKK protein.
Figure 28B:
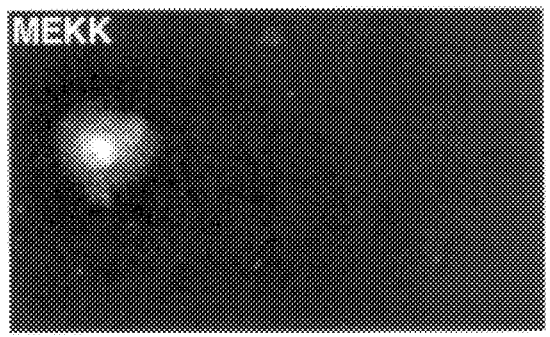
Figure 28C:
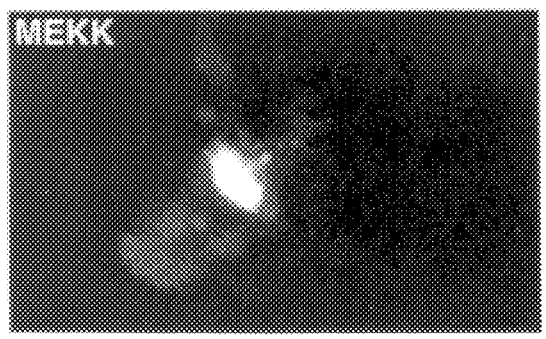
Figure 28D:
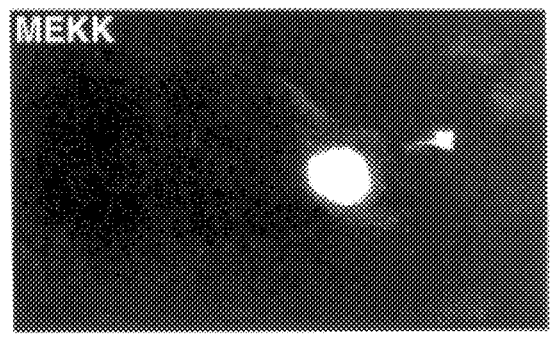

Swiss 3T3 cells and REF52 cells microinjected with a β-galatoctosidase expression plasmid, and an MEKK encoding plasmid or a BXB-Raf encoding plasmid, were treated and viewed using the method described above in Section A. An anti-β-Gal antibody (1:500, obtained from GIBCO, Gaithersburg Md.) was used to detect injected cells. Referring to FIG. 25, microscopic analysis of REF52 cells indicated that the cells expressing MEKK protein underwent cytoplasmic shrinkage and nuclear condensation leading to apoptotic death. In contrast, cells expressing BXB-Raf protein displayed normal morphology and did not undergo apoptosis. Similarly, referring to FIG. 26, microscopic analysis of Swiss 3T3 cells indicated that the cells expressing MEKK protein underwent cytoplasmic shrinkage and nuclear condensation leading to apoptotic death. In contrast, cells expressing BXB-Raf protein displayed normal morphology and did not undergo apoptosis.

FIG. 27 shows 3 representative fields of RFE52 cells expressing MEKK protein which have undergone substantial cytoplasmic shrinkage and nuclear condensation compared with a control cell not expressing MEKK. Similarly, FIG. 28 shows 3 representative fields of Swiss 3T3 cells expressing MEKK protein which have undergone substantial cytoplasmic shrinkage and nuclear condensation compared with a control cell not expressing MEKK. Thus, MEKK and not Raf protein can induce apoptotic programmed cell death.

Example 20

This Example describes regulation of MAPK activity by both MEKK and Raf protein.

COS cells were prepared using the method described in Example 3. In addition, COS cells were transfected with the pCVMV5 Raf construct (1 μg: Raf). FPLC MONO Q ion-exchange column fractions were prepared as described in Example 3 and assayed for MAPK activity according to the method described in Heasley et al., ibid.

Figure 29:
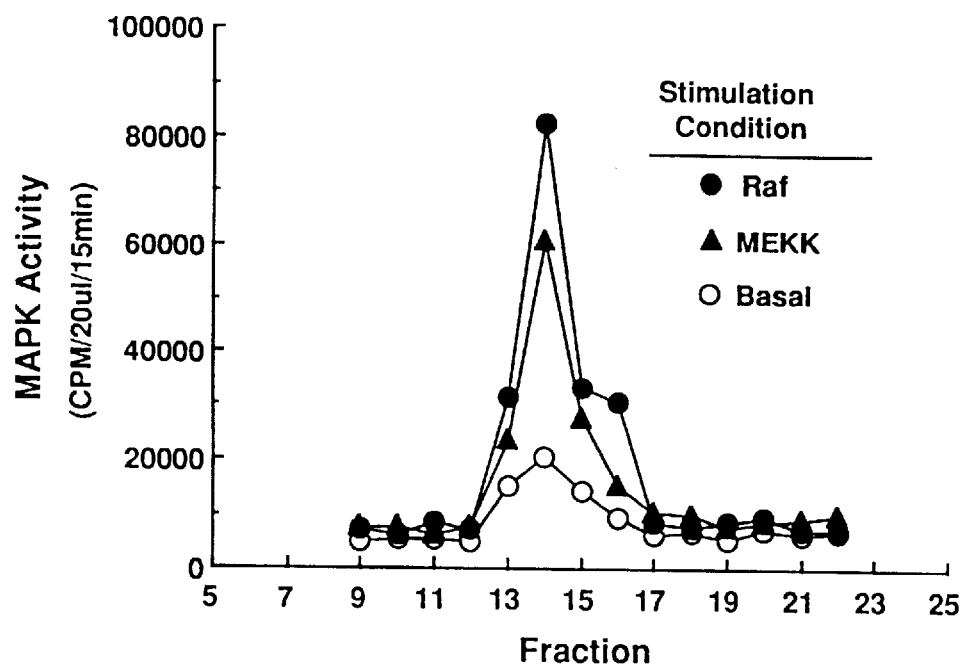
FIG. 29 shows similar stimulation of MAPK activity by MEKK protein and Raf protein.

Referring to FIG. 29, both MEKK and Raf overexpression in COS 1 cells resulted in similar levels of stimulation of MAPK activity over basal levels.

The foregoing description of the invention has been presented for purposes of illustration and description. Further, the description is not intended to limit the invention to the form disclosed herein. Consequently, variations and modifications commensurate with the above teachings, and the skill or knowledge in the relevant art are within the scope of the present invention. The preferred embodiment described herein above is further intended to explain the best mode known of practicing the invention and to enable others skilled in the art to utilize the invention in various embodiments and with various modifications required by their particular applications or uses of the invention. It is intended that the appended claims be construed to include alternate embodiments to the extent permitted by the prior art.

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 3260 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: MEKK
        ( B ) STRAIN: murine ( v i i ) IMMEDIATE SOURCE:
        ( A ) LIBRARY: mouse liver
        ( B ) CLONE: MEKK cDNA ( i x ) FEATURE:
        ( A ) NAME/KEY: 5'UTR
        ( B ) LOCATION: 1..485
        ( A ) NAME/KEY: CDS
        ( B ) LOCATION: 486..2501
        ( A ) NAME/KEY: 3'UTR
        ( B ) LOCATION: 2502..3260

( x i ) SEQUENCE DESCRIPTION: SEQ ID NO:1:

```
TACACTCCTT  GCCACAGTCT  GGCAGAAAGA  ATCAAACTTC  AGAGACTCCT  CCGGCCAGTT        60

GTAGACACTA  TCCTTGTCAA  GTGTGCAGAT  CCAACAGCCG  CACGAGTCAG  CTGTCCATAT       120

CTACAGTGCT  GGAACTCTGC  AAGGGCCAAG  CAGGAGAGCT  GGCGGTTGGG  AGAGAAATAC       180

TTAAAGCTGG  GTCCATCGGG  GTTGGTGGTG  TCGATTACGT  CTTAAGTTGT  ATCCTTGGAA       240

ACCAAGCTGA  ATCAAACAAC  TGGCAAGAAC  TGCTGGGTCG  CCTCTGTCTT  ATAGACAGGT       300

TGCTGTTGGA  ATTTCCTGCT  GAATTCTATC  CTCATATTGT  CAGTACTGAT  GTCTCACAAG       360

CTGAGCCTGT  TGAAATCAGG  TACAAGAAGC  TGCTCTCCCT  CTTAACCTTT  GCCTTGCAAT       420

CCATTGACAA  TTCCCACTCG  ATGGTTGGCA  AGCTCTCTCG  GAGGATATAT  CTGAGCTCTG       480

CCAGG  ATG  GTG  ACC  GCA  GTG  CCC  GCT  GTG  TTT  TCC  AAG  CTG  GTA  ACC       527
       Met  Val  Thr  Ala  Val  Pro  Ala  Val  Phe  Ser  Lys  Leu  Val  Thr
        1              5                        10

ATG  CTT  AAT  GCT  TCT  GGC  TCC  ACC  CAC  TTC  ACC  AGG  ATG  CGC  CGG  CGT       575
Met  Leu  Asn  Ala  Ser  Gly  Ser  Thr  His  Phe  Thr  Arg  Met  Arg  Arg  Arg
 15                   20                   25                        30
```

| | | | | | | | | | | | | | | | | |
|---|---|---|---|---|---|---|---|---|---|---|---|---|---|---|---|---|
| CTG | ATG | GCT | ATC | GCG | GAT | GAG | GTA | GAA | ATT | GCC | GAG | GTC | ATC | CAG | CTG | 623 |
| Leu | Met | Ala | Ile | Ala | Asp | Glu | Val | Glu | Ile | Ala | Glu | Val | Ile | Gln | Leu | |
| | | | 35 | | | | | 40 | | | | | | 45 | | |
| GGT | GTG | GAG | GAC | ACT | GTG | GAT | GGG | CAT | CAG | GAC | AGC | TTA | CAG | GCC | GTG | 671 |
| Gly | Val | Glu | Asp | Thr | Val | Asp | Gly | His | Gln | Asp | Ser | Leu | Gln | Ala | Val | |
| | | | | 50 | | | | | 55 | | | | | 60 | | |
| GCC | CCC | ACC | AGC | TGT | CTA | GAA | AAC | AGC | TCC | CTT | GAG | CAC | ACA | GTC | CAT | 719 |
| Ala | Pro | Thr | Ser | Cys | Leu | Glu | Asn | Ser | Ser | Leu | Glu | His | Thr | Val | His | |
| | | | | 65 | | | | | 70 | | | | | 75 | | |
| AGA | GAG | AAA | ACT | GGA | AAA | GGA | CTA | AGT | GCT | ACG | AGA | CTG | AGT | GCC | AGC | 767 |
| Arg | Glu | Lys | Thr | Gly | Lys | Gly | Leu | Ser | Ala | Thr | Arg | Leu | Ser | Ala | Ser | |
| | | 80 | | | | | 85 | | | | | 90 | | | | |
| TCG | GAG | GAC | ATT | TCT | GAC | AGA | CTG | GCC | GGC | GTC | TCT | GTA | GGA | CTT | CCC | 815 |
| Ser | Glu | Asp | Ile | Ser | Asp | Arg | Leu | Ala | Gly | Val | Ser | Val | Gly | Leu | Pro | |
| | 95 | | | | 100 | | | | | 105 | | | | | 110 | |
| AGC | TCA | ACA | ACA | ACA | GAA | CAA | CCA | AAG | CCA | GCG | GTT | CAA | ACA | AAA | GGC | 863 |
| Ser | Ser | Thr | Thr | Thr | Glu | Gln | Pro | Lys | Pro | Ala | Val | Gln | Thr | Lys | Gly | |
| | | | | 115 | | | | | 120 | | | | | 125 | | |
| AGA | CCC | CAC | AGT | CAG | TGT | TTG | AAC | TCC | TCC | CCT | TTG | TCT | CAT | GCT | CAA | 911 |
| Arg | Pro | His | Ser | Gln | Cys | Leu | Asn | Ser | Ser | Pro | Leu | Ser | His | Ala | Gln | |
| | | | 130 | | | | | 135 | | | | | 140 | | | |
| TTA | ATG | TTC | CCA | GCA | CCA | TCA | GCC | CCT | TGT | TCC | TCT | GCC | CCG | TCT | GTC | 959 |
| Leu | Met | Phe | Pro | Ala | Pro | Ser | Ala | Pro | Cys | Ser | Ser | Ala | Pro | Ser | Val | |
| | | 145 | | | | | 150 | | | | | 155 | | | | |
| CCA | GAT | ATT | TCT | AAG | CAC | AGA | CCC | CAG | GCA | TTT | GTT | CCC | TGC | AAA | ATA | 1007 |
| Pro | Asp | Ile | Ser | Lys | His | Arg | Pro | Gln | Ala | Phe | Val | Pro | Cys | Lys | Ile | |
| | 160 | | | | | 165 | | | | | 170 | | | | | |
| CCT | TCC | GCA | TCT | CCT | CAG | ACA | CAG | CGC | AAG | TTC | TCT | CTA | CAA | TTC | CAG | 1055 |
| Pro | Ser | Ala | Ser | Pro | Gln | Thr | Gln | Arg | Lys | Phe | Ser | Leu | Gln | Phe | Gln | |
| 175 | | | | | 180 | | | | | 185 | | | | | 190 | |
| AGG | AAC | TGC | TCT | GAA | CAC | CGA | GAC | TCA | GAC | CAG | CTC | TCC | CCA | GTC | TTC | 1103 |
| Arg | Asn | Cys | Ser | Glu | His | Arg | Asp | Ser | Asp | Gln | Leu | Ser | Pro | Val | Phe | |
| | | | | 195 | | | | | 200 | | | | | 205 | | |
| ACT | CAG | TCA | AGA | CCC | CCA | CCC | TCC | AGT | AAC | ATA | CAC | AGG | CCA | AAG | CCA | 1151 |
| Thr | Gln | Ser | Arg | Pro | Pro | Pro | Ser | Ser | Asn | Ile | His | Arg | Pro | Lys | Pro | |
| | | | 210 | | | | | 215 | | | | | 220 | | | |
| TCC | CGA | CCC | GTT | CCG | GGC | AGT | ACA | AGC | AAA | CTA | GGG | GAC | GCC | ACA | AAA | 1199 |
| Ser | Arg | Pro | Val | Pro | Gly | Ser | Thr | Ser | Lys | Leu | Gly | Asp | Ala | Thr | Lys | |
| | | 225 | | | | | 230 | | | | | 235 | | | | |
| AGT | AGC | ATG | ACA | CTT | GAT | CTG | GGC | AGT | GCT | TCC | AGG | TGT | GAC | GAC | AGC | 1247 |
| Ser | Ser | Met | Thr | Leu | Asp | Leu | Gly | Ser | Ala | Ser | Arg | Cys | Asp | Asp | Ser | |
| | 240 | | | | | 245 | | | | | 250 | | | | | |
| TTT | GGC | GGC | GGC | GGC | AAC | AGT | GGC | AAC | GCC | GTC | ATA | CCC | AGC | GAC | GAG | 1295 |
| Phe | Gly | Gly | Gly | Gly | Asn | Ser | Gly | Asn | Ala | Val | Ile | Pro | Ser | Asp | Glu | |
| 255 | | | | | 260 | | | | | 265 | | | | | 270 | |
| ACA | GTG | TTC | ACG | CCG | GTG | GAG | GAC | AAG | TGC | AGG | TTA | GAT | GTG | AAC | ACC | 1343 |
| Thr | Val | Phe | Thr | Pro | Val | Glu | Asp | Lys | Cys | Arg | Leu | Asp | Val | Asn | Thr | |
| | | | | 275 | | | | | 280 | | | | | 285 | | |
| GAG | CTC | AAC | TCC | AGC | ATC | GAG | GAC | CTT | CTT | GAA | GCA | TCC | ATG | CCT | TCA | 1391 |
| Glu | Leu | Asn | Ser | Ser | Ile | Glu | Asp | Leu | Leu | Glu | Ala | Ser | Met | Pro | Ser | |
| | | | 290 | | | | | 295 | | | | | 300 | | | |
| AGT | GAC | ACG | ACA | GTC | ACT | TTC | AAG | TCC | GAA | GTC | GCC | GTC | CTC | TCT | CCG | 1439 |
| Ser | Asp | Thr | Thr | Val | Thr | Phe | Lys | Ser | Glu | Val | Ala | Val | Leu | Ser | Pro | |
| | | 305 | | | | | 310 | | | | | 315 | | | | |
| GAA | AAG | GCC | GAA | AAT | GAC | GAC | ACC | TAC | AAA | GAC | GAC | GTC | AAT | CAT | AAT | 1487 |
| Glu | Lys | Ala | Glu | Asn | Asp | Asp | Thr | Tyr | Lys | Asp | Asp | Val | Asn | His | Asn | |
| | 320 | | | | | 325 | | | | | 330 | | | | | |
| CAA | AAG | TGC | AAA | GAA | AAG | ATG | GAA | GCT | GAA | GAG | GAG | GCT | TTA | GCG | | 1535 |
| Gln | Lys | Cys | Lys | Glu | Lys | Met | Glu | Ala | Glu | Glu | Glu | Ala | Leu | Ala | | |
| 335 | | | | | 340 | | | | | 345 | | | | | 350 | |

| | | | | | | | | | | | | | | | | |
|---|---|---|---|---|---|---|---|---|---|---|---|---|---|---|---|---|
| ATC | GCC | ATG | GCG | ATG | TCA | GCG | TCT | CAG | GAT | GCC | CTC | CCC | ATC | GTC | CCT | 1583 |
| Ile | Ala | Met | Ala | Met | Ser | Ala | Ser | Gln | Asp | Ala | Leu | Pro | Ile | Val | Pro | |
| | | | 355 | | | | | 360 | | | | | 365 | | | |
| CAG | CTG | CAG | GTG | GAA | AAT | GGA | GAA | GAT | ATT | ATC | ATC | ATT | CAG | CAG | GAC | 1631 |
| Gln | Leu | Gln | Val | Glu | Asn | Gly | Glu | Asp | Ile | Ile | Ile | Ile | Gln | Gln | Asp | |
| | | | 370 | | | | 375 | | | | | 380 | | | | |
| ACA | CCA | GAA | ACT | CTT | CCA | GGA | CAT | ACC | AAA | GCG | AAA | CAG | CCT | TAC | AGA | 1679 |
| Thr | Pro | Glu | Thr | Leu | Pro | Gly | His | Thr | Lys | Ala | Lys | Gln | Pro | Tyr | Arg | |
| | | 385 | | | | | 390 | | | | | 395 | | | | |
| GAA | GAC | GCT | GAG | TGG | CTG | AAA | GGC | CAG | CAG | ATA | GGC | CTC | GGA | GCA | TTT | 1727 |
| Glu | Asp | Ala | Glu | Trp | Leu | Lys | Gly | Gln | Gln | Ile | Gly | Leu | Gly | Ala | Phe | |
| | | 400 | | | | 405 | | | | | 410 | | | | | |
| TCT | TCC | TGT | TAC | CAA | GCA | CAG | GAT | GTG | GGG | ACT | GGG | ACT | TTA | ATG | GCT | 1775 |
| Ser | Ser | Cys | Tyr | Gln | Ala | Gln | Asp | Val | Gly | Thr | Gly | Thr | Leu | Met | Ala | |
| 415 | | | | 420 | | | | | 425 | | | | | 430 | | |
| GTG | AAA | CAG | GTG | ACG | TAC | GTC | AGA | AAC | ACA | TCC | TCC | GAG | CAG | GAG | GAG | 1823 |
| Val | Lys | Gln | Val | Thr | Tyr | Val | Arg | Asn | Thr | Ser | Ser | Glu | Gln | Glu | Glu | |
| | | | | 435 | | | | 440 | | | | | 445 | | | |
| GTG | GTG | GAA | GCG | TTG | AGG | GAA | GAG | ATC | CGG | ATG | ATG | GGT | CAC | CTC | AAC | 1871 |
| Val | Val | Glu | Ala | Leu | Arg | Glu | Glu | Ile | Arg | Met | Met | Gly | His | Leu | Asn | |
| | | | 450 | | | | 455 | | | | | 460 | | | | |
| CAT | CCA | AAC | ATC | ATC | CGG | ATG | CTG | GGG | GCC | ACG | TGC | GAG | AAG | AGC | AAC | 1919 |
| His | Pro | Asn | Ile | Ile | Arg | Met | Leu | Gly | Ala | Thr | Cys | Glu | Lys | Ser | Asn | |
| | | 465 | | | | | 470 | | | | | 475 | | | | |
| TAC | AAC | CTC | TTC | ATT | GAG | TGG | ATG | GCG | GGA | GGA | TCT | GTG | GCT | CAC | CTC | 1967 |
| Tyr | Asn | Leu | Phe | Ile | Glu | Trp | Met | Ala | Gly | Gly | Ser | Val | Ala | His | Leu | |
| | 480 | | | | | 485 | | | | | 490 | | | | | |
| TTG | AGT | AAA | TAC | GGA | GCT | TTC | AAG | GAG | TCA | GTC | GTC | ATT | AAC | TAC | ACT | 2015 |
| Leu | Ser | Lys | Tyr | Gly | Ala | Phe | Lys | Glu | Ser | Val | Val | Ile | Asn | Tyr | Thr | |
| 495 | | | | | 500 | | | | | 505 | | | | | 510 | |
| GAG | CAG | TTA | CTG | CGT | GGC | CTT | TCC | TAT | CTC | CAC | GAG | AAC | CAG | ATC | ATT | 2063 |
| Glu | Gln | Leu | Leu | Arg | Gly | Leu | Ser | Tyr | Leu | His | Glu | Asn | Gln | Ile | Ile | |
| | | | | 515 | | | | 520 | | | | | 525 | | | |
| CAC | AGA | GAC | GTC | AAA | GGT | GCC | AAC | CTG | CTC | ATT | GAC | AGC | ACC | GGT | CAG | 2111 |
| His | Arg | Asp | Val | Lys | Gly | Ala | Asn | Leu | Leu | Ile | Asp | Ser | Thr | Gly | Gln | |
| | | | 530 | | | | 535 | | | | | 540 | | | | |
| AGG | CTG | AGA | ATT | GCA | GAC | TTT | GGA | GCT | GCT | GCC | AGG | TTG | GCA | TCA | AAA | 2159 |
| Arg | Leu | Arg | Ile | Ala | Asp | Phe | Gly | Ala | Ala | Ala | Arg | Leu | Ala | Ser | Lys | |
| | | 545 | | | | | 550 | | | | | 555 | | | | |
| GGA | ACC | GGT | GCA | GGA | GAG | TTC | CAG | GGA | CAG | TTA | CTG | GGG | ACA | ATT | GCA | 2207 |
| Gly | Thr | Gly | Ala | Gly | Glu | Phe | Gln | Gly | Gln | Leu | Leu | Gly | Thr | Ile | Ala | |
| | 560 | | | | | 565 | | | | | 570 | | | | | |
| TTC | ATG | GCG | CCT | GAG | GTC | CTA | AGA | GGT | CAG | CAG | TAT | GGT | AGG | AGC | TGT | 2255 |
| Phe | Met | Ala | Pro | Glu | Val | Leu | Arg | Gly | Gln | Gln | Tyr | Gly | Arg | Ser | Cys | |
| 575 | | | | | 580 | | | | | 585 | | | | | 590 | |
| GAT | GTA | TGG | AGT | GTT | GGC | TGC | GCC | ATT | ATA | GAA | ATG | GCT | TGT | GCA | AAA | 2303 |
| Asp | Val | Trp | Ser | Val | Gly | Cys | Ala | Ile | Ile | Glu | Met | Ala | Cys | Ala | Lys | |
| | | | | 595 | | | | | 600 | | | | | 605 | | |
| CCA | CCT | TGG | AAT | GCA | GAA | AAA | CAC | TCC | AAT | CAT | CTC | GCC | TTG | ATA | TTT | 2351 |
| Pro | Pro | Trp | Asn | Ala | Glu | Lys | His | Ser | Asn | His | Leu | Ala | Leu | Ile | Phe | |
| | | | 610 | | | | 615 | | | | | 620 | | | | |
| AAG | ATT | GCT | AGC | GCA | ACT | ACT | GCA | CCG | TCC | ATC | CCG | TCA | CAC | CTG | TCC | 2399 |
| Lys | Ile | Ala | Ser | Ala | Thr | Thr | Ala | Pro | Ser | Ile | Pro | Ser | His | Leu | Ser | |
| | | 625 | | | | | 630 | | | | | 635 | | | | |
| CCG | GGT | CTG | CGC | GAC | GTG | GCC | GTG | CGC | TGC | TTA | GAA | CTT | CAG | CCT | CAG | 2447 |
| Pro | Gly | Leu | Arg | Asp | Val | Ala | Val | Arg | Cys | Leu | Glu | Leu | Gln | Pro | Gln | |
| | 640 | | | | 645 | | | | | 650 | | | | | | |
| GAC | CGG | CCT | CCG | TCC | AGA | GAG | CTG | CTG | AAA | CAT | CCG | GTC | TTC | CGT | ACC | 2495 |
| Asp | Arg | Pro | Pro | Ser | Arg | Glu | Leu | Leu | Lys | His | Pro | Val | Phe | Arg | Thr | |
| 655 | | | | | 660 | | | | | 665 | | | | | 670 | |

```
ACG TGG  TAGTTAATTG  TTCAGATCAG  CTCTAATGGA  GACAGGATAT  CGAACCGGGA      2551
Thr Trp

GAGAGAAAAG  AGAACTTGTG  GGCGACCATG  CCGCTAACCG  CAGCCCTCAC  GCCACTGAAC   2611

AGCCAGAAAC  GGGGCCAGCG  GGGAACCGTA  CCTAAGCATG  TGATTGACAA  ATCATGACCT   2671

GTACCTAAGC  TCGATATGCA  GACATCTACA  GCTCGTGCAG  GAACTGCACA  CCGTGCCTTT   2731

CACAGGACTG  GCTCTGGGGG  ACCAGGAAGG  CGATGGAGTT  TGCATGACTA  AAGAACAGAA   2791

GCATAAATTT  ATTTTGGAG   CACTTTTTCA  GCTAATCAGT  ATTACCATGT  ACATCAACAT   2851

GCCCGCCACA  TTTCAAACTC  AGACTGTCCC  AGATGTCAAG  ATCCACTGTG  TTTGAGTTTG   2911

TTTGCAGTTC  CCTCAGCTTG  CTGGTAATTG  TGGTGTTTTG  TTTTCGATGC  AAATGTGATG   2971

TAATATTCTT  ATTTTCTTTG  GATCAAAGCT  GGACTGAAAA  TTGTACTGTG  TAATTATTTT   3031

TGTGTTTTTA  ATGTTATTTG  GTACTCGAAT  TGTAAATAAC  GTCTACTGCT  GTTTATTCCA   3091

GTTCTACTA   CCTCAGGTGT  CCTATAGATT  TTTCTTCTAC  CAAAGTTCAC  TCTCAGAATG   3151

AAATTCTACG  TGCTGTGTGA  CTATGACTCC  TAAGACTTCC  AGGGCTTAAG  GGCTAACTCC   3211

TATTAGCACC  TTACTATGTA  AGCAAATGCT  ACAAAAAAAA  AAAAAAAA                 3260
```

(2) INFORMATION FOR SEQ ID NO:2:

(i) SEQUENCE CHARACTERISTICS:
        (A) LENGTH: 672 amino acids
        (B) TYPE: amino acid
        (D) TOPOLOGY: linear (ii) MOLECULE TYPE: protein (xi) SEQUENCE DESCRIPTION: SEQ ID NO:2:

```
Met Val Thr Ala Val Pro Ala Val Phe Ser Lys Leu Val Thr Met Leu
 1               5                  10                  15

Asn Ala Ser Gly Ser Thr His Phe Thr Arg Met Arg Arg Arg Leu Met
             20                  25                  30

Ala Ile Ala Asp Glu Val Glu Ile Ala Glu Val Ile Gln Leu Gly Val
         35                  40                  45

Glu Asp Thr Val Asp Gly His Gln Asp Ser Leu Gln Ala Val Ala Pro
     50                  55                  60

Thr Ser Cys Leu Glu Asn Ser Ser Leu Glu His Thr Val His Arg Glu
 65                  70                  75                  80

Lys Thr Gly Lys Gly Leu Ser Ala Thr Arg Leu Ser Ala Ser Ser Glu
                 85                  90                  95

Asp Ile Ser Asp Arg Leu Ala Gly Val Ser Val Gly Leu Pro Ser Ser
            100                 105                 110

Thr Thr Thr Glu Gln Pro Lys Pro Ala Val Gln Thr Lys Gly Arg Pro
        115                 120                 125

His Ser Gln Cys Leu Asn Ser Ser Pro Leu Ser His Ala Gln Leu Met
    130                 135                 140

Phe Pro Ala Pro Ser Ala Pro Cys Ser Ser Ala Pro Ser Val Pro Asp
145                 150                 155                 160

Ile Ser Lys His Arg Pro Gln Ala Phe Val Pro Cys Lys Ile Pro Ser
                165                 170                 175

Ala Ser Pro Gln Thr Gln Arg Lys Phe Ser Leu Gln Phe Gln Arg Asn
            180                 185                 190

Cys Ser Glu His Arg Asp Ser Asp Gln Leu Ser Pro Val Phe Thr Gln
        195                 200                 205
```

| | | | | | | | | | | | | | | |
|---|---|---|---|---|---|---|---|---|---|---|---|---|---|---|
| Ser | Arg 210 | Pro | Pro | Pro | Ser | Ser 215 | Asn | Ile | His | Arg | Pro 220 | Lys | Pro | Ser | Arg |
| Pro 225 | Val | Pro | Gly | Ser | Thr 230 | Ser | Lys | Leu | Gly | Asp 235 | Ala | Thr | Lys | Ser | Ser 240 |
| Met | Thr | Leu | Asp | Leu 245 | Gly | Ser | Ala | Ser | Arg 250 | Cys | Asp | Asp | Ser | Phe 255 | Gly |
| Gly | Gly | Gly | Asn 260 | Ser | Gly | Asn | Ala | Val 265 | Ile | Pro | Ser | Asp | Glu 270 | Thr | Val |
| Phe | Thr | Pro 275 | Val | Glu | Asp | Lys | Cys 280 | Arg | Leu | Asp | Val | Asn 285 | Thr | Glu | Leu |
| Asn | Ser 290 | Ser | Ile | Glu | Asp | Leu 295 | Leu | Glu | Ala | Ser | Met 300 | Pro | Ser | Ser | Asp |
| Thr 305 | Thr | Val | Thr | Phe | Lys 310 | Ser | Glu | Val | Ala | Val 315 | Leu | Ser | Pro | Glu | Lys 320 |
| Ala | Glu | Asn | Asp | Asp 325 | Thr | Tyr | Lys | Asp | Asp 330 | Val | Asn | His | Asn | Gln 335 | Lys |
| Cys | Lys | Glu | Lys 340 | Met | Glu | Ala | Glu | Glu 345 | Glu | Ala | Leu | Ala 350 | Ile | Ala |
| Met | Ala | Met 355 | Ser | Ala | Ser | Gln | Asp 360 | Ala | Leu | Pro | Ile | Val 365 | Pro | Gln | Leu |
| Gln | Val 370 | Glu | Asn | Gly | Glu | Asp 375 | Ile | Ile | Ile | Ile | Gln 380 | Gln | Asp | Thr | Pro |
| Glu 385 | Thr | Leu | Pro | Gly | His 390 | Thr | Lys | Ala | Lys | Gln 395 | Pro | Tyr | Arg | Glu | Asp 400 |
| Ala | Glu | Trp | Leu | Lys 405 | Gly | Gln | Gln | Ile | Gly 410 | Leu | Gly | Ala | Phe | Ser 415 | Ser |
| Cys | Tyr | Gln | Ala 420 | Gln | Asp | Val | Gly | Thr 425 | Gly | Thr | Leu | Met | Ala 430 | Val | Lys |
| Gln | Val | Thr 435 | Tyr | Val | Arg | Asn | Thr 440 | Ser | Ser | Glu | Gln | Glu 445 | Glu | Val | Val |
| Glu | Ala 450 | Leu | Arg | Glu | Glu | Ile 455 | Arg | Met | Met | Gly | His 460 | Leu | Asn | His | Pro |
| Asn 465 | Ile | Ile | Arg | Met | Leu 470 | Gly | Ala | Thr | Cys | Glu 475 | Lys | Ser | Asn | Tyr | Asn 480 |
| Leu | Phe | Ile | Glu | Trp 485 | Met | Ala | Gly | Gly | Ser 490 | Val | Ala | His | Leu | Leu 495 | Ser |
| Lys | Tyr | Gly | Ala 500 | Phe | Lys | Glu | Ser | Val 505 | Val | Ile | Asn | Tyr | Thr 510 | Glu | Gln |
| Leu | Leu | Arg 515 | Gly | Leu | Ser | Tyr | Leu 520 | His | Glu | Asn | Gln | Ile 525 | Ile | His | Arg |
| Asp | Val 530 | Lys | Gly | Ala | Asn 535 | Leu | Leu | Ile | Asp | Ser 540 | Thr | Gly | Gln | Arg | Leu |
| Arg 545 | Ile | Ala | Asp | Phe | Gly 550 | Ala | Ala | Ala | Arg | Leu 555 | Ala | Ser | Lys | Gly | Thr 560 |
| Gly | Ala | Gly | Glu | Phe 565 | Gln | Gly | Gln | Leu | Leu 570 | Gly | Thr | Ile | Ala | Phe 575 | Met |
| Ala | Pro | Glu | Val 580 | Leu | Arg | Gly | Gln | Gln 585 | Tyr | Gly | Arg | Ser | Cys 590 | Asp | Val |
| Trp | Ser | Val 595 | Gly | Cys | Ala | Ile | Ile 600 | Glu | Met | Ala | Cys | Ala 605 | Lys | Pro | Pro |
| Trp | Asn 610 | Ala | Glu | Lys | His | Ser 615 | Asn | His | Leu | Ala | Leu 620 | Ile | Phe | Lys | Ile |
| Ala 625 | Ser | Ala | Thr | Thr | Ala 630 | Pro | Ser | Ile | Pro | Ser 635 | His | Leu | Ser | Pro | Gly 640 |

| Leu | Arg | Asp | Val | Ala | Val | Arg | Cys | Leu | Glu | Leu | Gln | Pro | Gln | Asp | Arg |
|---|---|---|---|---|---|---|---|---|---|---|---|---|---|---|---|
| | | | | 645 | | | | | 650 | | | | | 655 | |

| Pro | Pro | Ser | Arg | Glu | Leu | Leu | Lys | His | Pro | Val | Phe | Arg | Thr | Thr | Trp |
|---|---|---|---|---|---|---|---|---|---|---|---|---|---|---|---|
| | | | 660 | | | | | 665 | | | | | 670 | | |

(2) INFORMATION FOR SEQ ID NO:3:

(i) SEQUENCE CHARACTERISTICS:
        (A) LENGTH: 2503 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 466..2325

(xi) SEQUENCE DESCRIPTION: SEQ ID NO:3:

```
GGTGGCGGCC GCTCTAGAAC TAGTGGATCC CCCGGGCTGC AGGAATTCGG CACGAGGGAC    60

GATCCAGCGG CAGAGTCGCC GCTTCCGCTT CGCTGCTTCT CCGGTCGGCG ACGCGGGCCC   120

GGGGCTTCCT TTTCATCGGC CCAGCTTATT CCGCGGGCCC CGGGGCTGCA GCTACCCAGA   180

AGCGGCGAAG AGGCCCTGGG CTGCGCGCCC GCTGTCCCAT GTGAAGCAGG TTGGGCCTGG   240

TCCCCGGCCC GTGCCCGGTT GTCTGCGGCC CTTCAGGCCT CAGGGACCCC CGCGAGGCGC   300

TGCTCCTGGG GGGCGCGGTG ACAGGCCGTG CGGGGCGGA  GGGGCCAGCT CGGTGGCCTC   360

CTCTCGGCCC TCGCGTCCGC GATCCCGCCC AGCGGCCGGG CAATAAAGAA TGTTGATGGG   420

AGAACCATTT TCCTAATTTT CAAATTATTG AGCTGGTCGC GCATA ATG GAT GAT       474
                                             Met Asp Asp
                                              1
```

| CAG | CAA | GCT | TTG | AAT | TCA | ATC | ATG | CAA | GAT | TTG | GCT | GTC | CTT | CAT | AAG | 522 |
|---|---|---|---|---|---|---|---|---|---|---|---|---|---|---|---|---|
| Gln | Gln | Ala | Leu | Asn | Ser | Ile | Met | Gln | Asp | Leu | Ala | Val | Leu | His | Lys | |
| | 5 | | | | | 10 | | | | | 15 | | | | | |

| CCA | GTC | GGC | CAG | CAT | TAT | CTT | TAC | AAG | AAA | CCA | GGA | AAG | CAA | AAC | CTT | 570 |
|---|---|---|---|---|---|---|---|---|---|---|---|---|---|---|---|---|
| Pro | Val | Gly | Gln | His | Tyr | Leu | Tyr | Lys | Lys | Pro | Gly | Lys | Gln | Asn | Leu | |
| 20 | | | | | 25 | | | | | 30 | | | | | 35 | |

| CAT | CAC | CAA | AAA | AAC | AGA | ATG | ATG | TTC | GAG | TCA | AAT | TTG | AAC | ATA | GAG | 618 |
|---|---|---|---|---|---|---|---|---|---|---|---|---|---|---|---|---|
| His | His | Gln | Lys | Asn | Arg | Met | Met | Phe | Glu | Ser | Asn | Leu | Asn | Ile | Glu | |
| | | | | 40 | | | | | 45 | | | | | 50 | | |

| GAG | GAA | AAA | AGG | ATC | CTG | CAG | GTT | ACT | AGA | CCA | GTT | AAA | CTA | GAA | GAC | 666 |
|---|---|---|---|---|---|---|---|---|---|---|---|---|---|---|---|---|
| Glu | Glu | Lys | Arg | Ile | Leu | Gln | Val | Thr | Arg | Pro | Val | Lys | Leu | Glu | Asp | |
| | | | 55 | | | | | 60 | | | | | 65 | | | |

| CTG | AGA | TCT | AAG | TCT | AAG | ATC | GCC | TTT | GGG | CAG | TCT | ATG | GAT | CTA | CAC | 714 |
|---|---|---|---|---|---|---|---|---|---|---|---|---|---|---|---|---|
| Leu | Arg | Ser | Lys | Ser | Lys | Ile | Ala | Phe | Gly | Gln | Ser | Met | Asp | Leu | His | |
| | | 70 | | | | | 75 | | | | | 80 | | | | |

| TAT | ACC | AAC | AAT | GAG | TTG | GTA | ATT | CCG | TTA | ACT | ACC | CAA | GAT | GAC | TTG | 762 |
|---|---|---|---|---|---|---|---|---|---|---|---|---|---|---|---|---|
| Tyr | Thr | Asn | Asn | Glu | Leu | Val | Ile | Pro | Leu | Thr | Thr | Gln | Asp | Asp | Leu | |
| | 85 | | | | | 90 | | | | | 95 | | | | | |

| GAC | AAA | GCT | GTG | GAA | CTG | CTG | GAT | CGC | AGT | ATT | CAC | ATG | AAG | AGT | CTC | 810 |
|---|---|---|---|---|---|---|---|---|---|---|---|---|---|---|---|---|
| Asp | Lys | Ala | Val | Glu | Leu | Leu | Asp | Arg | Ser | Ile | His | Met | Lys | Ser | Leu | |
| 100 | | | | | 105 | | | | | 110 | | | | | 115 | |

| AAG | ATA | TTA | CTT | GTA | GTA | AAT | GGG | AGT | ACA | CAG | GCT | ACT | AAT | TTA | GAA | 858 |
|---|---|---|---|---|---|---|---|---|---|---|---|---|---|---|---|---|
| Lys | Ile | Leu | Leu | Val | Val | Asn | Gly | Ser | Thr | Gln | Ala | Thr | Asn | Leu | Glu | |
| | | | | 120 | | | | | 125 | | | | | 130 | | |

| CCA | TCA | CCG | TCA | CCA | GAA | GAT | TTG | AAT | AAT | ACA | CCA | CTT | GGT | GCA | GAG | 906 |
|---|---|---|---|---|---|---|---|---|---|---|---|---|---|---|---|---|
| Pro | Ser | Pro | Ser | Pro | Glu | Asp | Leu | Asn | Asn | Thr | Pro | Leu | Gly | Ala | Glu | |
| | | 135 | | | | | 140 | | | | | 145 | | | | |

| | | | | | | | | | | | | | | | | |
|---|---|---|---|---|---|---|---|---|---|---|---|---|---|---|---|---|
| AGG | AAA | AAG | CGG | CTA | TCT | GTA | GTA | GGT | CCC | CCT | AAT | AGG | GAT | AGA | AGT | 954 |
| Arg | Lys | Lys | Arg | Leu | Ser | Val | Val | Gly | Pro | Pro | Asn | Arg | Asp | Arg | Ser | |
| | 150 | | | | | 155 | | | | | 160 | | | | | |
| TCC | CCT | CCT | CCA | GGA | TAC | ATT | CCA | GAC | ATA | CTA | CAC | CAG | ATT | GCC | CGG | 1002 |
| Ser | Pro | Pro | Pro | Gly | Tyr | Ile | Pro | Asp | Ile | Leu | His | Gln | Ile | Ala | Arg | |
| 165 | | | | | 170 | | | | | | 175 | | | | | |
| AAT | GGG | TCA | TTC | ACT | AGC | ATC | AAC | AGT | GAA | GGA | GAG | TTC | ATT | CCA | GAG | 1050 |
| Asn | Gly | Ser | Phe | Thr | Ser | Ile | Asn | Ser | Glu | Gly | Glu | Phe | Ile | Pro | Glu | |
| 180 | | | | | 185 | | | | | 190 | | | | | 195 | |
| AGC | ATG | GAC | CAA | ATG | CTG | GAT | CCA | TTG | TCT | TTA | AGC | AGC | CCT | GAA | AAT | 1098 |
| Ser | Met | Asp | Gln | Met | Leu | Asp | Pro | Leu | Ser | Leu | Ser | Ser | Pro | Glu | Asn | |
| | | | | 200 | | | | | 205 | | | | | 210 | | |
| TCT | GGC | TCA | GGA | AGC | TGT | CCG | TCA | CTT | GAT | AGT | CCT | TTG | GAT | GGA | GAA | 1146 |
| Ser | Gly | Ser | Gly | Ser | Cys | Pro | Ser | Leu | Asp | Ser | Pro | Leu | Asp | Gly | Glu | |
| | | | 215 | | | | 220 | | | | | 225 | | | | |
| AGC | TAC | CCA | AAA | TCA | CGG | ATG | CCT | AGG | GCA | CAG | AGC | TAC | CCA | GAT | AAT | 1194 |
| Ser | Tyr | Pro | Lys | Ser | Arg | Met | Pro | Arg | Ala | Gln | Ser | Tyr | Pro | Asp | Asn | |
| | | 230 | | | | | 235 | | | | | 240 | | | | |
| CAT | CAG | GAG | TTT | ACA | GAC | TAT | GAT | AAC | CCC | ATT | TTT | GAG | AAA | TTT | GGA | 1242 |
| His | Gln | Glu | Phe | Thr | Asp | Tyr | Asp | Asn | Pro | Ile | Phe | Glu | Lys | Phe | Gly | |
| 245 | | | | | 250 | | | | | | 255 | | | | | |
| AAA | GGA | GGA | ACA | TAT | CCA | AGA | AGG | TAC | CAC | GTT | TCC | TAT | CAT | CAC | CAG | 1290 |
| Lys | Gly | Gly | Thr | Tyr | Pro | Arg | Arg | Tyr | His | Val | Ser | Tyr | His | His | Gln | |
| 260 | | | | | 265 | | | | | 270 | | | | | 275 | |
| GAG | TAT | AAT | GAC | GGT | CGG | AAG | ACT | TTC | CCA | AGA | GCT | AGA | AGG | ACC | CAG | 1338 |
| Glu | Tyr | Asn | Asp | Gly | Arg | Lys | Thr | Phe | Pro | Arg | Ala | Arg | Arg | Thr | Gln | |
| | | | | 280 | | | | | 285 | | | | | 290 | | |
| GGC | ACC | AGT | TTC | CGG | TCT | CCT | GTG | AGC | TTC | AGT | CCT | ACT | GAT | CAC | TCC | 1386 |
| Gly | Thr | Ser | Phe | Arg | Ser | Pro | Val | Ser | Phe | Ser | Pro | Thr | Asp | His | Ser | |
| | | | 295 | | | | 300 | | | | | 305 | | | | |
| TTA | AGC | ACT | AGT | AGT | GGA | AGC | AGT | GTC | TTT | ACC | CCA | GAG | TAT | GAC | GAC | 1434 |
| Leu | Ser | Thr | Ser | Ser | Gly | Ser | Ser | Val | Phe | Thr | Pro | Glu | Tyr | Asp | Asp | |
| | | 310 | | | | | 315 | | | | | 320 | | | | |
| AGT | CGA | ATA | AGA | AGA | CGG | GGG | AGT | GAC | ATA | GAC | AAT | CCT | ACT | TTG | ACT | 1482 |
| Ser | Arg | Ile | Arg | Arg | Arg | Gly | Ser | Asp | Ile | Asp | Asn | Pro | Thr | Leu | Thr | |
| | 325 | | | | | 330 | | | | | 335 | | | | | |
| GTC | ACA | GAC | ATC | AGC | CCA | CCC | AGC | CGT | TCA | CCT | CGA | GCT | CCG | ACC | AAC | 1530 |
| Val | Thr | Asp | Ile | Ser | Pro | Pro | Ser | Arg | Ser | Pro | Arg | Ala | Pro | Thr | Asn | |
| 340 | | | | | 345 | | | | | 350 | | | | | 355 | |
| TGG | AGA | CTG | GGC | AAG | CTG | CTT | GGC | CAA | GGA | GCT | TTT | GGT | AGG | GTC | TAC | 1578 |
| Trp | Arg | Leu | Gly | Lys | Leu | Leu | Gly | Gln | Gly | Ala | Phe | Gly | Arg | Val | Tyr | |
| | | | | 360 | | | | | 365 | | | | | 370 | | |
| CTC | TGC | TAT | GAT | GTT | GAT | ACC | GGA | AGA | GAG | CTG | GCT | GTT | AAG | CAA | GTT | 1626 |
| Leu | Cys | Tyr | Asp | Val | Asp | Thr | Gly | Arg | Glu | Leu | Ala | Val | Lys | Gln | Val | |
| | | | 375 | | | | 380 | | | | | 385 | | | | |
| CAG | TTT | AAC | CCT | GAG | AGC | CCA | GAG | ACC | AGC | AAG | GAA | GTA | AAT | GCA | CTT | 1674 |
| Gln | Phe | Asn | Pro | Glu | Ser | Pro | Glu | Thr | Ser | Lys | Glu | Val | Asn | Ala | Leu | |
| | | 390 | | | | | 395 | | | | | 400 | | | | |
| GAG | TGT | GAA | ATT | CAG | TTG | TTG | AAA | AAC | TTG | TTG | CAT | GAG | CGA | ATT | GTT | 1722 |
| Glu | Cys | Glu | Ile | Gln | Leu | Leu | Lys | Asn | Leu | Leu | His | Glu | Arg | Ile | Val | |
| | 405 | | | | | 410 | | | | | 415 | | | | | |
| CAG | TAT | TAT | GGC | TGT | TTG | AGG | GAT | CCT | CAG | GAG | AAA | ACA | CTT | TCC | ATC | 1770 |
| Gln | Tyr | Tyr | Gly | Cys | Leu | Arg | Asp | Pro | Gln | Glu | Lys | Thr | Leu | Ser | Ile | |
| 420 | | | | | 425 | | | | | 430 | | | | | 435 | |
| TTT | ATG | GAG | CTC | TCG | CCA | GGG | GGT | TCA | ATT | AAG | GAC | CAA | CTA | AAA | GCC | 1818 |
| Phe | Met | Glu | Leu | Ser | Pro | Gly | Gly | Ser | Ile | Lys | Asp | Gln | Leu | Lys | Ala | |
| | | | | 440 | | | | | 445 | | | | | 450 | | |
| TAC | GGA | GCT | CTT | ACT | GAG | AAC | GTG | ACG | AGG | AAG | TAC | ACC | CGT | CAG | ATT | 1866 |
| Tyr | Gly | Ala | Leu | Thr | Glu | Asn | Val | Thr | Arg | Lys | Tyr | Thr | Arg | Gln | Ile | |
| | | | 455 | | | | | 460 | | | | | 465 | | | |

| | | | | | | | | | | | | | | | |
|---|---|---|---|---|---|---|---|---|---|---|---|---|---|---|---|
|CTG|GAG|GGG|GTC|CAT|TAT|TTG|CAT|AGT|AAT|ATG|ATT|GTC|CAT|AGA|GAT|1914
|Leu|Glu|Gly|Val|His|Tyr|Leu|His|Ser|Asn|Met|Ile|Val|His|Arg|Asp|
| | |470| | | |475| | | |480| | | | | |
|ATC|AAA|GGA|GCA|AAT|ATC|TTA|AGG|GAT|TCC|ACA|GGC|AAT|ATC|AAG|TTA|1962
|Ile|Lys|Gly|Ala|Asn|Ile|Leu|Arg|Asp|Ser|Thr|Gly|Asn|Ile|Lys|Leu|
| |485| | | | |490| | | | |495| | | | |
|GGA|GAC|TTT|GGG|GCT|AGT|AAA|CGG|CTT|CAG|ACC|ATC|TGT|CTC|TCA|GGC|2010
|Gly|Asp|Phe|Gly|Ala|Ser|Lys|Arg|Leu|Gln|Thr|Ile|Cys|Leu|Ser|Gly|
|500| | | | |505| | | | |510| | | | |515|
|ACA|GGA|ATG|AAG|TCT|GTC|ACA|GGC|ACG|CCA|TAC|TGG|ATG|AGT|CCT|GAG|2058
|Thr|Gly|Met|Lys|Ser|Val|Thr|Gly|Thr|Pro|Tyr|Trp|Met|Ser|Pro|Glu|
| | | | |520| | | | |525| | | | |530| |
|GTC|ATC|AGT|GGA|GAA|GGC|TAT|GGA|AGA|AAA|GCA|GAC|ATC|TGG|AGT|GTA|2106
|Val|Ile|Ser|Gly|Glu|Gly|Tyr|Gly|Arg|Lys|Ala|Asp|Ile|Trp|Ser|Val|
| | | |535| | | | |540| | | | |545| | |
|GCA|TGT|ACT|GTG|GTA|GAA|ATG|CTA|ACT|GAA|AAG|CCA|CCT|TGG|GCT|GAA|2154
|Ala|Cys|Thr|Val|Val|Glu|Met|Leu|Thr|Glu|Lys|Pro|Pro|Trp|Ala|Glu|
| | |550| | | | |555| | | | |560| | | |
|TTT|GAA|GCA|ATG|GCT|GCC|ATC|TTT|AAG|ATC|GCC|ACT|CAG|CCA|ACG|AAC|2202
|Phe|Glu|Ala|Met|Ala|Ala|Ile|Phe|Lys|Ile|Ala|Thr|Gln|Pro|Thr|Asn|
| |565| | | | |570| | | | |575| | | | |
|CCA|AAG|CTG|CCA|CCT|CAT|GTC|TCA|GAC|TAT|ACT|CGG|GAC|TTC|CTC|AAA|2250
|Pro|Lys|Leu|Pro|Pro|His|Val|Ser|Asp|Tyr|Thr|Arg|Asp|Phe|Leu|Lys|
|580| | | | |585| | | | |590| | | | |595|
|CGG|ATT|TTT|GTA|GAG|GCC|AAA|CTT|CGA|CCT|TCA|GCG|GAG|GAG|CTC|TTG|2298
|Arg|Ile|Phe|Val|Glu|Ala|Lys|Leu|Arg|Pro|Ser|Ala|Glu|Glu|Leu|Leu|
| | | |600| | | | |605| | | | |610| | |
|CGG|CAC|ATG|TTT|GTG|CAT|TAT|CAC|TAGCAGCGGC|GGCTTCGGTC|CTCCACCAGC| | | | | |2352
|Arg|His|Met|Phe|Val|His|Tyr|His| | | | | | | | |
| | | |615| | | |620| | | | | | | | |

TCCATCCTCG CGGCCACCTT CTCTCTTACT GCACTTTCCT TTTTTATAAA AAAGAGAGAT        2412

GGGGAGAAAA AGACAAGAGG GAAAATATTT CTCTTGATTC TTGGTTAAAT TTGTTTAATA        2472

ATAATAGTAA ACTAAAAAAA AAAAAAAAAA A                                       2503

( 2 ) INFORMATION FOR SEQ ID NO:4:

( i ) SEQUENCE CHARACTERISTICS:
        ( A ) LENGTH: 619 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
|Met|Asp|Asp|Gln|Gln|Ala|Leu|Asn|Ser|Ile|Met|Gln|Asp|Leu|Ala|Val|
|1| | | |5| | | | |10| | | | |15| |
|Leu|His|Lys|Pro|Val|Gly|Gln|His|Tyr|Leu|Tyr|Lys|Lys|Pro|Gly|Lys|
| | | |20| | | | |25| | | | |30| | |
|Gln|Asn|Leu|His|His|Gln|Lys|Asn|Arg|Met|Met|Phe|Glu|Ser|Asn|Leu|
| | |35| | | | |40| | | | |45| | | |
|Asn|Ile|Glu|Glu|Glu|Lys|Arg|Ile|Leu|Gln|Val|Thr|Arg|Pro|Val|Lys|
| |50| | | | |55| | | | |60| | | | |
|Leu|Glu|Asp|Leu|Arg|Ser|Lys|Ser|Lys|Ile|Ala|Phe|Gly|Gln|Ser|Met|
|65| | | | |70| | | | |75| | | | |80|
|Asp|Leu|His|Tyr|Thr|Asn|Asn|Glu|Leu|Val|Ile|Pro|Leu|Thr|Thr|Gln|
| | | |85| | | | |90| | | | |95| | |
|Asp|Asp|Leu|Asp|Lys|Ala|Val|Glu|Leu|Leu|Asp|Arg|Ser|Ile|His|Met|
| | | |100| | | | |105| | | | |110| | |

```
Lys  Ser  Leu  Lys  Ile  Leu  Leu  Val  Val  Asn  Gly  Ser  Thr  Gln  Ala  Thr
          115                120                     125

Asn  Leu  Glu  Pro  Ser  Pro  Ser  Pro  Glu  Asp  Leu  Asn  Asn  Thr  Pro  Leu
130                     135                     140

Gly  Ala  Glu  Arg  Lys  Lys  Arg  Leu  Ser  Val  Val  Gly  Pro  Pro  Asn  Arg
145                     150                     155                          160

Asp  Arg  Ser  Ser  Pro  Pro  Gly  Tyr  Ile  Pro  Asp  Ile  Leu  His  Gln
               165                170                          175

Ile  Ala  Arg  Asn  Gly  Ser  Phe  Thr  Ser  Ile  Asn  Ser  Glu  Gly  Glu  Phe
               180                185                          190

Ile  Pro  Glu  Ser  Met  Asp  Gln  Met  Leu  Asp  Pro  Leu  Ser  Leu  Ser  Ser
          195                200                     205

Pro  Glu  Asn  Ser  Gly  Ser  Gly  Ser  Cys  Pro  Ser  Leu  Asp  Ser  Pro  Leu
     210                215                     220

Asp  Gly  Glu  Ser  Tyr  Pro  Lys  Ser  Arg  Met  Pro  Arg  Ala  Gln  Ser  Tyr
225                     230                     235                          240

Pro  Asp  Asn  His  Gln  Glu  Phe  Thr  Asp  Tyr  Asp  Asn  Pro  Ile  Phe  Glu
               245                250                          255

Lys  Phe  Gly  Lys  Gly  Gly  Thr  Tyr  Pro  Arg  Arg  Tyr  His  Val  Ser  Tyr
               260                265                          270

His  His  Gln  Glu  Tyr  Asn  Asp  Gly  Arg  Lys  Thr  Phe  Pro  Arg  Ala  Arg
               275                280                          285

Arg  Thr  Gln  Gly  Thr  Ser  Phe  Arg  Ser  Pro  Val  Ser  Phe  Ser  Pro  Thr
     290                     295                     300

Asp  His  Ser  Leu  Ser  Thr  Ser  Ser  Gly  Ser  Ser  Val  Phe  Thr  Pro  Glu
305                     310                     315                          320

Tyr  Asp  Asp  Ser  Arg  Ile  Arg  Arg  Arg  Gly  Ser  Asp  Ile  Asp  Asn  Pro
               325                330                          335

Thr  Leu  Thr  Val  Thr  Asp  Ile  Ser  Pro  Pro  Ser  Arg  Ser  Pro  Arg  Ala
               340                345                          350

Pro  Thr  Asn  Trp  Arg  Leu  Gly  Lys  Leu  Leu  Gly  Gln  Gly  Ala  Phe  Gly
          355                360                     365

Arg  Val  Tyr  Leu  Cys  Tyr  Asp  Val  Asp  Thr  Gly  Arg  Glu  Leu  Ala  Val
     370                375                     380

Lys  Gln  Val  Gln  Phe  Asn  Pro  Glu  Ser  Pro  Glu  Thr  Ser  Lys  Glu  Val
385                     390                     395                          400

Asn  Ala  Leu  Glu  Cys  Glu  Ile  Gln  Leu  Leu  Lys  Asn  Leu  Leu  His  Glu
               405                410                          415

Arg  Ile  Val  Gln  Tyr  Tyr  Gly  Cys  Leu  Arg  Asp  Pro  Gln  Glu  Lys  Thr
               420                425                          430

Leu  Ser  Ile  Phe  Met  Glu  Leu  Ser  Pro  Gly  Gly  Ser  Ile  Lys  Asp  Gln
          435                440                     445

Leu  Lys  Ala  Tyr  Gly  Ala  Leu  Thr  Glu  Asn  Val  Thr  Arg  Lys  Tyr  Thr
     450                     455                     460

Arg  Gln  Ile  Leu  Glu  Gly  Val  His  Tyr  Leu  His  Ser  Asn  Met  Ile  Val
465                     470                     475                          480

His  Arg  Asp  Ile  Lys  Gly  Ala  Asn  Ile  Leu  Arg  Asp  Ser  Thr  Gly  Asn
               485                490                          495

Ile  Lys  Leu  Gly  Asp  Phe  Gly  Ala  Ser  Lys  Arg  Leu  Gln  Thr  Ile  Cys
               500                505                          510

Leu  Ser  Gly  Thr  Gly  Met  Lys  Ser  Val  Thr  Gly  Thr  Pro  Tyr  Trp  Met
          515                520                     525

Ser  Pro  Glu  Val  Ile  Ser  Gly  Glu  Gly  Tyr  Gly  Arg  Lys  Ala  Asp  Ile
     530                     535                     540
```

```
Trp  Ser  Val  Ala  Cys  Thr  Val  Val  Glu  Met  Leu  Thr  Glu  Lys  Pro  Pro
545                 550                 555                 560

Trp  Ala  Glu  Phe  Glu  Ala  Met  Ala  Ala  Ile  Phe  Lys  Ile  Ala  Thr  Gln
                    565                 570                 575

Pro  Thr  Asn  Pro  Lys  Leu  Pro  Pro  His  Val  Ser  Asp  Tyr  Thr  Arg  Asp
               580                 585                 590

Phe  Leu  Lys  Arg  Ile  Phe  Val  Glu  Ala  Lys  Leu  Arg  Pro  Ser  Ala  Glu
          595                 600                 605

Glu  Leu  Leu  Arg  His  Met  Phe  Val  His  Tyr  His
          610                 615
```

( 2 ) INFORMATION FOR SEQ ID NO:5:

( i ) SEQUENCE CHARACTERISTICS:
        ( A ) LENGTH: 3089 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 400..2280

( x i ) SEQUENCE DESCRIPTION: SEQ ID NO:5:

```
AGGGAACAAA  AGCTGGAGCT  CCACCGCGGT  GGCGGCCGCT  CTAGAACTAG  TGGATCCCCC      60

GGGCTGCAGG  AATTCGGCAC  GAGGAACAGT  GGCCGGTCGG  AGCGTCTTCT  GGACTTCAGG     120

ACTCGCAGGC  GGCCCGGTCG  AGTGGCGCCG  CCGAGGCCGG  GTTGGGCCGA  GCCTGGGAGC     180

GCCGGGGATG  TAGCGGGCCA  ACCTGCTCAT  GCCACAGCGC  CCGGCCGCGG  CCGAGCCGGA     240

GCCTGGGGAG  GCGGCGGGGG  CCCCGAGCGC  AGCCCACGGC  CCCCGCGCGG  AGCCAGGCCC     300

GCTGCCGTCC  CCGCCGCCCG  CTCCCCCGGC  ATGCAGCCCC  GGCTGCGGAG  GTGACACTTC     360

TGGGCTGTAG  TCGCCACCGC  CGCCTCCGCC  ATCGCCACC  ATG GAT GAA CAA GAG          414
                                               Met Asp Glu Gln Glu
                                                 1               5

GCA TTA GAC TCG ATC ATG AAG GAC CTG GTG GCC CTC CAG ATG AGC CGA              462
Ala Leu Asp Ser Ile Met Lys Asp Leu Val Ala Leu Gln Met Ser Arg
             10                  15                  20

CGA ACC CGG TTG TCT GGA TAT GAG ACC ATG AAG AAT AAG GAC ACA GGT              510
Arg Thr Arg Leu Ser Gly Tyr Glu Thr Met Lys Asn Lys Asp Thr Gly
                 25                  30                  35

CAC CCA AAC AGG CAG AGT GAC GTC AGA ATC AAG TTT GAA CAC AAT GGG              558
His Pro Asn Arg Gln Ser Asp Val Arg Ile Lys Phe Glu His Asn Gly
             40                  45                  50

GAG AGA CGA ATT ATA GCA TTC AGC CGG CCT GTG AGA TAC GAA GAT GTG              606
Glu Arg Arg Ile Ile Ala Phe Ser Arg Pro Val Arg Tyr Glu Asp Val
     55                  60                  65

GAG CAC AAG GTG ACA ACA GTC TTT GGG CAG CCT CTT GAT TTG CAT TAT              654
Glu His Lys Val Thr Thr Val Phe Gly Gln Pro Leu Asp Leu His Tyr
 70                  75                  80                  85

ATG AAT AAT GAG CTC TCC ATC CTG TTG AAA AAC CAA GAT GAT CTC GAT              702
Met Asn Asn Glu Leu Ser Ile Leu Leu Lys Asn Gln Asp Asp Leu Asp
                 90                  95                 100

AAA GCC ATT GAC ATT TTG GAT AGA AGC TCA AGT ATG AAA AGC CTT AGG              750
Lys Ala Ile Asp Ile Leu Asp Arg Ser Ser Ser Met Lys Ser Leu Arg
             105                 110                 115

ATA CTA CTG TTA TCC CAA GAC AGA AAC CAT ACT AGT TCC TCT CCC CAC              798
Ile Leu Leu Leu Ser Gln Asp Arg Asn His Thr Ser Ser Ser Pro His
         120                 125                 130
```

| | | | | | | | | | | | | | | | | |
|---|---|---|---|---|---|---|---|---|---|---|---|---|---|---|---|---|
| TCT | GGA | GTG | TCC | AGG | CAG | GTT | CGG | ATC | AAG | CCT | TCC | CAG | TCT | GCA | GGG | 846 |
| Ser | Gly | Val | Ser | Arg | Gln | Val | Arg | Ile | Lys | Pro | Ser | Gln | Ser | Ala | Gly | |
| | 135 | | | | 140 | | | | | 145 | | | | | | |
| GAT | ATA | AAT | ACC | ATC | TAC | CAA | GCT | CCT | GAG | CCC | AGA | AGC | AGG | CAC | CTG | 894 |
| Asp | Ile | Asn | Thr | Ile | Tyr | Gln | Ala | Pro | Glu | Pro | Arg | Ser | Arg | His | Leu | |
| 150 | | | | | 155 | | | | | 160 | | | | | 165 | |
| TCT | GTC | AGC | TCC | CAG | AAC | CCT | GGC | CGA | AGC | TCT | CCT | CCC | CCG | GGA | TAT | 942 |
| Ser | Val | Ser | Ser | Gln | Asn | Pro | Gly | Arg | Ser | Ser | Pro | Pro | Pro | Gly | Tyr | |
| | | | | 170 | | | | | 175 | | | | | 180 | | |
| GTA | CCT | GAG | CGA | CAA | CAG | CAC | ATT | GCC | CGG | CAA | GGA | TCC | TAT | ACG | AGC | 990 |
| Val | Pro | Glu | Arg | Gln | Gln | His | Ile | Ala | Arg | Gln | Gly | Ser | Tyr | Thr | Ser | |
| | | | 185 | | | | | 190 | | | | | 195 | | | |
| ATC | AAC | AGC | GAA | GGT | GAA | TTC | ATC | CCA | GAG | ACC | AGC | GAA | CAG | TGT | ATG | 1038 |
| Ile | Asn | Ser | Glu | Gly | Glu | Phe | Ile | Pro | Glu | Thr | Ser | Glu | Gln | Cys | Met | |
| | | 200 | | | | | 205 | | | | | 210 | | | | |
| CTA | GAT | CCC | CTC | AGC | AGT | GCC | GAA | AAT | TCC | TTG | TCA | GGA | AGC | TGC | CAA | 1086 |
| Leu | Asp | Pro | Leu | Ser | Ser | Ala | Glu | Asn | Ser | Leu | Ser | Gly | Ser | Cys | Gln | |
| | 215 | | | | | 220 | | | | | 225 | | | | | |
| TCC | TTG | GAC | AGG | TCA | GCA | GAC | AGC | CCA | TCC | TTC | AGG | AAA | TCA | CAA | ATG | 1134 |
| Ser | Leu | Asp | Arg | Ser | Ala | Asp | Ser | Pro | Ser | Phe | Arg | Lys | Ser | Gln | Met | |
| 230 | | | | | 235 | | | | | 240 | | | | | 245 | |
| TCC | CGA | GCC | CGG | AGC | TTC | CCA | GAC | AAC | AGA | AAG | GAA | TGC | TCA | GAT | CGG | 1182 |
| Ser | Arg | Ala | Arg | Ser | Phe | Pro | Asp | Asn | Arg | Lys | Glu | Cys | Ser | Asp | Arg | |
| | | | | 250 | | | | | 255 | | | | | 260 | | |
| GAG | ACC | CAG | CTC | TAT | GAT | AAA | GGT | GTC | AAA | GGT | GGA | ACC | TAT | CCC | AGG | 1230 |
| Glu | Thr | Gln | Leu | Tyr | Asp | Lys | Gly | Val | Lys | Gly | Gly | Thr | Tyr | Pro | Arg | |
| | | | 265 | | | | | 270 | | | | | 275 | | | |
| CGC | TAC | CAT | GTG | TCT | GTG | CAT | CAC | AAA | GAC | TAC | AAT | GAT | GGC | AGA | AGA | 1278 |
| Arg | Tyr | His | Val | Ser | Val | His | His | Lys | Asp | Tyr | Asn | Asp | Gly | Arg | Arg | |
| | | 280 | | | | | 285 | | | | | 290 | | | | |
| ACA | TTT | CCC | CGA | ATA | CGA | CGG | CAT | CAA | GGC | AAC | CTA | TTC | ACT | CTG | GTG | 1326 |
| Thr | Phe | Pro | Arg | Ile | Arg | Arg | His | Gln | Gly | Asn | Leu | Phe | Thr | Leu | Val | |
| | 295 | | | | | 300 | | | | | 305 | | | | | |
| CCC | TCA | AGT | CGC | TCC | TTG | AGC | ACA | AAT | GGC | GAG | AAC | ATG | GGT | GTA | GCT | 1374 |
| Pro | Ser | Ser | Arg | Ser | Leu | Ser | Thr | Asn | Gly | Glu | Asn | Met | Gly | Val | Ala | |
| 310 | | | | | 315 | | | | | 320 | | | | | 325 | |
| GTG | CAA | TAC | CTG | GAC | CCC | CGT | GGG | CGC | CTA | CGG | AGT | GCA | GAC | AGT | GAG | 1422 |
| Val | Gln | Tyr | Leu | Asp | Pro | Arg | Gly | Arg | Leu | Arg | Ser | Ala | Asp | Ser | Glu | |
| | | | | 330 | | | | | 335 | | | | | 340 | | |
| AAT | GCC | CTC | ACT | GTG | CAG | GAA | AGG | AAT | GTG | CCA | ACC | AAA | TCT | CCT | AGT | 1470 |
| Asn | Ala | Leu | Thr | Val | Gln | Glu | Arg | Asn | Val | Pro | Thr | Lys | Ser | Pro | Ser | |
| | | | 345 | | | | | 350 | | | | | 355 | | | |
| GCT | CCC | ATC | AAT | TGG | CGT | CGG | GGG | AAG | CTC | CTG | GGT | CAA | GGT | GCC | TTC | 1518 |
| Ala | Pro | Ile | Asn | Trp | Arg | Arg | Gly | Lys | Leu | Leu | Gly | Gln | Gly | Ala | Phe | |
| | | 360 | | | | | 365 | | | | | 370 | | | | |
| GGC | AGG | GTC | TAC | TTG | TGC | TAT | GAT | GTG | GAC | ACA | GGA | CGT | GAA | CTT | GCT | 1566 |
| Gly | Arg | Val | Tyr | Leu | Cys | Tyr | Asp | Val | Asp | Thr | Gly | Arg | Glu | Leu | Ala | |
| | 375 | | | | | 380 | | | | | 385 | | | | | |
| TCT | AAG | CAG | GTC | CAG | TTT | GAC | CCA | GAT | AGT | CCT | GAG | ACA | AGC | AAG | GAG | 1614 |
| Ser | Lys | Gln | Val | Gln | Phe | Asp | Pro | Asp | Ser | Pro | Glu | Thr | Ser | Lys | Glu | |
| 390 | | | | | 395 | | | | | 400 | | | | | 405 | |
| GTG | AGT | GCT | CTG | GAG | TGT | GAG | ATC | CAG | TTG | CTG | AAG | AAC | CTG | CAG | CAT | 1662 |
| Val | Ser | Ala | Leu | Glu | Cys | Glu | Ile | Gln | Leu | Leu | Lys | Asn | Leu | Gln | His | |
| | | | | 410 | | | | | 415 | | | | | 420 | | |
| GAG | CGC | ATT | GTG | CAG | TAC | TAC | GGC | TGC | CTG | CGG | GAC | CGT | GCT | GAG | AAG | 1710 |
| Glu | Arg | Ile | Val | Gln | Tyr | Tyr | Gly | Cys | Leu | Arg | Asp | Arg | Ala | Glu | Lys | |
| | | | 425 | | | | | 430 | | | | | 435 | | | |
| ATC | CTC | ACC | ATC | TTT | ATG | GAG | TAT | ATG | CCA | GGG | GGC | TCT | GTA | AAA | GAC | 1758 |
| Ile | Leu | Thr | Ile | Phe | Met | Glu | Tyr | Met | Pro | Gly | Gly | Ser | Val | Lys | Asp | |
| | | 440 | | | | | 445 | | | | | 450 | | | | |

| | | | | | | | | | | | | | | | | |
|---|---|---|---|---|---|---|---|---|---|---|---|---|---|---|---|---|
|CAG|TTG|AAG|GCC|TAC|GGA|GCT|CTG|ACA|GAG|AGT|GTG|ACC|CGC|AAG|TAC|1806|
|Gln|Leu|Lys|Ala|Tyr|Gly|Ala|Leu|Thr|Glu|Ser|Val|Thr|Arg|Lys|Tyr| |
| |455| | | | |460| | | | |465| | | | | |
|ACC|CGG|CAG|ATT|CTG|GAG|GGC|ATG|TCA|TAC|CTG|CAC|AGC|AAC|ATG|ATT|1854|
|Thr|Arg|Gln|Ile|Leu|Glu|Gly|Met|Ser|Tyr|Leu|His|Ser|Asn|Met|Ile| |
|470| | | | |475| | | | |480| | | | |485| |
|GTG|CAT|CGG|GAC|ATC|AAG|GGA|GCC|AAT|ATC|CTC|CGA|GAC|TCA|GCT|GGG|1902|
|Val|His|Arg|Asp|Ile|Lys|Gly|Ala|Asn|Ile|Leu|Arg|Asp|Ser|Ala|Gly| |
| | | | |490| | | | |495| | | | |500| | |
|AAT|GTG|AAG|CTT|GGG|GAT|TTT|GGG|GCC|AGC|AAA|CGC|CTA|CAG|ACC|ATC|1950|
|Asn|Val|Lys|Leu|Gly|Asp|Phe|Gly|Ala|Ser|Lys|Arg|Leu|Gln|Thr|Ile| |
| | | |505| | | | |510| | | | |515| | | |
|TGC|ATG|TCA|GGG|ACA|GGC|ATT|CGC|TCT|GTC|ACT|GGC|ACA|CCC|TAC|TGG|1998|
|Cys|Met|Ser|Gly|Thr|Gly|Ile|Arg|Ser|Val|Thr|Gly|Thr|Pro|Tyr|Trp| |
| | |520| | | | |525| | | | |530| | | | |
|ATG|AGT|CCT|GAA|GTC|ATC|AGT|GGC|GAG|GGC|TAT|GGA|AGA|AAG|GCA|GAC|2046|
|Met|Ser|Pro|Glu|Val|Ile|Ser|Gly|Glu|Gly|Tyr|Gly|Arg|Lys|Ala|Asp| |
| |535| | | | |540| | | | |545| | | | | |
|GTG|TGG|AGC|CTG|GGC|TGT|ACT|GTG|GTG|GAA|ATG|CTG|ACA|GAG|AAA|CCA|2094|
|Val|Trp|Ser|Leu|Gly|Cys|Thr|Val|Val|Glu|Met|Leu|Thr|Glu|Lys|Pro| |
|550| | | | |555| | | | |560| | | | |565| |
|CCT|TGG|GCA|GAG|TAT|GAA|GCT|ATG|GCT|GCC|ATT|TTC|AAG|ATT|GCC|ACC|2142|
|Pro|Trp|Ala|Glu|Tyr|Glu|Ala|Met|Ala|Ala|Ile|Phe|Lys|Ile|Ala|Thr| |
| | | | |570| | | | |575| | | | |580| | |
|CAG|CCT|ACC|AAT|CCT|CAG|CTG|CCC|TCT|CAC|ATC|TCA|GAA|CAC|GGC|AGG|2190|
|Gln|Pro|Thr|Asn|Pro|Gln|Leu|Pro|Ser|His|Ile|Ser|Glu|His|Gly|Arg| |
| | | |585| | | | |590| | | | |595| | | |
|GAC|TTC|CTG|AGG|CGC|ATA|TTT|GTG|GAA|GCT|CGT|CAG|AGA|CCC|TCA|GCT|2238|
|Asp|Phe|Leu|Arg|Arg|Ile|Phe|Val|Glu|Ala|Arg|Gln|Arg|Pro|Ser|Ala| |
| | |600| | | | |605| | | | |610| | | | |
|GAG|GAG|CTG|CTC|ACA|CAC|CAC|TTT|GCA|CAG|CTA|GTG|TAC|TGAGCTCTCA| | |2287|
|Glu|Glu|Leu|Leu|Thr|His|His|Phe|Ala|Gln|Leu|Val|Tyr| | | | |
| |615| | | | |620| | | | |625| | | | | |

| | | | | |
|---|---|---|---|---|
|AGGCTATCAG|GCTGCCAGCT|GCCACCTGCT|GAGCAGGCAA|GGGGCTGCTG|TCAGGCTCAG|2347|
|TGAAGTTGCT|GCTTCTTCCA|GGCAAGGCTA|TGACCAGTGG|AGCATCGGTC|CAGCCATTGT|2407|
|TTGTCTGTGC|CCCATCTGCC|ACTGGGACTC|AAAGCCAGGA|TGGGATAGCT|CTGGCATCAA|2467|
|GACTGGGAGC|TCCAGCCTGT|AAGACCCAAG|AGCTTTAGCA|CCTTAAGCTC|AGTATGGCGG|2527|
|GAAGGGCTGG|AAACAGTATG|CAAGACTGCC|ATGGGTCCTG|CCTACCCTCA|GATGTGTCCT|2587|
|AACACTGCAG|ACAGCACTGA|AGTCAAGAGG|GACTGGGGCA|CAGGAGGTCC|TCAAGGGTAT|2647|
|GAATAGTGTT|ACTTCATTCA|GAGTGTTACT|TTGTTTCTCT|CCCAATGTTT|GGAGACCACC|2707|
|AGCCTGTCTC|TGGGCTGCAA|GCCTGAGGTA|AAGCCCAGCA|TCCCCCAGCC|AACAGAAGGT|2767|
|AGAGGTTTGG|GCTACCCCAC|TATAGCTTCC|AGGTATTCGG|TGTCAGTCCT|GTCTTACCAA|2827|
|AGATGAATGA|AGCAAATGTT|ACACTGCCTT|ATTCTGGGAA|GGAGGAGCTA|CTCGGATAAG|2887|
|CAGGGCCTGA|GAGATGGAGC|TGCCTCCAGA|AACTGGGGAG|ACCCAGTCTT|GTCAATGCAA|2947|
|TTGTCTCTGT|TTTACAAGTT|GGAGTCACTC|TTATGCTGTT|CCCAGTTTTA|AAACTGGAGA|3007|
|CTTTGCCCTC|TGAGCTCTGG|AGACCCATGT|GGGCTTAGGC|TTGGACTGGA|TGGAAGAGCT|3067|
|GATGGCCTCT|GCCCCTGGCC|TG| | | |3089|

( 2 ) INFORMATION FOR SEQ ID NO:6:

( i ) SEQUENCE CHARACTERISTICS:
        ( A ) LENGTH: 626 amino acids
        ( B ) TYPE: amino acid
        ( D ) TOPOLOGY: linear (ii) MOLECULE TYPE: protein (xi) SEQUENCE DESCRIPTION: SEQ ID NO:6:

| Met | Asp | Glu | Gln | Glu | Ala | Leu | Asp | Ser | Ile | Met | Lys | Asp | Leu | Val | Ala |
|---|---|---|---|---|---|---|---|---|---|---|---|---|---|---|---|
| 1 | | | | 5 | | | | | 10 | | | | | 15 | |
| Leu | Gln | Met | Ser | Arg | Arg | Thr | Arg | Leu | Ser | Gly | Tyr | Glu | Thr | Met | Lys |
| | | | 20 | | | | 25 | | | | | 30 | | | |
| Asn | Lys | Asp | Thr | Gly | His | Pro | Asn | Arg | Gln | Ser | Asp | Val | Arg | Ile | Lys |
| | | 35 | | | | | 40 | | | | | 45 | | | |
| Phe | Glu | His | Asn | Gly | Glu | Arg | Arg | Ile | Ile | Ala | Phe | Ser | Arg | Pro | Val |
| | 50 | | | | | 55 | | | | | | 60 | | | |
| Arg | Tyr | Glu | Asp | Val | Glu | His | Lys | Val | Thr | Thr | Val | Phe | Gly | Gln | Pro |
| 65 | | | | | 70 | | | | | 75 | | | | | 80 |
| Leu | Asp | Leu | His | Tyr | Met | Asn | Asn | Glu | Leu | Ser | Ile | Leu | Leu | Lys | Asn |
| | | | | 85 | | | | | 90 | | | | | 95 | |
| Gln | Asp | Asp | Leu | Asp | Lys | Ala | Ile | Asp | Ile | Leu | Asp | Arg | Ser | Ser | Ser |
| | | | | 100 | | | | 105 | | | | | 110 | | |
| Met | Lys | Ser | Leu | Arg | Ile | Leu | Leu | Leu | Ser | Gln | Asp | Arg | Asn | His | Thr |
| | | 115 | | | | | 120 | | | | | 125 | | | |
| Ser | Ser | Ser | Pro | His | Ser | Gly | Val | Ser | Arg | Gln | Val | Arg | Ile | Lys | Pro |
| | 130 | | | | | 135 | | | | | 140 | | | | |
| Ser | Gln | Ser | Ala | Gly | Asp | Ile | Asn | Thr | Ile | Tyr | Gln | Ala | Pro | Glu | Pro |
| 145 | | | | | 150 | | | | | 155 | | | | | 160 |
| Arg | Ser | Arg | His | Leu | Ser | Val | Ser | Ser | Gln | Asn | Pro | Gly | Arg | Ser | Ser |
| | | | | 165 | | | | | 170 | | | | | 175 | |
| Pro | Pro | Pro | Gly | Tyr | Val | Pro | Glu | Arg | Gln | Gln | His | Ile | Ala | Arg | Gln |
| | | | 180 | | | | | 185 | | | | | 190 | | |
| Gly | Ser | Tyr | Thr | Ser | Ile | Asn | Ser | Glu | Gly | Glu | Phe | Ile | Pro | Glu | Thr |
| | | | 195 | | | | | 200 | | | | | 205 | | |
| Ser | Glu | Gln | Cys | Met | Leu | Asp | Pro | Leu | Ser | Ser | Ala | Glu | Asn | Ser | Leu |
| | | 210 | | | | | 215 | | | | | 220 | | | |
| Ser | Gly | Ser | Cys | Gln | Ser | Leu | Asp | Arg | Ser | Ala | Asp | Ser | Pro | Ser | Phe |
| 225 | | | | | 230 | | | | | 235 | | | | | 240 |
| Arg | Lys | Ser | Gln | Met | Ser | Arg | Ala | Arg | Ser | Phe | Pro | Asp | Asn | Arg | Lys |
| | | | | 245 | | | | | 250 | | | | | 255 | |
| Glu | Cys | Ser | Asp | Arg | Glu | Thr | Gln | Leu | Tyr | Asp | Lys | Gly | Val | Lys | Gly |
| | | | 260 | | | | | 265 | | | | | 270 | | |
| Gly | Thr | Tyr | Pro | Arg | Arg | Tyr | His | Val | Ser | Val | His | His | Lys | Asp | Tyr |
| | | 275 | | | | | 280 | | | | | 285 | | | |
| Asn | Asp | Gly | Arg | Arg | Thr | Phe | Pro | Arg | Ile | Arg | Arg | His | Gln | Gly | Asn |
| | 290 | | | | | 295 | | | | | 300 | | | | |
| Leu | Phe | Thr | Leu | Val | Pro | Ser | Ser | Arg | Ser | Leu | Ser | Thr | Asn | Gly | Glu |
| 305 | | | | | 310 | | | | | 315 | | | | | 320 |
| Asn | Met | Gly | Val | Ala | Val | Gln | Tyr | Leu | Asp | Pro | Arg | Gly | Arg | Leu | Arg |
| | | | | 325 | | | | | 330 | | | | | 335 | |
| Ser | Ala | Asp | Ser | Glu | Asn | Ala | Leu | Thr | Val | Gln | Glu | Arg | Asn | Val | Pro |
| | | | 340 | | | | | 345 | | | | | 350 | | |
| Thr | Lys | Ser | Pro | Ser | Ala | Pro | Ile | Asn | Trp | Arg | Arg | Gly | Lys | Leu | Leu |
| | | 355 | | | | | 360 | | | | | 365 | | | |
| Gly | Gln | Gly | Ala | Phe | Gly | Arg | Val | Tyr | Leu | Cys | Tyr | Asp | Val | Asp | Thr |
| | 370 | | | | | 375 | | | | | 380 | | | | |
| Gly | Arg | Glu | Leu | Ala | Ser | Lys | Gln | Val | Gln | Phe | Asp | Pro | Asp | Ser | Pro |
| 385 | | | | | 390 | | | | | 395 | | | | | 400 |

| | | | | | | | | | | | | | | |
|---|---|---|---|---|---|---|---|---|---|---|---|---|---|---|
| Glu | Thr | Ser | Lys 405 | Glu | Val | Ser | Ala | Leu 410 | Glu | Cys | Glu | Ile | Gln 415 | Leu Leu |
| Lys | Asn | Leu | Gln 420 | His | Glu | Arg | Ile | Val 425 | Gln | Tyr | Tyr | Gly | Cys 430 | Leu Arg |
| Asp | Arg | Ala 435 | Glu | Lys | Ile | Leu | Thr 440 | Ile | Phe | Met | Glu | Tyr 445 | Met | Pro Gly |
| Gly | Ser 450 | Val | Lys | Asp | Gln | Leu 455 | Lys | Ala | Tyr | Gly | Ala 460 | Leu | Thr | Glu Ser |
| Val 465 | Thr | Arg | Lys | Tyr | Thr 470 | Arg | Gln | Ile | Leu | Glu 475 | Gly | Met | Ser | Tyr Leu 480 |
| His | Ser | Asn | Met | Ile 485 | Val | His | Arg | Asp | Ile 490 | Lys | Gly | Ala | Asn | Ile Leu 495 |
| Arg | Asp | Ser | Ala 500 | Gly | Asn | Val | Lys | Leu 505 | Gly | Asp | Phe | Gly | Ala 510 | Ser Lys |
| Arg | Leu | Gln 515 | Thr | Ile | Cys | Met | Ser 520 | Gly | Thr | Gly | Ile | Arg 525 | Ser | Val Thr |
| Gly | Thr 530 | Pro | Tyr | Trp | Met | Ser 535 | Pro | Glu | Val | Ile | Ser 540 | Gly | Glu | Gly Tyr |
| Gly 545 | Arg | Lys | Ala | Asp | Val 550 | Trp | Ser | Leu | Gly | Cys 555 | Thr | Val | Val | Glu Met 560 |
| Leu | Thr | Glu | Lys | Pro 565 | Pro | Trp | Ala | Glu | Tyr 570 | Glu | Ala | Met | Ala 575 | Ala Ile |
| Phe | Lys | Ile | Ala 580 | Thr | Gln | Pro | Thr | Asn 585 | Pro | Gln | Leu | Pro 590 | Ser | His Ile |
| Ser | Glu | His 595 | Gly | Arg | Asp | Phe | Leu 600 | Arg | Arg | Ile | Phe | Val 605 | Glu | Ala Arg |
| Gln | Arg 610 | Pro | Ser | Ala | Glu | Glu 615 | Leu | Leu | Thr | His | His 620 | Phe | Ala | Gln Leu |
| Val 625 | Tyr | | | | | | | | | | | | | |

( 2 ) INFORMATION FOR SEQ ID NO:7:

( i ) SEQUENCE CHARACTERISTICS:
        ( A ) LENGTH: 3913 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 747..3417
        ( A ) NAME/KEY: N = G,A,C or T
        ( B ) LOCATION: 1094
        ( A ) NAME/KEY: Xaa = Any amino acid
        ( B ) LOCATION: 116

( x i ) SEQUENCE DESCRIPTION: SEQ ID NO:7:

| | | | | | | |
|---|---|---|---|---|---|---|
| AATTCGGCAC | GAGAACCTAT | CAGACATTGG | CTGGCCAGTG | TTTGAAATCC | CCTCCCCTCG | 60 |
| GCCGTCCAAG | GGCTACGAGC | CAGAGGACGA | GGTCGAGGAC | ACGGAGGTTG | AGCTGAGGGA | 120 |
| GCTGGAGAGC | GGGACGGAGG | AGAGTGACGA | GGAGCCAACC | CCCAGTCCGA | GGGTGCCAGA | 180 |
| GCTCAGGCTG | TCCACAGACA | CCATCTTGGA | CAGTCGCTCC | CAGGGCTGCG | TCTCCAGGAA | 240 |
| GCTGGAGAGG | CTCGAGTCAG | AGGAAGATTC | CATAGGCTGG | GGGACAGCGG | ACTGTGGCCC | 300 |
| TGAAGCCAGC | AGGCATTGTT | TGACTTCTAT | CTATAGACCA | TTCGTGGACA | AAGCACTGAA | 360 |
| GCAAATGGGG | CTAAGAAAGT | TAATTTTACG | ACTTCATAAG | CTTATGAATG | GGTCCTTGCA | 420 |

-continued

```
AAGAGCTCGT GTAGCTCTGG TGAAGGACGA CCGTCAGTGG AGTTCTCTGA CTTTCCAGGT      480

CCCATGTGGG GCTCGGATTA TGTGCAGTTG TCGGGAACAC CTCCTTCCTC AGAGCAGAAG      540

TGTAGCGCTG TGTCCTGGGA AGAACTGAGA GCCATGGACC TGCCTTCCTT TGAGCCCGCC      600

TTCCTGGTGC TCTGTCGGGT CCTGCTGAAC GTGATCCACG AGTGCCTGAA GCTGCGGCTG      660

GAACAGAGGC TGCCGGGGAG CCTTCCCTCT TGAGTATCAA ACAGCTAGTG CGAGAGTGTA      720

AAGAGGTCCT AAAGGGCGGG CTCCTG ATG AAG CAG TAT TAC CAG TTC ATG CTG      773
                              Met Lys Gln Tyr Tyr Gln Phe Met Leu
                               1                   5
```

| | | | | | | | | | | | | | | | | |
|---|---|---|---|---|---|---|---|---|---|---|---|---|---|---|---|---|
| CAG | GAG | GTC | CTG | GGC | GGA | CTG | GAG | AAG | ACC | GAC | TGC | AAC | ATG | GAT | GCC | 821 |
| Gln | Glu | Val | Leu | Gly | Gly | Leu | Glu | Lys | Thr | Asp | Cys | Asn | Met | Asp | Ala | |
| 10 | | | | 15 | | | | 20 | | | | | | | 25 | |
| TTT | GAG | GAG | GAC | CTG | CAG | AAG | ATG | CTG | ATG | GTG | TAT | TTT | GAT | TAC | ATG | 869 |
| Phe | Glu | Glu | Asp | Leu | Gln | Lys | Met | Leu | Met | Val | Tyr | Phe | Asp | Tyr | Met | |
| | | | | 30 | | | | | 35 | | | | | 40 | | |
| AGA | AGC | TGG | ATC | CAA | ATG | CTA | CAG | CAG | TTA | CCT | CAG | GCT | TCC | CAT | AGC | 917 |
| Arg | Ser | Trp | Ile | Gln | Met | Leu | Gln | Gln | Leu | Pro | Gln | Ala | Ser | His | Ser | |
| | | | 45 | | | | | 50 | | | | | 55 | | | |
| TTA | AAA | AAC | CTG | CTA | GAA | GAG | GAA | TGG | AAT | TTC | ACC | AAA | GAA | ATA | ACC | 965 |
| Leu | Lys | Asn | Leu | Leu | Glu | Glu | Glu | Trp | Asn | Phe | Thr | Lys | Glu | Ile | Thr | |
| | | 60 | | | | | 65 | | | | | 70 | | | | |
| CAT | TAT | ATC | CGT | GGC | GGA | GAA | GCG | CAG | GCT | GGA | AAG | CTT | TTC | TGT | GAC | 1013 |
| His | Tyr | Ile | Arg | Gly | Gly | Glu | Ala | Gln | Ala | Gly | Lys | Leu | Phe | Cys | Asp | |
| | 75 | | | | | 80 | | | | | 85 | | | | | |
| ATC | GCA | GGG | ATG | CTG | CTG | AAA | TCC | ACA | GGG | AGC | TTT | CTG | GAA | TCC | GGC | 1061 |
| Ile | Ala | Gly | Met | Leu | Leu | Lys | Ser | Thr | Gly | Ser | Phe | Leu | Glu | Ser | Gly | |
| 90 | | | | | 95 | | | | | 100 | | | | | 105 | |
| CTG | CAG | GAG | AGC | TGT | GCT | GAG | CTG | TGG | ACC | AGN | GCC | GAC | GAC | AAC | GGT | 1109 |
| Leu | Gln | Glu | Ser | Cys | Ala | Glu | Leu | Trp | Thr | Xaa | Ala | Asp | Asp | Asn | Gly | |
| | | | | 110 | | | | | 115 | | | | | 120 | | |
| GCT | GCC | GAC | GAG | CTA | AGG | AGA | TCT | GTC | ATC | GAG | ATC | AGC | CGA | GCA | CTC | 1157 |
| Ala | Ala | Asp | Glu | Leu | Arg | Arg | Ser | Val | Ile | Glu | Ile | Ser | Arg | Ala | Leu | |
| | | | 125 | | | | | 130 | | | | | 135 | | | |
| AAG | GAG | CTC | TTC | CAC | GAA | GCC | AGG | GAA | AGA | GCC | TCC | AAG | GCC | CTG | GGC | 1205 |
| Lys | Glu | Leu | Phe | His | Glu | Ala | Arg | Glu | Arg | Ala | Ser | Lys | Ala | Leu | Gly | |
| | | 140 | | | | | 145 | | | | | 150 | | | | |
| TTT | GCT | AAA | ATG | CTG | AGG | AAG | GAC | CTA | GAA | ATA | GCA | GCA | GAG | TTC | GTG | 1253 |
| Phe | Ala | Lys | Met | Leu | Arg | Lys | Asp | Leu | Glu | Ile | Ala | Ala | Glu | Phe | Val | |
| | 155 | | | | | 160 | | | | | 165 | | | | | |
| CTA | TCT | GCA | TCA | GCC | CGA | GAG | CTC | CTG | GAC | GCT | CTG | AAA | GCA | AAG | CAG | 1301 |
| Leu | Ser | Ala | Ser | Ala | Arg | Glu | Leu | Leu | Asp | Ala | Leu | Lys | Ala | Lys | Gln | |
| 170 | | | | 175 | | | | | 180 | | | | | 185 | | |
| TAT | GTT | AAG | GTA | CAG | ATT | CCC | GGG | TTA | GAG | AAT | TTG | CAC | GTG | TTT | GTC | 1349 |
| Tyr | Val | Lys | Val | Gln | Ile | Pro | Gly | Leu | Glu | Asn | Leu | His | Val | Phe | Val | |
| | | | | 190 | | | | | 195 | | | | | 200 | | |
| CCC | GAC | AGC | CTC | GCT | GAG | GAG | AAG | AAA | ATT | ATT | TTG | CAG | CTA | CTC | AAT | 1397 |
| Pro | Asp | Ser | Leu | Ala | Glu | Glu | Lys | Lys | Ile | Ile | Leu | Gln | Leu | Leu | Asn | |
| | | | 205 | | | | | 210 | | | | | 215 | | | |
| GCT | GCC | ACA | GGA | AAG | GAC | TGC | TCA | AAG | GAT | CCA | GAC | GAC | GTC | TTC | ATG | 1445 |
| Ala | Ala | Thr | Gly | Lys | Asp | Cys | Ser | Lys | Asp | Pro | Asp | Asp | Val | Phe | Met | |
| | | 220 | | | | | 225 | | | | | 230 | | | | |
| GAT | GCC | TTC | CTG | CTC | CTG | ACC | AAG | CAT | GGG | GAC | CGA | GCC | CGT | GAC | TCA | 1493 |
| Asp | Ala | Phe | Leu | Leu | Leu | Thr | Lys | His | Gly | Asp | Arg | Ala | Arg | Asp | Ser | |
| | 235 | | | | | 240 | | | | | 245 | | | | | |
| GAA | GAT | GGC | TGG | GGC | ACA | TGG | GAA | GCT | CGG | GCT | GTC | AAA | ATT | GTG | CCT | 1541 |
| Glu | Asp | Gly | Trp | Gly | Thr | Trp | Glu | Ala | Arg | Ala | Val | Lys | Ile | Val | Pro | |
| 250 | | | | 255 | | | | | 260 | | | | | 265 | | |

| | | | | | | | | | | | | | | | | |
|---|---|---|---|---|---|---|---|---|---|---|---|---|---|---|---|---|
| CAG | GTG | GAG | ACT | GTG | GAC | ACC | CTG | AGA | AGC | ATG | CAG | GTG | GAC | AAC | CTT | 1589 |
| Gln | Val | Glu | Thr | Val | Asp | Thr | Leu | Arg | Ser | Met | Gln | Val | Asp | Asn | Leu | |
| | | | 270 | | | | | 275 | | | | | 280 | | | |
| CTG | CTG | GTT | GTC | ATG | GAG | TCT | GCT | CAC | CTC | GTA | CTT | CAG | AGA | AAA | GCC | 1637 |
| Leu | Leu | Val | Val | Met | Glu | Ser | Ala | His | Leu | Val | Leu | Gln | Arg | Lys | Ala | |
| | | | 285 | | | | 290 | | | | | 295 | | | | |
| TTC | CAG | CAG | TCC | ATT | GAG | GGG | CTG | ATG | ACT | GTA | CGC | CAT | GAG | CAG | ACA | 1685 |
| Phe | Gln | Gln | Ser | Ile | Glu | Gly | Leu | Met | Thr | Val | Arg | His | Glu | Gln | Thr | |
| | | 300 | | | | 305 | | | | | 310 | | | | | |
| TCT | AGC | CAG | CCC | ATC | ATC | GCC | AAA | GGT | TTG | CAG | CAG | CTC | AAG | AAC | GAT | 1733 |
| Ser | Ser | Gln | Pro | Ile | Ile | Ala | Lys | Gly | Leu | Gln | Gln | Leu | Lys | Asn | Asp | |
| | 315 | | | | 320 | | | | | 325 | | | | | | |
| GCA | CTT | GAG | CTA | TGC | AAC | AGA | ATC | AGC | GAT | GCC | ATC | GAC | CGT | GTG | GAC | 1781 |
| Ala | Leu | Glu | Leu | Cys | Asn | Arg | Ile | Ser | Asp | Ala | Ile | Asp | Arg | Val | Asp | |
| 330 | | | | 335 | | | | | 340 | | | | | 345 | | |
| CAC | ATG | TTC | ACC | CTG | GAG | TTC | GAT | GCT | GAG | GTC | GAG | GAG | TCT | GAG | TCG | 1829 |
| His | Met | Phe | Thr | Leu | Glu | Phe | Asp | Ala | Glu | Val | Glu | Glu | Ser | Glu | Ser | |
| | | | | 350 | | | | | 355 | | | | | 360 | | |
| GCC | ACG | CTG | CAG | CAG | TAC | TAC | CGA | GAA | GCC | ATG | ATT | CAG | GGC | TAC | AAC | 1877 |
| Ala | Thr | Leu | Gln | Gln | Tyr | Tyr | Arg | Glu | Ala | Met | Ile | Gln | Gly | Tyr | Asn | |
| | | | 365 | | | | | 370 | | | | | 375 | | | |
| TTT | GGG | TTT | GAG | TAT | CAT | AAA | GAA | GTT | GTT | CGT | TTG | ATG | TCT | GGG | GAA | 1925 |
| Phe | Gly | Phe | Glu | Tyr | His | Lys | Glu | Val | Val | Arg | Leu | Met | Ser | Gly | Glu | |
| | | 380 | | | | | 385 | | | | | 390 | | | | |
| TTC | AGG | CAG | AAG | ATA | GGA | GAC | AAA | TAT | ATA | ACG | TTC | GCC | CAG | AAG | TGG | 1973 |
| Phe | Arg | Gln | Lys | Ile | Gly | Asp | Lys | Tyr | Ile | Thr | Phe | Ala | Gln | Lys | Trp | |
| | 395 | | | | | 400 | | | | | 405 | | | | | |
| ATG | AAT | TAC | GTG | CTG | ACC | AAA | TGC | GAG | AGC | GGC | AGA | GGC | ACA | AGA | CCC | 2021 |
| Met | Asn | Tyr | Val | Leu | Thr | Lys | Cys | Glu | Ser | Gly | Arg | Gly | Thr | Arg | Pro | |
| 410 | | | | | 415 | | | | | 420 | | | | | 425 | |
| AGA | TGG | GCC | ACC | CAA | GGA | TTT | GAT | TTC | CTA | CAA | GCC | ATT | GAA | CCT | GCC | 2069 |
| Arg | Trp | Ala | Thr | Gln | Gly | Phe | Asp | Phe | Leu | Gln | Ala | Ile | Glu | Pro | Ala | |
| | | | | 430 | | | | | 435 | | | | | 440 | | |
| TTT | ATT | TCA | GCT | TTA | CCA | GAA | GAT | GAC | TTC | TTG | AGT | TTG | CAA | GCC | CTG | 2117 |
| Phe | Ile | Ser | Ala | Leu | Pro | Glu | Asp | Asp | Phe | Leu | Ser | Leu | Gln | Ala | Leu | |
| | | | 445 | | | | | 450 | | | | | 455 | | | |
| ATG | AAT | GAG | TGC | ATC | GGG | CAC | GTC | ATA | GGA | AAG | CCA | CAC | AGC | CCT | GTC | 2165 |
| Met | Asn | Glu | Cys | Ile | Gly | His | Val | Ile | Gly | Lys | Pro | His | Ser | Pro | Val | |
| | | 460 | | | | | 465 | | | | | 470 | | | | |
| ACA | GCT | ATC | CAT | CGG | AAC | AGC | CCC | CGC | CCT | GTG | AAG | GTG | CCC | CGA | TGC | 2213 |
| Thr | Ala | Ile | His | Arg | Asn | Ser | Pro | Arg | Pro | Val | Lys | Val | Pro | Arg | Cys | |
| | 475 | | | | | 480 | | | | | 485 | | | | | |
| CAC | AGT | GAC | CCT | CCT | AAC | CCT | CAC | CTC | ATC | ATC | CCG | ACT | CCA | GAG | GGA | 2261 |
| His | Ser | Asp | Pro | Pro | Asn | Pro | His | Leu | Ile | Ile | Pro | Thr | Pro | Glu | Gly | |
| 490 | | | | | 495 | | | | | 500 | | | | | 505 | |
| TTC | AGG | GGT | TCC | AGT | GTC | CCT | GAA | AAC | GAC | CGC | TTG | GCC | TCC | ATA | GCT | 2309 |
| Phe | Arg | Gly | Ser | Ser | Val | Pro | Glu | Asn | Asp | Arg | Leu | Ala | Ser | Ile | Ala | |
| | | | | 510 | | | | | 515 | | | | | 520 | | |
| GCA | GAA | CTG | CAG | TTC | AGG | TCT | CTG | AGT | CGG | CAC | TCA | AGC | CCC | ACG | GAA | 2357 |
| Ala | Glu | Leu | Gln | Phe | Arg | Ser | Leu | Ser | Arg | His | Ser | Ser | Pro | Thr | Glu | |
| | | | 525 | | | | | 530 | | | | | 535 | | | |
| GAG | CGA | GAC | GAG | CCA | GCG | TAT | CCT | CGG | AGT | GAC | TCA | AGT | GGA | TCA | ACT | 2405 |
| Glu | Arg | Asp | Glu | Pro | Ala | Tyr | Pro | Arg | Ser | Asp | Ser | Ser | Gly | Ser | Thr | |
| | | 540 | | | | | 545 | | | | | 550 | | | | |
| CGG | AGA | AGC | TGG | GAA | CTT | CGA | ACA | CTC | ATC | AGC | CAG | ACC | AAA | GAC | TCG | 2453 |
| Arg | Arg | Ser | Trp | Glu | Leu | Arg | Thr | Leu | Ile | Ser | Gln | Thr | Lys | Asp | Ser | |
| | 555 | | | | | 560 | | | | | 565 | | | | | |
| GCC | TCT | AAG | CAG | GGG | CCC | ATA | GAA | GCT | ATC | CAG | AAG | TCA | GTC | CGA | CTG | 2501 |
| Ala | Ser | Lys | Gln | Gly | Pro | Ile | Glu | Ala | Ile | Gln | Lys | Ser | Val | Arg | Leu | |
| 570 | | | | | 575 | | | | | 580 | | | | | 585 | |

| | | | | | | | | | | | | | | | | |
|---|---|---|---|---|---|---|---|---|---|---|---|---|---|---|---|---|
| TTT | GAA | GAG | AGG | AGG | TAT | CGA | GAG | ATG | AGG | AGA | AAG | AAT | ATC | ATC | GGC | 2549 |
| Phe | Glu | Glu | Arg | Arg | Tyr | Arg | Glu | Met | Arg | Arg | Lys | Asn | Ile | Ile | Gly | |
| | | | 590 | | | | | 595 | | | | | | | 600 | |
| CAA | GTG | TGC | GAT | ACC | CCT | AAG | TCC | TAT | GAT | AAC | GTC | ATG | CAT | GTT | GGA | 2597 |
| Gln | Val | Cys | Asp | Thr | Pro | Lys | Ser | Tyr | Asp | Asn | Val | Met | His | Val | Gly | |
| | | | 605 | | | | | 610 | | | | | 615 | | | |
| CTG | AGG | AAG | GTG | ACA | TTT | AAG | TGG | CAA | AGA | GGA | AAC | AAA | ATT | GGA | GAA | 2645 |
| Leu | Arg | Lys | Val | Thr | Phe | Lys | Trp | Gln | Arg | Gly | Asn | Lys | Ile | Gly | Glu | |
| | | 620 | | | | | 625 | | | | | 630 | | | | |
| GGA | CAG | TAT | GGA | AAA | GTA | TAC | ACC | TGC | ATC | AGT | GTT | GAC | ACA | GGG | GAG | 2693 |
| Gly | Gln | Tyr | Gly | Lys | Val | Tyr | Thr | Cys | Ile | Ser | Val | Asp | Thr | Gly | Glu | |
| | 635 | | | | | 640 | | | | | 645 | | | | | |
| CTG | ATG | GCC | ATG | AAG | GAG | ATT | CGA | TTT | CAG | CCT | AAC | GAC | CAC | AAG | ACT | 2741 |
| Leu | Met | Ala | Met | Lys | Glu | Ile | Arg | Phe | Gln | Pro | Asn | Asp | His | Lys | Thr | |
| 650 | | | | 655 | | | | | 660 | | | | | 665 | | |
| ATC | AAG | GAG | ACT | GCA | GAC | GAG | TTG | AAA | ATA | TTT | GAA | GGC | ATC | AAG | CAC | 2789 |
| Ile | Lys | Glu | Thr | Ala | Asp | Glu | Leu | Lys | Ile | Phe | Glu | Gly | Ile | Lys | His | |
| | | | | 670 | | | | 675 | | | | | 680 | | | |
| CCC | AAC | CTG | GTC | CGG | TAT | TTT | GGC | GTG | GAG | CTT | CAC | AGG | GAA | GAG | ATG | 2837 |
| Pro | Asn | Leu | Val | Arg | Tyr | Phe | Gly | Val | Glu | Leu | His | Arg | Glu | Glu | Met | |
| | | | 685 | | | | | 690 | | | | | 695 | | | |
| TAC | ATC | TTC | ATG | GAG | TAC | TGT | GAT | GAG | GGT | ACA | CTA | GAG | GAG | GTG | TCA | 2885 |
| Tyr | Ile | Phe | Met | Glu | Tyr | Cys | Asp | Glu | Gly | Thr | Leu | Glu | Glu | Val | Ser | |
| | | 700 | | | | | 705 | | | | | 710 | | | | |
| CGA | CTG | GGC | CTG | CAG | GAG | CAC | GTC | ATC | AGG | TTA | TAT | ACC | AAG | CAG | ATC | 2933 |
| Arg | Leu | Gly | Leu | Gln | Glu | His | Val | Ile | Arg | Leu | Tyr | Thr | Lys | Gln | Ile | |
| 715 | | | | | 720 | | | | | 725 | | | | | | |
| ACT | GTC | GCC | ATC | AAC | GTC | CTC | CAT | GAG | CAC | GGC | ATC | GTT | CAC | CGA | GAC | 2981 |
| Thr | Val | Ala | Ile | Asn | Val | Leu | His | Glu | His | Gly | Ile | Val | His | Arg | Asp | |
| 730 | | | | | 735 | | | | | 740 | | | | | 745 | |
| ATC | AAA | GGT | GCC | AAT | ATC | TTC | CTT | ACG | TCA | TCT | GGA | CTA | ATC | AAG | CTG | 3029 |
| Ile | Lys | Gly | Ala | Asn | Ile | Phe | Leu | Thr | Ser | Ser | Gly | Leu | Ile | Lys | Leu | |
| | | | | 750 | | | | | 755 | | | | | 760 | | |
| GGA | GAT | TTT | GGA | TGC | TCT | GTA | AAA | CTT | AAA | AAC | AAC | GCC | CAG | ACC | ATG | 3077 |
| Gly | Asp | Phe | Gly | Cys | Ser | Val | Lys | Leu | Lys | Asn | Asn | Ala | Gln | Thr | Met | |
| | | | 765 | | | | | 770 | | | | | 775 | | | |
| CCC | GGA | GAG | GTG | AAC | AGC | ACC | CTA | GGG | ACA | GCA | GCT | TAC | ATG | GCC | CCT | 3125 |
| Pro | Gly | Glu | Val | Asn | Ser | Thr | Leu | Gly | Thr | Ala | Ala | Tyr | Met | Ala | Pro | |
| | | | 780 | | | | | 785 | | | | | 790 | | | |
| GAA | GTT | ATT | ACC | CGA | GCC | AAA | GGA | GAA | GGC | CAC | GGA | CGT | GCG | GCA | GAT | 3173 |
| Glu | Val | Ile | Thr | Arg | Ala | Lys | Gly | Glu | Gly | His | Gly | Arg | Ala | Ala | Asp | |
| | | 795 | | | | | 800 | | | | | 805 | | | | |
| ATC | TGG | AGT | CTG | GGG | TGC | GTC | GTC | ATA | GAG | ATG | GTG | ACT | GGC | AAG | CGG | 3221 |
| Ile | Trp | Ser | Leu | Gly | Cys | Val | Val | Ile | Glu | Met | Val | Thr | Gly | Lys | Arg | |
| 810 | | | | | 815 | | | | | 820 | | | | | 825 | |
| CCT | TGG | CAT | GAG | TAT | GAA | CAC | AAC | TTT | CAG | ATT | ATG | TAC | AAG | GTG | GGG | 3269 |
| Pro | Trp | His | Glu | Tyr | Glu | His | Asn | Phe | Gln | Ile | Met | Tyr | Lys | Val | Gly | |
| | | | | 830 | | | | | 835 | | | | | 840 | | |
| ATG | GGA | CAC | AAG | CCA | CCA | ATC | CCG | GAA | AGG | CTA | AGC | CCT | GAA | GGA | AAG | 3317 |
| Met | Gly | His | Lys | Pro | Pro | Ile | Pro | Glu | Arg | Leu | Ser | Pro | Glu | Gly | Lys | |
| | | | 845 | | | | | 850 | | | | | 855 | | | |
| GCC | TTT | CTC | TCG | CAC | TGC | CTG | GAA | AGT | GAC | CCG | AAG | ATA | CGG | TGG | ACA | 3365 |
| Ala | Phe | Leu | Ser | His | Cys | Leu | Glu | Ser | Asp | Pro | Lys | Ile | Arg | Trp | Thr | |
| | | | 860 | | | | | 865 | | | | | 870 | | | |
| GCC | AGC | CAG | CTC | CTC | GAC | CAC | GCT | TTT | GTC | AAG | GTT | TGC | ACA | GAT | GAA | 3413 |
| Ala | Ser | Gln | Leu | Leu | Asp | His | Ala | Phe | Val | Lys | Val | Cys | Thr | Asp | Glu | |
| | 875 | | | | | 880 | | | | | 885 | | | | | |
| GAG | T | GAAGTGAACC | AGTCCGTGGC | CTAGTAGTGT | GTGGACAGAA | TCCCGTGATC | | | | | | | | | | 3467 |
| Glu | | | | | | | | | | | | | | | | |
| 890 | | | | | | | | | | | | | | | | |

-continued

```
ACTACTGTAT GTAATATTTA CATAAAGACT GCAGCGCAGG CGGCCTTCCT AACCTCCCAG    3527
GACTGAAGAC TACAGGGGTG ACAAGCCTCA CTTCTGCTGC TCCTGTCGCC TGCTGAGTGA    3587
CAGTGCTGAG GTTAAAGGAG CCGCACGTTA AGTGCCATTA CTACTGTACA CGGCCACCGC    3647
CTCTGTCCCC TCCGACCCTC TCGTGACTGA GAACCAACCG TGTCATCAGC ACAGTGTTTT    3707
TGAGCTCCTG GGGTTCAGAA GAACATGTAG TGTTCCCGGG TGTCCGGGAC GTTTATTTCA    3767
ACCTCCTGGT CGTTGGCTCT GACTGTGGAG CCTCCTTGTT CGAAAGCTGC AGGTTTGTTA    3827
TGCAAAGGCT CGTAAGTGAA GCTGAAGAAA AGGTTCTTTT TCAATAAATG GTTTATTTTA    3887
GGAAAGCGAA AAAAAAAAAA AAAAA                                          3913
```

( 2 ) INFORMATION FOR SEQ ID NO:8:

( i ) SEQUENCE CHARACTERISTICS:
( A ) LENGTH: 890 amino acids
( B ) TYPE: amino acid
( D ) TOPOLOGY: linear ( i i ) MOLECULE TYPE: protein ( i x ) FEATURE:
( A ) NAME/KEY: Xaa = Any amino acid
( B ) LOCATION: 116

( x i ) SEQUENCE DESCRIPTION: SEQ ID NO:8:

```
Met Lys Gln Tyr Tyr Gln Phe Met Leu Gln Glu Val Leu Gly Gly Leu
 1               5                  10                  15

Glu Lys Thr Asp Cys Asn Met Asp Ala Phe Glu Glu Asp Leu Gln Lys
                20                  25                  30

Met Leu Met Val Tyr Phe Asp Tyr Met Arg Ser Trp Ile Gln Met Leu
            35                  40                  45

Gln Gln Leu Pro Gln Ala Ser His Ser Leu Lys Asn Leu Leu Glu Glu
        50                  55                  60

Glu Trp Asn Phe Thr Lys Glu Ile Thr His Tyr Ile Arg Gly Gly Glu
 65                 70                  75                  80

Ala Gln Ala Gly Lys Leu Phe Cys Asp Ile Ala Gly Met Leu Leu Lys
                85                  90                  95

Ser Thr Gly Ser Phe Leu Glu Ser Gly Leu Gln Glu Ser Cys Ala Glu
               100                 105                 110

Leu Trp Thr Xaa Ala Asp Asp Asn Gly Ala Ala Asp Glu Leu Arg Arg
           115                 120                 125

Ser Val Ile Glu Ile Ser Arg Ala Leu Lys Glu Leu Phe His Glu Ala
       130                 135                 140

Arg Glu Arg Ala Ser Lys Ala Leu Gly Phe Ala Lys Met Leu Arg Lys
145                 150                 155                 160

Asp Leu Glu Ile Ala Ala Glu Phe Val Leu Ser Ala Ser Ala Arg Glu
                165                 170                 175

Leu Leu Asp Ala Leu Lys Ala Lys Gln Tyr Val Lys Val Gln Ile Pro
            180                 185                 190

Gly Leu Glu Asn Leu His Val Phe Val Pro Asp Ser Leu Ala Glu Glu
        195                 200                 205

Lys Lys Ile Ile Leu Gln Leu Leu Asn Ala Ala Thr Gly Lys Asp Cys
    210                 215                 220

Ser Lys Asp Pro Asp Asp Val Phe Met Asp Ala Phe Leu Leu Leu Thr
225                 230                 235                 240

Lys His Gly Asp Arg Ala Arg Asp Ser Glu Asp Gly Trp Gly Thr Trp
                245                 250                 255
```

```
Glu Ala Arg Ala Val Lys Ile Val Pro Gln Val Glu Thr Val Asp Thr
            260                 265                 270
Leu Arg Ser Met Gln Val Asp Asn Leu Leu Leu Val Val Met Glu Ser
            275                 280             285
Ala His Leu Val Leu Gln Arg Lys Ala Phe Gln Gln Ser Ile Glu Gly
290             295                         300
Leu Met Thr Val Arg His Glu Gln Thr Ser Ser Gln Pro Ile Ile Ala
305                 310                 315                 320
Lys Gly Leu Gln Gln Leu Lys Asn Asp Ala Leu Glu Leu Cys Asn Arg
                325                 330                 335
Ile Ser Asp Ala Ile Asp Arg Val Asp His Met Phe Thr Leu Glu Phe
            340                 345                 350
Asp Ala Glu Val Glu Glu Ser Glu Ser Ala Thr Leu Gln Gln Tyr Tyr
            355                 360                 365
Arg Glu Ala Met Ile Gln Gly Tyr Asn Phe Gly Phe Glu Tyr His Lys
            370                 375                 380
Glu Val Val Arg Leu Met Ser Gly Glu Phe Arg Gln Lys Ile Gly Asp
385                 390                 395                 400
Lys Tyr Ile Thr Phe Ala Gln Lys Trp Met Asn Tyr Val Leu Thr Lys
            405                 410                 415
Cys Glu Ser Gly Arg Gly Thr Arg Pro Arg Trp Ala Thr Gln Gly Phe
            420                 425                 430
Asp Phe Leu Gln Ala Ile Glu Pro Ala Phe Ile Ser Ala Leu Pro Glu
            435                 440                 445
Asp Asp Phe Leu Ser Leu Gln Ala Leu Met Asn Glu Cys Ile Gly His
    450                 455                 460
Val Ile Gly Lys Pro His Ser Pro Val Thr Ala Ile His Arg Asn Ser
465                 470                 475                 480
Pro Arg Pro Val Lys Val Pro Arg Cys His Ser Asp Pro Pro Asn Pro
                485                 490                 495
His Leu Ile Ile Pro Thr Pro Glu Gly Phe Arg Gly Ser Ser Val Pro
            500                 505                 510
Glu Asn Asp Arg Leu Ala Ser Ile Ala Ala Glu Leu Gln Phe Arg Ser
            515                 520                 525
Leu Ser Arg His Ser Ser Pro Thr Glu Glu Arg Asp Glu Pro Ala Tyr
530                 535                 540
Pro Arg Ser Asp Ser Ser Gly Ser Thr Arg Arg Ser Trp Glu Leu Arg
545                 550                 555                 560
Thr Leu Ile Ser Gln Thr Lys Asp Ser Ala Ser Lys Gln Gly Pro Ile
                565                 570                 575
Glu Ala Ile Gln Lys Ser Val Arg Leu Phe Glu Glu Arg Arg Tyr Arg
            580                 585                 590
Glu Met Arg Arg Lys Asn Ile Ile Gly Gln Val Cys Asp Thr Pro Lys
            595                 600                 605
Ser Tyr Asp Asn Val Met His Val Gly Leu Arg Lys Val Thr Phe Lys
610                 615                 620
Trp Gln Arg Gly Asn Lys Ile Gly Glu Gly Gln Tyr Gly Lys Val Tyr
625                 630                 635                 640
Thr Cys Ile Ser Val Asp Thr Gly Glu Leu Met Ala Met Lys Glu Ile
                645                 650                 655
Arg Phe Gln Pro Asn Asp His Lys Thr Ile Lys Glu Thr Ala Asp Glu
            660                 665                 670
Leu Lys Ile Phe Glu Gly Ile Lys His Pro Asn Leu Val Arg Tyr Phe
            675                 680                 685
```

| | | | | | | | | | | | | | |
|---|---|---|---|---|---|---|---|---|---|---|---|---|---|
| Gly | Val | Glu | Leu | His | Arg | Glu | Glu | Met | Tyr | Ile | Phe | Met | Glu | Tyr | Cys |
| | 690 | | | | | 695 | | | | 700 | | | | |
| Asp | Glu | Gly | Thr | Leu | Glu | Glu | Val | Ser | Arg | Leu | Gly | Leu | Gln | Glu | His |
| 705 | | | | | 710 | | | | | 715 | | | | | 720 |
| Val | Ile | Arg | Leu | Tyr | Thr | Lys | Gln | Ile | Thr | Val | Ala | Ile | Asn | Val | Leu |
| | | | | 725 | | | | | 730 | | | | | 735 | |
| His | Glu | His | Gly | Ile | Val | His | Arg | Asp | Ile | Lys | Gly | Ala | Asn | Ile | Phe |
| | | | 740 | | | | | 745 | | | | | 750 | | |
| Leu | Thr | Ser | Ser | Gly | Leu | Ile | Lys | Leu | Gly | Asp | Phe | Gly | Cys | Ser | Val |
| | | 755 | | | | | 760 | | | | | 765 | | | |
| Lys | Leu | Lys | Asn | Asn | Ala | Gln | Thr | Met | Pro | Gly | Glu | Val | Asn | Ser | Thr |
| | 770 | | | | | 775 | | | | | 780 | | | | |
| Leu | Gly | Thr | Ala | Ala | Tyr | Met | Ala | Pro | Glu | Val | Ile | Thr | Arg | Ala | Lys |
| 785 | | | | | 790 | | | | | 795 | | | | | 800 |
| Gly | Glu | Gly | His | Gly | Arg | Ala | Ala | Asp | Ile | Trp | Ser | Leu | Gly | Cys | Val |
| | | | | 805 | | | | | 810 | | | | | 815 | |
| Val | Ile | Glu | Met | Val | Thr | Gly | Lys | Arg | Pro | Trp | His | Glu | Tyr | Glu | His |
| | | | 820 | | | | | 825 | | | | | 830 | | |
| Asn | Phe | Gln | Ile | Met | Tyr | Lys | Val | Gly | Met | Gly | His | Lys | Pro | Pro | Ile |
| | | 835 | | | | | 840 | | | | | 845 | | | |
| Pro | Glu | Arg | Leu | Ser | Pro | Glu | Gly | Lys | Ala | Phe | Leu | Ser | His | Cys | Leu |
| | 850 | | | | | 855 | | | | | 860 | | | | |
| Glu | Ser | Asp | Pro | Lys | Ile | Arg | Trp | Thr | Ala | Ser | Gln | Leu | Leu | Asp | His |
| 865 | | | | | 870 | | | | | 875 | | | | | 880 |
| Ala | Phe | Val | Lys | Val | Cys | Thr | Asp | Glu | Glu | | | | | | |
| | | | | 885 | | | | | 890 | | | | | | |

( 2 ) INFORMATION FOR SEQ ID NO:9:

( i ) SEQUENCE CHARACTERISTICS:
        ( A ) LENGTH: 4592 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 355..4095

( x i ) SEQUENCE DESCRIPTION: SEQ ID NO:9:

```
AAGAAGAAGG ACAGGGAGCA GAGGGGACAA GAAAACACGG CTGCTTTCTG GTTCAACCGA      60

TCGAACGAAC TGATCTGGTT AGAACTGCAG GCCTGGCACG CGGGCCGCAC CATCAATGAC     120

CAGGACCTCT TTCTCTACAC AGCCCGCCAG GCCATCCCAG ACATCATCAA TGAGATCCTC     180

ACCTTCAAAG TTAACTACGG GAGCATTGCC TTCTCCAGCA ATGGAGCCGG TTTCAACGGG     240

CCCTTGGTAG AAGGCCAGTG CAGAACCCCT CAGGAGACAA ACCGTGTGGG CTGCTCATCG     300

TACCACGAGC ACCTCCAGCG CCAGAGGGTC TCGTTTGAGC AGGTGAAGCG GATA ATG      357
                                                              Met
                                                               1
```

| GAG | CTG | CTG | GAG | TAC | ATG | GAG | GCA | CTT | TAC | CCA | TCC | TTG | CAG | GCT | CTG | 405 |
|---|---|---|---|---|---|---|---|---|---|---|---|---|---|---|---|---|
| Glu | Leu | Leu | Glu | Tyr | Met | Glu | Ala | Leu | Tyr | Pro | Ser | Leu | Gln | Ala | Leu | |
| | | | | 5 | | | | | 10 | | | | | 15 | | |

| CAG | AAG | GAC | TAT | GAA | CGG | TAC | GCC | GCC | AAG | GAC | TTT | GAG | GAC | AGA | GTG | 453 |
|---|---|---|---|---|---|---|---|---|---|---|---|---|---|---|---|---|
| Gln | Lys | Asp | Tyr | Glu | Arg | Tyr | Ala | Ala | Lys | Asp | Phe | Glu | Asp | Arg | Val | |
| | | 20 | | | | | 25 | | | | | 30 | | | | |

-continued

| | | | | | | | | | | | | | | | | |
|---|---|---|---|---|---|---|---|---|---|---|---|---|---|---|---|---|
| CAG | GCG | CTC | TGC | CTG | TGG | CTC | AAC | ATC | ACG | AAA | GAT | CTA | AAT | CAG | AAG | 501 |
| Gln | Ala | Leu | Cys | Leu | Trp | Leu | Asn | Ile | Thr | Lys | Asp | Leu | Asn | Gln | Lys | |
| | 35 | | | | 40 | | | | 45 | | | | | | | |

| CTG | CGG | ATC | ATG | GGC | ACC | GTG | CTG | GGC | ATC | AAG | TTC | CTA | TCA | GAC | ATT | 549 |
| Leu | Arg | Ile | Met | Gly | Thr | Val | Leu | Gly | Ile | Lys | Phe | Leu | Ser | Asp | Ile | |
| 50 | | | | | 55 | | | | | 60 | | | | | 65 | |

| GGC | TGG | CCA | GTG | AAA | GAA | ATC | CCC | TCC | CCT | CGG | CCG | TCC | AAG | GGC | TAC | 597 |
| Gly | Trp | Pro | Val | Lys | Glu | Ile | Pro | Ser | Pro | Arg | Pro | Ser | Lys | Gly | Tyr | |
| | | | | 70 | | | | | 75 | | | | | | 80 | |

| GAG | CCA | GAG | GAC | GAG | GTC | GAG | GAC | ACG | GAG | GTT | GAG | CTG | AGG | GAG | CTG | 645 |
| Glu | Pro | Glu | Asp | Glu | Val | Glu | Asp | Thr | Glu | Val | Glu | Leu | Arg | Glu | Leu | |
| | | | 85 | | | | | 90 | | | | | 95 | | | |

| GAG | AGC | GGG | ACG | GAG | GAG | AGT | GAC | GAG | GAG | CCA | ACC | CCC | AGT | CCG | AGG | 693 |
| Glu | Ser | Gly | Thr | Glu | Glu | Ser | Asp | Glu | Glu | Pro | Thr | Pro | Ser | Pro | Arg | |
| | | 100 | | | | | 105 | | | | | 110 | | | | |

| GTG | CCA | GAG | CTC | AGG | CTG | TCC | ACA | GAC | ACC | ATC | TTG | GAC | AGT | CGC | TCC | 741 |
| Val | Pro | Glu | Leu | Arg | Leu | Ser | Thr | Asp | Thr | Ile | Leu | Asp | Ser | Arg | Ser | |
| | 115 | | | | | 120 | | | | | 125 | | | | | |

| CAG | GGC | TGC | GTC | TCC | AGG | AAG | CTG | GAG | AGG | CTC | GAG | TCA | GAG | GAA | GAT | 789 |
| Gln | Gly | Cys | Val | Ser | Arg | Lys | Leu | Glu | Arg | Leu | Glu | Ser | Glu | Glu | Asp | |
| 130 | | | | | 135 | | | | | 140 | | | | | 145 | |

| TCC | ATA | GGC | TGG | GGG | ACA | GCG | GAC | TGT | GGC | CCT | GAA | GCC | AGC | AGG | CAT | 837 |
| Ser | Ile | Gly | Trp | Gly | Thr | Ala | Asp | Cys | Gly | Pro | Glu | Ala | Ser | Arg | His | |
| | | | | 150 | | | | | 155 | | | | | 160 | | |

| TGT | TTG | ACT | TCT | ATG | TAT | AGA | CCA | TTC | GTG | GAC | AAA | GCA | CTG | AAG | CAA | 885 |
| Cys | Leu | Thr | Ser | Met | Tyr | Arg | Pro | Phe | Val | Asp | Lys | Ala | Leu | Lys | Gln | |
| | | | | 165 | | | | | 170 | | | | | 175 | | |

| ATG | GGG | CTA | AGA | AAG | TTA | ATT | TTA | CGA | CTT | CAT | AAG | CTT | ATG | AAT | GGG | 933 |
| Met | Gly | Leu | Arg | Lys | Leu | Ile | Leu | Arg | Leu | His | Lys | Leu | Met | Asn | Gly | |
| | | 180 | | | | | 185 | | | | | 190 | | | | |

| TCC | TTG | CAA | AGA | GCT | CGT | GTA | GCT | CTG | GTG | AAG | GAC | GAC | CGT | CCA | GTG | 981 |
| Ser | Leu | Gln | Arg | Ala | Arg | Val | Ala | Leu | Val | Lys | Asp | Asp | Arg | Pro | Val | |
| | 195 | | | | | 200 | | | | | 205 | | | | | |

| GAG | TTC | TCT | GAC | TTT | CCA | GGT | CCC | ATG | TGG | GGC | TCG | GAT | TAT | GTG | CAG | 1029 |
| Glu | Phe | Ser | Asp | Phe | Pro | Gly | Pro | Met | Trp | Gly | Ser | Asp | Tyr | Val | Gln | |
| 210 | | | | | 215 | | | | | 220 | | | | | 225 | |

| TTG | TCG | GGA | ACA | CCT | CCT | TCC | TCA | GAG | CAG | AAG | TGT | AGC | GCT | GTG | TCC | 1077 |
| Leu | Ser | Gly | Thr | Pro | Pro | Ser | Ser | Glu | Gln | Lys | Cys | Ser | Ala | Val | Ser | |
| | | | | 230 | | | | | 235 | | | | | 240 | | |

| TGG | GAA | GAA | CTG | AGA | GCC | ATG | GAC | CTG | CCT | TCC | TTT | GAG | CCC | GCC | TTC | 1125 |
| Trp | Glu | Glu | Leu | Arg | Ala | Met | Asp | Leu | Pro | Ser | Phe | Glu | Pro | Ala | Phe | |
| | | | | 245 | | | | | 250 | | | | | 255 | | |

| CTG | GTG | CTC | TGT | CGG | GTC | CTG | CTG | AAC | GTG | ATC | CAC | GAG | TGC | CTG | AAG | 1173 |
| Leu | Val | Leu | Cys | Arg | Val | Leu | Leu | Asn | Val | Ile | His | Glu | Cys | Leu | Lys | |
| | | | | 260 | | | | | 265 | | | | | 270 | | |

| CTG | CGG | CTG | GAA | CAG | AGG | CCT | GCC | GGG | GAG | CCT | TCC | CTC | TTG | AGT | ATC | 1221 |
| Leu | Arg | Leu | Glu | Gln | Arg | Pro | Ala | Gly | Glu | Pro | Ser | Leu | Leu | Ser | Ile | |
| | | 275 | | | | | 280 | | | | | 285 | | | | |

| AAA | CAG | CTA | GTG | CGA | GAG | TGT | AAA | GAG | GTC | CTA | AAG | GGC | GGG | CTC | CTG | 1269 |
| Lys | Gln | Leu | Val | Arg | Glu | Cys | Lys | Glu | Val | Leu | Lys | Gly | Gly | Leu | Leu | |
| 290 | | | | | 295 | | | | | 300 | | | | | 305 | |

| ATG | AAG | CAG | TAT | TAC | CAG | TTC | ATG | CTG | CAG | GAG | GTC | CTG | GGC | GGA | CTG | 1317 |
| Met | Lys | Gln | Tyr | Tyr | Gln | Phe | Met | Leu | Gln | Glu | Val | Leu | Gly | Gly | Leu | |
| | | | | 310 | | | | | 315 | | | | | 320 | | |

| GAG | AAG | ACC | GAC | TGC | AAC | ATG | GAT | GCC | TTT | GAG | GAG | GAC | CTG | CAG | AAG | 1365 |
| Glu | Lys | Thr | Asp | Cys | Asn | Met | Asp | Ala | Phe | Glu | Glu | Asp | Leu | Gln | Lys | |
| | | | | 325 | | | | | 330 | | | | | 335 | | |

| ATG | CTG | ATG | GTG | TAT | TTT | GAT | TAC | ATG | AGA | AGC | TGG | ATC | CAA | ATG | CTA | 1413 |
| Met | Leu | Met | Val | Tyr | Phe | Asp | Tyr | Met | Arg | Ser | Trp | Ile | Gln | Met | Leu | |
| | | 340 | | | | | 345 | | | | | 350 | | | | |

| | | | | | | | | | | | | | | | |
|---|---|---|---|---|---|---|---|---|---|---|---|---|---|---|---|
| CAG | CAG | TTA | CCT | CAG | GCT | TCC | CAT | AGC | TTA | AAA | AAC | CTG | CTA | GAA | GAG | 1461 |
| Gln | Gln | Leu | Pro | Gln | Ala | Ser | His | Ser | Leu | Lys | Asn | Leu | Leu | Glu | Glu | |
| | 355 | | | | 360 | | | | | 365 | | | | | | |
| GAA | TGG | AAT | TTC | ACC | AAA | GAA | ATA | ACC | CAT | TAT | ATC | CGT | GGC | GGA | GAA | 1509 |
| Glu | Trp | Asn | Phe | Thr | Lys | Glu | Ile | Thr | His | Tyr | Ile | Arg | Gly | Gly | Glu | |
| 370 | | | | | 375 | | | | | 380 | | | | | 385 | |
| GCG | CAG | GCT | GGA | AAG | CTT | TTC | TGT | GAC | ATC | GCA | GGG | ATG | CTG | CTG | AAA | 1557 |
| Ala | Gln | Ala | Gly | Lys | Leu | Phe | Cys | Asp | Ile | Ala | Gly | Met | Leu | Leu | Lys | |
| | | | | 390 | | | | | 395 | | | | | 400 | | |
| TCC | ACA | GGG | AGC | TTT | CTG | GAA | TCC | GGC | CTG | CAG | GAG | AGC | TGT | GCT | GAG | 1605 |
| Ser | Thr | Gly | Ser | Phe | Leu | Glu | Ser | Gly | Leu | Gln | Glu | Ser | Cys | Ala | Glu | |
| | | | 405 | | | | | 410 | | | | | 415 | | | |
| CTG | TGG | ACC | AGC | GCC | GAC | GAC | AAC | GGT | GCT | GCC | GAC | GAG | CTA | AGG | AGA | 1653 |
| Leu | Trp | Thr | Ser | Ala | Asp | Asp | Asn | Gly | Ala | Ala | Asp | Glu | Leu | Arg | Arg | |
| | | 420 | | | | | 425 | | | | | 430 | | | | |
| TCT | GTC | ATC | GAG | ATC | AGC | CGA | GCA | CTC | AAG | GAG | CTC | TTC | CAC | GAA | GCC | 1701 |
| Ser | Val | Ile | Glu | Ile | Ser | Arg | Ala | Leu | Lys | Glu | Leu | Phe | His | Glu | Ala | |
| | 435 | | | | | 440 | | | | | 445 | | | | | |
| AGG | GAA | AGA | GCC | TCC | AAG | GCC | CTG | GGC | TTT | GCT | AAA | ATG | CTG | AGG | AAG | 1749 |
| Arg | Glu | Arg | Ala | Ser | Lys | Ala | Leu | Gly | Phe | Ala | Lys | Met | Leu | Arg | Lys | |
| 450 | | | | | 455 | | | | | 460 | | | | | 465 | |
| GAC | CTA | GAA | ATA | GCA | GCA | GAG | TTC | GTG | CTA | TCT | GCA | TCA | GCC | CGA | GAG | 1797 |
| Asp | Leu | Glu | Ile | Ala | Ala | Glu | Phe | Val | Leu | Ser | Ala | Ser | Ala | Arg | Glu | |
| | | | | 470 | | | | | 475 | | | | | 480 | | |
| CTC | CTG | GAC | GCT | CTG | AAA | GCA | AAG | CAG | TAT | GTT | AAG | GTA | CAG | ATT | CCC | 1845 |
| Leu | Leu | Asp | Ala | Leu | Lys | Ala | Lys | Gln | Tyr | Val | Lys | Val | Gln | Ile | Pro | |
| | | | 485 | | | | | 490 | | | | | 495 | | | |
| GGG | TTA | GAG | AAT | TTG | CAC | GTG | TTT | GTC | CCC | GAC | AGC | CTC | GCT | GAG | GAG | 1893 |
| Gly | Leu | Glu | Asn | Leu | His | Val | Phe | Val | Pro | Asp | Ser | Leu | Ala | Glu | Glu | |
| | | | 500 | | | | | 505 | | | | | 510 | | | |
| AAG | AAA | ATT | ATT | TTG | CAG | CTA | CTC | AAT | GCT | GCC | ACA | GGA | AAG | GAC | TGC | 1941 |
| Lys | Lys | Ile | Ile | Leu | Gln | Leu | Leu | Asn | Ala | Ala | Thr | Gly | Lys | Asp | Cys | |
| | 515 | | | | | 520 | | | | | 525 | | | | | |
| TCA | AAG | GAT | CCA | GAC | GAC | GTC | TTC | ATG | GAT | GCC | TTC | CTG | CTC | CTG | ACC | 1989 |
| Ser | Lys | Asp | Pro | Asp | Asp | Val | Phe | Met | Asp | Ala | Phe | Leu | Leu | Leu | Thr | |
| 530 | | | | | 535 | | | | | 540 | | | | | 545 | |
| AAG | CAT | GGG | GAC | CGA | GCC | CGT | GAC | TCA | GAA | GAT | GGC | TGG | GGC | ACA | TGG | 2037 |
| Lys | His | Gly | Asp | Arg | Ala | Arg | Asp | Ser | Glu | Asp | Gly | Trp | Gly | Thr | Trp | |
| | | | | 550 | | | | | 555 | | | | | 560 | | |
| GAA | GCT | CGG | GCT | GTC | AAA | ATT | GTG | CCT | CAG | GTG | GAG | ACT | GTG | GAC | ACC | 2085 |
| Glu | Ala | Arg | Ala | Val | Lys | Ile | Val | Pro | Gln | Val | Glu | Thr | Val | Asp | Thr | |
| | | | 565 | | | | | 570 | | | | | 575 | | | |
| CTG | AGA | AGC | ATG | CAG | GTG | GAC | AAC | CTT | CTG | CTG | GTT | GTC | ATG | GAG | TCT | 2133 |
| Leu | Arg | Ser | Met | Gln | Val | Asp | Asn | Leu | Leu | Leu | Val | Val | Met | Glu | Ser | |
| | | | 580 | | | | | 585 | | | | | 590 | | | |
| GCT | CAC | CTC | GTA | CTT | CAG | AGA | AAA | GCC | TTC | CAG | CAG | TCC | ATT | GAG | GGG | 2181 |
| Ala | His | Leu | Val | Leu | Gln | Arg | Lys | Ala | Phe | Gln | Gln | Ser | Ile | Glu | Gly | |
| | 595 | | | | | 600 | | | | | 605 | | | | | |
| CTG | ATG | ACT | GTA | CGC | CAT | GAG | CAG | ACA | TCT | AGC | CAG | CCC | ATC | ATC | GCC | 2229 |
| Leu | Met | Thr | Val | Arg | His | Glu | Gln | Thr | Ser | Ser | Gln | Pro | Ile | Ile | Ala | |
| 610 | | | | | 615 | | | | | 620 | | | | | 625 | |
| AAA | GGT | TTG | CAG | CAG | CTC | AAG | AAC | GAT | GCA | CTT | GAG | CTA | TGC | AAC | AGA | 2277 |
| Lys | Gly | Leu | Gln | Gln | Leu | Lys | Asn | Asp | Ala | Leu | Glu | Leu | Cys | Asn | Arg | |
| | | | | 630 | | | | | 635 | | | | | 640 | | |
| ATC | AGC | GAT | GCC | ATC | GAC | CGT | GTG | GAC | CAC | ATG | TTC | ACC | CTG | GAG | TTC | 2325 |
| Ile | Ser | Asp | Ala | Ile | Asp | Arg | Val | Asp | His | Met | Phe | Thr | Leu | Glu | Phe | |
| | | | 645 | | | | | 650 | | | | | 655 | | | |
| GAT | GCT | GAG | GTC | GAG | GAG | TCT | GAG | TCG | GCC | ACG | CTG | CAG | CAG | TAC | TAC | 2373 |
| Asp | Ala | Glu | Val | Glu | Glu | Ser | Glu | Ser | Ala | Thr | Leu | Gln | Gln | Tyr | Tyr | |
| | | | 660 | | | | | 665 | | | | | 670 | | | |

| | | | | | | | | | | | | | | | | |
|---|---|---|---|---|---|---|---|---|---|---|---|---|---|---|---|---|
| CGA | GAA | GCC | ATG | ATT | CAG | GGC | TAC | AAC | TTT | GGG | TTT | GAG | TAT | CAT | AAA | 2421 |
| Arg | Glu | Ala | Met | Ile | Gln | Gly | Tyr | Asn | Phe | Gly | Phe | Glu | Tyr | His | Lys | |
| 675 | | | | | 680 | | | | | 685 | | | | | | |
| GAA | GTT | GTT | CGT | TTG | ATG | TCT | GGG | GAA | TTC | AGG | CAG | AAG | ATA | GGA | GAC | 2469 |
| Glu | Val | Val | Arg | Leu | Met | Ser | Gly | Glu | Phe | Arg | Gln | Lys | Ile | Gly | Asp | |
| 690 | | | | | 695 | | | | | 700 | | | | | 705 | |
| AAA | TAT | ATA | AGC | TTC | GCC | CAG | AAG | TGG | ATG | AAT | TAC | GTG | CTG | ACC | AAA | 2517 |
| Lys | Tyr | Ile | Ser | Phe | Ala | Gln | Lys | Trp | Met | Asn | Tyr | Val | Leu | Thr | Lys | |
| | | | | 710 | | | | | 715 | | | | | 720 | | |
| TGC | GAG | AGC | GGC | AGA | GGC | ACA | AGA | CCC | AGA | TGG | GCC | ACC | CAA | GGA | TTT | 2565 |
| Cys | Glu | Ser | Gly | Arg | Gly | Thr | Arg | Pro | Arg | Trp | Ala | Thr | Gln | Gly | Phe | |
| | | | 725 | | | | | 730 | | | | | 735 | | | |
| GAT | TTC | CTA | CAA | GCC | ATT | GAA | CCT | GCC | TTT | ATT | TCA | GCT | TTA | CCA | GAA | 2613 |
| Asp | Phe | Leu | Gln | Ala | Ile | Glu | Pro | Ala | Phe | Ile | Ser | Ala | Leu | Pro | Glu | |
| | | 740 | | | | | 745 | | | | | 750 | | | | |
| GAT | GAC | TTC | TTG | AGT | TTG | CAA | GCC | CTG | ATG | AAT | GAG | TGC | ATC | GGG | CAC | 2661 |
| Asp | Asp | Phe | Leu | Ser | Leu | Gln | Ala | Leu | Met | Asn | Glu | Cys | Ile | Gly | His | |
| | 755 | | | | | 760 | | | | | 765 | | | | | |
| GTC | ATA | GGA | AAG | CCA | CAC | AGC | CCT | GTC | ACA | GCT | ATC | CAT | CGG | AAC | AGC | 2709 |
| Val | Ile | Gly | Lys | Pro | His | Ser | Pro | Val | Thr | Ala | Ile | His | Arg | Asn | Ser | |
| 770 | | | | | 775 | | | | | 780 | | | | | 785 | |
| CCC | CGC | CCT | GTG | AAG | GTG | CCC | CGA | TGC | CAC | AGT | GAC | CCT | CCT | AAC | CCT | 2757 |
| Pro | Arg | Pro | Val | Lys | Val | Pro | Arg | Cys | His | Ser | Asp | Pro | Pro | Asn | Pro | |
| | | | | 790 | | | | | 795 | | | | | 800 | | |
| CAC | CTC | ATC | ATC | CCG | ACT | CCA | GAG | GGA | TTC | AGC | ACC | CGG | AGC | GTG | CCT | 2805 |
| His | Leu | Ile | Ile | Pro | Thr | Pro | Glu | Gly | Phe | Ser | Thr | Arg | Ser | Val | Pro | |
| | | | 805 | | | | | 810 | | | | | 815 | | | |
| TCC | GAC | GCT | CGG | ACC | CAT | GGC | AAC | TCT | GTT | GCT | GCT | GCT | GCT | GCT | GTT | 2853 |
| Ser | Asp | Ala | Arg | Thr | His | Gly | Asn | Ser | Val | Ala | Ala | Ala | Ala | Ala | Val | |
| | | 820 | | | | | 825 | | | | | 830 | | | | |
| CGT | GCC | GCC | GCC | ACC | ACT | GCT | GCT | GGC | CGC | CCT | GGC | CCA | GGT | GGT | GGT | 2901 |
| Arg | Ala | Ala | Ala | Thr | Thr | Ala | Ala | Gly | Arg | Pro | Gly | Pro | Gly | Gly | Gly | |
| | 835 | | | | | 840 | | | | | 845 | | | | | |
| GAC | TCT | GTG | CCA | GCC | AAA | CCT | GTC | AAC | ACT | GCC | CCT | GAT | ACC | AGG | GGT | 2949 |
| Asp | Ser | Val | Pro | Ala | Lys | Pro | Val | Asn | Thr | Ala | Pro | Asp | Thr | Arg | Gly | |
| 850 | | | | | 855 | | | | | 860 | | | | | 865 | |
| TCC | AGT | GTC | CCT | GAA | AAC | GAC | CGC | TTG | GCC | TCC | ATA | GCT | GCA | GAA | CTG | 2997 |
| Ser | Ser | Val | Pro | Glu | Asn | Asp | Arg | Leu | Ala | Ser | Ile | Ala | Ala | Glu | Leu | |
| | | | | 870 | | | | | 875 | | | | | 880 | | |
| CAG | TTC | AGG | TCT | CTG | AGT | CGG | CAC | TCA | AGC | CCC | ACG | GAA | GAG | CGA | GAC | 3045 |
| Gln | Phe | Arg | Ser | Leu | Ser | Arg | His | Ser | Ser | Pro | Thr | Glu | Glu | Arg | Asp | |
| | | | 885 | | | | | 890 | | | | | 895 | | | |
| GAG | CCA | GCG | TAT | CCT | CGG | AGT | GAC | TCA | AGT | GGA | TCA | ACT | CGG | AGA | AGC | 3093 |
| Glu | Pro | Ala | Tyr | Pro | Arg | Ser | Asp | Ser | Ser | Gly | Ser | Thr | Arg | Arg | Ser | |
| | | 900 | | | | | 905 | | | | | 910 | | | | |
| TGG | GAA | CTT | CGA | ACA | CTC | ATC | AGC | CAG | ACC | AAA | GAC | TCG | GCC | TCT | AAG | 3141 |
| Trp | Glu | Leu | Arg | Thr | Leu | Ile | Ser | Gln | Thr | Lys | Asp | Ser | Ala | Ser | Lys | |
| | 915 | | | | | 920 | | | | | 925 | | | | | |
| CAG | GGG | CCC | ATA | GAA | GCT | ATC | CAG | AAG | TCA | GTC | CGA | CTG | TTT | GAA | GAG | 3189 |
| Gln | Gly | Pro | Ile | Glu | Ala | Ile | Gln | Lys | Ser | Val | Arg | Leu | Phe | Glu | Glu | |
| 930 | | | | | 935 | | | | | 940 | | | | | 945 | |
| AGG | AGG | TAT | CGA | GAG | ATG | AGG | AGA | AAG | AAT | ATC | ATC | GGC | CAA | GTG | TGC | 3237 |
| Arg | Arg | Tyr | Arg | Glu | Met | Arg | Arg | Lys | Asn | Ile | Ile | Gly | Gln | Val | Cys | |
| | | | | 950 | | | | | 955 | | | | | 960 | | |
| GAT | ACC | CCT | AAG | TCC | TAT | GAT | AAC | GTC | ATG | CAT | GTT | GGA | CTG | AGG | AAG | 3285 |
| Asp | Thr | Pro | Lys | Ser | Tyr | Asp | Asn | Val | Met | His | Val | Gly | Leu | Arg | Lys | |
| | | | 965 | | | | | 970 | | | | | 975 | | | |
| GTG | ACA | TTT | AAG | TGG | CAA | AGA | GGA | AAC | AAA | ATT | GGA | GAA | GGA | CAG | TAT | 3333 |
| Val | Thr | Phe | Lys | Trp | Gln | Arg | Gly | Asn | Lys | Ile | Gly | Glu | Gly | Gln | Tyr | |
| | | 980 | | | | | 985 | | | | | 990 | | | | |

-continued

| | | | | | | | | | | | | | | | | |
|---|---|---|---|---|---|---|---|---|---|---|---|---|---|---|---|---|
| GGA | AAA | GTA | TAC | ACC | TGC | ATC | AGT | GTT | GAC | ACA | GGG | GAG | CTG | ATG | GCC | 3381 |
| Gly | Lys | Val | Tyr | Thr | Cys | Ile | Ser | Val | Asp | Thr | Gly | Glu | Leu | Met | Ala | |
| | 995 | | | | 1000 | | | | | 1005 | | | | | | |
| ATG | AAG | GAG | ATT | CGA | TTT | CAG | CCT | AAC | GAC | CAC | AAG | ACT | ATC | AAG | GAG | 3429 |
| Met | Lys | Glu | Ile | Arg | Phe | Gln | Pro | Asn | Asp | His | Lys | Thr | Ile | Lys | Glu | |
| 1010 | | | | | 1015 | | | | | 1020 | | | | | 1025 | |
| ACT | GCA | GAC | GAG | TTG | AAA | ATA | TTT | GAA | GGC | ATC | AAG | CAC | CCC | AAC | CTG | 3477 |
| Thr | Ala | Asp | Glu | Leu | Lys | Ile | Phe | Glu | Gly | Ile | Lys | His | Pro | Asn | Leu | |
| | | | 1030 | | | | | 1035 | | | | | 1040 | | | |
| GTC | CGG | TAT | TTT | GGC | GTG | GAG | CTT | CAC | AGG | GAA | GAG | ATG | TAC | ATC | TTC | 3525 |
| Val | Arg | Tyr | Phe | Gly | Val | Glu | Leu | His | Arg | Glu | Glu | Met | Tyr | Ile | Phe | |
| | | | | 1045 | | | | | 1050 | | | | | 1055 | | |
| ATG | GAG | TAC | TGT | GAT | GAG | GGT | ACA | CTA | GAG | GAG | GTG | TCA | CGA | CTG | GGC | 3573 |
| Met | Glu | Tyr | Cys | Asp | Glu | Gly | Thr | Leu | Glu | Glu | Val | Ser | Arg | Leu | Gly | |
| | | | | 1060 | | | | | 1065 | | | | | 1070 | | |
| CTG | CAG | GAG | CAC | GTC | ATC | AGG | TTA | TAT | ACC | AAG | CAG | ATC | ACT | GTC | GCC | 3621 |
| Leu | Gln | Glu | His | Val | Ile | Arg | Leu | Tyr | Thr | Lys | Gln | Ile | Thr | Val | Ala | |
| | | 1075 | | | | | 1080 | | | | | 1085 | | | | |
| ATC | AAC | GTC | CTC | CAT | GAG | CAC | GGC | ATC | GTT | CAC | CGA | GAC | ATC | AAA | GGT | 3669 |
| Ile | Asn | Val | Leu | His | Glu | His | Gly | Ile | Val | His | Arg | Asp | Ile | Lys | Gly | |
| 1090 | | | | | 1095 | | | | | 1100 | | | | | 1105 | |
| GCC | AAT | ATC | TTC | CTT | ACG | TCA | TCT | GGA | CTA | ATC | AAG | CTG | GGA | GAT | TTT | 3717 |
| Ala | Asn | Ile | Phe | Leu | Thr | Ser | Ser | Gly | Leu | Ile | Lys | Leu | Gly | Asp | Phe | |
| | | | | 1110 | | | | | 1115 | | | | | 1120 | | |
| GGA | TGC | TCT | GTA | AAA | CTT | AAA | AAC | AAC | GCC | CAG | ACC | ATG | CCC | GGA | GAG | 3765 |
| Gly | Cys | Ser | Val | Lys | Leu | Lys | Asn | Asn | Ala | Gln | Thr | Met | Pro | Gly | Glu | |
| | | | | 1125 | | | | | 1130 | | | | | 1135 | | |
| GTG | AAC | AGC | ACC | CTA | GGG | ACA | GCA | GCT | TAC | ATG | GCC | CCT | GAA | GTT | ATT | 3813 |
| Val | Asn | Ser | Thr | Leu | Gly | Thr | Ala | Ala | Tyr | Met | Ala | Pro | Glu | Val | Ile | |
| | | | | 1140 | | | | | 1145 | | | | | 1150 | | |
| ACC | CGA | GCC | AAA | GGA | GAA | GGC | CAC | GGA | CGT | GCG | GCA | GAT | ATC | TGG | AGT | 3861 |
| Thr | Arg | Ala | Lys | Gly | Glu | Gly | His | Gly | Arg | Ala | Ala | Asp | Ile | Trp | Ser | |
| | | 1155 | | | | | 1160 | | | | | 1165 | | | | |
| CTG | GGG | TGC | GTC | GTC | ATA | GAG | ATG | GTG | ACT | GGC | AAG | CGG | CCT | TGG | CAT | 3909 |
| Leu | Gly | Cys | Val | Val | Ile | Glu | Met | Val | Thr | Gly | Lys | Arg | Pro | Trp | His | |
| 1170 | | | | | 1175 | | | | | 1180 | | | | | 1185 | |
| GAG | TAT | GAA | CAC | AAC | TTT | CAG | ATT | ATG | TAC | AAG | GTG | GGG | ATG | GGA | CAC | 3957 |
| Glu | Tyr | Glu | His | Asn | Phe | Gln | Ile | Met | Tyr | Lys | Val | Gly | Met | Gly | His | |
| | | | | 1190 | | | | | 1195 | | | | | 1200 | | |
| AAG | CCA | CCA | ATC | CCG | GAA | AGG | CTA | AGC | CCT | GAA | GGA | AAG | GCC | TTT | CTC | 4005 |
| Lys | Pro | Pro | Ile | Pro | Glu | Arg | Leu | Ser | Pro | Glu | Gly | Lys | Ala | Phe | Leu | |
| | | | | 1205 | | | | | 1210 | | | | | 1215 | | |
| TCG | CAC | TGC | CTG | GAA | AGT | GAC | CCG | AAG | ATA | CGG | TGG | ACA | GCC | AGC | CAG | 4053 |
| Ser | His | Cys | Leu | Glu | Ser | Asp | Pro | Lys | Ile | Arg | Trp | Thr | Ala | Ser | Gln | |
| | | | 1220 | | | | | 1225 | | | | | 1230 | | | |
| CTC | CTC | GAC | CAC | GCT | TTT | GTC | AAG | GTT | TGC | ACA | GAT | GAA | GAG | | | 4095 |
| Leu | Leu | Asp | His | Ala | Phe | Val | Lys | Val | Cys | Thr | Asp | Glu | Glu | | | |
| | | | 1235 | | | | | 1240 | | | | | 1245 | | | |

| | | | | |
|---|---|---|---|---|
| TGAAGTGAAC | CAGTCCGTGG | CCTAGTAGTG | TGTGGACAGA | ATCCCGTGAT | CACTACTGTA | 4155 |
| TGTAATATTT | ACATAAAGAC | TGCAGCGCAG | GCGGCCTTCC | TAACCTCCCA | GGACTGAAGA | 4215 |
| CTACAGGGGT | GACAAGCCTC | ACTTCTGCTG | CTCCTGTCGC | CTGCTGAGTG | ACAGTGCTGA | 4275 |
| GGTTAAAGGA | GCCGCACGTT | AAGTGCCATT | ACTACTGTAC | ACGGCCACCG | CCTCTGTCCC | 4335 |
| CTCCGACCCT | CTCGTGACTG | AGAACCAACC | GTGTCATCAG | CACAGTGTTT | TGAGCTCCT | 4395 |
| GGGGTTCAGA | AGAACATGTA | GTGTTCCCGG | GTGTCCGGGA | CGTTTATTTC | AACCTCCTGG | 4455 |
| TCGTTGGCTC | TGACTGTGGA | GCCTCCTTGT | TCGAAAGCTG | CAGGTTTGTT | ATGCAAGGC | 4515 |
| TCGTAAGTGA | AGCTGAAGAA | AAGGTTCTTT | TTCAATAAAT | GGTTTATTTT | AGGAAAGCGA | 4575 |

AAAAAAAAA AAAAAA											4 5 9 2

( 2 ) INFORMATION FOR SEQ ID NO:10:

( i ) SEQUENCE CHARACTERISTICS:
        ( A ) LENGTH: 1247 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

| Met | Glu | Leu | Leu | Glu | Tyr | Met | Glu | Ala | Leu | Tyr | Pro | Ser | Leu | Gln | Ala |
|---|---|---|---|---|---|---|---|---|---|---|---|---|---|---|---|
| 1 | | | | 5 | | | | | 10 | | | | | 15 | |
| Leu | Gln | Lys | Asp | Tyr | Glu | Arg | Tyr | Ala | Ala | Lys | Asp | Phe | Glu | Asp | Arg |
| | | | 20 | | | | | 25 | | | | | 30 | | |
| Val | Gln | Ala | Leu | Cys | Leu | Trp | Leu | Asn | Ile | Thr | Lys | Asp | Leu | Asn | Gln |
| | | | 35 | | | | 40 | | | | | 45 | | | |
| Lys | Leu | Arg | Ile | Met | Gly | Thr | Val | Leu | Gly | Ile | Lys | Phe | Leu | Ser | Asp |
| | | 50 | | | | | 55 | | | | | 60 | | | |
| Ile | Gly | Trp | Pro | Val | Lys | Glu | Ile | Pro | Ser | Pro | Arg | Pro | Ser | Lys | Gly |
| 65 | | | | | 70 | | | | | 75 | | | | | 80 |
| Tyr | Glu | Pro | Glu | Asp | Glu | Val | Glu | Asp | Thr | Glu | Val | Glu | Leu | Arg | Glu |
| | | | | 85 | | | | | 90 | | | | | 95 | |
| Leu | Glu | Ser | Gly | Thr | Glu | Glu | Ser | Asp | Glu | Glu | Pro | Thr | Pro | Ser | Pro |
| | | | | 100 | | | | | 105 | | | | | 110 | |
| Arg | Val | Pro | Glu | Leu | Arg | Leu | Ser | Thr | Asp | Thr | Ile | Leu | Asp | Ser | Arg |
| | | | 115 | | | | | 120 | | | | | 125 | | |
| Ser | Gln | Gly | Cys | Val | Ser | Arg | Lys | Leu | Glu | Arg | Leu | Glu | Ser | Glu | Glu |
| | 130 | | | | | 135 | | | | | 140 | | | | |
| Asp | Ser | Ile | Gly | Trp | Gly | Thr | Ala | Asp | Cys | Gly | Pro | Glu | Ala | Ser | Arg |
| 145 | | | | | 150 | | | | | 155 | | | | | 160 |
| His | Cys | Leu | Thr | Ser | Met | Tyr | Arg | Pro | Phe | Val | Asp | Lys | Ala | Leu | Lys |
| | | | | 165 | | | | | 170 | | | | | 175 | |
| Gln | Met | Gly | Leu | Arg | Lys | Leu | Ile | Leu | Arg | Leu | His | Lys | Leu | Met | Asn |
| | | | 180 | | | | | 185 | | | | | 190 | | |
| Gly | Ser | Leu | Gln | Arg | Ala | Arg | Val | Ala | Leu | Val | Lys | Asp | Asp | Arg | Pro |
| | | | 195 | | | | | 200 | | | | | 205 | | |
| Val | Glu | Phe | Ser | Asp | Phe | Pro | Gly | Pro | Met | Trp | Gly | Ser | Asp | Tyr | Val |
| | 210 | | | | | 215 | | | | | 220 | | | | |
| Gln | Leu | Ser | Gly | Thr | Pro | Pro | Ser | Ser | Glu | Gln | Lys | Cys | Ser | Ala | Val |
| 225 | | | | | 230 | | | | | 235 | | | | | 240 |
| Ser | Trp | Glu | Glu | Leu | Arg | Ala | Met | Asp | Leu | Pro | Ser | Phe | Glu | Pro | Ala |
| | | | | 245 | | | | | 250 | | | | | 255 | |
| Phe | Leu | Val | Leu | Cys | Arg | Val | Leu | Leu | Asn | Val | Ile | His | Glu | Cys | Leu |
| | | | 260 | | | | | 265 | | | | | 270 | | |
| Lys | Leu | Arg | Leu | Glu | Gln | Arg | Pro | Ala | Gly | Glu | Pro | Ser | Leu | Leu | Ser |
| | | 275 | | | | | 280 | | | | | 285 | | | |
| Ile | Lys | Gln | Leu | Val | Arg | Glu | Cys | Lys | Glu | Val | Leu | Lys | Gly | Gly | Leu |
| | 290 | | | | | 295 | | | | | 300 | | | | |
| Leu | Met | Lys | Gln | Tyr | Tyr | Gln | Phe | Met | Leu | Gln | Glu | Val | Leu | Gly | Gly |
| 305 | | | | | 310 | | | | | 315 | | | | | 320 |
| Leu | Glu | Lys | Thr | Asp | Cys | Asn | Met | Asp | Ala | Phe | Glu | Glu | Asp | Leu | Gln |
| | | | | 325 | | | | | 330 | | | | | 335 | |
| Lys | Met | Leu | Met | Val | Tyr | Phe | Asp | Tyr | Met | Arg | Ser | Trp | Ile | Gln | Met |
| | | | 340 | | | | | 345 | | | | | 350 | | |

```
Leu Gln Gln Leu Pro Gln Ala Ser His Ser Leu Lys Asn Leu Leu Glu
        355             360             365

Glu Glu Trp Asn Phe Thr Lys Glu Ile Thr His Tyr Ile Arg Gly Gly
    370             375             380

Glu Ala Gln Ala Gly Lys Leu Phe Cys Asp Ile Ala Gly Met Leu Leu
385             390             395                         400

Lys Ser Thr Gly Ser Phe Leu Glu Ser Gly Leu Gln Glu Ser Cys Ala
                405             410             415

Glu Leu Trp Thr Ser Ala Asp Asn Gly Ala Ala Asp Glu Leu Arg
            420             425             430

Arg Ser Val Ile Glu Ile Ser Arg Ala Leu Lys Glu Leu Phe His Glu
            435             440             445

Ala Arg Glu Arg Ala Ser Lys Ala Leu Gly Phe Ala Lys Met Leu Arg
    450             455             460

Lys Asp Leu Glu Ile Ala Ala Glu Phe Val Leu Ser Ala Ser Ala Arg
465             470             475                         480

Glu Leu Leu Asp Ala Leu Lys Ala Lys Gln Tyr Val Lys Val Gln Ile
            485             490             495

Pro Gly Leu Glu Asn Leu His Val Phe Val Pro Asp Ser Leu Ala Glu
                500             505             510

Glu Lys Lys Ile Ile Leu Gln Leu Leu Asn Ala Ala Thr Gly Lys Asp
        515             520             525

Cys Ser Lys Asp Pro Asp Asp Val Phe Met Asp Ala Phe Leu Leu Leu
    530             535             540

Thr Lys His Gly Asp Arg Ala Arg Asp Ser Glu Asp Gly Trp Gly Thr
545             550             555                         560

Trp Glu Ala Arg Ala Val Lys Ile Val Pro Gln Val Glu Thr Val Asp
                565             570             575

Thr Leu Arg Ser Met Gln Val Asp Asn Leu Leu Leu Val Val Met Glu
            580             585             590

Ser Ala His Leu Val Leu Gln Arg Lys Ala Phe Gln Gln Ser Ile Glu
        595             600             605

Gly Leu Met Thr Val Arg His Glu Gln Thr Ser Ser Gln Pro Ile Ile
    610             615             620

Ala Lys Gly Leu Gln Gln Leu Lys Asn Asp Ala Leu Glu Leu Cys Asn
625             630             635                         640

Arg Ile Ser Asp Ala Ile Asp Arg Val Asp His Met Phe Thr Leu Glu
                645             650             655

Phe Asp Ala Glu Val Glu Glu Ser Glu Ser Ala Thr Leu Gln Gln Tyr
            660             665             670

Tyr Arg Glu Ala Met Ile Gln Gly Tyr Asn Phe Gly Phe Glu Tyr His
        675             680             685

Lys Glu Val Val Arg Leu Met Ser Gly Glu Phe Arg Gln Lys Ile Gly
    690             695             700

Asp Lys Tyr Ile Ser Phe Ala Gln Lys Trp Met Asn Tyr Val Leu Thr
705             710             715                         720

Lys Cys Glu Ser Gly Arg Gly Thr Arg Pro Arg Trp Ala Thr Gln Gly
                725             730             735

Phe Asp Phe Leu Gln Ala Ile Glu Pro Ala Phe Ile Ser Ala Leu Pro
            740             745             750

Glu Asp Asp Phe Leu Ser Leu Gln Ala Leu Met Asn Glu Cys Ile Gly
        755             760             765

His Val Ile Gly Lys Pro His Ser Pro Val Thr Ala Ile His Arg Asn
    770             775             780
```

```
Ser  Pro  Arg  Pro  Val  Lys  Val  Pro  Arg  Cys  His  Ser  Asp  Pro  Pro  Asn
785                 790                 795                      800

Pro  His  Leu  Ile  Ile  Pro  Thr  Pro  Glu  Gly  Phe  Ser  Thr  Arg  Ser  Val
                    805                 810                      815

Pro  Ser  Asp  Ala  Arg  Thr  His  Gly  Asn  Ser  Val  Ala  Ala  Ala  Ala  Ala
               820                 825                      830

Val  Arg  Ala  Ala  Ala  Thr  Thr  Ala  Ala  Gly  Arg  Pro  Gly  Pro  Gly  Gly
          835                 840                           845

Gly  Asp  Ser  Val  Pro  Ala  Lys  Pro  Val  Asn  Thr  Ala  Pro  Asp  Thr  Arg
850                      855                      860

Gly  Ser  Ser  Val  Pro  Glu  Asn  Asp  Arg  Leu  Ala  Ser  Ile  Ala  Ala  Glu
865                      870                 875                           880

Leu  Gln  Phe  Arg  Ser  Leu  Ser  Arg  His  Ser  Ser  Pro  Thr  Glu  Glu  Arg
               885                      890                           895

Asp  Glu  Pro  Ala  Tyr  Pro  Arg  Ser  Asp  Ser  Ser  Gly  Ser  Thr  Arg  Arg
               900                      905                      910

Ser  Trp  Glu  Leu  Arg  Thr  Leu  Ile  Ser  Gln  Thr  Lys  Asp  Ser  Ala  Ser
          915                      920                      925

Lys  Gln  Gly  Pro  Ile  Glu  Ala  Ile  Gln  Lys  Ser  Val  Arg  Leu  Phe  Glu
          930                      935                      940

Glu  Arg  Arg  Tyr  Arg  Glu  Met  Arg  Arg  Lys  Asn  Ile  Ile  Gly  Gln  Val
945                      950                      955                      960

Cys  Asp  Thr  Pro  Lys  Ser  Tyr  Asp  Asn  Val  Met  His  Val  Gly  Leu  Arg
               965                      970                           975

Lys  Val  Thr  Phe  Lys  Trp  Gln  Arg  Gly  Asn  Lys  Ile  Gly  Glu  Gly  Gln
               980                      985                           990

Tyr  Gly  Lys  Val  Tyr  Thr  Cys  Ile  Ser  Val  Asp  Thr  Gly  Glu  Leu  Met
          995                      1000                     1005

Ala  Met  Lys  Glu  Ile  Arg  Phe  Gln  Pro  Asn  Asp  His  Lys  Thr  Ile  Lys
          1010                     1015                     1020

Glu  Thr  Ala  Asp  Glu  Leu  Lys  Ile  Phe  Glu  Gly  Ile  Lys  His  Pro  Asn
1025                     1030                     1035                     1040

Leu  Val  Arg  Tyr  Phe  Gly  Val  Glu  Leu  His  Arg  Glu  Glu  Met  Tyr  Ile
               1045                     1050                     1055

Phe  Met  Glu  Tyr  Cys  Asp  Glu  Gly  Thr  Leu  Glu  Glu  Val  Ser  Arg  Leu
               1060                     1065                     1070

Gly  Leu  Gln  Glu  His  Val  Ile  Arg  Leu  Tyr  Thr  Lys  Gln  Ile  Thr  Val
               1075                     1080                     1085

Ala  Ile  Asn  Val  Leu  His  Glu  His  Gly  Ile  Val  His  Arg  Asp  Ile  Lys
          1090                     1095                     1100

Gly  Ala  Asn  Ile  Phe  Leu  Thr  Ser  Ser  Gly  Leu  Ile  Lys  Leu  Gly  Asp
1105                     1110                     1115                     1120

Phe  Gly  Cys  Ser  Val  Lys  Leu  Lys  Asn  Asn  Ala  Gln  Thr  Met  Pro  Gly
               1125                     1130                     1135

Glu  Val  Asn  Ser  Thr  Leu  Gly  Thr  Ala  Ala  Tyr  Met  Ala  Pro  Glu  Val
               1140                     1145                     1150

Ile  Thr  Arg  Ala  Lys  Gly  Glu  Gly  His  Gly  Arg  Ala  Ala  Asp  Ile  Trp
               1155                     1160                     1165

Ser  Leu  Gly  Cys  Val  Val  Ile  Glu  Met  Val  Thr  Gly  Lys  Arg  Pro  Trp
          1170                     1175                     1180

His  Glu  Tyr  Glu  His  Asn  Phe  Gln  Ile  Met  Tyr  Lys  Val  Gly  Met  Gly
1185                     1190                     1195                     1200
```

| His | Lys | Pro | Pro | Ile<br>1205 | Pro | Glu | Arg | Leu | Ser | Pro<br>1210 | Glu | Gly | Lys | Ala | Phe<br>1215 |
| Leu | Ser | His | Cys<br>1220 | Leu | Glu | Ser | Asp | Pro | Lys<br>1225 | Ile | Arg | Trp | Thr<br>1230 | Ala | Ser |
| Gln | Leu | Leu<br>1235 | Asp | His | Ala | Phe | Val | Lys<br>1240 | Val | Cys | Thr | Asp<br>1245 | Glu | Glu | |

What is claimed:

1. An isolated MEKK protein comprising the amino acid sequence of SEQ ID NO:4.

2. An isolated MEKK regulatory domain comprising amino acids 1–162 of SEQ ID NO:4.

3. An isolated MEKK catalytic domain comprising amino acids 351–619 of SEQ ID NO:4.

4. An isolated MEKK kinase domain comprising amino acids 386–480 of SEQ ID NO:4.

5. An isolated MEKK protein comprising the amino acid sequence of SEQ ID NO:6.

6. An isolated MEKK regulatory domain comprising amino acids 1–174 of SEQ ID NO:6.

7. An isolated MEKK catalytic domain comprising amino acids 357–626 of SEQ ID NO:6.

8. An isolated MFKK kinase domain comprising amino acids 392–486 of SEQ ID NO:6.

9. An isolated MEKK protein comprising the amino acid sequence of SEQ ID NO:8.

10. An isolated MEKK protein comprising the amino acid sequence of SEQ ID NO:10.

11. An isolated MEKK kinase domain comprising amino acids 656–742 of SEQ ID NO:8.

* * * * *